United States Patent
Liu et al.

(10) Patent No.: US 12,162,848 B2
(45) Date of Patent: Dec. 10, 2024

(54) INHIBITORS OF PROTEIN TYROSINE PHOSPHATASE, COMPOSITIONS, AND METHODS OF USE

(71) Applicant: BRISTOL-MYERS SQUIBB COMPANY, Princeton, NJ (US)

(72) Inventors: Haibo Liu, Lexington, MA (US); Laura Akullian D'Agostino, Sudbury, MA (US); Shoshana L. Posy, Highland Park, NJ (US); Annapurna Pendri, South Glastonbury, CT (US); Swanee E. Jacutin-Porte, Madison, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 18/161,184

(22) Filed: Jan. 30, 2023

(65) Prior Publication Data
US 2023/0322695 A1 Oct. 12, 2023

Related U.S. Application Data

(60) Provisional application No. 63/305,022, filed on Jan. 31, 2022.

(51) Int. Cl.
| | |
|---|---|
| C07D 285/06 | (2006.01) |
| A61K 45/06 | (2006.01) |
| A61P 35/00 | (2006.01) |
| C07D 417/10 | (2006.01) |
| C07D 417/12 | (2006.01) |

(52) U.S. Cl.
CPC ............ *C07D 285/06* (2013.01); *A61K 45/06* (2013.01); *A61P 35/00* (2018.01); *C07D 417/10* (2013.01); *C07D 417/12* (2013.01)

(58) Field of Classification Search
CPC .................................................. C07D 285/06
USPC ....................................................... 514/361
See application file for complete search history.

(56) References Cited

U.S. PATENT DOCUMENTS 8,252,820 B2 * 8/2012 Barnes ................ A61P 19/10
548/135

FOREIGN PATENT DOCUMENTS

| WO | 2007067612 A1 | 6/2007 |
| WO | 2014/031170 A1 * | 2/2014 |
| WO | 2022056281 A1 | 3/2022 |
| WO | 2022/261145 A1 * | 12/2022 |
| WO | 2022261145 | 12/2022 |

OTHER PUBLICATIONS

King, Med. Chem., Principle and Practice (1994), pp. 206-208.*
Patani et al., Chem. Rev. (1996) 96, p. 3149.*
Abdel-Magid, Ahmed F., "The Inhibitors of Protein Tyrosine Phosphatase Nonreceptor Type 2 (PTPN2) as Potential Enhancers of Cancer Immunotherapy and Type 1 (PTPN1) as Treatment of Metabolic Diseases", ACS Medicinal Chemistry Letters, vol. 13 (2022), pp. 19-21.
Flosbach, Markus et al., "PTPN2 Deficiency Enhances Programmed T Cell Expansion and Survival Capacity of Activated T Cells", Cell Reports, vol. 32 (2020), pp. 1-17.
Hering, Larissa et al., "Protein Tyrosine Phosphatase Non-Receptor Type 2 Function in Dendritic Cells Is Crucial to Maintain Tissue Tolerance", Frontiers in Immunology, vol. 11, Article 1856 (2020), pp. 1-15.
Kearney, Conor J., et al., "Tumor immune evasion arises through loss of TNF sensitivity", Science Immunology, vol. 3, eaar3451, (2018), pp. 1-14.
LaFleur, Martin W., et al., "PTPN2 regulates the generation of exhausted CD8+ T cell subpopulations and restrains tumor immunity", Nature Immunology, vol. 20 (2019), pp. 1335-1347.
Manguso, Robert T. et al., "In vivo CRISPR screening identifies Ptpn2 as a cancer immunotherapy target", Nature, vol. 547 (2017), pp. 413-429.
Pan, Deng et al., "A major chromatin regulator determines resistance of tumor cells to T cell-mediated killing", Science, vol. 359 (2018), pp. 1-6.
Poorebrahim, Mansour et al., "Counteracting CAR T cell dysfunction", Oncogene, vol. 40 (2021), pp. 421-435.
Sceneay, Jaclyn et al., "The future of immune checkpoint combinations with tumor-targeted small molecule drugs", Emerging Topics in Life Sciences (2021) vol. 5, pp. 675-680.
Spalinger, Marianne R., et al., "PTPN2 Regulates Inflammasome Activation and Controls Onset of Intestinal Inflammation and Colon Cancer", Cell Reports, vol. 22 (2018), pp. 1835-1848.
Wiede, Florian et al., "PTPN2 phosphatase deletion in T cells promotes anti-tumour immunity and CAR T-cell efficacy in solid tumours", The EMBO Journal, vol. 39, e103637 (2020), pp. 1-26.
Wiede, Florian, et al., "PTPN2 attenuates T-cell lymphopenia-induced proliferation", Nature Communications, 5:3073, (2014), pp. 1-15.

(Continued)

*Primary Examiner* — Taofiq A Solola
(74) *Attorney, Agent, or Firm* — Robert Kajubi

(57) ABSTRACT

Disclosed are compounds of Formula (I)

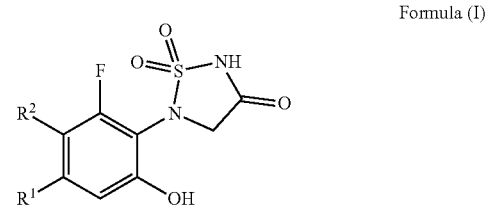

Formula (I)

pharmaceutically acceptable salts thereof are defined herein, and pharmaceutical compositions thereof and combinations thereof, and methods of using the same as inhibitors of protein tyrosine phosphatases (PTPN2). These compounds are useful in treating cancer and diseases susceptible to PNPT2 inhibition.

17 Claims, No Drawings

(56) References Cited

OTHER PUBLICATIONS

Wiede, Florian, et al., "T cell protein tyrosine phosphatase attenuates T cell signaling to maintain tolerance in mice", The Journal of Clinical Investigation, vol. 121 (12) (2011), pp. 4758-4774.

* cited by examiner

INHIBITORS OF PROTEIN TYROSINE PHOSPHATASE, COMPOSITIONS, AND METHODS OF USE

CROSS REFERENCE TO RELATED APPLICATIONS

This application claims the benefit of U.S. Provisional Application Ser. No. 63/305,022 filed Jan. 31, 2022 which is incorporated herein in its entirety.

FIELD OF THE INVENTION

Disclosed are compounds, pharmaceutically acceptable salts thereof, pharmaceutical compositions thereof and combinations thereof, and methods of using the same as inhibitors of protein tyrosine phosphatases.

BACKGROUND

Immune checkpoint blockade (ICB) is an innovative approach to immunotherapy that targets immune evasion mechanisms to improve clinical responses in cancer patients. For example, checkpoint blockade antibodies target cytotoxic T lymphocyte antigen 4 (CTLA-4), programmed cell death 1 (PD-1), and its ligands, such as programmed cell death ligand 1 (PD-L1), in the treatment of multiple types of cancer to significantly improve the treatment and survival outcomes of patients affected by these malignancies.

A majority of patients who undergo ICB, however, are either refractory to treatment or eventually acquire resistance. In particular, mutation or loss of interferon-gamma (IFNγ) signaling pathway represents a significant mechanism of clinical ICB resistance (Zaretsky, *N. Engl. J. Med.* 375, 819-829). IFNγ is a T-cell-derived cytokine that signals through the Janus kinase/signal transducer and activator of transcription pathway (JAK/STAT) to restrict tumor growth directly. Furthermore, IFNγ indirectly restricts tumor growth by promoting upregulation of major histocompatibility complex class I (MHC-I), thereby enabling antigen (Ag) presentation to T-cells. In vivo CRISPR screening using syngeneic mouse models have revealed enrichment of the IFNγ pathway in tumors resistant to anti-PD-1. These studies identified the aforementioned IFNγ pathway members (JAK1/2 and STAT1) and Interferon Gamma Receptor (IFNGR1/IFNGR2) as resistance hits, in addition to newly identified negative regulators—such as PTPN2 and Apelin Receptor (APLNR)—which represent novel therapeutic targets (Charles Sinclair et al. *Emerg Top Life Sci.* (2021) 5 (5): 675-680).

Data pooled from in vivo genetic screening using CRISPR-Cas9 genome editing to identify genes that cause resistance to checkpoint blockade identified that deletion of the protein tyrosine phosphatase (PTPN2) gene in tumor cells increased the efficacy of immunotherapy. The PTPN2 gene encodes a protein tyrosine phosphatase that regulates a range of intracellular processes. Loss of PTPN2 in tumor cells promotes amplified IFNγ signaling, antigen presentation to T cells and growth arrest in response to cytokines; these data suggest that PTPN2 therapeutic inhibition may potentiate the effect of immunotherapies that invoke an IFNγ response (Manguso, Robert T et al. Nature vol. 547, 7664 (2017): 413-418).

Protein tyrosine phosphatase non-receptor type 2 (PTPN2), also known as T cell protein tyrosine phosphatase (TCPTP), is an intracellular member of the class 1 subfamily phospho-tyrosine specific phosphatases that control multiple cellular regulatory processes by removing phosphate groups from tyrosine substrates. PTPN2 is ubiquitously expressed, but expression is highest in hematopoietic and placental cells (Mosinger, B. Jr. et al., *Proc Natl Acad Sci USA* (1992) 89:499-503). In humans, PTPN2 expression is controlled post-transcriptionally by the existence of two splice variants: a 45 kDa form that contains a nuclear localization signal at the C-terminus upstream of the splice junction and a 48 kDa canonical form which has a C-terminal ER retention motif (Tillmann U. et al., *Mol Cell Biol* (1994) 14:3030-3040). The 45 kDa isoform can passively transfuse into the cytosol under certain cellular stress conditions. Both isoforms share an N-terminal phospho-tyrosine phosphatase catalytic domain, and as a critical negative regulator of the JAK-STAT pathway, PTPN2 directly regulates signaling through cytokine receptors. The PTPN2 catalytic domain shares 74% sequence homology with PTPN1 (also called PTP1B) and shares similar enzymatic kinetics (Romsicki Y. et al., *Arch Biochem Biophys* (2003) 414:40-50).

T cell protein tyrosine phosphatase PTPN2 has been further identified as a key negative regulator of TCR signaling, underscoring an association between PTPN2 Single nucleotide polymorphisms (SNPs) and autoimmune disease (Wiede F et al., *J Clin Invest*. (2011); 121(12):4758-4774). PTPN2 dephosphorylates and inactivates Src family kinases to regulate T cell responses. PTPN2 deficiency has been demonstrated to lower the in vivo threshold for TCR-dependent $CD8^+$ T cell proliferation. Consistent with these findings, T cell-specific PTPN2-deficient mice have been shown to develop widespread inflammation and autoimmunity. This autoimmunity is associated with increased serum levels of proinflammatory cytokines, anti-nuclear antibodies, T cell infiltrates in non-lymphoid tissues, and liver disease. These data further indicate that PTPN2 is a critical negative regulator of TCR signaling that sets the threshold for TCR-induced naive T cell responses to prevent autoimmune and inflammatory disorders.

In addition to PTPN2 encoding T cell PTP (TCPTP) as a susceptibility locus for autoimmune diseases, SNPs in PTPN2 have been linked to the development of type 1 diabetes, rheumatoid arthritis, and Crohn's disease. Moreover, a type 1 diabetes-linked PTPN2 variant rs1893217(C) has also been associated with decreased PTPN2 expression in T cells (Florian Wiede *J Clin Invest.* 2011; 121(12):4758-4774).

The above findings suggest that inhibition of PTPN2 is a potential therapeutic strategy to improve the efficacy of cancer therapy regimens associated with ICB resistance.

SUMMARY

The present disclosure is directed to compounds pharmaceutically acceptable salts thereof, pharmaceutical compositions thereof, and combinations thereof, are effective inhibitors of protein tyrosine phosphatases, e.g., protein tyrosine phosphatase non-receptor type 2 (PTPN2) and/or protein tyrosine phosphatase non-receptor type 1 ((PTPN1), also known as protein tyrosine phosphatase-1B (PTP1B)). The invention further provides methods of treating, preventing, or ameliorating cancers comprising administering to a subject in need thereof an effective amount of PTPN2/PTPN1 inhibitors disclosed herein. In a preferred embodiment, the compounds have a mono-cyclic core structure compared to literature-reported compounds, where compounds contain fused bicyclic cores.

In some embodiments, disclosed herein is an inhibitor of protein tyrosine phosphatase, e.g., PTPN2 and/or PTP1B, comprising a compound disclosed herein, e.g., a compound of Formula (I). In other embodiments, disclosed herein are methods of treating a disease or disorder, e.g., cancer, type-2 diabetes, obesity, a metabolic disease, or any other disease, disorder or ailment favorably responsive to PTPN2 or PTP1B inhibitor treatment, comprising administering an effective amount of a compound disclosed herein, e.g., a compound of Formula (I). These and other features of the invention will be set forth in expanded form as the disclosure continues.

The first aspect of the present invention provides at least one compound of Formula (I):

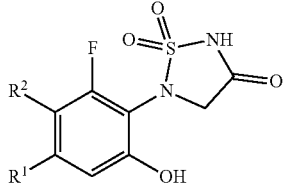

Formula (I)

wherein:

$R^1$ is selected from the group consisting of: —H, -heteroaryl, —CONHR$^3$, —CH$_2$N(R$^5$)CH$_2$R$^4$, 4-aminopiperidin-1-yl,

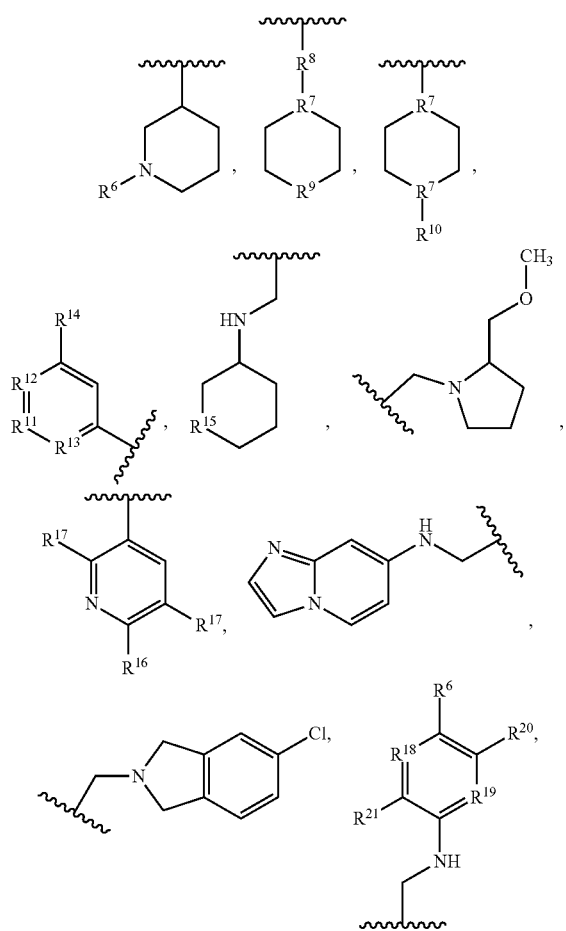

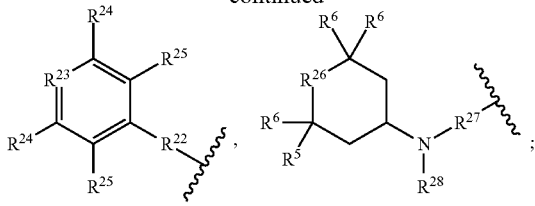

$R^2$ is selected from the group consisting of —H,

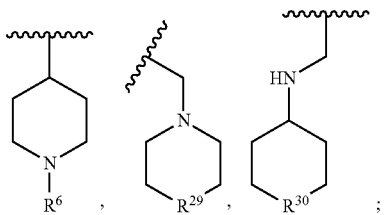

$R^3$ is selected from the group consisting of -heteroalicyclyl and —CH$_2$CH$_2$N(CH$_3$)$_2$;
$R^4$ is selected from the group consisting of -alkyl, -heteroaryl, -carboalicyclyl, and 1-methyl-1H-pyrazol-4-yl;
$R^5$ is selected from the group consisting of -alkyl and -carboalicyclyl;
$R^6$ is selected from the group consisting of —H and -alkyl;
$R^7$ is selected from the group consisting of CH and N;
$R^8$ is selected from the group consisting of —CH$_2$—, —NH—, —CH$_2$CH$_2$NHCH$_2$—,

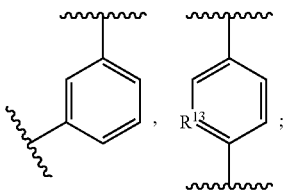

$R^9$ is selected from the group consisting of —CH$_2$—, —NH—, —O—, —CH(R$^{31}$)—, and —N(R$^{32}$)—;
$R^{10}$ is selected from the group consisting of —H, -alkyl, —N(CH$_3$)$_2$, and —CH$_2$CH$_2$OCH$_3$;
$R^{11}$ is selected from the group consisting of —CH═, —N═, and —C(R$^{33}$)═;
$R^{12}$ is selected from the group consisting of —CH═, —N═, and —C(R$^{34}$)═;
$R^{13}$ is selected from the group consisting of —CH═ and —N═;
$R^{14}$ is selected from the group consisting of —H, -alkyl, phenoxy, and

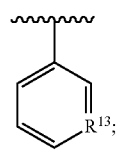

$R^{15}$ is selected from the group consisting of —NH—, —O—, and —N($R^{35}$)—;

$R^{16}$ is selected from the group consisting of —H, —OH, —OCH$_3$, and —N(CH$_3$)$_2$;

$R^{17}$ is selected from the group consisting of —H and —OCH$_3$;

$R^{18}$ is selected from the group consisting of —CH═, —N═, and

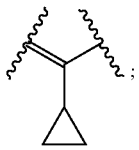 [SMILES: *C(=*)C1CC1]

$R^{19}$ is selected from the group consisting of —CH═, —N═, and —CCH$_3$═;

$R^{20}$ is selected from the group consisting of —H and —CN;

$R^{21}$ is selected from the group consisting of —H, -alkyl, and -halogen;

$R^{22}$ is selected from the group consisting of —NHCH$_2$—, —CH$_2$N($R^6$)CH$_2$—, and

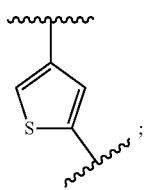 [SMILES: *c1csc(*)c1]

$R^{23}$ is selected from the group consisting of —CH═, —N═, and —C($R^{36}$)═;

$R^{24}$ is selected from the group consisting of —H, -alkyl, -halogen, and —CN;

$R^{25}$ is selected from the group consisting of —H and -halogen;

$R^{26}$ is selected from the group consisting of —CH$_2$—, —NH—, —O—, —CH($R^{37}$)—, —C(CH$_3$)$_2$—, and

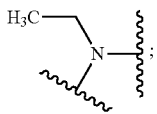

$R^{27}$ is selected from the group consisting of —CH$_2$— and —CO—;

$R^{28}$ is selected from the group consisting of —H, -alkyl, and -carboalicyclyl;

$R^{29}$ is selected from the group consisting of —O—, —CH($R^{38}$)—, and —N($R^{39}$)—;

$R^{31}$ is selected from the group consisting of —CH$_2$—, —O—, and —C(CH$_3$)$_2$—;

$R^{31}$ is selected from the group consisting of —OH, -halogen, -carboaryl, —OCH$_3$, —N(CH$_3$)$_2$, —CH$_2$N(CH$_3$)$_2$, —OCH(CH$_3$)$_2$, and —CH$_2$CH$_2$R$^{40}$CH$_3$;

$R^{32}$ is selected from the group consisting of -alkyl, —CCH$_3$O, —CH$_2$CH$_2$OCH$_3$, —CH$_2$CONHCH$_3$, and —R$^{27}$CH$_2$CH(CH$_3$)$_2$;

$R^{33}$ is selected from the group consisting of -halogen, —OCH$_3$, and cyclopropylmethoxy;

$R^{34}$ is selected from the group consisting of -alkyl, -halogen, —OCH$_2$CH$_3$, —C(CH$_3$)$_2$R$^{41}$, —CH$_2$NHCCH$_3$O, (pyrrolidin-1-yl)methyl, benzyl,

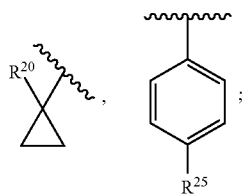

$R^{35}$ is selected from the group consisting of —CCH$_3$O, —R$^{27}$CH$_2$R$^{42}$, and —SO$_2$R$^{43}$;

$R^{36}$ is selected from the group consisting of -halogen and —CN;

$R^{37}$ is selected from the group consisting of —NH$_2$, —N(CH$_3$)$_2$, —CONHCH$_3$, and —NHCCH$_3$O;

$R^{38}$ is selected from the group consisting of -halogen and —N(CH$_3$)$_2$;

$R^{39}$ is -alkyl;

$R^{40}$ is selected from the group consisting of —CH$_2$— and —O—;

$R^{41}$ is selected from the group consisting of —OH, -alkyl, and —CN;

$R^{42}$ is selected from the group consisting of -alkyl and —COOH;

$R^{43}$ is selected from the group consisting of -alkyl, -carboalicyclyl, and 3-fluorophenyl.

Further disclosed is a compound selected from a group consisting of:

5-(2-fluoro-6-hydroxy-4-(piperidin-3-yl)phenyl)-1,2,5-thiadiazolidin-3-one 1,1-dioxide:

5-[2-fluoro-6-hydroxy-4-(4-piperidyl)phenyl]-1,1-dioxo-1, 2,5-thiadiazolidin-3-one;

5-(2-fluoro-6-hydroxy-4-(1-methylpiperidin-3-yl)phenyl)-1,2,5-thiadiazolidin-3-one 1,1-dioxide;

5-[2-fluoro-6-hydroxy-4-(1-methyl-4-piperidyl)phenyl]-1, 1-dioxo-1,2,5-thiadiazolidin-3-one;

5-(2-fluoro-6-hydroxy-4-(1-isopentylpiperidin-3-yl)phenyl)-1,2,5-thiadiazolidin-3-one 1,1-dioxide;

5-[2-fluoro-6-hydroxy-4-(1-isopentyl-4-piperidyl)phenyl]-1,1-dioxo-1,2,5-thiadiazolidin-3-one;

5-(2-fluoro-6-hydroxy-4-(pyridin-2-yl)phenyl)-1,2,5-thiadiazolidin-3-one 1,1-dioxide;

5-(2-fluoro-6-hydroxy-4-(pyridin-3-yl)phenyl)-1,2,5-thiadiazolidin-3-one 1,1-dioxide;

5-(2-fluoro-6-hydroxy-4-(pyridin-4-yl)phenyl)-1,2,5-thiadiazolidin-3-one 1,1-dioxide;

5-[4-(4-benzylphenyl)-2-fluoro-6-hydroxy-phenyl]-1,1-dioxo-1,2,5-thiadiazolidin-3-one;

5-[2-fluoro-6-hydroxy-4-(3-phenylphenyl)phenyl]-1,1-dioxo-1,2,5-thiadiazolidin-3-one;

5-[2-fluoro-4-[4-(4-fluorophenyl)phenyl]-6-hydroxy-phenyl]-1,1-dioxo-1,2,5-thiadiazolidin-3-one;

5-[2-fluoro-6-hydroxy-4-(4-morpholinophenyl)phenyl]-1,1-dioxo-1,2,5-thiadiazolidin-3-one; 5-[2-fluoro-6-hydroxy-4-(3-phenoxyphenyl)phenyl]-1,1-dioxo-1,2,5-thiadiazolidin-3-one;

5-[2-fluoro-6-hydroxy-4-(4-isobutylphenyl)phenyl]-1,1-dioxo-1,2,5-thiadiazolidin-3-one;

5-[2-fluoro-6-hydroxy-4-(3-morpholinophenyl)phenyl]-1,1-dioxo-1,2,5-thiadiazolidin-3-one;

5-[4-(4-cyclopropylphenyl)-2-fluoro-6-hydroxy-phenyl]-1,1-dioxo-1,2,5-thiadiazolidin-3-one;
5-[2-fluoro-6-hydroxy-4-(4-phenyl-2-thienyl)phenyl]-1,1-dioxo-1,2,5-thiadiazolidin-3-one;
5-[2-fluoro-6-hydroxy-4-[4-(pyrrolidin-1-ylmethyl)phenyl]phenyl]-1,1-dioxo-1,2,5-thiadiazolidin-3-one;
5-[2-fluoro-6-hydroxy-4-(2-phenyl-4-pyridyl)phenyl]-1,1-dioxo-1,2,5-thiadiazolidin-3-one;
5-[4-[3-(cyclopropylmethoxy)-5-methyl-phenyl]-2-fluoro-6-hydroxy-phenyl]-1,1-dioxo-1,2,5-thiadiazolidin-3-one;
5-[2-fluoro-6-hydroxy-4-[4-(1-hydroxy-1-methyl-ethyl)phenyl]phenyl]-1,1-dioxo-1,2,5-thiadiazolidin-3-one;
5-[2-fluoro-6-hydroxy-4-(6-methoxy-3-pyridyl)phenyl]-1,1-dioxo-1,2,5-thiadiazolidin-3-one;
5-[2-fluoro-6-hydroxy-4-(3-quinolyl)phenyl]-1,1-dioxo-1,2,5-thiadiazolidin-3-one;
5-[2-fluoro-6-hydroxy-4-(2-methoxy-3-pyridyl)phenyl]-1,1-dioxo-1,2,5-thiadiazolidin-3-one;
5-[2-fluoro-6-hydroxy-4-(6-hydroxy-3-pyridyl)phenyl]-1,1-dioxo-1,2,5-thiadiazolidin-3-one;
5-[2-fluoro-6-hydroxy-4-[6-(4-methylpiperazin-1-yl)-3-pyridyl]phenyl]-1,1-dioxo-1,2,5-thiadiazolidin-3-one;
5-[2-fluoro-6-hydroxy-4-(5-methoxy-3-pyridyl)phenyl]-1,1-dioxo-1,2,5-thiadiazolidin-3-one;
5-[4-[6-(dimethylamino)-3-pyridyl]-2-fluoro-6-hydroxy-phenyl]-1,1-dioxo-1,2,5-thiadiazolidin-3-one;
5-[2-fluoro-6-hydroxy-4-(6-phenyl-3-pyridyl)phenyl]-1,1-dioxo-1,2,5-thiadiazolidin-3-one;
5-(2-fluoro-6-hydroxy-4-((4-methylpiperazin-1-yl)methyl)phenyl)-1,2,5-thiadiazolidin-3-one 1,1-dioxide;
5-(2-fluoro-6-hydroxy-4-((4-isopentylpiperazin-1-yl)methyl)phenyl)-1,2,5-thiadiazolidin-3-one 1,1-dioxide;
5-(4-((4-(dimethylamino)piperidin-1-yl)methyl)-2-fluoro-6-hydroxyphenyl)-1,2,5-thiadiazolidin-3-one 1,1-dioxide;
5-[4-[(cyclohexylamino)methyl]-2-fluoro-6-hydroxy-phenyl]-1,1-dioxo-1,2,5-thiadiazolidin-3-one;
5-[2-fluoro-6-hydroxy-4-[(tetrahydropyran-4-ylamino)methyl]phenyl]-1,1-dioxo-1,2,5-thiadiazolidin-3-one;
5-(2-fluoro-6-hydroxy-4-((4-(3-methylbutanoyl)piperazin-1-yl)methyl)phenyl)-1,2,5-thiadiazolidin-3-one 1,1-dioxide;
5-(4-(((4,4-dimethylcyclohexyl)amino)methyl)-2-fluoro-6-hydroxyphenyl)-1,2,5-thiadiazolidin-3-one 1,1-dioxide;
5-(4-((4-acetylpiperazin-1-yl)methyl)-2-fluoro-6-hydroxyphenyl)-1,2,5-thiadiazolidin-3-one 1,1-dioxide;
5-(2-fluoro-6-hydroxy-4-((piperidin-4-ylamino)methyl)phenyl)-1,2,5-thiadiazolidin-3-one 1,1-dioxide;
5-(4-(((1-ethylpiperidin-4-yl)amino)methyl)-2-fluoro-6-hydroxyphenyl)-1,2,5-thiadiazolidin-3-one 1,1-dioxide;
5-(2-fluoro-6-hydroxy-4-(morpholinomethyl)phenyl)-1,2,5-thiadiazolidin-3-one 1,1-dioxide;
5-(2-fluoro-4-((4-fluoropiperidin-1-yl)methyl)-6-hydroxyphenyl)-1,2,5-thiadiazolidin-3-one 1,1-dioxide;
5-(4-((cyclohexyl(methyl)amino)methyl)-2-fluoro-6-hydroxyphenyl)-1,2,5-thiadiazolidin-3-one 1,1-dioxide;
5-(2-fluoro-6-hydroxy-4-((4-(2-methoxyethyl)piperazin-1-yl)methyl)phenyl)-1,2,5-thiadiazolidin-3-one 1,1-dioxide;
2-fluoro-5-[[[3-fluoro-5-hydroxy-4-(1,1,4-trioxo-1,2,5-thiadiazolidin-2-yl)phenyl]methylamino]methyl]benzonitrile;
5-[2-fluoro-6-hydroxy-4-[[2-(1-methyl-4-piperidyl)ethylamino]methyl]phenyl]-1,1-dioxo-1,2,5-thiadiazolidin-3-one;
5-[2-fluoro-6-hydroxy-4-[(4-phenyl-1-piperidyl)methyl]phenyl]-1,1-dioxo-1,2,5-thiadiazolidin-3-one;

5-[4-[[cyclopropyl(propyl)amino]methyl]-2-fluoro-6-hydroxy-phenyl]-1,1-dioxo-1,2,5-thiadiazolidin-3-one;
5-[4-[[cyclobutylmethyl(methyl)amino]methyl]-2-fluoro-6-hydroxy-phenyl]-1,1-dioxo-1,2,5-thiadiazolidin-3-one;
3-[[[3-fluoro-5-hydroxy-4-(1,1,4-trioxo-1,2,5-thiadiazolidin-2-yl)phenyl]methyl-methyl-amino]methyl]benzonitrile;
5-[4-[[[(1R)-3,3-dimethylcyclohexyl]amino]methyl]-2-fluoro-6-hydroxy-phenyl]-1,1-dioxo-1,2,5-thiadiazolidin-3-one;
5-[2-fluoro-6-hydroxy-4-[(4-hydroxy-1-piperidyl)methyl]phenyl]-1,1-dioxo-1,2,5-thiadiazolidin-3-one;
5-[2-fluoro-6-hydroxy-4-[(4-methoxy-1-piperidyl)methyl]phenyl]-1,1-dioxo-1,2,5-thiadiazolidin-3-one;
5-[2-fluoro-6-hydroxy-4-[(4-isopropoxy-1-piperidyl)methyl]phenyl]-1,1-dioxo-1,2,5-thiadiazolidin-3-one;
5-[2-fluoro-6-hydroxy-4-[[4-(2-methoxyethyl)-1-piperidyl]methyl]phenyl]-1,1-dioxo-1,2,5-thiadiazolidin-3-one;
5-[4-[[4-[(dimethylamino)methyl]-1-piperidyl]methyl]-2-fluoro-6-hydroxy-phenyl]-1,1-dioxo-1,2,5-thiadiazolidin-3-one;
5-[4-[(4-butyl-1-piperidyl)methyl]-2-fluoro-6-hydroxy-phenyl]-1,1-dioxo-1,2,5-thiadiazolidin-3-one;
(1r,4r)-4-((4-(1,1-dioxido-4-oxo-1,2,5-thiadiazolidin-2-yl)-3-fluoro-5-hydroxybenzyl)amino)-N-methylcyclohexane-1-carboxamide;
2-(4-(4-(1,1-dioxido-4-oxo-1,2,5-thiadiazolidin-2-yl)-3-fluoro-5-hydroxybenzyl)piperazin-1-yl)-N-methylacetamide;
N-((1r,4r)-4-((4-(1,1-dioxido-4-oxo-1,2,5-thiadiazolidin-2-yl)-3-fluoro-5-hydroxybenzyl)amino)cyclohexyl)acetamide;
(R)-5-(2-fluoro-6-hydroxy-4-((piperidin-3-ylamino)methyl)phenyl)-1,2,5-thiadiazolidin-3-one 1,1-dioxide;
(R)-5-(2-fluoro-6-hydroxy-4-(((1-isopentylpiperidin-3-yl)amino)methyl)phenyl)-1,2,5-thiadiazolidin-3-one 1,1-dioxide;
5-[2-fluoro-6-hydroxy-4-[[[(3S)-1-isopentyl-3-piperidyl]amino]methyl]phenyl]-1,1-dioxo-1,2,5-thiadiazolidin-3-one;
(R)-5-(2-fluoro-6-hydroxy-4-(((tetrahydro-2H-pyran-3-yl)amino)methyl)phenyl)-1,2,5-thiadiazolidin-3-one 1,1-dioxide;
(S)-5-(2-fluoro-6-hydroxy-4-((piperidin-3-ylamino)methyl)phenyl)-1,2,5-thiadiazolidin-3-one 1,1-dioxide;
(S)-5-(4-(((3,3-dimethylcyclohexyl)amino)methyl)-2-fluoro-6-hydroxyphenyl)-1,2,5-thiadiazolidin-3-one 1,1-dioxide;
(S)-5-(2-fluoro-6-hydroxy-4-(((tetrahydro-2H-pyran-3-yl)amino)methyl)phenyl)-1,2,5-thiadiazolidin-3-one 1,1-dioxide;
5-[4-[[[(3R)-1-acetyl-3-piperidyl]amino]methyl]-2-fluoro-6-hydroxy-phenyl]-1,1-dioxo-1,2,5-thiadiazolidin-3-one;
5-[2-fluoro-4-[[[(3R)-1-(3-fluorophenyl)sulfonyl-3-piperidyl]amino]methyl]-6-hydroxy-phenyl]-1,1-dioxo-1,2,5-thiadiazolidin-3-one;
5-[2-fluoro-4-[[[(3S)-1-(3-fluorophenyl)sulfonyl-3-piperidyl]amino]methyl]-6-hydroxy-phenyl]-1,1-dioxo-1,2,5-thiadiazolidin-3-one;
5-[4-[[[(3S)-1-acetyl-3-piperidyl]amino]methyl]-2-fluoro-6-hydroxy-phenyl]-1,1-dioxo-1,2,5-thiadiazolidin-3-one;
5-[2-fluoro-6-hydroxy-4-[[[(3R)-1-methylsulfonyl-3-piperidyl]amino]methyl]phenyl]-1,1-dioxo-1,2,5-thiadiazolidin-3-one;
5-[4-[[[(3S)-1-cyclopropylsulfonyl-3-piperidyl]amino]methyl]-2-fluoro-6-hydroxy-phenyl]-1,1-dioxo-1,2,5-thiadiazolidin-3-one;

5-[4-[[[(3R)-1-cyclopropylsulfonyl-3-piperidyl]amino]
methyl]-2-fluoro-6-hydroxy-phenyl]-1,1-dioxo-1,2,5-
thiadiazolidin-3-one;
5-[2-fluoro-6-hydroxy-4-[[[(3S)-1-methylsulfonyl-3-pip-
eridyl]amino]methyl]phenyl]-1,1-dioxo-1,2,5-thiadiazo-
lidin-3-one;
3-[(3S)-3-[[3-fluoro-5-hydroxy-4-(1,1,4-trioxo-1,2,5-thiadi-
azolidin-2-yl) phenyl]methylamino]-1-piperidyl]-3-oxo-
propanoic acid;
5-[4-[[(4,4-dimethylcyclohexyl)-methyl-amino]methyl]-2-
fluoro-6-hydroxy-phenyl]-1,1-dioxo-1,2,5-thiadiazoli-
din-3-one;
5-[4-[[cyclobutylmethyl(propyl)amino]methyl]-2-fluoro-6-
hydroxy-phenyl]-1,1-dioxo-1,2,5-thiadiazolidin-3-one;
5-[[3-fluoro-5-hydroxy-4-(1,1,4-trioxo-1,2,5-thiadiazolidin-
2-yl)phenyl]methylamino]pyridine-3-carbonitrile;
5-[4-[(2-chloro-5-fluoro-anilino)methyl]-2-fluoro-6-hy-
droxy-phenyl]-1,1-dioxo-1,2,5-thiadiazolidin-3-one;
4-chloro-3-[[3-fluoro-5-hydroxy-4-(1,1,4-trioxo-1,2,5-thia-
diazolidin-2-yl) phenyl]methylamino]benzonitrile;
5-[4-[[(4-cyclopropyl-2-pyridyl)amino]methyl]-2-fluoro-6-
hydroxy-phenyl]-1,1-dioxo-1,2,5-thiadiazolidin-3-one;
5-(2-fluoro-6-hydroxy-4-(4-isopentylpiperazin-1-yl)phe-
nyl)-1,2,5-thiadiazolidin-3-one 1,1-dioxide;
5-(4-(4-aminopiperidin-1-yl)-2-fluoro-6-hydroxyphenyl)-1,
2,5-thiadiazolidin-3-one 1,1-dioxide;
5-(2-fluoro-6-hydroxy-4-(piperazin-1-yl)phenyl)-1,2,5-thia-
diazolidin-3-one 1,1-dioxide;
5-(2-fluoro-6-hydroxy-4-(4-(2-methoxyethyl)piperazin-1-
yl)phenyl)-1,2,5-thiadiazolidin-3-one 1,1-dioxide;
5-(4-(4-(dimethylamino)piperidin-1-yl)-2-fluoro-6-hy-
droxyphenyl)-1,2,5-thiadiazolidin-3-one 1,1-dioxide;
5-(2-fluoro-6-hydroxy-4-(piperidin-4-ylamino)phenyl)-1,2,
5-thiadiazolidin-3-one 1,1-dioxide;
5-(2-fluoro-6-hydroxy-4-((1-isopentylpiperidin-4-yl)amino)
phenyl)-1,2,5-thiadiazolidin-3-one 1,1-dioxide;
5-(2-fluoro-6-hydroxy-4-((1-(2-methoxyethyl)piperidin-4-
yl)amino)phenyl)-1,2,5-thiadiazolidin-3-one 1,1-dioxide;
N-(2-(dimethylamino)ethyl)-4-(1,1-dioxido-4-oxo-1,2,5-
thiadiazolidin-2-yl)-3-fluoro-5-hydroxybenzamide;
4-(1,1-dioxido-4-oxo-1,2,5-thiadiazolidin-2-yl)-3-fluoro-5-
hydroxy-N-(piperidin-4-yl)benzamide;
(S)-4-(1,1-dioxido-4-oxo-1,2,5-thiadiazolidin-2-yl)-3-
fluoro-5-hydroxy-N-(piperidin-3-yl)benzamide;
(R)-4-(1,1-dioxido-4-oxo-1,2,5-thiadiazolidin-2-yl)-3-
fluoro-5-hydroxy-N-(piperidin-3-yl)benzamide;
N-((1r,4r)-4-aminocyclohexyl)-4-(1,1-dioxido-4-oxo-1,2,5-
thiadiazolidin-2-yl)-3-fluoro-5-hydroxybenzamide;
N-((1r,4r)-4-(dimethylamino)cyclohexyl)-4-(1,1-dioxido-4-
oxo-1,2,5-thiadiazolidin-2-yl)-3-fluoro-5-hydroxybenz-
amide;
5-(3-(((4,4-dimethylcyclohexyl)amino)methyl)-2-fluoro-6-
hydroxyphenyl)-1,2,5-thiadiazolidin-3-one 1,1-dioxide;
5-(2-fluoro-3-((4-fluoropiperidin-1-yl)methyl)-6-hydroxy-
phenyl)-1,2,5-thiadiazolidin-3-one 1,1-dioxide;
5-(2-fluoro-6-hydroxy-3-(morpholinomethyl)phenyl)-1,2,5-
thiadiazolidin-3-one 1,1-dioxide;
5-(3-((cyclohexylamino)methyl)-2-fluoro-6-hydroxyphe-
nyl)-1,2,5-thiadiazolidin-3-one 1,1-dioxide;
5-(2-fluoro-6-hydroxy-3-(((tetrahydro-2H-pyran-4-yl)
amino)methyl)phenyl)-1,2,5-thiadiazolidin-3-one 1,1-di-
oxide;
5-(3-((4-(dimethylamino)piperidin-1-yl)methyl)-2-fluoro-6-
hydroxyphenyl)-1,2,5-thiadiazolidin-3-one 1,1-dioxide;
5-(2-fluoro-6-hydroxy-3-((4-methylpiperazin-1-yl)methyl)
phenyl)-1,2,5-thiadiazolidin-3-one 1,1-dioxide;

5-[2-fluoro-6-hydroxy-3-[(4-isopentylpiperazin-1-yl)
methyl]phenyl]-1,1-dioxo-1,2,5-thiadiazolidin-3-one;
5-(2-fluoro-6-hydroxy-3-(piperidin-4-yl)phenyl)-1,2,5-thia-
diazolidin-3-one 1,1-dioxide; and,
5-(2-fluoro-6-hydroxy-3-(1-methylpiperidin-4-yl)phenyl)-
1,2,5-thiadiazolidin-3-one 1,1-dioxide.

In some embodiments, the compound of Formula (I) is formulated as a pharmaceutically acceptable composition comprising the compound of Formula (I) and a pharmaceutically acceptable carrier.

Also disclosed herein is a method of treating cancer in a patient in need thereof, comprising administering to the patient an effective amount of the compound of formula (I) disclosed herein in combination with an additional therapeutic agent. In some embodiments, the additional therapeutic agent is an immunotherapeutic agent. For example, in some embodiments, the immunotherapeutic agent is an antibody.

Also disclosed herein is a method of treating cancer in a patient in need thereof, comprising administering to the patient an effective amount of a compound disclosed herein, e.g., a compound of Formula (I).

Further disclosed herein is a method of treating a metabolic disease in a patient in need thereof, comprising administering to the patient an effective amount of a compound disclosed herein, e.g., a compound of Formula (I).

In some embodiments, the method comprises the treatment of cancer. In some embodiments, the cancer comprises pancreatic cancer, breast cancer, multiple myeloma, melanoma, or a cancer of the secretory cells.

Also disclosed herein is a composition for use in treating cancer in a patient in need thereof, wherein the composition comprises a compound disclosed herein, e.g., a compound of Formula (I) in combination with an additional therapeutic agent. In some embodiments, the additional therapeutic agent is an immunotherapeutic agent. For example, in some embodiments, the immunotherapeutic agent is selected from the group consisting of an anti-PD-1 antibody, an anti-PD-L1 antibody.

Further disclosed herein is a composition for use in treating a metabolic disease in a patient in need thereof, wherein the composition comprises a compound disclosed herein, e.g., a compound of Formula (I).

DETAILED DESCRIPTION

The present disclosure is directed to compounds pharmaceutically acceptable salts thereof, pharmaceutical compositions thereof, and combinations thereof, are effective inhibitors of protein tyrosine phosphatases, e.g., protein tyrosine phosphatase non-receptor type 2 (PTPN2) and/or protein tyrosine phosphatase non-receptor type 1 ((PTPN1), also known as protein tyrosine phosphatase-1B (PTP1B)). The invention further provides methods of treating, preventing, or ameliorating cancers comprising administering to a subject in need thereof an effective amount of PTPN2/PTPN1 inhibitors disclosed herein. In a preferred embodiment, the compounds have a mono-cyclic core structure compared to literature-reported compounds, where compounds contain fused bicyclic cores.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., and specific functional groups are generally defined as described therein. Additionally, general principles of organic chemistry, as well as specific functional moieties and reactivity, are described in Thomas Sorrell, Organic Chemistry, University Science Books, Sausalito, 1999; Smith and March, *March's Advanced Organic Chemistry*, 5th Edition, John Wiley & Sons, Inc., New York, 2001: Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

The abbreviations used herein have their conventional meaning within the chemical and biological arts. The chemical structures and formulae set forth herein are constructed according to the standard rules of chemical valency known in the chemical arts.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or a mixture of stereoisomers, including racemic mixtures and mixtures enriched in one or more stereoisomer. Isomers can be isolated from mixtures by methods known to those skilled in the art, including chiral high-pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, IN 1972). The disclosure additionally encompasses compounds described herein as individual isomers substantially free of other isomers, and alternatively, as mixtures of various isomers.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound.

The features and advantages of the invention as described in this disclosure may be more readily understood by those of ordinary skill in the art in view of the following definitions. Certain features of the invention described within the context of separate embodiments may also be combined to form a single or extrapolated to include multiple embodiments. Embodiments identified herein as exemplary or preferred are illustrative and not limiting.

Unless expressly stated otherwise herein, references made in the singular may also include the plural. For example, "a" and "an" may refer to either one, or one or more.

As used herein, the phrase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.
The term "amino" refers to the group —NH$_2$.
The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —CF$_3$ and —CH$_2$CF$_3$.

The term "cyanoalkyl" includes both branched and straight-chain saturated alkyl groups substituted with one or more cyano groups. For example, "cyanoalkyl" includes —CH$_2$CN, —CH$_2$CH$_2$CN, and $C_{1-4}$ cyanoalkyl.

The term "aminoalkyl" includes both branched and straight-chain saturated alkyl groups substituted with one or more amine groups. For example, "aminoalkyl" includes —CH$_2$NH$_2$, —CH$_2$CH$_2$NH$_2$, and $C_{1-4}$ aminoalkyl.

The term "hydroxyalkyl" includes both branched and straight-chain saturated alkyl groups substituted with one or more hydroxyl groups. For example, "hydroxyalkyl" includes —CH$_2$OH, —CH$_2$CH$_2$OH, and $C_{1-4}$ hydroxyalkyl.

The term "hydroxy-fluoroalkyl" includes both branched and straight-chain saturated alkyl groups substituted with one or more hydroxyl groups and one or more fluorine atoms. For example, "hydroxy-fluoroalkyl" includes —CHFCH$_2$OH, —CH$_2$CHFC(CH$_3$)$_2$OH, and $C_{1-4}$ hydroxy-fluoroalkyl.

The term "cycloalkyl," "carbocyclic" "carbocyclyl" as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl.

When numbers appear in a subscript after the symbol "C", the subscript defines with more specificity the number of carbon atoms that a particular cycloalkyl group may contain. For example, "$C_3$-$C_6$ cycloalkyl" denotes cycloalkyl groups with three to six carbon atoms.

The term "heterocyclic" as used herein, refers to organic compounds with cyclic structures of both carbon atoms and non-carbon atoms such as oxygen, nitrogen.

The term "alkoxy," as used herein, refers to an alkyl group attached to the parent molecular moiety through an oxygen atom, for example, methoxy group (—$OCH_3$). For example, "$C_{1-3}$ alkoxy" denotes alkoxy groups with one to three carbon atoms.

The term "alkoxyalkyl," as used herein, refers to an alkoxy group attached through its oxygen atom to an alkyl group, which is attached to the parent molecular moiety, for example, methoxymethyl group (—$CH_2OCH_3$). For example, "$C_{2-4}$ alkoxyalkyl" denotes alkoxyalkyl groups with two to four carbon atoms, such as —$CH_2OCH_3$, —$CH_2CH_2OCH_3$, —$CH_2OCH_2CH_3$, and —$CH_2CH_2OCH_2CH_3$.

The term "heteroaryl" as used herein, refers to an aromatic heterocycle ring of 5 to 10 members and having at least one heteroatom selected from nitrogen, oxygen and sulfur, and containing at least 1 carbon atom, including both mono- and bicyclic ring systems.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:
a) *The Practice of Medicinal Chemistry*, Camille G. Wermuth et al., Ch 31, (Academic Press, 1996);
b) *Design of Prodrugs*, edited by H. Bundgaard, (Elsevier, 1985);
c) *A Textbook of Drug Design and Development*, P. Krogsgaard-Larson and H. Bundgaard, eds. Ch 5, pgs 113-191 (Harwood Academic Publishers, 1991); and
d) *Hydrolysis in Drug and Prodrug Metabolism*, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor or effective to treat or ameliorate cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—$CH_3$) also includes deuterated methyl groups such as —$CD_3$.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt.

As defined herein, the term "inhibition". "inhibit", "inhibiting" and the like in reference to a protein-inhibitor (e.g., antagonist) interaction means negatively affecting (e.g., decreasing) the activity or function of the protein relative to the activity or function of the protein in the absence of the inhibitor. In some embodiments, inhibition refers to reduction of a disease or symptoms of disease. In some embodiments, inhibition refers to a reduction in the activity of a signal transduction pathway or signaling pathway. Thus, inhibition includes, at least in part, partially or totally blocking stimulation, decreasing, preventing, or delaying activation, or inactivating, desensitizing, or down-regulating signal transduction or enzymatic activity or the amount of a protein. In some embodiments, inhibition refers to a decrease in the activity of a protein tyrosine phosphatase, e.g., protein tyrosine phosphatase non-receptor type 2 (PTPN2) or protein tyrosine phosphatase non-receptor type I (PTP1B). Thus, inhibition may include, at least in part, partially or totally decreasing stimulation, decreasing or reducing activation, or inactivating, desensitizing, or down-regulating signal transduction or enzymatic activity or the amount of a protein tyrosine phosphatase, e.g., protein tyrosine phosphatase non-receptor type 2 (PTPN2) or protein tyrosine phosphatase non-receptor type I (PTP1B).

"Patient" or "subject" in need thereof refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In some embodiments, a patient is human. In some embodiments, a patient is a domesticated animal. In some embodiments, a patient is a dog. In some embodiments, a patient is a parrot. In some embodiments, a patient is livestock animal. In some embodiments, a patient is a mammal. In some embodiments, a patient is a cat. In some embodiments, a patient is a horse. In some embodiments, a patient is bovine. In some embodiments, a patient is a canine. In some embodiments, a patient is a feline. In some embodiments, a patient is an ape. In some embodiments, a patient is a monkey. In some embodiments, a patient is a mouse. In some embodiments, a patient is an experimental animal. In some embodiments, a patient is a rat. In some embodiments, a patient is a hamster. In some embodiments, a patient is a test animal. In some embodiments, a patient is a newborn animal. In some embodiments, a patient is a newborn human. In some embodiments, a patient is a newborn mammal. In some embodiments, a patient is an elderly animal. In some embodiments, a patient is an elderly human. In some embodiments, a patient is an elderly mammal. In some embodiments, a patient is a geriatric patient.

"Disease", "disorder" or "condition" refers to a state of being or health status of a patient or subject capable of being treated with a compound, pharmaceutical composition, or method provided herein. In some embodiments, the compounds and methods described herein comprise reduction or elimination of one or more symptoms of the disease, disorder, or condition, e.g., through administration of a compound disclosed herein, a pharmaceutically acceptable salt thereof, or a pharmaceutical composition comprising a compound disclosed herein, or a pharmaceutically acceptable salt thereof, and a pharmaceutically acceptable carrier.

The term "signaling pathway" as used herein refers to a series of interactions between cellular and optionally extracellular components (e.g., proteins, nucleic acids, small molecules, ions, lipids) that conveys a change in one component to one or more other components, which in turn may convey a change to additional components, which is optionally propagated to other signaling pathway components.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's solution, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, welling agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it.

Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arterial, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a compound or composition described herein is administered at the same time, just prior to, or just after the administration of one or more additional therapies (e.g., anti-cancer agent, chemotherapeutic, or immunotherapeutic agent). The compounds or compositions described herein can be administered alone or can be coadministered to the patient. Coadministration is meant to include simultaneous or sequential administration of the compound or composition individually or in combination (more than one compound or agent). Thus, the preparations can also be combined, when desired, with other active substances (e.g., to reduce metabolic degradation).

Pharmaceutical compositions described herein can be prepared by any method known in the art of pharmacology. In general, such preparatory methods include the steps of bringing a disclosed compound (the "active ingredient") into association with a carrier and/or one or more other accessory ingredients, and then, if necessary and/or desirable, shaping and/or packaging the product into a desired single- or multi-dose unit. Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Methods of Treatment

The present disclosure features compounds, compositions, and methods comprising a compound disclosed herein, e.g., a compound of Formula (I). In some embodiments, the compounds, compositions, and methods disclosed herein are used in the prevention or treatment of a disease, disorder, or condition. Exemplary diseases, disorders, or conditions include, but are not limited to cancer, type-2 diabetes, metabolic syndrome, obesity, or a metabolic disease.

Cancer

In some embodiments, a compound disclosed herein, e.g., a compound of Formula (I), is used to treat cancer. As used herein, "cancer" refers to human cancers and carcinomas, sarcomas, adenocarcinomas (e.g., papillary adenocarcinomas), lymphomas, leukemias, melanomas, etc., including solid and lymphoid cancers, kidney, breast, lung, bladder, colon, ovarian, prostate, pancreas, stomach, brain, head and neck, skin, uterine, testicular, glioma, esophagus, liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), and/or multiple myeloma. In some further instances, "cancer" refers to lung cancer, breast cancer, ovarian cancer, epithelial ovarian cancer, leukemia, lymphoma, melanoma, pancreatic cancer, sarcoma, bladder cancer, bone cancer, biliary tract cancer, adrenal gland cancer, salivary gland cancer, bronchus cancer, oral cancer, cancer of the oral cavity or pharynx, laryngeal cancer, renal cancer, gynecologic cancers, brain cancer, central nervous system cancer, peripheral nervous system cancer, cancer of the hematological tissues, small bowel or appendix cancer, cervical cancer, colon cancer, esophageal cancer, gastric cancer, liver cancer, head and neck cancer, kidney cancer, myeloma, thyroid cancer, prostate cancer, metastatic cancer, or carcinoma.

Exemplary cancers that may be treated with a compound, pharmaceutical composition, or method provided herein include lymphoma, B-cell lymphoma, heavy chain disease, alpha chain disease, gamma chain disease, mu chain disease, Waldenstrom's macroglobulinemia, benign monoclonal gammopathy, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g., ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g., non-small cell lung carcinoma, squamous cell lung carcinoma, adenocarcinoma, large cell lung carcinoma, small cell lung carcinoma, carcinoid, sarcoma), glioblastoma multiforme, acoustic neuroma, retinoblastoma, astrocytoma, craniopharyngioma, hemangioblastoma, pinealoma, ependymoma, oligodendroglioma, meningioma, glioma, or melanoma. Additional examples include, cancer of the thyroid, endocrine system, brain, breast, cervix, colon, head & neck, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, immunocytic amyloidosis, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, and hepatocellular carcinoma.

The first aspect of the present invention provides at least one compound of Formula (I):

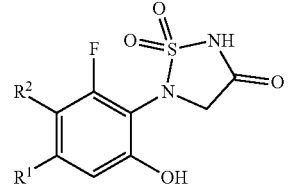

Formula (I)

wherein:

$R^1$ is selected from the group consisting of: —H, -heteroaryl, —CONHR$^3$, —CH$_2$N(R$^5$)CH$_2$R$^4$, 4-aminopiperidin-1-yl,

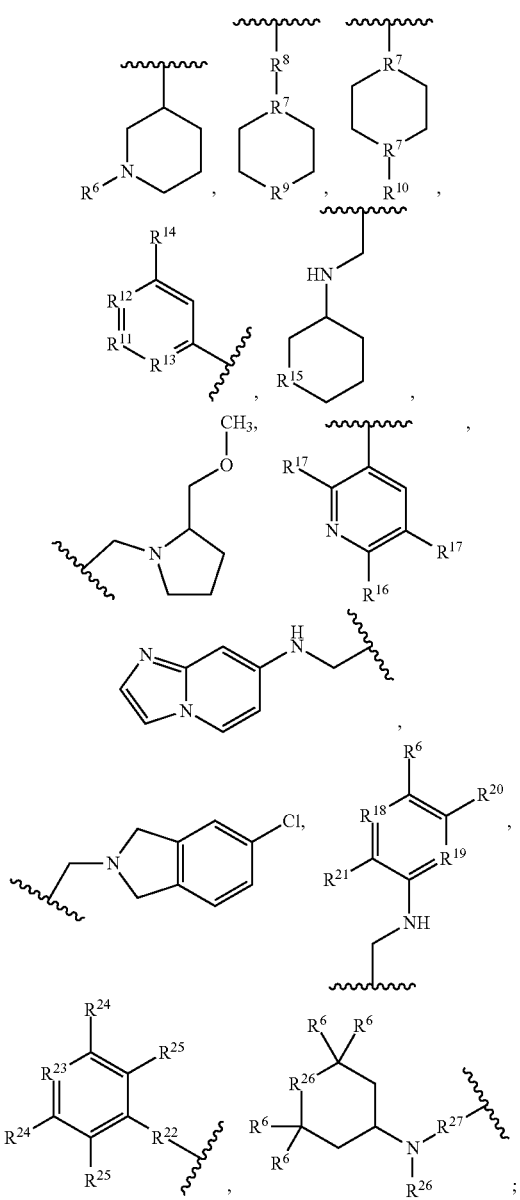

$R^2$ is selected from the group consisting of —H,

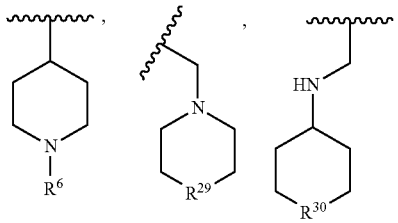

$R^3$ is selected from the group consisting of -heteroalicyclyl and —CH$_2$CH$_2$N(CH$_3$)$_2$;
$R^4$ is selected from the group consisting of -alkyl, -heteroaryl, -carboalicyclyl, and 1-methyl-1H-pyrazol-4-yl;
$R^5$ is selected from the group consisting of -alkyl and -carboalicyclyl;
$R^6$ is selected from the group consisting of —H and -alkyl;
$R^7$ is selected from the group consisting of CH and N;
$R^8$ is selected from the group consisting of —CH$_2$—, —NH—, —CH$_2$CH$_2$NHCH$_2$—,

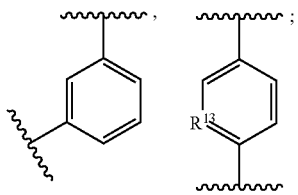

$R^9$ is selected from the group consisting of —CH$_2$—, —NH—, —O—, —CH($R^{31}$)—, and —N($R^{32}$)—;
$R^{10}$ is selected from the group consisting of —H, -alkyl, —N(CH$_3$)$_2$, and —CH$_2$CH$_2$OCH$_3$;
$R^{11}$ is selected from the group consisting of —CH=, —N=, and —C($R^{33}$)=;
$R^{12}$ is selected from the group consisting of —CH=, —N=, and —C($R^{34}$)=;
$R^{13}$ is selected from the group consisting of —CH= and —N=;
$R^{14}$ is selected from the group consisting of —H, -alkyl, phenoxy, and

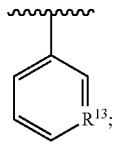

$R^{15}$ is selected from the group consisting of —NH—, —O—, and —N($R^{35}$)—;
$R^{16}$ is selected from the group consisting of —H, —OH, —OCH$_3$, and —N(CH$_3$)$_2$;
$R^{17}$ is selected from the group consisting of —H and —OCH$_3$;
$R^{18}$ is selected from the group consisting of —CH=, —N=, and

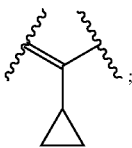

$R^{19}$ is selected from the group consisting of —CH=, —N=, and —CCH$_3$=;
$R^{20}$ is selected from the group consisting of —H and —CN;
$R^{21}$ is selected from the group consisting of —H, -alkyl, and -halogen;
$R^{22}$ is selected from the group consisting of —NHCH$_2$—, —CH$_2$N($R^6$)CH$_2$—, and

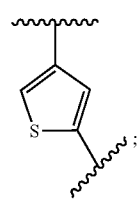 [SMILES: *c1csc(*)c1]

$R^{23}$ is selected from the group consisting of —CH=, —N=, and —C($R^{36}$)—;
$R^{24}$ is selected from the group consisting of —H, -alkyl, -halogen, and —CN;
$R^{25}$ is selected from the group consisting of —H and -halogen;
$R^{26}$ is selected from the group consisting of —CH$_2$—, —NH—, —O—, —CH($R^{37}$)—, —C(CH$_3$)$_2$—, and

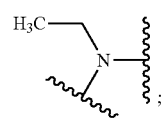

$R^{27}$ is selected from the group consisting of —CH$_2$— and —CO—;
$R^{28}$ is selected from the group consisting of —H, -alkyl, and -carboalicyclyl;
$R^{29}$ is selected from the group consisting of —O—, —CH($R^{38}$)—, and —N($R^{39}$)—.
$R^{30}$ is selected from the group consisting of —CH$_2$—, —O—, and —C(CH$_3$)$_2$—;
$R^{31}$ is selected from the group consisting of —OH, -halogen, -carboaryl, —OCH$_3$, —N(CH$_3$)$_2$, —CH$_2$N(CH$_3$)$_2$, —OCH(CH$_3$)$_2$, and —CH$_2$CH$_2$R$^{40}$CH$_3$;
$R^{32}$ is selected from the group consisting of -alkyl, —CCH$_{3O}$, —CH$_2$CH$_2$OCH$_3$, —CH$_2$CONHCH$_3$, and —R$^{27}$CH$_2$CH(CH$_3$)$_2$;
$R^{33}$ is selected from the group consisting of -halogen, —OCH$_3$, and cyclopropylmethoxy;
$R^{34}$ is selected from the group consisting of -alkyl, -halogen, —OCH$_2$CH$_3$, —C(CH$_3$)$_2$R$^{41}$, —CH$_2$NHCCH$_3$O, (pyrrolidin-1-yl)methyl, benzyl,

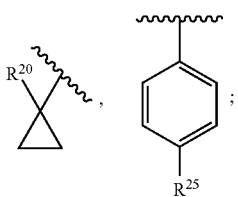

$R^{35}$ is selected from the group consisting of —CCH$_3$O, —R$^{27}$CH$_2$R$^{42}$, and —SO$_2$R$^{43}$;

$R^{36}$ is selected from the group consisting of -halogen and —CN;

$R^{37}$ is selected from the group consisting of —NH$_2$, —N(CH$_3$)$_2$, —CONHCH$_3$, and —NHCCH$_3$O;

$R^{38}$ is selected from the group consisting of -halogen and —N(CH$_3$)$_2$;

$R^{39}$ is -alkyl;

$R^{40}$ is selected from the group consisting of —CH$_2$— and —O—;

$R^{41}$ is selected from the group consisting of —OH, -alkyl, and —CN;

$R^{42}$ is selected from the group consisting of -alkyl and —COOH;

$R^{43}$ is selected from the group consisting of -alkyl, -carboalicyclyl, and 3-fluorophenyl.

In another embodiment of the compound of formula (I) $R^1$ is selected from the group consisting of —H, 1H-pyrrol-2-yl, furan-2-yl, 1H-imidazol-5-yl, 1,2-oxazol-5-yl, 1H-1,2,3-triazol-5-yl, 1,3,4-oxadiazol-2-yl, 1H-1,2,3,4-tetrazol-5-yl, thiophen-2-yl, 1,3-thiazol-2-yl, 1,3,4-thiadiazol-2-yl, pyridin-2-yl, pyrimidin-4-yl, 1,3,5-triazin-2-yl, 1,2,4-triazin-3-yl, 1λ$^4$-pyran-1-ylium-4-yl, —CONHR$^3$, —CH$_2$N(R$^5$)CH$_2$R$^4$, 4-aminopiperidin-1-yl,

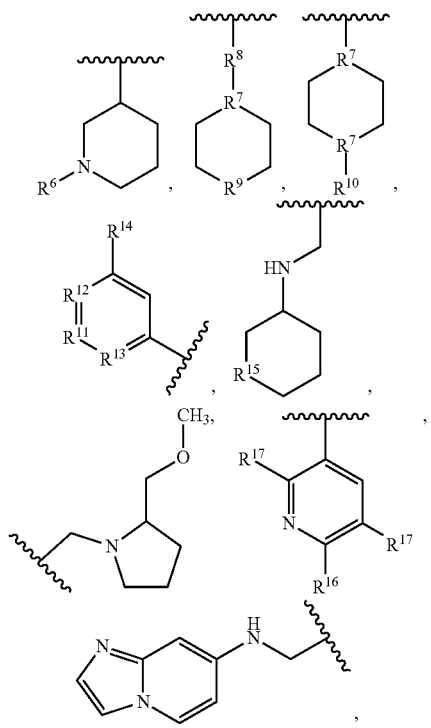

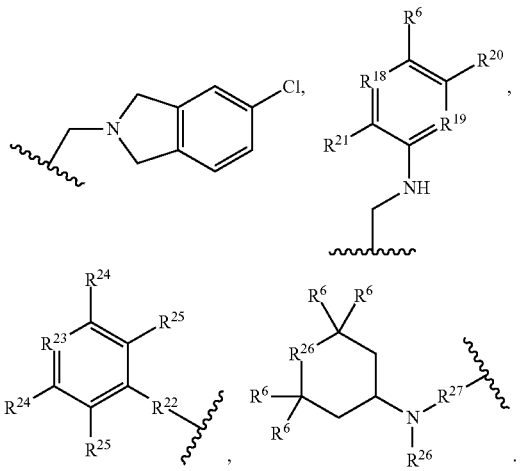

In one embodiment of the compound of formula (I):

$R^3$ is selected from the group consisting of aziridin-1-yl, 2,5-dihydro-1H-pyrrol-1-yl, 2,5-dihydrofuran-3-yl, 4,5-dihydro-1H-imidazol-2-yl, pyrrolidin-1-yl, oxolan-2-yl, imidazolidin-4-yl, 1,3-dioxolan-2-yl, 1,3-thiazolidin-3-yl, piperidin-1-yl, oxan-2-yl, 1,3-diazinan-5-yl, morpholin-4-yl, 1,3,5-triazinan-2-yl, 1,3-dioxan-2-yl, and —CH$_2$CH$_2$N(CH$_3$)$_2$.

In another embodiment of the compound of formula (I):

$R^3$ is selected from the group consisting of aziridin-1-yl, 2,5-dihydro-1H-pyrrol-1-yl, 2,5-dihydrofuran-3-yl, 4,5-dihydro-1H-imidazol-2-yl, pyrrolidin-1-yl, oxolan-2-yl, imidazolidin-4-yl, 1,3-dioxolan-2-yl, 1,3-thiazolidin-3-yl, piperidin-1-yl, oxan-2-yl, 1,3-diazinan-5-yl, morpholin-4-yl, 1,3,5-triazinan-2-yl, 1,3-dioxan-2-yl, and —CH$_2$CH$_2$N(CH$_3$)$_2$;

$R^4$ is selected from the group consisting of —CH$_3$, —CH$_2$CH$_3$, —CH$_2$CH$_2$CH$_3$, —CH$_2$CH$_2$CH$_2$CH$_3$, —C(CH$_3$)$_3$, pentyl, —CH$_2$CH$_2$CH(CH$_3$)$_2$, —CH$_2$C(CH$_3$)$_3$, hexyl, heptyl, 6-methylheptan-2-yl, decyl, hexadecyl, 4,8,12-trimethyltridecyl, 1H-pyrrol-2-yl, furan-2-yl, 1H-imidazol-5-yl, 1,2-oxazol-5-yl, 1H-1,2,3-triazol-5-yl, 1,3,4-oxadiazol-2-yl, thiophen-2-yl, 1,3-thiazol-2-yl, 1,3,4-thiadiazol-2-yl, pyridin-2-yl, pyrimidin-4-yl, 1,3,5-triazin-2-yl, 1,2,4-triazin-3-yl, 1λ$^4$-pyran-1-ylium-4-yl, cyclopropyl, cyclobutyl, cyclopent-2-en-1-yl, cyclopentyl, cyclohexa-1,4-dien-1-yl, cyclohex-3-en-1-yl, cyclohexyl, adamantan-1-yl, decahydronaphthalen-1-yl, 1-methyl-1H-pyrazol-4-yl,

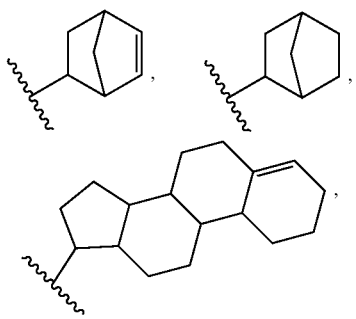

-continued

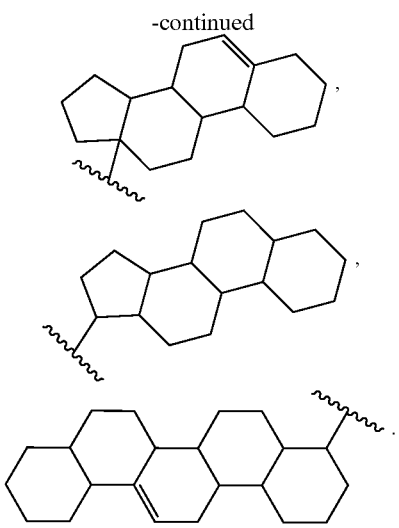

In one embodiment of compound of formula (I):
R$^5$ is selected from the group consisting of —CH$_3$, —CH$_2$CH$_3$, —CH$_2$CH$_2$CH$_3$, —CH$_2$CH$_2$CH$_2$CH$_3$, —C(CH$_3$)$_3$, pentyl, —CH$_2$CH$_2$CH(CH$_3$)$_2$, —CH$_2$C(CH$_3$)$_3$, hexyl, heptyl, 6-methylheptan-2-yl, decyl, hexadecyl, 4,8,12-trimethyltridecyl, cyclopropyl, cyclobutyl, cyclopent-2-en-1-yl, cyclopentyl, cyclohexa-1,4-dien-1-yl, cyclohex-3-en-1-yl, cyclohexyl, adamantan-1-yl, decahydronaphthalen-1-yl,

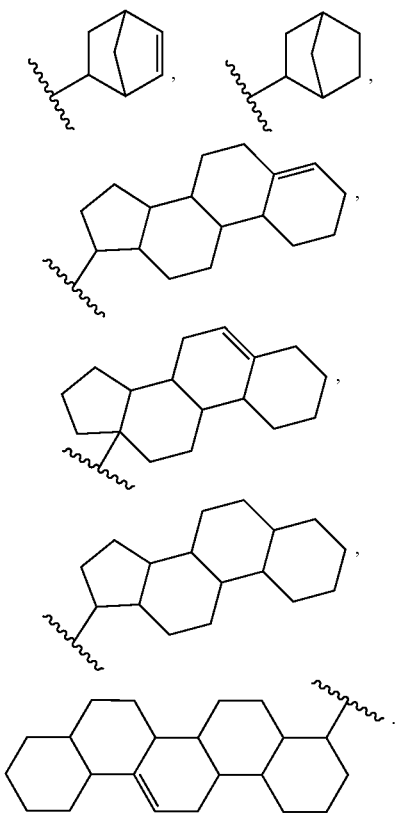

In another embodiment of the compound of formula (I):
R$^6$ is selected from the group consisting of —H, —CH$_3$, —CH$_2$CH$_3$, —CH$_2$CH$_2$CH$_3$, —CH$_2$CH$_2$CH$_2$CH$_3$, —C(CH$_3$)$_3$, pentyl, —CH$_2$CH$_2$CH(CH$_3$)$_2$, —CH$_2$C(CH$_3$)$_3$, hexyl, heptyl, 6-methylheptan-2-yl, decyl, hexadecyl, and 4,8,12-trimethyltridecyl.

In one embodiment of the compound of formula (I):
R$^{31}$ is selected from the group consisting of —OH, —F, —Cl, —Br, —I, phenyl, 2,3-dihydro-1H-inden-5-yl, naphthalen-1-yl, azulen-1-yl, 1,2-dihydroacenaphthylen-5-yl, 9H-fluoren-2-yl, phenanthren-3-yl, anthracen-9-yl, pyren-1-yl, fluoranthen-3-yl, tetraphen-7-yl, —OCH$_3$, —N(CH$_3$)$_2$, —CH$_2$N(CH$_3$)$_2$, —OCH(CH$_3$)$_2$, —CH$_2$CH$_2$R$^{40}$CH$_3$,

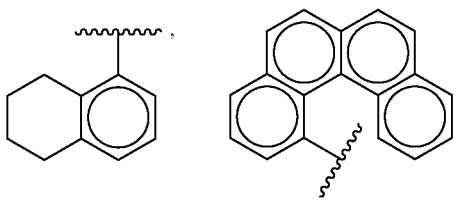

In another embodiment of the compound of formula (I):
R$^{32}$ is selected from the group consisting of —CH$_3$, —CH$_2$CH$_3$, —CH$_2$CH$_2$CH$_3$, —CH$_2$CH$_2$CH$_2$CH$_3$, —C(CH$_3$)$_3$, pentyl, —CH$_2$CH$_2$CH(CH$_3$)$_2$, —CH$_2$C(CH$_3$)$_3$, hexyl, heptyl, 6-methylheptan-2-yl, decyl, hexadecyl, 4,8,12-trimethyltridecyl, —CCH$_{30}$, —CH$_2$CH$_2$OCH$_3$, —CH$_2$CONHCH$_3$, and —R$^{27}$CH$_2$CH(CH$_3$)$_2$.

In one embodiment of the compound of formula (I):
R$^{10}$ is selected from the group consisting of —H, —CH$_3$, —CH$_2$CH$_3$, —CH$_2$CH$_2$CH$_3$, —CH$_2$CH$_2$CH$_2$CH$_3$, —C(CH$_3$)$_3$, pentyl, —CH$_2$CH$_2$CH(CH$_3$)$_2$, —CH$_2$C(CH$_3$)$_3$, hexyl, heptyl, 6-methylheptan-2-yl, decyl, hexadecyl, 4,8,12-trimethyltridecyl, —N(CH$_3$)$_2$, and —CH$_2$CH$_2$OCH$_3$.

In another embodiment of the compound of formula (I):
R$^{10}$ is selected from the group consisting of —H, —CH$_3$, —CH$_2$CH$_3$, —CH$_2$CH$_2$CH$_3$, —CH$_2$CH$_2$CH$_2$CH$_3$, —C(CH$_3$)$_3$, pentyl, —CH$_2$CH$_2$CH(CH$_3$)$_2$, —CH$_2$C(CH$_3$)$_3$, hexyl, heptyl, 6-methylheptan-2-yl, decyl, hexadecyl, 4,8,12-trimethyltridecyl, —N(CH$_3$)$_2$, and —CH$_2$CH$_2$OCH$_3$;

R$^{33}$ is selected from the group consisting of —F, —Cl, —Br, —I, —OCH$_3$, and cyclopropylmethoxy.

In one embodiment of the compound of formula (I):
R$^{34}$ is selected from the group consisting of —CH$_3$, —CH$_2$CH$_3$, —CH$_2$CH$_2$CH$_3$, —CH$_2$CH$_2$CH$_2$CH$_3$, —C(CH$_3$)$_3$, pentyl, —CH$_2$CH$_2$CH(CH$_3$)$_2$, —CH$_2$C(CH$_3$)$_3$, hexyl, heptyl, 6-methylheptan-2-yl, decyl, hexadecyl, 4,8,12-trimethyltridecyl, —F, —Cl, —Br, —I, —OCH$_2$CH$_3$, —C(CH$_3$)$_2$R$^{41}$, —CH$_2$NHCCH$_3$O, (pyrrolidin-1-yl)methyl, benzyl,

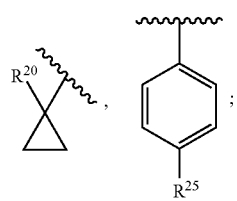

In another embodiment of the compound of formula (I):
R$^{14}$ is selected from the group consisting of —H, —CH$_3$, —CH$_2$CH$_3$, —CH$_2$CH$_2$CH$_3$, —CH$_2$CH$_2$CH$_2$CH$_3$, —C(CH$_3$)$_3$, pentyl, —CH$_2$CH$_2$CH(CH$_3$)$_2$, —CH$_2$C(CH$_3$)$_3$, hexyl, heptyl, 6-methylheptan-2-yl, decyl, hexadecyl, 4,8,12-trimethyltridecyl, phenoxy, and

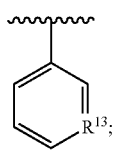

R$^{25}$ is selected from the group consisting of —H, —F, —Cl, —Br, and —I;
R$^{41}$ is selected from the group consisting of —OH, —CH$_3$, —CH$_2$CH$_3$, —CH$_2$CH$_2$CH$_3$, —CH$_2$CH$_2$CH$_2$CH$_3$, —C(CH$_3$)$_3$, pentyl, —CH$_2$CH$_2$CH(CH$_3$)$_2$, —CH$_2$C(CH$_3$)$_3$, hexyl, heptyl, 6-methylheptan-2-yl, decyl, hexadecyl, 4,8,12-trimethyltridecyl, and —CN.
In another embodiment of the compound of formula (I):
R$^{42}$ is selected from the group consisting of —CH$_3$, —CH$_2$CH$_3$, —CH$_2$CH$_2$CH$_3$, —CH$_2$CH$_2$CH$_2$CH$_3$, —C(CH$_3$)$_3$, pentyl, —CH$_2$CH$_2$CH(CH$_3$)$_2$, —CH$_2$C(CH$_3$)$_3$, hexyl, heptyl, 6-methylheptan-2-yl, decyl, hexadecyl, 4,8,12-trimethyltridecyl, and —COOH.
In one embodiment of the compound of formula (I):
R$^{43}$ is selected from the group consisting of —CH$_3$, —CH$_2$CH$_3$, —CH$_2$CH$_2$CH$_3$, —CH$_2$CH$_2$CH$_2$CH$_3$, —C(CH$_3$)$_3$, pentyl, —CH$_2$CH$_2$CH(CH$_3$)$_2$, —CH$_2$C(CH$_3$)$_3$, hexyl, heptyl, 6-methylheptan-2-yl, decyl, hexadecyl, 4,8,12-trimethyltridecyl, -carboalicyclyl, and 3-fluorophenyl.
In another embodiment of the compound of formula (I):
R$^6$ is selected from the group consisting of —H, —CH$_3$, —CH$_2$CH$_3$, —CH$_2$CH$_2$CH$_3$, —CH$_2$CH$_2$CH$_2$CH$_3$, —C(CH$_3$)$_3$, pentyl, —CH$_2$CH$_2$CH(CH$_3$)$_2$, —CH$_2$C(CH$_3$)$_3$, hexyl, heptyl, 6-methylheptan-2-yl, decyl, hexadecyl, and 4,8,12-trimethyltridecyl;
R$^{21}$ is selected from the group consisting of —H, —CH$_3$, —CH$_2$CH$_3$, —CH$_2$CH$_2$CH$_3$, —CH$_2$CH$_2$CH$_2$CH$_3$, —C(CH$_3$)$_3$, pentyl, —CH$_2$CH$_2$CH(CH$_3$)$_2$, —CH$_2$C(CH$_3$)$_3$, hexyl, heptyl, 6-methylheptan-2-yl, decyl, hexadecyl, 4,8,12-trimethyltridecyl, —F, —Cl, —Br, and —I;
R$^{21}$ is selected from the group consisting of —H, —CH$_3$, —CH$_2$CH$_3$, —CH$_2$CH$_2$CH$_3$, —CH$_2$CH$_2$CH$_2$CH$_3$, —C(CH$_3$)$_3$, pentyl, —CH$_2$CH$_2$CH(CH$_3$)$_2$, —CH$_2$C(CH$_3$)$_3$, hexyl, heptyl, 6-methylheptan-2-yl, decyl, hexadecyl, 4,8,12-trimethyltridecyl, —F, —Cl, —Br, —I, and —CN;
R$^{28}$ is selected from the group consisting of —H, —CH$_3$, —CH$_2$CH$_3$, —CH$_2$CH$_2$CH$_3$, —CH$_2$CH$_2$CH$_2$CH$_3$, —C(CH$_3$)$_3$, pentyl, —CH$_2$CH$_2$CH(CH$_3$)$_2$, —CH$_2$C(CH$_3$)$_3$, hexyl, heptyl, 6-methylheptan-2-yl, decyl, hexadecyl, 4,8,12-trimethyltridecyl, and -carboalicyclyl;
R$^{36}$ is selected from the group consisting of —F, —Cl, —Br, —I, and —CN;
R$^{38}$ is selected from the group consisting of —F, —Cl, —Br, —I, and —N(CH$_3$)$_2$;
R$^{39}$ is selected from the group consisting of —CH$_3$, —CH$_2$CH$_3$, —CH$_2$CH$_2$CH$_3$, —CH$_2$CH$_2$CH$_2$CH$_3$, —C(CH$_3$)$_3$, pentyl, —CH$_2$CH$_2$CH(CH$_3$)$_2$, —CH$_2$C(CH$_3$)$_3$, hexyl, heptyl, 6-methylheptan-2-yl, decyl, hexadecyl, and 4,8,12-trimethyltridecyl.

In one embodiment, the invention comprises a pharmaceutical composition comprising a compound of Formula (I) or a pharmaceutically acceptable salt thereof, and at least one pharmaceutically acceptable carrier.

In another embodiment, the invention comprises a method for treating cancer comprising administering to a patient a therapeutically effective amount of a compound of Formula (I) or a pharmaceutically acceptable salt thereof wherein the cancer/disease is selected from: human cancers, carcinomas, sarcomas, adenocarcinomas, papillary adenocarcinomas, lymphomas, leukemias, melanomas, solid lymphoid cancers, kidney cancer, breast cancer, lung cancer, bladder cancer, colon cancer, ovarian cancer, prostate cancer, pancreatic cancer, stomach cancer, brain cancer, head and neck cancer, skin cancer, uterine, testicular, glioma, esophagus, liver cancer, including hepatocarcinoma, lymphoma, including B-acute lymphoblastic lymphoma, non-Hodgkin's lymphomas, Burkitt's lymphoma, Small lymphomas, Hodgkin's lymphoma, leukemia and multiple myeloma.

In another embodiment, the invention comprises a method of treating cancer in a patient in need thereof, comprising administering to the patient an effective amount of a compound of the compound of formula (I) in combination with an additional therapeutic agent.

In one embodiment the additional therapeutic agent is an immunotherapeutic agent.

In another embodiment the immunotherapeutic agent is selected from the group consisting of an anti-PD-1 antibody, an anti-PD-L1 antibody and an anti-CTLA-4 antibody.

In one embodiment, the method of treating cancer in a patient in need thereof, comprises administering to the patient an effective amount of a pharmaceutically acceptable composition comprising formula (I).

In another embodiment of the method of treating cancer the one or more other cancer treatments include radiation, surgery, chemotherapy or administration of a biologic drug.

In one embodiment of the method, the one or more other cancer treatments is the administration of a biologic drug and the biologic drug is a drug that stimulates the immune system wherein the method comprises administering to the subject an inhibitor of DGKα and/or DGKζ, an antagonist of the PD1/PD-L1 axis and an antagonist of CTLA4.

Further disclosed is a compound selected from a group consisting of: Further disclosed is a compound selected from a group consisting of:
5-(2-fluoro-6-hydroxy-4-(piperidin-3-yl)phenyl)-1,2,5-thiadiazolidin-3-one 1,1-dioxide:
5-[2-fluoro-6-hydroxy-4-(4-piperidyl)phenyl]-1,1-dioxo-1,2,5-thiadiazolidin-3-one;
5-(2-fluoro-6-hydroxy-4-(1-methylpiperidin-3-yl)phenyl)-1,2,5-thiadiazolidin-3-one 1,1-dioxide;
5-[2-fluoro-6-hydroxy-4-(1-methyl-4-piperidyl)phenyl]-1,1-dioxo-1,2,5-thiadiazolidin-3-one;
5-(2-fluoro-6-hydroxy-4-(1-isopentylpiperidin-3-yl)phenyl)-1,2,5-thiadiazolidin-3-one 1,1-dioxide;
5-[2-fluoro-6-hydroxy-4-(1-isopentyl-4-piperidyl)phenyl]-1,1-dioxo-1,2,5-thiadiazolidin-3-one;
5-(2-fluoro-6-hydroxy-4-(pyridin-2-yl)phenyl)-1,2,5-thiadiazolidin-3-one 1,1-dioxide;
5-(2-fluoro-6-hydroxy-4-(pyridin-3-yl)phenyl)-1,2,5-thiadiazolidin-3-one 1,1-dioxide;
5-(2-fluoro-6-hydroxy-4-(pyridin-4-yl)phenyl)-1,2,5-thiadiazolidin-3-one 1,1-dioxide;
5-[4-(4-benzylphenyl)-2-fluoro-6-hydroxy-phenyl]-1,1-dioxo-1,2,5-thiadiazolidin-3-one;

5-[2-fluoro-6-hydroxy-4-(3-phenylphenyl)phenyl]-1,1-di-oxo-1,2,5-thiadiazolidin-3-one;
5-[2-fluoro-4-[4-(4-fluorophenyl)phenyl]-6-hydroxy-phenyl]-1,1-dioxo-1,2,5-thiadiazolidin-3-one;
5-[2-fluoro-6-hydroxy-4-(4-morpholinophenyl)phenyl]-1,1-dioxo-1,2,5-thiadiazolidin-3-one; 5-[2-fluoro-6-hydroxy-4-(3-phenoxyphenyl)phenyl]-1,1-dioxo-1,2,5-thiadiazolidin-3-one;
5-[2-fluoro-6-hydroxy-4-(4-isobutylphenyl)phenyl]-1,1-dioxo-1,2,5-thiadiazolidin-3-one;
5-[2-fluoro-6-hydroxy-4-(3-morpholinophenyl)phenyl]-1,1-dioxo-1,2,5-thiadiazolidin-3-one;
5-[4-(4-cyclopropylphenyl)-2-fluoro-6-hydroxy-phenyl]-1,1-dioxo-1,2,5-thiadiazolidin-3-one;
5-[2-fluoro-6-hydroxy-4-(4-phenyl-2-thienyl)phenyl]-1,1-dioxo-1,2,5-thiadiazolidin-3-one;
5-[2-fluoro-6-hydroxy-4-[4-(pyrrolidin-1-ylmethyl)phenyl]phenyl]-1,1-dioxo-1,2,5-thiadiazolidin-3-one;
5-[2-fluoro-6-hydroxy-4-(2-phenyl-4-pyridyl)phenyl]-1,1-dioxo-1,2,5-thiadiazolidin-3-one;
5-[4-[3-(cyclopropylmethoxy)-5-methyl-phenyl]-2-fluoro-6-hydroxy-phenyl]-1,1-dioxo-1,2,5-thiadiazolidin-3-one;
5-[2-fluoro-6-hydroxy-4-[4-(1-hydroxy-1-methyl-ethyl)phenyl]phenyl]-1,1-dioxo-1,2,5-thiadiazolidin-3-one;
5-[2-fluoro-6-hydroxy-4-(6-methoxy-3-pyridyl)phenyl]-1,1-dioxo-1,2,5-thiadiazolidin-3-one;
5-[2-fluoro-6-hydroxy-4-(3-quinolyl)phenyl]-1,1-dioxo-1,2,5-thiadiazolidin-3-one;
5-[2-fluoro-6-hydroxy-4-(2-methoxy-3-pyridyl)phenyl]-1,1-dioxo-1,2,5-thiadiazolidin-3-one;
5-[2-fluoro-6-hydroxy-4-(6-hydroxy-3-pyridyl)phenyl]-1,1-dioxo-1,2,5-thiadiazolidin-3-one;
5-[2-fluoro-6-hydroxy-4-[6-(4-methylpiperazin-1-yl)-3-pyridyl]phenyl]-1,1-dioxo-1,2,5-thiadiazolidin-3-one;
5-[2-fluoro-6-hydroxy-4-(5-methoxy-3-pyridyl)phenyl]-1,1-dioxo-1,2,5-thiadiazolidin-3-one;
5-[4-[6-(dimethylamino)-3-pyridyl]-2-fluoro-6-hydroxy-phenyl]-1,1-dioxo-1,2,5-thiadiazolidin-3-one;
5-[2-fluoro-6-hydroxy-4-(6-phenyl-3-pyridyl)phenyl]-1,1-dioxo-1,2,5-thiadiazolidin-3-one;
5-(2-fluoro-6-hydroxy-4-((4-methylpiperazin-1-yl)methyl)phenyl)-1,2,5-thiadiazolidin-3-one 1,1-dioxide;
5-(2-fluoro-6-hydroxy-4-((4-isopentylpiperazin-1-yl)methyl)phenyl)-1,2,5-thiadiazolidin-3-one 1,1-dioxide;
5-(4-((4-(dimethylamino)piperidin-1-yl)methyl)-2-fluoro-6-hydroxyphenyl)-1,2,5-thiadiazolidin-3-one 1,1-dioxide;
5-[4-[(cyclohexylamino)methyl]-2-fluoro-6-hydroxy-phenyl]-1,1-dioxo-1,2,5-thiadiazolidin-3-one;
5-[2-fluoro-6-hydroxy-4-[(tetrahydropyran-4-ylamino)methyl]phenyl]-1,1-dioxo-1,2,5-thiadiazolidin-3-one;
5-(2-fluoro-6-hydroxy-4-((4-(3-methylbutanoyl)piperazin-1-yl)methyl)phenyl)-1,2,5-thiadiazolidin-3-one 1,1-dioxide;
5-(4-(((4,4-dimethylcyclohexyl)amino)methyl)-2-fluoro-6-hydroxyphenyl)-1,2,5-thiadiazolidin-3-one 1,1-dioxide;
5-(4-((4-acetylpiperazin-1-yl)methyl)-2-fluoro-6-hydroxyphenyl)-1,2,5-thiadiazolidin-3-one 1,1-dioxide;
5-(2-fluoro-6-hydroxy-4-((piperidin-4-ylamino)methyl)phenyl)-1,2,5-thiadiazolidin-3-one 1,1-dioxide;
5-(4-(((1-ethylpiperidin-4-yl)amino)methyl)-2-fluoro-6-hydroxyphenyl)-1,2,5-thiadiazolidin-3-one 1,1-dioxide;
5-(2-fluoro-6-hydroxy-4-(morpholinomethyl)phenyl)-1,2,5-thiadiazolidin-3-one 1,1-dioxide;
5-(2-fluoro-4-((4-fluoropiperidin-1-yl)methyl)-6-hydroxyphenyl)-1,2,5-thiadiazolidin-3-one 1,1-dioxide;
5-(4-((cyclohexyl(methyl)amino)methyl)-2-fluoro-6-hydroxyphenyl)-1,2,5-thiadiazolidin-3-one 1,1-dioxide;
5-(2-fluoro-6-hydroxy-4-((4-(2-methoxyethyl)piperazin-1-yl)methyl)phenyl)-1,2,5-thiadiazolidin-3-one 1,1-dioxide;
2-fluoro-5-[[[3-fluoro-5-hydroxy-4-(1,1,4-trioxo-1,2,5-thiadiazolidin-2-yl)phenyl]methylamino]methyl]benzonitrile;
5-[2-fluoro-6-hydroxy-4-[[2-(1-methyl-4-piperidyl)ethylamino]methyl]phenyl]-1,1-dioxo-1,2,5-thiadiazolidin-3-one;
5-[2-fluoro-6-hydroxy-4-[(4-phenyl-1-piperidyl)methyl]phenyl]-1,1-dioxo-1,2,5-thiadiazolidin-3-one;
5-[4-[[cyclopropyl(propyl)amino]methyl]-2-fluoro-6-hydroxy-phenyl]-1,1-dioxo-1,2,5-thiadiazolidin-3-one;
5-[4-[[cyclobutylmethyl(methyl)amino]methyl]-2-fluoro-6-hydroxy-phenyl]-1,1-dioxo-1,2,5-thiadiazolidin-3-one;
3-[[[3-fluoro-5-hydroxy-4-(1,1,4-trioxo-1,2,5-thiadiazolidin-2-yl)phenyl]methyl-methyl-amino]methyl]benzonitrile;
5-[4-[[[(1R)-3,3-dimethylcyclohexyl]amino]methyl]-2-fluoro-6-hydroxy-phenyl]-1,1-dioxo-1,2,5-thiadiazolidin-3-one;
5-[2-fluoro-6-hydroxy-4-[(4-hydroxy-1-piperidyl)methyl]phenyl]-1,1-dioxo-1,2,5-thiadiazolidin-3-one;
5-[2-fluoro-6-hydroxy-4-[(4-methoxy-1-piperidyl)methyl]phenyl]-1,1-dioxo-1,2,5-thiadiazolidin-3-one;
5-[2-fluoro-6-hydroxy-4-[(4-isopropoxy-1-piperidyl)methyl]phenyl]-1,1-dioxo-1,2,5-thiadiazolidin-3-one;
5-[2-fluoro-6-hydroxy-4-[[4-(2-methoxyethyl)-1-piperidyl]methyl]phenyl]-1,1-dioxo-1,2,5-thiadiazolidin-3-one;
5-[4-[[4-[(dimethylamino)methyl]-1-piperidyl]methyl]-2-fluoro-6-hydroxy-phenyl]-1,1-dioxo-1,2,5-thiadiazolidin-3-one;
5-[4-[(4-butyl-1-piperidyl)methyl]-2-fluoro-6-hydroxy-phenyl]-1,1-dioxo-1,2,5-thiadiazolidin-3-one;
(1r,4r)-4-((4-(1,1-dioxido-4-oxo-1,2,5-thiadiazolidin-2-yl)-3-fluoro-5-hydroxybenzyl)amino)-N-methylcyclohexane-1-carboxamide;
2-(4-(4-(1,1-dioxido-4-oxo-1,2,5-thiadiazolidin-2-yl)-3-fluoro-5-hydroxybenzyl)piperazin-1-yl)-N-methylacetamide;
N-((1r,4r)-4-((4-(1,1-dioxido-4-oxo-1,2,5-thiadiazolidin-2-yl)-3-fluoro-5-hydroxybenzyl)amino)cyclohexyl)acetamide;
(R)-5-(2-fluoro-6-hydroxy-4-((piperidin-3-ylamino)methyl)phenyl)-1,2,5-thiadiazolidin-3-one 1,1-dioxide;
(R)-5-(2-fluoro-6-hydroxy-4-(((1-isopentylpiperidin-3-yl)amino)methyl)phenyl)-1,2,5-thiadiazolidin-3-one 1,1-dioxide;
5-[2-fluoro-6-hydroxy-4-[[[(3S)-1-isopentyl-3-piperidyl]amino]methyl]phenyl]-1,1-dioxo-1,2,5-thiadiazolidin-3-one;
(R)-5-(2-fluoro-6-hydroxy-4-(((tetrahydro-2H-pyran-3-yl)amino)methyl)phenyl)-1,2,5-thiadiazolidin-3-one 1,1-dioxide;
(S)-5-(2-fluoro-6-hydroxy-4-((piperidin-3-ylamino)methyl)phenyl)-1,2,5-thiadiazolidin-3-one 1,1-dioxide;
(S)-5-(4-(((3,3-dimethylcyclohexyl)amino)methyl)-2-fluoro-6-hydroxyphenyl)-1,2,5-thiadiazolidin-3-one 1,1-dioxide;
(S)-5-(2-fluoro-6-hydroxy-4-(((tetrahydro-2H-pyran-3-yl)amino)methyl)phenyl)-1,2,5-thiadiazolidin-3-one 1,1-dioxide;
5-[4-[[[(3R)-1-acetyl-3-piperidyl]amino]methyl]-2-fluoro-6-hydroxy-phenyl]-1,1-dioxo-1,2,5-thiadiazolidin-3-one;
5-[2-fluoro-4-[[[(3R)-1-(3-fluorophenyl)sulfonyl-3-piperidyl]amino]methyl]-6-hydroxy-phenyl]-1,1-dioxo-1,2,5-thiadiazolidin-3-one;

5-[2-fluoro-4-[[[(3S)-1-(3-fluorophenyl)sulfonyl-3-piperidyl]amino]methyl]-6-hydroxy-phenyl]-1,1-dioxo-1,2,5-thiadiazolidin-3-one;
5-[4-[[[(3S)-1-acetyl-3-piperidyl]amino]methyl]-2-fluoro-6-hydroxy-phenyl]-1,1-dioxo-1,2,5-thiadiazolidin-3-one;
5-[2-fluoro-6-hydroxy-4-[[[(3R)-1-methylsulfonyl-3-piperidyl]amino]methyl]phenyl]-1,1-dioxo-1,2,5-thiadiazolidin-3-one;
5-[4-[[[(3S)-1-cyclopropylsulfonyl-3-piperidyl]amino]methyl]-2-fluoro-6-hydroxy-phenyl]-1,1-dioxo-1,2,5-thiadiazolidin-3-one;
5-[4-[[[(3R)-1-cyclopropylsulfonyl-3-piperidyl]amino]methyl]-2-fluoro-6-hydroxy-phenyl]-1,1-dioxo-1,2,5-thiadiazolidin-3-one;
5-[2-fluoro-6-hydroxy-4-[[[(3S)-1-methylsulfonyl-3-piperidyl]amino]methyl]phenyl]-1,1-dioxo-1,2,5-thiadiazolidin-3-one;
3-[(3S)-3-[[3-fluoro-5-hydroxy-4-(1,1,4-trioxo-1,2,5-thiadiazolidin-2-yl) phenyl]methylamino]-1-piperidyl]-3-oxopropanoic acid;
5-[4-[[(4,4-dimethylcyclohexyl)-methyl-amino]methyl]-2-fluoro-6-hydroxy-phenyl]-1,1-dioxo-1,2,5-thiadiazolidin-3-one;
5-[4-[[cyclobutylmethyl(propyl)amino]methyl]-2-fluoro-6-hydroxy-phenyl]-1,1-dioxo-1,2,5-thiadiazolidin-3-one;
5-[[3-fluoro-5-hydroxy-4-(1,1,4-trioxo-1,2,5-thiadiazolidin-2-yl)phenyl]methylamino]pyridine-3-carbonitrile;
5-[4-[(2-chloro-5-fluoro-anilino)methyl]-2-fluoro-6-hydroxy-phenyl]-1,1-dioxo-1,2,5-thiadiazolidin-3-one;
4-chloro-3-[[3-fluoro-5-hydroxy-4-(1,1,4-trioxo-1,2,5-thiadiazolidin-2-yl) phenyl]methylamino]benzonitrile;
5-[4-[[(4-cyclopropyl-2-pyridyl)amino]methyl]-2-fluoro-6-hydroxy-phenyl]-1,1-dioxo-1,2,5-thiadiazolidin-3-one;
5-(2-fluoro-6-hydroxy-4-(4-isopentylpiperazin-1-yl)phenyl)-1,2,5-thiadiazolidin-3-one 1,1-dioxide;
5-(4-(4-aminopiperidin-1-yl)-2-fluoro-6-hydroxyphenyl)-1,2,5-thiadiazolidin-3-one 1,1-dioxide;
5-(2-fluoro-6-hydroxy-4-(piperazin-1-yl)phenyl)-1,2,5-thiadiazolidin-3-one 1,1-dioxide;
5-(2-fluoro-6-hydroxy-4-(4-(2-methoxyethyl)piperazin-1-yl)phenyl)-1,2,5-thiadiazolidin-3-one 1,1-dioxide;
5-(4-(4-(dimethylamino)piperidin-1-yl)-2-fluoro-6-hydroxyphenyl)-1,2,5-thiadiazolidin-3-one 1,1-dioxide;
5-(2-fluoro-6-hydroxy-4-(piperidin-4-ylamino)phenyl)-1,2,5-thiadiazolidin-3-one 1,1-dioxide;
5-(2-fluoro-6-hydroxy-4-((1-isopentylpiperidin-4-yl)amino)phenyl)-1,2,5-thiadiazolidin-3-one 1,1-dioxide;
5-(2-fluoro-6-hydroxy-4-((1-(2-methoxyethyl)piperidin-4-yl)amino)phenyl)-1,2,5-thiadiazolidin-3-one 1,1-dioxide;
N-(2-(dimethylamino)ethyl)-4-(1,1-dioxido-4-oxo-1,2,5-thiadiazolidin-2-yl)-3-fluoro-5-hydroxybenzamide;
4-(1,1-dioxido-4-oxo-1,2,5-thiadiazolidin-2-yl)-3-fluoro-5-hydroxy-N-(piperidin-4-yl)benzamide;
(S)-4-(1,1-dioxido-4-oxo-1,2,5-thiadiazolidin-2-yl)-3-fluoro-5-hydroxy-N-(piperidin-3-yl)benzamide;
(R)-4-(1,1-dioxido-4-oxo-1,2,5-thiadiazolidin-2-yl)-3-fluoro-5-hydroxy-N-(piperidin-3-yl)benzamide;
N-((1r,4r)-4-aminocyclohexyl)-4-(1,1-dioxido-4-oxo-1,2,5-thiadiazolidin-2-yl)-3-fluoro-5-hydroxybenzamide;
N-((1r,4r)-4-(dimethylamino)cyclohexyl)-4-(1,1-dioxido-4-oxo-1,2,5-thiadiazolidin-2-yl)-3-fluoro-5-hydroxybenzamide;
5-(3-(((4,4-dimethylcyclohexyl)amino)methyl)-2-fluoro-6-hydroxyphenyl)-1,2,5-thiadiazolidin-3-one 1,1-dioxide;
5-(2-fluoro-3-((4-fluoropiperidin-1-yl)methyl)-6-hydroxyphenyl)-1,2,5-thiadiazolidin-3-one 1,1-dioxide;
5-(2-fluoro-6-hydroxy-3-(morpholinomethyl)phenyl)-1,2,5-thiadiazolidin-3-one 1,1-dioxide;
5-(3-((cyclohexylamino)methyl)-2-fluoro-6-hydroxyphenyl)-1,2,5-thiadiazolidin-3-one 1,1-dioxide;
5-(2-fluoro-6-hydroxy-3-(((tetrahydro-2H-pyran-4-yl)amino)methyl)phenyl)-1,2,5-thiadiazolidin-3-one 1,1-dioxide;
5-(3-((4-(dimethylamino)piperidin-1-yl)methyl)-2-fluoro-6-hydroxyphenyl)-1,2,5-thiadiazolidin-3-one 1,1-dioxide;
5-(2-fluoro-6-hydroxy-3-((4-methylpiperazin-1-yl)methyl)phenyl)-1,2,5-thiadiazolidin-3-one 1,1-dioxide;
5-[2-fluoro-6-hydroxy-3-[(4-isopentylpiperazin-1-yl)methyl]phenyl]-1,1-dioxo-1,2,5-thiadiazolidin-3-one;
5-(2-fluoro-6-hydroxy-3-(piperidin-4-yl)phenyl)-1,2,5-thiadiazolidin-3-one 1,1-dioxide; and,
5-(2-fluoro-6-hydroxy-3-(1-methylpiperidin-4-yl)phenyl)-1,2,5-thiadiazolidin-3-one 1,1-dioxide.

Synthetic Methods

The compounds of the invention may be prepared by the methods and examples presented below and by methods known to those of ordinary skill in the art. In each of the examples below, the R groups are as defined above for each formula unless noted. Optimum reaction conditions and reaction times may vary according to reactants used. Unless otherwise specified, solvents, temperatures, pressures, and other reaction conditions may be readily selected by one of ordinary skill in the art.

The intermediates used in the syntheses below are either commercially available or easily prepared by methods known to those skilled in the art. Reaction progress may be monitored by conventional methods such as thin-layer chromatography (TLC) or high-pressure liquid chromatography-mass spec (HPLC-MS). Intermediates and products may be purified by methods known in the art, including column chromatography, HPLC, preparative TLC or Preparatory HPLC.

Preparation of Examples

Example 1: 5-(2-fluoro-6-hydroxy-4-(piperidin-3-yl)phenyl)-1,2,5-thiadiazolidin-3-one 1,1-dioxide

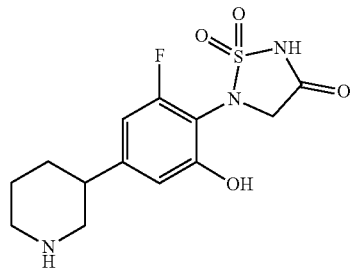 [SMILES: O=C1CN(c2c(O)cc(C3CCCNC3)cc2F)S(=O)(=O)N1]

Scheme 6

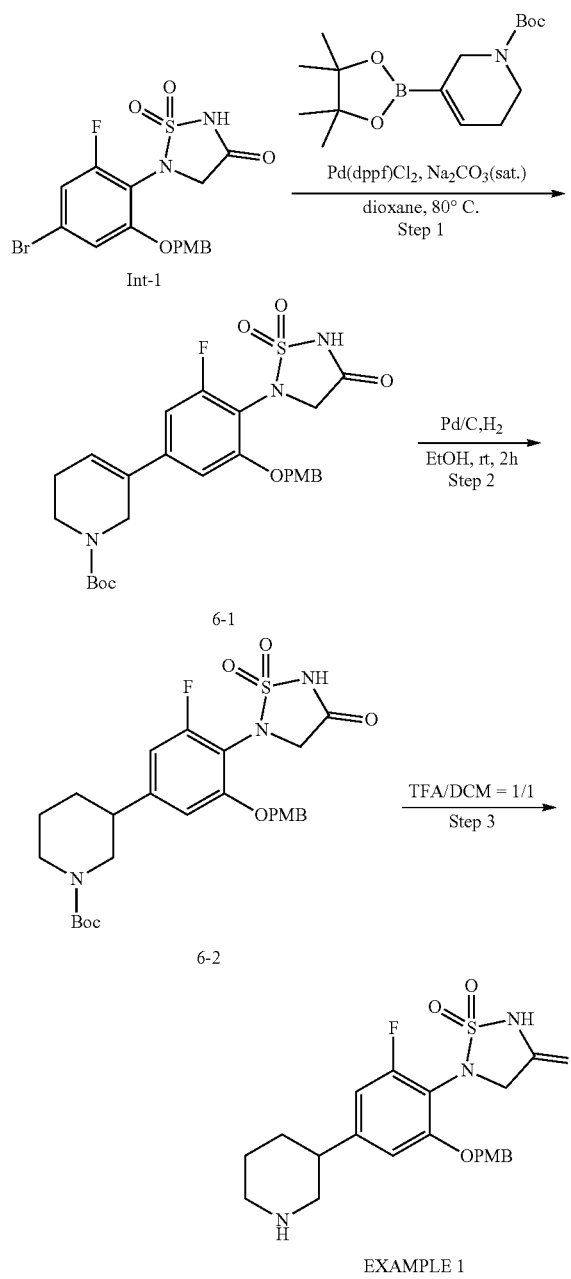

Step 1: To a solution of 5-[4-bromo-2-fluoro-6-[(4-methoxyphenyl)methoxy]phenyl]-1,1-dioxo-1,2,5-thiadiazolidin-3-one (Int-1, 200 mg, 0.45 mmol) in 1,4-Dioxane (3 mL) and Water (0.30 mL) was added tert-butyl 5-(4,4,5,5-tetramethyl-1,3,2-dioxaborolan-2-yl)-3,6-dihydro-2H-pyridine-1-carboxylate (208.33 mg, 0.67 mmol), Pd(dppf)Cl$_2$ (73.36 mg, 0.09 mmol), Na$_2$CO$_3$ (142.84 mg, 1.35 mmol). The resulting mixture was stirred at 80° C. for 3 h under nitrogen atmosphere. Upon completion, the mixture was cooled at r.t. and then filtered. The organic solution was evaporated and the crude residue was purified by reversed flash (0.5% TFA in H$_2$O and MeCN) to obtain tert-butyl 5-[3-fluoro-5-[(4-methoxyphenyl)methoxy]-4-(1,1,4-trioxo-1,2,5-thiadiazolidin-2-yl)phenyl]-3,6-dihydro-2H-pyridine-1-carboxylate (100 mg, 0.18 mmol, 41% yield) as alight-yellow oil. MS: m/z: Calc'd for C$_{26}$H$_{30}$FN$_3$O$_7$S [M−H]$^+$ 546; Found 546.

Step 2: Under a nitrogen atmosphere, Pd/C (90 mg, 0.85 mmol) was added to a solution of tert-butyl 5-[3-fluoro-5-[(4-methoxyphenyl)methoxy]-4-(1,1,4-trioxo-1,2,5-thiadiazolidin-2-yl)phenyl]-3,6-dihydro-2H-pyridine-1-carboxylate (90 mg, 0.16 mmol) in Ethanol (5 mL), H$_2$ was subsequently introduced into the reaction system, and the resulting mixture was stirred at r.t. for 2 h. The reaction mixture was filtered to obtain tert-butyl 3-[3-fluoro-5-hydroxy-4-(1,1,4-trioxo-1,2,5-thiadiazolidin-2-yl)phenyl]piperidine-1-carboxylate (70 mg, 0.15 mmol, 94% yield) as a light yellow solid. MS: m/z: Calc'd for C$_{18}$H$_{24}$FN$_3$O$_6$S [M−H]$^+$ 428; Found 428.

Step 3: To a solution of tert-butyl 3-[3-fluoro-5-hydroxy-4-(1,1,4-trioxo-1,2,5-thiadiazolidin-2-yl)phenyl]piperidine-1-carboxylate (65 mg, 0.15 mmol) in DCM (2 mL) was added TFA (2 mL) at 0° C., the mixture was stirred at r.t. for 2 h. After solvent evaporation, the residue was purified by Prep-HPLC to obtain 5-[2-fluoro-6-hydroxy-4-(3-piperidyl)phenyl]-1,1-dioxo-1,2,5-thiadiazolidin-3-one (28.4 mg, 0.0823 mmol, 54% yield) as an off-white solid. MS: m/z: Calc'd for C$_{13}$H$_{16}$FN$_3$O$_4$ [M−H]$^+$ 328; Found 328. $^1$H NMR (400 MHz, DMSO-d6) δ 7.37-7.24 (m, 2H), 6.65-6.56 (m, 2H), 3.94 (s, 2H), 3.16-3.12 (m, 2H), 2.77-2.71 (m, 3H), 1.86-1.80 (m, 2H), 1.65-1.51 (m, 2H).

Prep-HPLC conditions: XBridge Prep OBD C18 Column, 30*150 mm, 5 μm; Mobile Phase A: Water (10 mmol/L NH$_4$HCO$_3$), Mobile Phase B: ACN; Flow rate: 60 mL/min; Gradient: 2% B to 20% B in 7 min, 20% B; Wave Length: 254/220 nm.

Example 2: 5-[2-fluoro-6-hydroxy-4-(4-piperidyl)phenyl]-1,1-dioxo-1,2,5-thiadiazolidin-3-one

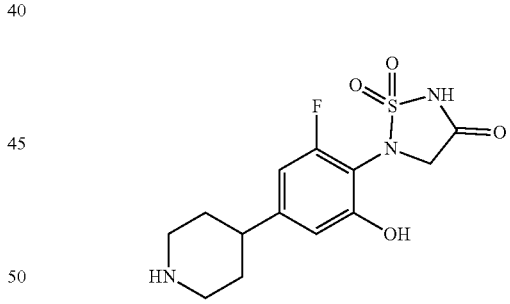

The title compound was prepared in 14% overall yield as a white solid according to the preparation of EXAMPLE 1 using tert-butyl 4-(4,4,5,5-tetramethyl-1,3,2-dioxaborolan-2-yl)-3,6-dihydro-2H-pyridine-1-carboxylate in STEP 1. MS: m/z: Calc'd for C$_{13}$H$_{16}$FN$_3$O$_4$S [M+H]$^+$ 330; Found 330. $^1$H NMR (400 MHz, DMSO-d6) δ 9.69 (s, 1H), 8.58-8.53 (m, 1H), 8.29 (d, J=12.0 Hz, 1H), 6.55 (d, J=1.9 Hz, 2H), 4.04 (s, 2H), 3.37 (d, J=12.5 Hz, 2H), 3.11-2.95 (m, 2H), 2.81-2.76 (m, 1H), 1.93 (d, J=13.7 Hz, 2H), 1.80-1.65 (m, 2H) Prep-HPLC conditions: Column: Xselect CSH OBD Column 30*150 mm 5 um, n; Mobile Phase A: Water (0.05% TFA), Mobile Phase B: ACN; Flow rate: 60 mL/min; Gradient: 2% B to 20% B in 7 min, 20% B; Wave Length: 254/220 nm.

Example 3: 5-(2-fluoro-6-hydroxy-4-(1-methylpiperidin-3-yl)phenyl)-1,2,5-thiadiazolidin-3-one 1,1-dioxide

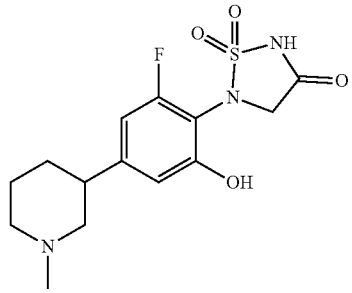 [SMILES: CN1CCCC(c2cc(O)c(N3CC(=O)NS3(=O)=O)c(F)c2)C1]

The title compound was prepared in 10% overall yield as an off-white solid according to the preparation of EXAMPLE 1 using 1-methyl-5-(4,4,5,5-tetramethyl-1,3,2-dioxaborolan-2-yl)-1,2,3,6-tetrahydropyridine in STEP 1. MS: m/z: Calc'd for $C_{14}H_{18}FN_3O_4$ [M–H]⁻ 342; Found 342 ¹H NMR (400 MHz, DMSO-d6) δ 9.50-9.31 (m, 1H), 6.66-6.62 (m, 2H), 3.94 (s, 2H), 2.96-2.92 (m, 2H), 2.76-2.72 (m, 1H), 2.39-2.36 (m, 3H), 2.20-2.18 (m, 2H), 1.78-1.72 (m, 2H), 1.68-1.58 (m, 1H), 1.49-1.33 (m, 1H). Prep-HPLC conditions: XBridge Prep OBD C18 Column, 30*150 mm, 5 μm; Mobile Phase A: Water (10 mmol/L $NH_3 \cdot H_2O$), Mobile Phase B: ACN; Flow rate: 60 mL/min; Gradient: 2% B to 22% B in 7 min, 22% B; Wave Length: 254/220 nm.

Example 4: 5-[2-fluoro-6-hydroxy-4-(1-methyl-4-piperidyl)phenyl]-1,1-dioxo-1,2,5-thiadiazolidin-3-one

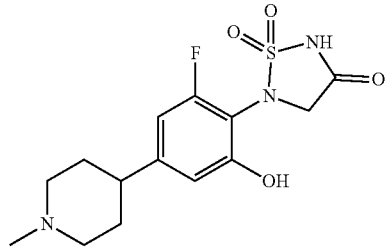 [SMILES: CN1CCC(c2cc(O)c(N3CC(=O)NS3(=O)=O)c(F)c2)CC1]

The title compound was prepared in 9% overall yield as a white solid according to the preparation of EXAMPLE 1 using 1-methyl-4-(4,4,5,5-tetramethyl-1,3,2-dioxaborolan-2-yl)-3,6-dihydro-2H-pyridine in STEP 1. MS: m/z: Calc'd for $C_{14}H_{18}FN_3O_4S$ [M+H]⁺ 344; Found 344. ¹H NMR (400 MHz, DMSO-d6) δ 9.85 (s, 1H), 9.41-9.30 (m, 1H), 6.64-6.57 (m, 2H), 4.16-4.08 (m, 2H), 3.51 (d, J=12.0 Hz, 2H), 3.10-3.05 (m, 2H), 2.81 (d, J=4.3 Hz, 2H), 2.76-2.68 (m, 2H), 2.00 (d, J=14.0 Hz, 2H), 1.89-1.68 (m, 2H).

Prep-HPLC conditions: Xselect CSH OBD Column 30*150 mm 5 um, n; Mobile Phase A: Water (0.05% TFA), Mobile Phase B: ACN; Flow rate: 60 mL/min; Gradient: 2% B to 22% B in 7 min, 22% B; Wave Length: 254/220 nm.

Example 5: 5-(2-fluoro-6-hydroxy-4-(1-isopentylpiperidin-3-yl)phenyl)-1,2,5-thiadiazolidin-3-one 1,1-dioxide

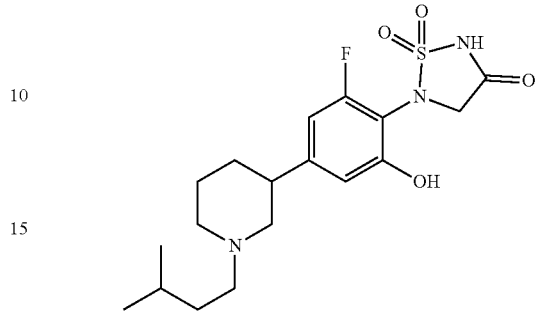

To a stirred solution of 5-[2-fluoro-6-hydroxy-4-(3-piperidyl)phenyl]-1,1-dioxo-1,2,5-thiadiazolidin-3-one; hydrochloride EXAMPLE 1, 35 mg, 0.10 mmol) and 3-methylbutanal (16.48 mg, 0.19 mmol) in DCM (2 mL) were added DIEA (0.02 mL, 0.190 mmol) and AcOH (0.02 mL, 0.290 mmol) at room temperature. The resulting mixture was stirred at room temperature for 1 h. $NaBH(OAc)_3$ (40.56 mg, 0.190 mmol) was added to the mixture at 0° C. and was allowed to stirred at room temperature for 1 h. The reaction mixture was concentrated and the resulting crude product was purified by Prep-HPLC to afford 5-[2-fluoro-6-hydroxy-4-(1-isopentyl-3-piperidyl)phenyl]-1,1-dioxo-1,2,5-thiadiazolidin-3-one (10.2 mg, yield: 226%) as a white solid. MS: m/z: Calc'd for $C_{18}H_{26}FN_3O_4S$ [M+H]⁺ 400, found 400. ¹H NMR (400 MHz, DMSO-d6) δ 9.90 (s, 1H), 9.22 (s, 1H), 6.70-6.44 (dd, J=11.0, 1.9 Hz, 2H), 4.11 (d, J=2.6 Hz, 2H), 3.51 (d, J=11.4 Hz, 2H), 3.11-2.97 (m, 3H), 2.95-2.84 (m, 2H), 2.00-1.75 (t, J=13.6 Hz, 3H), 1.68-1.51 (m, 4H), 0.90 (d, J=5.1 Hz, 6H).

Example 6: 5-[2-fluoro-6-hydroxy-4-(1-isopentyl-4-piperidyl)phenyl]-1,1-dioxo-1,2,5-thiadiazolidin-3-one

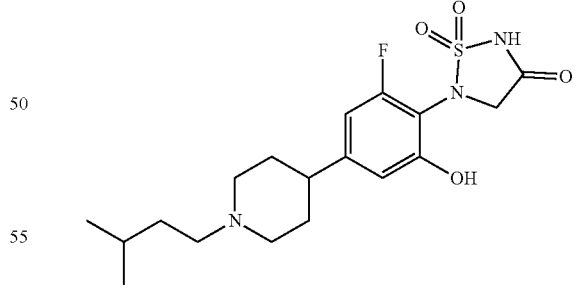

The title compound was prepared in 27% overall yield as a white solid according to the preparation of EXAMPLE 5 using 5-[2-fluoro-6-hydroxy-4-(4-piperidyl)phenyl]-1,1-dioxo-1,2,5-thiadiazolidin-3-one in STEP 1. MS: m/z: Calc'd for $C_{18}H_{26}FN_3O_4S$ [M+H]⁺ 400; Found 400. ¹H NMR (300 MHz, DMSO-d6) δ 9.92 (s, 1H), 9.10 (s, 1H), 6.66-6.55 (m, 2H), 4.14 (s, 2H), 3.59 (d, J=12.0 Hz, 2H), 3.31-2.93 (m, 4H), 2.77 (t, J=12.3 Hz, 1H), 2.01 (d, J=13.8 Hz, 2H), 1.89-1.72 (m, 2H), 1.68-1.40 (m, 3H), 0.99-0.93 (m, 6H).

Prep-HPLC conditions: Xselect CSH OBD Column 30*150 mm 5 um, n; Mobile Phase A: Water (0.05% TFA), Mobile Phase B: ACN; Flow rate: 60 mL/min; Gradient: 10% B to 35% B in 7 min, 35% B; Wave Length: 254/220 nm.

Example 7: 5-(2-fluoro-6-hydroxy-4-(pyridin-2-yl)phenyl)-1,2,5-thiadiazolidin-3-one 1,1-dioxide

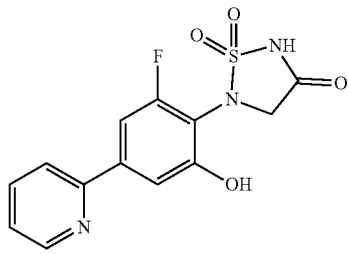 [SMILES: O=C1CN(c2c(O)cc(-c3ccccn3)cc2F)S(=O)(=O)N1]

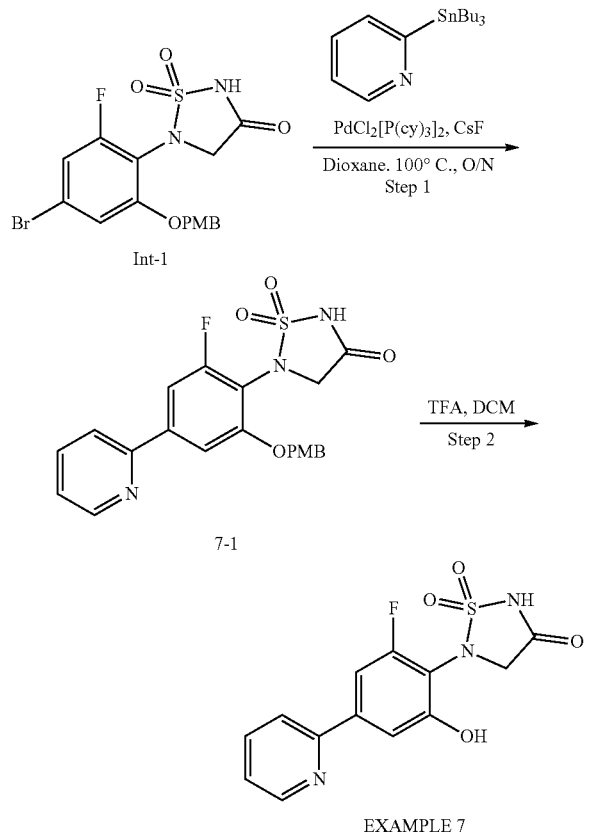

Step 1: To a solution of 5-[4-bromo-2-fluoro-6-[(4-methoxyphenyl)methoxy]phenyl]-1,1-dioxo-1,2,5-thiadiazolidin-3-one (Int-1, 120 mg, 0.27 mmol) and tributyl(2-pyridyl)stannane (198 mg, 0.54 mmol) in Dioxane (6 mL) were added CsF (123 mg, 0.81 mmol), and PdCl$_2$[P(cy)$_3$]$_2$ (20 mg, 0.03 mmol) at room temperature. The resulting suspension was degassed via vacuum/nitrogen backfills for 3 times and stirred at 100° C. for 16 h. The reaction mixture was concentrated and the resulting residue was purified by reversed-phase column (0.05% NH$_4$HCO$_3$ in water, MeCN) to obtain 5-[2-fluoro-6-[(4-methoxyphenyl)methoxy]-4-(2-pyridyl)phenyl]-1,1-dioxo-1,2,5-thiadiazolidin-3-one (100 mg, 0.23 mmol, 84% yield). MS: m/z: Calc'd for C$_{21}$H$_{18}$FN$_3$O$_5$S [M+H]$^+$ 444; found 444.

Step 2: The title compound was prepared in 23.97% yield as an off-white solid according to the preparation of EXAMPLE 1 using 7-1 in STEP 3. MS: m/z: Calc'd for C$_{13}$H$_{10}$FN$_3$O$_4$S [M+H]$^+$ 324; Found 324. $^1$H NMR (400 MHz, DMSO-d6) δ 8.72 (s, 1H), 7.89-7.86 (m, 2H), 7.23-7.48 (m, 3H), 4.06 (s, 2H).

Prep-HPLC purification conditions: Xselect CSH OBD Column 30*150 mm 5 um; Mobile Phase A: Water (0.05% NH$_4$HCO$_3$), Mobile Phase B: ACN; Flow rate: 60 mL/min; Gradient: 5% B to 20% B in 10 min, 20% B; Wave Length: 254/220 nm.

Example 8: 5-(2-fluoro-6-hydroxy-4-(pyridin-3-yl)phenyl)-1,2,5-thiadiazolidin-3-one 1,1-dioxide

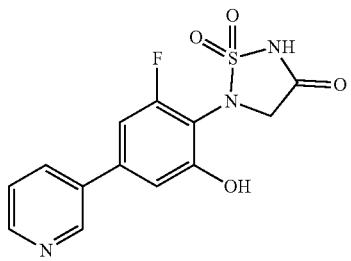 [SMILES: O=C1CN(c2c(O)cc(-c3cccnc3)cc2F)S(=O)(=O)N1]

The title compound was prepared in 22% overall yield as an off-white solid according to the preparation of EXAMPLE 7 using 3-(tributylstannyl)pyridine in STEP 1. MS: m/z: Calc'd for C$_{13}$H$_{10}$FN$_3$O$_4$S [M+H]$^+$ 324; Found 324. $^1$H NMR (400 MHz, DMSO-d6) δ 8.79 (d, J=2.4 Hz, 1H), 8.54 (dd, J=4.8, 1.6 Hz, 1H), 8.03 (dt, J=8.1, 1.8 Hz, 1H), 7.49 (dd, J=8.0, 4.8 Hz, 1H), 7.06 (dd, J=11.0, 2.1 Hz, 1H), 6.99 (t, J=1.6 Hz, 1H), 4.04 (s, 2H). Prep-HPLC purification conditions: Xselect CSH OBD Column 30*150 mm 5 um; Mobile Phase A: Water (0.05% NH$_4$HCO$_3$), Mobile Phase B: ACN; Flow rate: 60 mL/min; Gradient: 5% B to 25% B in 12 min, 25% B; Wave Length: 254/220 nm.

Example 9: 5-(2-fluoro-6-hydroxy-4-(pyridin-4-yl)phenyl)-1,2,5-thiadiazolidin-3-one 1,1-dioxide

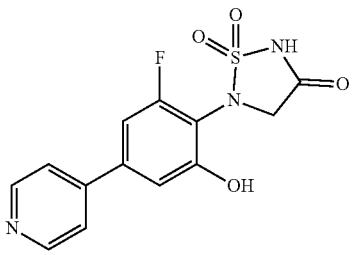 [SMILES: O=C1CN(c2c(O)cc(-c3ccncc3)cc2F)S(=O)(=O)N1]

Scheme 8

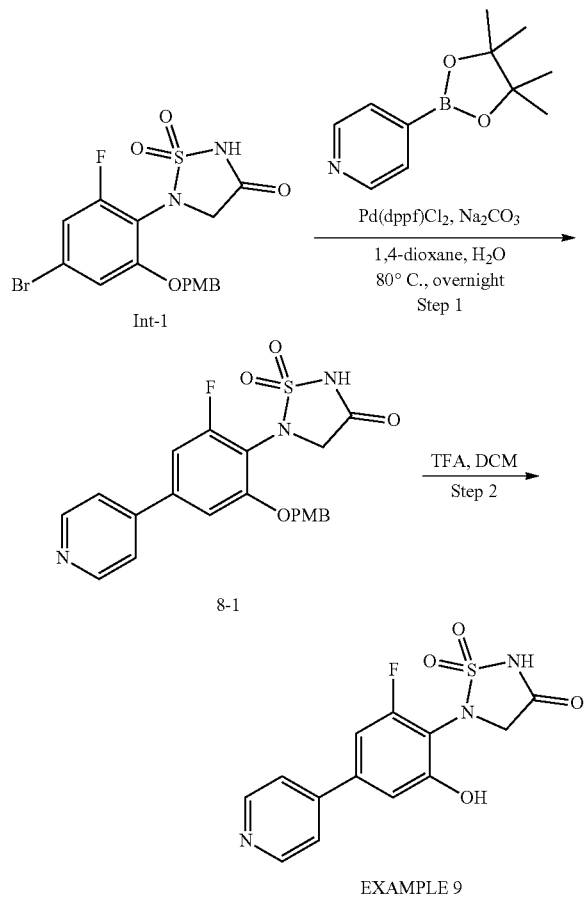

EXAMPLE 9

Step 1: To a seal tube were added 5-[4-bromo-2-fluoro-6-[(4-methoxyphenyl) methoxy]phenyl]-1,1-dioxo-1,2,5-thiadiazolidin-3-one (Int-1, 120 mg, 0.27 mmol), 4-(4,4,5,5-tetramethyl-1,3,2-dioxaborolan-2-yl) pyridine (83 mg, 0.40 mmol), $Na_2CO_3$ (90 mg, 0.81 mmol), 1,4-Dioxane (12 mL), Water (2 mL), and Pd(dppf)Cl$_2$ (22 mg, 0.03 mmol). The reaction was purged with $N_2$ and stirred at 80° C. for overnight. Upon completion the reaction mixture was filtered, concentrated in vacuo. The crude product was purified by reversed-phase column (0.05% $NH_4HCO_3$ in $H_2O$, MeCN) to afford 5-[2-fluoro-6-[(4-methoxyphenyl) methoxy]-4-(4-pyridyl)phenyl]-1,1-dioxo-1,2,5-thiadiazolidin-3-one (50 mg, 0.11 mmol, 42% yield) as off-white solid. MS: m/z: Calc'd for $C_{21}H_{18}FN_3O_4S$, $[M+H]^+$ 444; Found 444.

Step 2: To a stirred solution of 5-[2-fluoro-6-[(4-methoxyphenyl)methoxy]-4-(4-pyridyl)phenyl]-1,1-dioxo-1,2,5-thiadiazolidin-3-one (35 mg, 0.08 mmol) in DCM (6 mL) was added TFA (6 mL) at 0° C., and stirred at room temperature for 6 h. The reaction was concentrated and the resulting residue was purified by Prep-HPLC to afford 5-[2-fluoro-6-hydroxy-4-(4-pyridyl)phenyl]-1,1-dioxo-1,2,5-thiadiazolidin-3-one (11.5 mg, 0.03 mmol, 44% yield) as a yellow solid. MS: m/z: Calc'd for $C_{13}H_{10}FN_3O_4S$, $[M+H]^+$ 324; Found 324. $^1H$ NMR (400 MHz, DMSO-d6) δ 10.41 (s, 1H), 8.83 (s, 2H), 8.04 (d, J=5.6 Hz, 2H), 7.42-7.35 (m, 1H), 7.23-7.17 (m, 1H), 4.23 (s, 2H).

Prep-HPLC purification conditions: Xselect CSH OBD Column 30*150 mm 5 um, n; Mobile Phase A: Water (0.05% TFA), Mobile Phase B: ACN; Flow rate: 60 mL/min; Gradient: 20% B to 34% B in 10 min, 34% B to 100% B in 5 min; Wavelength: 254/220 nm.

Example 10: 5-[4-(4-benzylphenyl)-2-fluoro-6-hydroxy-phenyl]-1,1-dioxo-1,2,5-thiadiazolidin-3-one

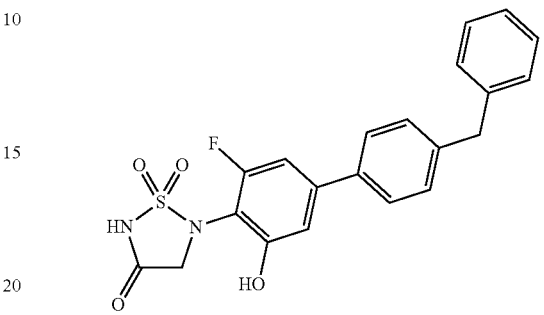

The title compound was prepared in 26% overall yield as a white solid according to the preparation of EXAMPLE 9 using (4-benzylphenyl)boronic acid in STEP 1. MS: m/z: Calc'd for $C_{21}H_{17}FN_2O_4S$ $[M+H]^+$ 413; Found 413. $^1H$ NMR (400 MHz, DMSO-d6+D2O) δ 7.58-7.52 (m, 2H), 7.37-7.16 (m, 7H), 6.96 (d, J=10.5 Hz, 2H), 4.05-3.97 (m, 4H). Prep-HPLC purification conditions: XBridge Prep OBD C18 Column, 30*150 mm, 5 μm; Mobile Phase A: Water (10 mmol/L $NH_4HCO_3$+0.1% $NH_3·H_2O$), Mobile Phase B: ACN; Flow rate: 60 mL/min; Gradient: 33% B to 43% B in 8 min, 43% B; Wave Length: 254/220 nm.

Example 11: 5-[2-fluoro-6-hydroxy-4-(3-phenylphenyl)phenyl]-1,1-dioxo-1,2,5-thiadiazolidin-3-one

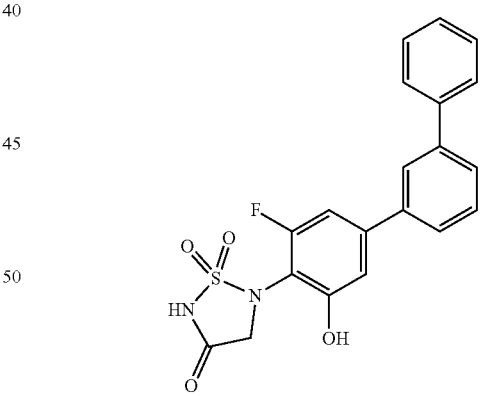

The title compound was prepared in 31% overall yield as a white solid according to the preparation of EXAMPLE 9 using (3-phenylphenyl)boronic acid in STEP 1. MS: m/z: Calc'd for $C_{20}H_{15}FN_2O_4S$ $[M-H]^-$ 397; Found 397. $^1H$ NMR (300 MHz, DMSO-d6) δ 7.85 (t, J=1.8 Hz, 1H), 7.82-7.73 (m, 2H), 7.72-7.69 (m, 1H), 7.67-7.57 (m, 2H), 7.55-7.46 (m, 2H), 7.45-7.36 (m, 1H), 7.17-7.04 (m, 2H), 4.08 (s, 2H).

Prep-HPLC purification conditions: XBridge Prep OBD C18 Column, 30*150 mm, 5 μm; Mobile Phase A: Water (10 mmol/L $NH_4HCO_3$+0.1% $NH_3·H_2O$), Mobile Phase B:

ACN; Flow rate: 60 mL/min; Gradient: 30% B to 40% B in 8 min, 40% B; Wave Length: 254/220 nm.

Example 12: 5-[2-fluoro-4-[4-(4-fluorophenyl)phenyl]-6-hydroxy-phenyl]-1,1-dioxo-1,2,5-thiadiazolidin-3-one

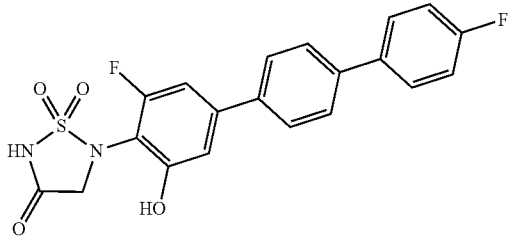 [SMILES: O=C1CN(c2c(O)cc(-c3ccc(-c4ccc(F)cc4)cc3)cc2F)S(=O)(=O)N1]

The title compound was prepared in 34% overall yield as a white solid according to the preparation of EXAMPLE 9 using [4-(4-fluorophenyl)phenyl]boronic acid in STEP 1. MS: m/z: Calc'd for $C_{20}H_{14}F_2N_2O_4S$, $[M-H]^-$ 415; Found 415. $^1H$ NMR (300 MHz, DMSO-d6) δ 7.83-7.67 (m, 6H), 7.32 (dd, J=9.8, 7.9 Hz, 1H), 7.23 (s, 1H), 7.11-6.98 (m, 2H), 4.01 (s, 2H).

Prep-HPLC purification conditions: XBridge Prep OBD C18 Column, 30*150 mm, 5 μm; Mobile Phase A: Water (10 mmol/L $NH_4HCO_3$+0.1% $NH_3·H_2O$), Mobile Phase B: ACN; Flow rate: 60 mL/min; Gradient: 30% B to 42% B in 9 min, 42% B; Wave Length: 254/220 nm.

Example 13: 5-[2-fluoro-6-hydroxy-4-(4-morpholinophenyl)phenyl]-1,1-dioxo-1,2,5-thiadiazolidin-3-one

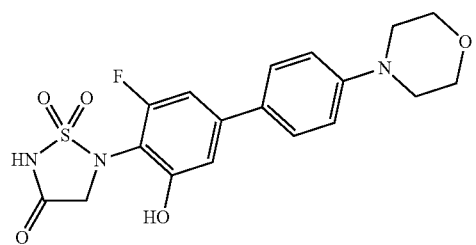 [SMILES: O=C1CN(c2c(O)cc(-c3ccc(N4CCOCC4)cc3)cc2F)S(=O)(=O)N1]

The title compound was prepared in 18% overall yield as a white solid according to the preparation of EXAMPLE 9 using (4-morpholinophenyl)boronic acid in STEP 1. MS: m/z: Calc'd for $C_{18}H_{18}FN_3O_5S$, $[M+H]^+$ 408; Found 408. $^1H$ NMR (400 MHz, DMSO-d6+D2O) δ 7.33-7.29 (t, J=7.9 Hz, 1H), 7.11-7.04 (m, J=2.1 Hz, 1H), 7.02-7.00 (m, J=7.2, 1.6 Hz, 1H), 6.98-6.72 (m, 3H), 4.01 (s, 2H), 3.79-3.72 (m, 4H), 3.21-3.15 (m, 4H).

Prep-HPLC purification conditions: XBridge Prep OBD C18 Column, 30*150 mm, 5 μm; Mobile Phase A: Water (10 mmol/L $NH_4HCO_3$+0.1% $NH_3·H_2O$), Mobile Phase B: ACN; Flow rate: 60 mL/min; Gradient: 17% B to 30% B in 8 min, 30% B; Wave Length: 254/220 nm.

Example 14: 5-[2-fluoro-6-hydroxy-4-(3-phenoxyphenyl)phenyl]-1,1-dioxo-1,2,5-thiadiazolidin-3-one

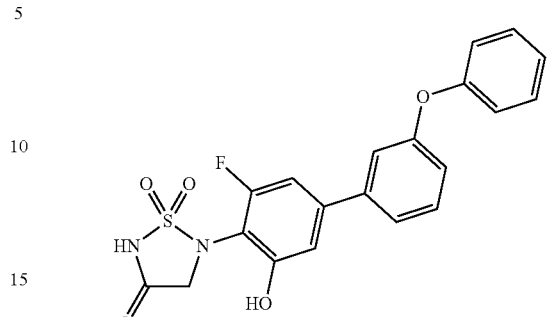

The title compound was prepared in 33% overall yield as a white solid according to the preparation of EXAMPLE 9 using (3-phenoxyphenyl)boronic acid in STEP 1. MS: m/z: Calc'd for $C_{20}H_{15}FN_2O_5S$, $[M-H]^-$ 413; Found 413. $^1H$ NMR (400 MHz, DMSO-d6+D2O) δ 7.50-7.38 (m, 4H), 7.24-7.2 (d, J=2.1 Hz, 1H), 7.19-7.17 (m, 1H), 7.16-7.07 (m, 2H), 7.03-6.97 (m, 2H), 6.93 (t, J=1.6 Hz, 1H), 4.00 (s, 2H).

Prep-HPLC purification conditions: XBridge Prep OBD C18 Column, 30*150 mm, 5 μm; Mobile Phase A: Water (10 mmol/L $NH_4HCO_3$+0.1% $NH_3·H_2O$), Mobile Phase B: ACN; Flow rate: 60 mL/min; Gradient: 32% B to 42% B in 8 min, 42% B; Wave Length: 254/220 nm.

Example 15: 5-[2-fluoro-6-hydroxy-4-(4-isobutylphenyl)phenyl]-1,1-dioxo-1,2,5-thiadiazolidin-3-one

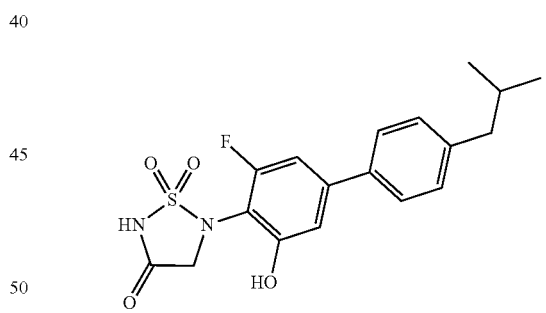

The title compound was prepared in 19% overall yield as a white solid according to the preparation of EXAMPLE 9 using (4-isobutylphenyl)boronic acid in STEP 1. MS: m/z: Calc'd for $C_{18}H_{19}FN_2O_4S$, $[M-H]^-$ 377; Found 377. $^1H$ NMR (400 MHz, DMSO-d6+$D_2O$) δ 7.50-7.38 (m, 4H), 7.24-7.2 (d, J=2.1 Hz, 1H), 7.19-7.17 (m, 1H), 7.16-7.07 (m, 2H), 7.03-6.97 (m, 2H), 6.93 (t, J=1.6 Hz, 1H), 4.00 (s, 2H).

Prep-HPLC purification conditions: XBridge Prep OBD C18 Column, 30*150 mm, 5 μm; Mobile Phase A: Water (10 mmol/L $NH_4HCO_3$+0.1% $NH_3·H_2O$), Mobile Phase B: ACN; Flow rate: 60 mL/min; Gradient: 32% B to 42% B in 8 min, 42% B; Wave Length: 254/220 nm.

Example 16: 5-[2-fluoro-6-hydroxy-4-(3-morpholinophenyl)phenyl]-1,1-dioxo-1,2,5-thiadiazolidin-3-one

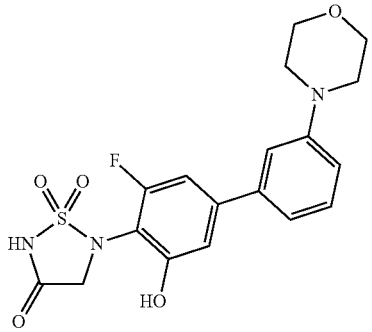 [SMILES: O=C1CN(c2c(O)cc(-c3cccc(N4CCOCC4)c3)cc2F)S(=O)(=O)N1]

The title compound was prepared in 31% overall yield as a white solid according to the preparation of EXAMPLE 9 using (3-morpholinophenyl)boronic acid in STEP 1. MS: m/z: Calc'd for $C_{18}H_{18}FN_3O_5S$, $[M+H]^+$ 408; Found 408. $^1H$ NMR (400 MHz, DMSO-d6+D2O) δ 7.55-7.47 (m, 2H), 7.05-6.98 (m, 2H), 6.97-6.91 (m, 2H), 4.00 (s, 2H), 3.82-3.72 (m, 4H), 3.20-3.13 (m, 4H).

Prep-HPLC purification conditions: XBridge Prep OBD C18 Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 20% B to 30% B in 8 min, 30% B; Wave Length: 254/220 nm.

Example 17: 5-[4-(4-cyclopropylphenyl)-2-fluoro-6-hydroxy-phenyl]-1,1-dioxo-1,2,5-thiadiazolidin-3-one

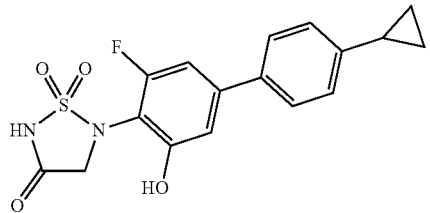 [SMILES: O=C1CN(c2c(O)cc(-c3ccc(C4CC4)cc3)cc2F)S(=O)(=O)N1]

The title compound was prepared in 37% overall yield as a white solid according to the preparation of EXAMPLE 9 using (4-cyclopropylphenyl)boronic acid in STEP 1. MS: m/z: Calc'd for $C_{17}H_{15}FN_2O_4S$, $[M-H]^-$ 361; Found 361. $^1H$ NMR (300 MHz, DMSO-d6) δ 7.50 (d, J=8.0 Hz, 2H), 7.16 (d, J=8.1 Hz, 2H), 7.01-6.91 (m, 2H), 4.02 (s, 2H), 2.08-1.85 (m, 1H), 1.12-0.82 (m, 2H), 0.76-0.65 (m, 2H).

Prep-HPLC purification conditions: XBridge Prep OBD C18 Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 27% B to 47% B in 8 min, 47% B; Wave Length: 254/220 nm.

Example 18: 5-[2-fluoro-6-hydroxy-4-(4-phenyl-2-thienyl)phenyl]-1,1-dioxo-1,2,5-thiadiazolidin-3-one

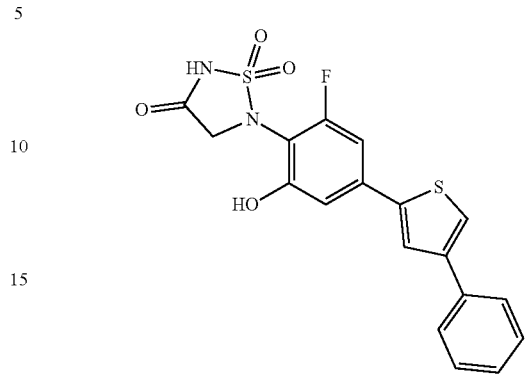

The title compound was prepared in 13% overall yield as a white solid according to the preparation of EXAMPLE 9 using (4-phenyl-2-thienyl)boronic acid in STEP 1. MS: m/z: Calc'd for $C_{18}H_{13}FN_2O_4S_2$, $[M-H]^-$ 403; Found 403. $^1H$ NMR (300 MHz, DMSO-d6) δ 7.99 (d, J=1.5 Hz, 1H), 7.88 (d, J=1.4 Hz, 1H), 7.83-7.74 (m, 2H), 7.45 (t, J=7.6 Hz, 2H), 7.33 (t, J=7.3 Hz, 1H), 7.16 (dd, J=11.2, 2.1 Hz, 1H), 7.02 (t, J=1.6 Hz, 1H), 4.03 (s, 2H).

Prep-HPLC purification conditions: XBridge Prep OBD C18 Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 30% B to 40% B in 8 min, 40% B; Wave Length: 254/220 nm.

Example 19: 5-[2-fluoro-6-hydroxy-4-[4-(pyrrolidin-1-ylmethyl)phenyl]phenyl]-1,1-dioxo-1,2,5-thiadiazolidin-3-one

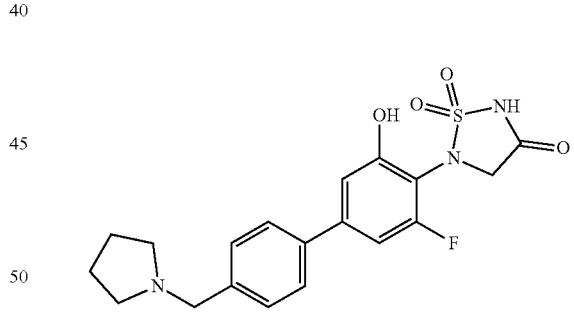

The title compound was prepared in 25% overall yield as a white solid according to the preparation of EXAMPLE 9 using 1-[[4-(4,4,5,5-tetramethyl-1,3,2-dioxaborolan-2-yl)phenyl]methyl]pyrrolidine in STEP 1. MS: m/z: Calc'd for $C_{19}H_{20}FN_3O_4S$, $[M+H]^+$ 406; Found 406. $^1H$ NMR (400 MHz, DMSO-d6) δ 9.73-9.68 (m, 2H), 7.77-7.71 (m, 2H), 7.63-7.57 (m, 2H), 7.09-6.96 (m, 2H), 4.39 (d, J=4.1 Hz, 2H), 4.01 (s, 2H), 3.41-3.34 (m, 2H), 3.13 (s, 1H), 2.05 (s, 2H), 1.87 (s, 2H).

Prep-HPLC purification conditions: Xselect CSH $C_{18}$ OBD Column 30*150 mm 5 μm; Mobile Phase A: Water (0.05% TFA), Mobile Phase B: ACN; Flow rate: 60 mL/min; Gradient: 5% B to 35% B in 10 min, 35% B; Wave Length: 254 nm.

Example 20: 5-[2-fluoro-6-hydroxy-4-(2-phenyl-4-pyridyl)phenyl]-1,1-dioxo-1,2,5-thiadiazolidin-3-one

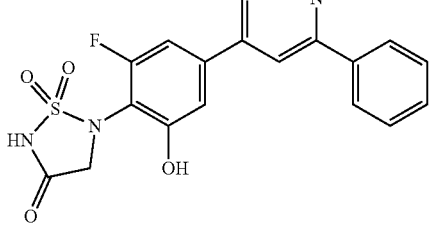

Scheme 9

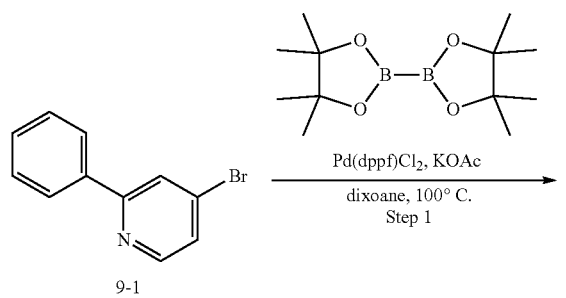

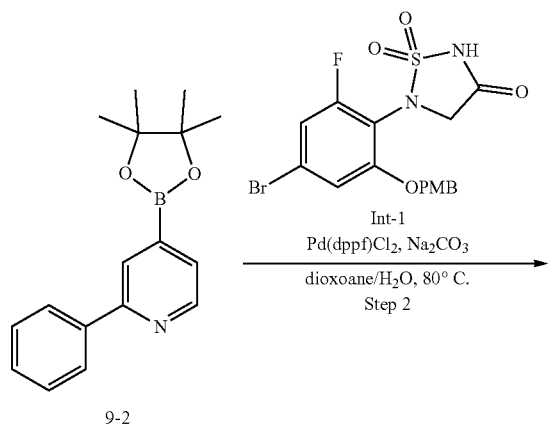

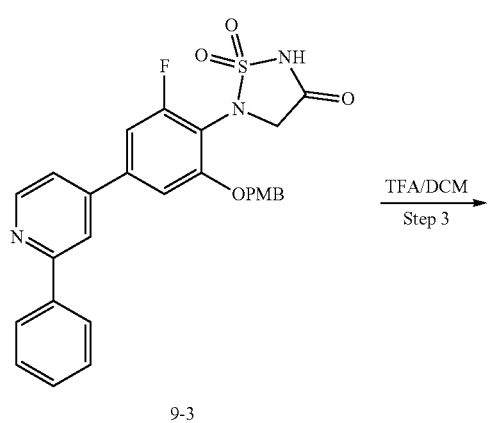

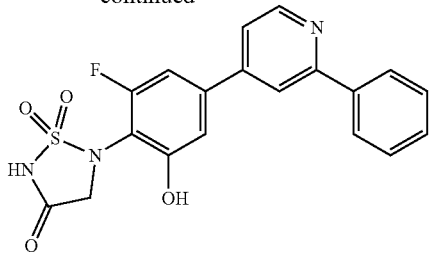

EXAMPLE 20

Step 1: To a stirred mixture of 4-bromo-2-phenyl-pyridine (300 mg, 1.28 mmol) and bis(pinacolato)diboron (488.16 mg, 1.92 mmol) in 1,4-Dioxane (6 mL) were added KOAc (377.32 mg, 3.84 mmol) and Pd(dppf)Cl$_2$ (0.21 g, 0.26 mmol). The resulting mixture was subsequently degassed by bubbling nitrogen through the solution for 5 minutes and then stirred at 100° C. for 16 h. LCMS showed the reaction was completed. The resulting mixture was filtered and the filtrate was concentrated. The residue was purified by reverse flash to obtain 2-phenyl-4-(4,4,5,5-tetramethyl-1,3,2-dioxaborolan-2-yl)pyridine (320 mg, 1.6 mmol, 88% yield) as a light yellow oil. MS: m/z: Calc'd for $C_{17}H_{20}BNO_2$, [M−83]$^-$ 198; Found 198.

Step 2: The compound 9-3 was prepared in 86% yield as a yellow solid according to the preparation of EXAMPLE 9 using 2-phenyl-4-(4,4,5,5-tetramethyl-1,3,2-dioxaborolan-2-yl)pyridine in STEP 1. MS: m/z: Calc'd for $C_{27}H_{22}FN_3O_5S$, [M+H]$^+$ 520; Found 520.

Step 3: The title compound was prepared in 24% yield as a white solid according to the preparation of EXAMPLE 9 using 9-3 in STEP 2. MS: m/z: Calc'd for $C_{19}H_{14}FN_3O_4S$, [M+H]$^+$ 400; Found 400. $^1$H NMR (300 MHz, DMSO-d6) δ 8.73 (d, J=5.2 Hz, 1H), 8.31-8.18 (m, 3H), 7.63 (dd, J=5.2, 1.7 Hz, 1H), 7.59-7.42 (m, 3H), 7.32 (dd, J=11.1, 2.0 Hz, 1H), 7.20 (t, J=1.7 Hz, 1H), 4.07 (s, 2H).

Prep-HPLC purification conditions: XBridge Prep OBD C18 Column, 30*150 mm, 5 μm; Mobile Phase A: Water (10 mmol/L NH$_4$HCO$_3$+0.1% NH$_3$·H$_2$O), Mobile Phase B: ACN; Flow rate: 60 mL/min; Gradient: 23% B to 33% B in 8 min, 33% B; Wave Length: 254/220 nm.

Example 21: 5-[4-[3-(cyclopropylmethoxy)-5-methyl-phenyl]-2-fluoro-6-hydroxy-phenyl]-1,1-dioxo-1,2,5-thiadiazolidin-3-one

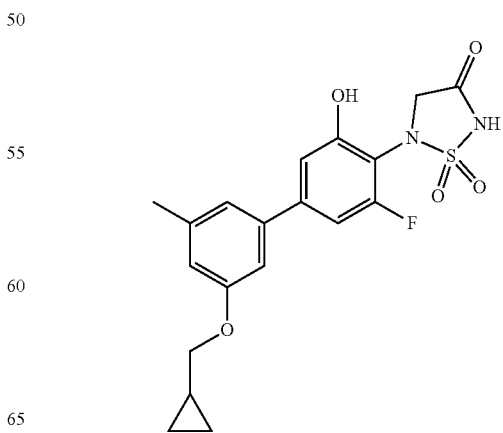

Scheme 10

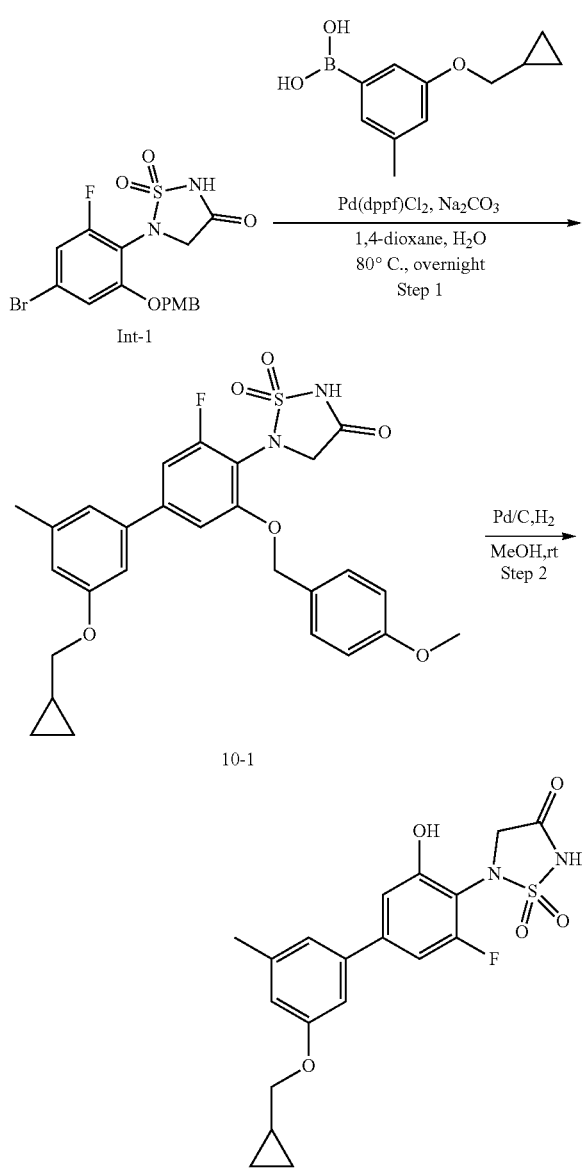

EXAMPLE 21

Step 1: The compound 10-1 was prepared in 85% yield as a brown semi-solid according to the preparation of EXAMPLE 9 using [3-(cyclopropylmethoxy)-5-methyl-phenyl]boronic acid in STEP 1. MS: m/z: Calc'd for $C_{19}H_{19}FN_2O_5S$, [M–H]$^-$ 525; Found 525.

Step 2: To a stirred solution of 5-[4-[3-(cyclopropyl-methoxy)-5-methyl-phenyl]-2-fluoro-6-[(4-methoxyphenyl)methoxy]phenyl]-1,1-dioxo-1,2,5-thiadiazolidin-3-one (10-1, 90 mg, 0.17 mmol) in Methanol (15 mL) was added Pd/C (80. mg, 0.75 mmol) under $N_2$. $H_2$ was subsequently introduced into the reaction system, and the resulting mixture was stirred at ambient temperature for 2 h. LCMS showed the starting material was consumed completely. The mixture was filtrated and the filtrate was concentrated. The residue was purified by Prep-HPLC to obtain 5-[4-[3-(cyclopropylmethoxy)-5-methyl-phenyl]-2-fluoro-6-hydroxy-phenyl]-1,1-dioxo-1,2,5-thiadiazolidin-3-one (31.1 mg, 0.07 mmol) as a white solid. MS: m/z: Calc'd for $C_{19}H_{19}FN_2O_5S$, [M–H]$^-$ 405; Found 405. $^1$H NMR (400 MHz, DMSO-d6+ D$_2$O) δ 7.01-6.93 (m, 3H), 6.91 (t, J=2.0 Hz, 1H), 6.80-6.75 (m, 1H), 4.05 (s, 2H), 3.86 (d, J=7.0 Hz, 2H), 2.33 (s, 3H), 1.26-1.20 (m, 1H), 0.63-0.50 (m, 2H), 0.37-0.29 (m, 2H).

Prep-HPLC purification conditions: XBridge Prep OBD C18 Column, 30*150 mm, 5 μm; Mobile Phase A: Water (10 mmol/L NH$_4$HCO$_3$+0.1% NH$_3$·H$_2$O), Mobile Phase B: ACN; Flow rate: 60 mL/min; Gradient: 30% B to 40% B in 8 min, 40% B; Wave Length: 254/220 nm.

Example 22: 5-[2-fluoro-6-hydroxy-4-[4-(1-hydroxy-1-methyl-ethyl)phenyl]phenyl]-1,1-dioxo-1,2,5-thiadiazolidin-3-one

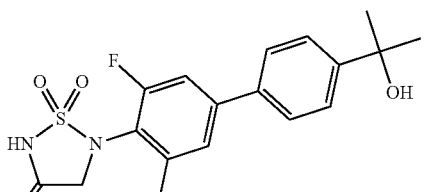

The title compound was prepared in 66% overall yield as a white solid according to the preparation of EXAMPLE 19 using [4-(1-hydroxy-1-methyl-ethyl)phenyl]boronic acid in STEP 1. MS: m/z: Calc'd for $C_{17}H_{17}FN_2O_5S$, [M–H]$^-$ 379; Found 379. $^1$H NMR (400 MHz, DMSO-d6) δ 7.53 (d, J=2.2 Hz, 4H), 6.96 (d, J=8.6 Hz, 2H), 4.04 (s, 2H), 1.43 (s, 6H).

Prep-HPLC purification conditions: XBridge Prep OBD C18 Column, 30*150 mm, 5 μm; Mobile Phase A: Water (10 mmol/L NH$_4$HCO$_3$+0.1% NH$_3$·H$_2$O), Mobile Phase B: ACN; Flow rate: 60 mL/min; Gradient: 2% B to 23% B in 8 min, 23% B; Wave Length: 254/220 nm.

Example 23: 5-[2-fluoro-6-hydroxy-4-(6-methoxy-3-pyridyl)phenyl]-1,1-dioxo-1,2,5-thiadiazolidin-3-one

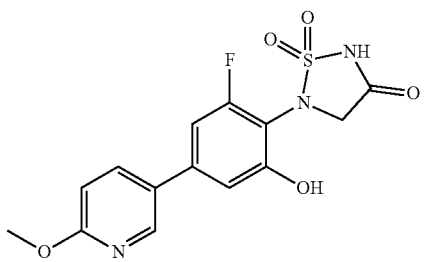 [SMILES: COc1ccc(-c2cc(O)c(N3CC(=O)NS3(=O)=O)c(F)c2)cn1]

The title compound was prepared in 40% overall yield as a white solid according to the preparation of EXAMPLE 9 using 2-methoxy-5-(4,4,5,5-tetramethyl-1,3,2-dioxaborolan-2-yl)pyridine in STEP 1. MS: m/z: Calc'd for $C_{14}H_{12}FN_3O_5S$, [M+H]$^+$ 354; Found 354. $^1$H NMR (300 MHz, DMSO-d6) δ 8.45 (d, J=2.5 Hz, 1H), 7.98 (dd, J=8.7, 2.6 Hz, 1H), 7.04-7.00 (m, 1H), 6.98-6.87 (m, 2H), 4.01 (s, 2H), 3.90 (s, 3H).

Prep-HPLC purification conditions: XBridge Prep OBD C18 Column, 30*150 mm, 5 μm; Mobile Phase A: Water (10 mmol/L NH$_4$HCO$_3$+0.1% NH$_3$·H$_2$O), Mobile Phase B:

ACN; Flow rate: 60 mL/min; Gradient: 15% B to 20% B in 8 min, 20% B; Wave Length: 254/220 nm.

Example 24: 5-[2-fluoro-6-hydroxy-4-(3-quinolyl)phenyl]-1,1-dioxo-1,2,5-thiadiazolidin-3-one

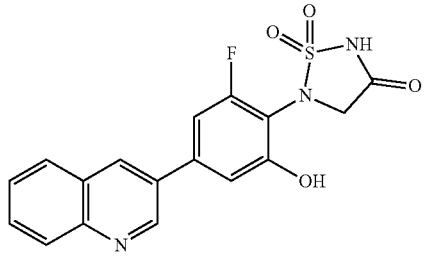 [SMILES: O=C1CN(c2c(O)cc(-c3cnc4ccccc4c3)cc2F)S(=O)(=O)N1]

The title compound was prepared in 14% overall yield as a white solid according to the preparation of EXAMPLE 9 using 3-quinolylboronic acid in STEP 1. MS: m/z: Calc'd for $C_{17}H_{12}FN_3O_4S$, $[M+H]^+$ 374; Found 374. $^1$H NMR (300 MHz, DMSO-d6) δ 9.21 (d, J=2.3 Hz, 1H), 8.65 (d, J=2.4 Hz, 1H), 8.11-8.02 (m, 2H), 7.80 (t, J=7.7 Hz, 1H), 7.67 (t, J=7.5 Hz, 1H), 7.27 (dd, J=11.4, 1.9 Hz, 1H), 7.20 (s, 1H), 4.05 (s, 2H).

Prep-HPLC purification conditions: XBridge Prep OBD C18 Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 16% B to 23% B in 9 min, 23% B; Wave Length: 254/220 nm.

Example 25: 5-[2-fluoro-6-hydroxy-4-(2-methoxy-3-pyridyl)phenyl]-1,1-dioxo-1,2,5-thiadiazolidin-3-one

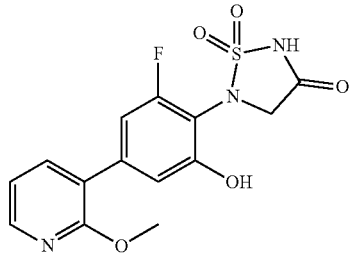 [SMILES: COc1ncccc1-c1cc(O)c(N2CC(=O)NS2(=O)=O)c(F)c1]

The title compound was prepared in 38% overall yield as a white solid according to the preparation of EXAMPLE 9 using (2-methoxy-3-pyridyl)boronic acid in STEP 1. MS: m/z: Calc'd for $C_{14}H_{12}FN_3O_5S$, $[M+H]^+$ 354; Found 354. $^1$H NMR (400 MHz, DMSO-d6) δ 8.19 (dd, J=4.9, 1.9 Hz, 1H), 7.75 (dd, J=7.4, 1.9 Hz, 1H), 7.11 (dd, J=7.3, 5.0 Hz, 1H), 6.93-6.85 (m, 2H), 4.05 (s, 2H), 3.90 (s, 3H).

Prep-HPLC purification conditions: XBridge Prep Phenyl OBD Column, 19*250 mm, 5 μm; Mobile Phase A: Water (10 mmol/L $NH_4HCO_3$), Mobile Phase B: ACN; Flow rate: 25 mL/min; Gradient: 5% B to 10% B in 7 min, 10% B; Wave Length: 254/220 nm.

Example 26: 5-[2-fluoro-6-hydroxy-4-(6-hydroxy-3-pyridyl)phenyl]-1,1-dioxo-1,2,5-thiadiazolidin-3-one

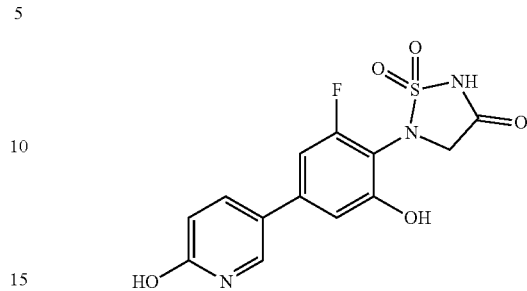

The title compound was prepared in 22% overall yield as an off-white solid according to the preparation of EXAMPLE 9 using 5-(4,4,5,5-tetramethyl-1,3,2-dioxaborolan-2-yl)pyridin-2-ol in STEP 1. MS: m/z: Calc'd for $C_{13}H_{10}FN_3O_5S$, $[M-H]^-$ 338; Found 338. $^1$H NMR (300 MHz, DMSO-d6) δ 7.83 (dd, J=9.5, 2.8 Hz, 1H), 7.73 (d, J=2.8 Hz, 1H), 6.94 (dd, J=11.5, 2.1 Hz, 1H), 6.89-6.82 (m, 1H), 6.48 (d, J=9.5 Hz, 1H), 4.02 (s, 2H).

Prep-HPLC purification conditions: XBridge Prep OBD C18 Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 2% B to 15% B in 8 min, 15% B; Wave Length: 254/220 nm.

Example 27: 5-[2-fluoro-6-hydroxy-4-[6-(4-methylpiperazin-1-yl)-3-pyridyl]phenyl]-1,1-dioxo-1,2,5-thiadiazolidin-3-one

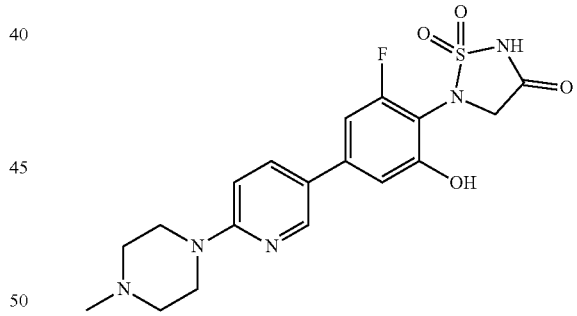

The title compound was prepared in 23% overall yield as a white solid according to the preparation of EXAMPLE 9 using 1-methyl-4-[5-(4,4,5,5-tetramethyl-1,3,2-dioxaborolan-2-yl)-2-pyridyl]piperazine in STEP 1. MS: m/z: Calc'd for $C_{18}H_{20}FN_5O_4S$, $[M+H]^+$ 422; Found 422. $^1$H NMR (400 MHz, DMSO-d6) δ 9.52 (s, 1H), 8.43 (d, 1H), 7.86 (m, 1H), 7.02-6.92 (m, 3H), 3.99 (d, 2H), 3.71-3.67 (m, 4H), 2.90-2.85 (d, 4H), 2.58-2.47 (m, 3H).

Prep-HPLC purification conditions: Xselect Peptide CSH C18 19*150 mm 5 μm; Mobile Phase A: Water (10 mmol/L $NH_4HCO_3$), Mobile Phase B: ACN; Flow rate: 60 mL/min; Gradient: 12% B to 42% B in 10 min, 42% B; Wave Length: 254 nm.

Example 28: 5-[2-fluoro-6-hydroxy-4-(5-methoxy-3-pyridyl)phenyl]-1,1-dioxo-1,2,5-thiadiazolidin-3-one

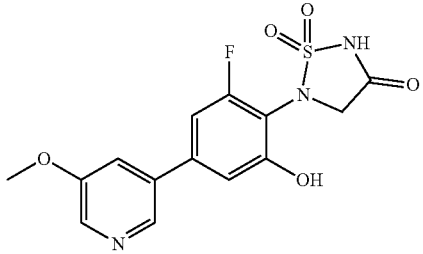 [SMILES: COc1cncc(-c2cc(O)c(N3CC(=O)NS3(=O)=O)c(F)c2)c1]

The title compound was prepared in 44% overall yield as a white solid according to the preparation of EXAMPLE 9 using 3-methoxy-5-(4,4,5,5-tetramethyl-1,3,2-dioxaborolan-2-yl)pyridine in STEP 1. MS: m/z: Calc'd for $C_{14}H_{12}FN_3O_5S$, $[M+H]^+$ 354; Found 354. $^1$H NMR (300 MHz, DMSO-d6) δ 8.43 (d, J=1.8 Hz, 1H), 8.30 (d, J=2.7 Hz, 1H), 7.59 (dd, J=2.8, 1.9 Hz, 1H), 7.13 (dd, J=11.3, 2.1 Hz, 1H), 7.08-7.01 (m, 1H), 4.02 (s, 2H), 3.91 (s, 3H).

Prep-HPLC purification conditions: XBridge Prep OBD C18 Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 16% B to 23% B in 9 min, 23% B; Wave Length: 254/220 nm.

Example 29: 5-[4-[6-(dimethylamino)-3-pyridyl]-2-fluoro-6-hydroxy-phenyl]-1,1-dioxo-1,2,5-thiadiazolidin-3-one

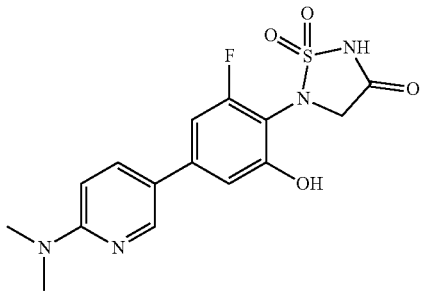 [SMILES: CN(C)c1ccc(-c2cc(O)c(N3CC(=O)NS3(=O)=O)c(F)c2)cn1]

The title compound was prepared in 27% overall yield as a white solid according to the preparation of EXAMPLE 9 using N,N-dimethyl-5-(4,4,5,5-tetramethyl-1,3,2-dioxaborolan-2-yl)pyridin-2-amine in STEP 1. MS: m/z: Calc'd for $C_{15}H_{15}FN_4O_4S$, $[M+H]^+$ 367; Found 367. 1H NMR (400 MHz, DMSO-d6) δ 8.38 (d, 1H), 7.78 (m, 1H), 6.98-6.88 (m, 2H), 6.71 (d, 1H), 3.99 (s, 2H), 3.06 (s, 6H).

Prep-HPLC purification conditions: X select CSH $C_{18}$ OBD Column 30*150 mm 5 μm; Mobile Phase A: Water (10 mmol/L $NH_4HCO_3$), Mobile Phase B: ACN; Flow rate: 60 mL/min; Gradient: 12% B to 42% B in 10 min, 42% B; Wave Length: 254 nm.

Example 30: 5-[2-fluoro-6-hydroxy-4-(6-phenyl-3-pyridyl)phenyl]-1,1-dioxo-1,2,5-thiadiazolidin-3-one

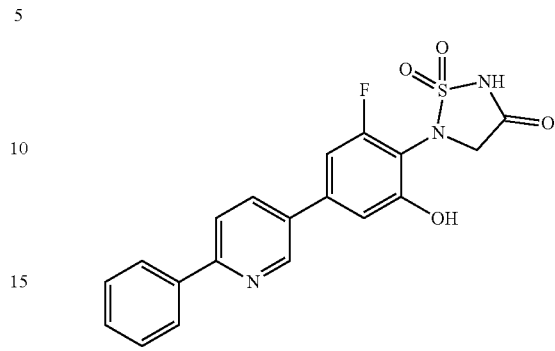

The title compound was prepared in 25% overall yield as a light-yellow solid according to the preparation of EXAMPLE 9 using (6-phenyl-3-pyridyl)boronic acid in STEP 1. MS: m/z: Calc'd for $C_{19}H_{14}FN_3O_4S$, $[M+H]^+$ 400; Found 400. $^1$H NMR (400 MHz, DMSO-d6) δ 10.58 (s, 1H), 8.96 (d, J=2.4 Hz, 1H), 8.15 (dd, J=5.9, 2.9 Hz, 3H), 8.09 (d, J=8.4 Hz, 1H), 7.53 (t, J=7.4 Hz, 2H), 7.47 (dd, J=8.2, 6.0 Hz, 1H), 7.25 (dd, J=11.0, 1.9 Hz, 1H), 7.11 (s, 1H), 4.39 (s, 2H).

Prep-HPLC purification conditions: Xselect Peptide CSH C18 19*150 mm 5 μm, 1; Mobile Phase A: Water (0.05% TFA), Mobile Phase B: ACN; Flow rate: 60 mL/min; Gradient: 30% B to 30% B in 7 min, 30% B; Wave Length: 254 nm.

Example 31: 5-(2-fluoro-6-hydroxy-4-((4-methylpiperazin-1-yl)methyl)phenyl)-1,2,5-thiadiazolidin-3-one 1,1-dioxide

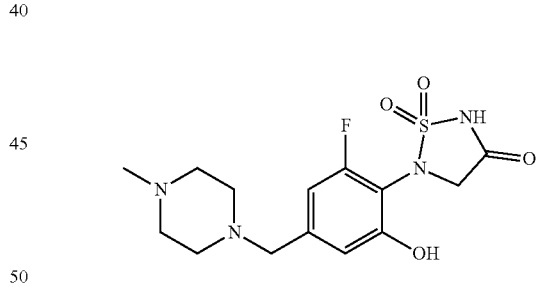

Scheme 11

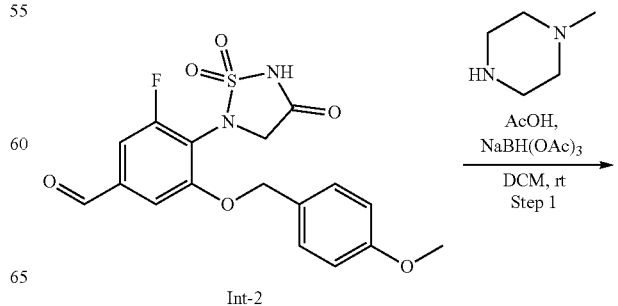

-continued

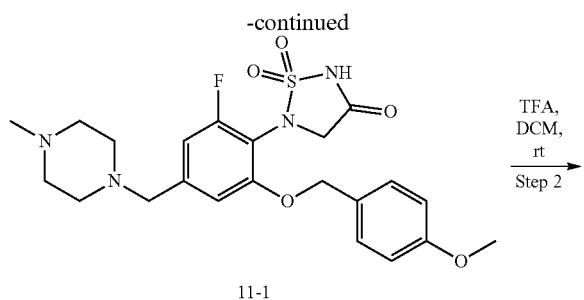

11-1

↓ TFA, DCM, rt
Step 2

Example 32: 5-(2-fluoro-6-hydroxy-4-((4-isopentylpiperazin-1-yl)methyl)phenyl)-1,2,5-thiadiazolidin-3-one 1,1-dioxide

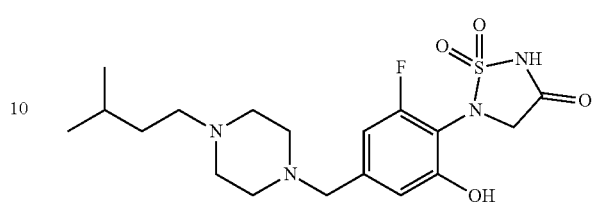

The title compound was prepared in 9.7% overall yield as a white solid according to the preparation of EXAMPLE 31 using 1-isopentylpiperazine hydrochloride in STEP 1. MS: m/z Calc'd for $C_{18}H_{27}FN_4O_4S$, $[M+H]^+$ 415, found 415. $^1H$ NMR (400 MHz, DMSO-d6) δ 9.91 (s, 1H) 6.71 (d, J=3.8 Hz, 2H), 4.12 (s, 2H), 3.64-3.44 (m, 6H), 3.07 (s, 6H), 1.65-1.45 (m, 3H), 0.90 (d, J=6.5 Hz, 6H).

Prep-HPLC purification conditions: Atlantis Prep T3 OBD Column, 19*250 mm 10 u; Mobile Phase A: Water (0.05% TFA), Mobile Phase B: ACN; Flow rate: 25 mL/min; Gradient: 5% B to 35% B in 7 min, 35% B; Wave Length: 254/210 nm.

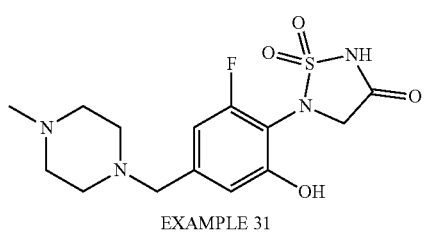

EXAMPLE 31

Step 1: To a stirred solution of 3-fluoro-5-[(4-methoxyphenyl)methoxy]-4-(1,1,4-trioxo-1,2,5-thiadiazolidin-2-yl)benzaldehyde (Int-2, 65 mg, 0.16 mmol) and 1-methylpiperazine (33.02 mg, 0.33 mmol) in DCM (2 mL) was added AcOH (0.02 mL, 0.33 mmol), the resulting mixture was stirred at 0° C. for 1 h. Then NaBH(OAc)₃ (69.86 mg, 0.33 mmol) was added at 0° C. and the resulting mixture was stirred at RT for 1 h. The mixture was concentrated and directly purified by reversed-phase column (0.05% NH₄HCO₃ in water and acetonitrile) to obtain 5-[2-fluoro-6-[(4-methoxyphenyl)methoxy]-4-[(4-methylpiperazin-1-yl)methyl]phenyl]-1,1-dioxo-1,2,5-thiadiazolidin-3-one (70 mg, 0.15 mmol, 89% yield) as a brown solid. MS: m/z Calc'd for $C_{22}H_{27}FN_4O_5S$, $[M+H]^+$ 479, found 479.

Step 2: To a stirred solution of 5-[2-fluoro-6-[(4-methoxyphenyl)methoxy]-4-[(4-methylpiperazin-1-yl)methyl]phenyl]-1,1-dioxo-1,2,5-thiadiazolidin-3-one (70 mg, 0.15 mmol) in DCM (2 mL) was added TFA (1 mL) at 0° C. The resulting mixture was stirred at RT for 2 h. Upon completion, the reaction mixture was concentrated in vacuo, and the residue was purified by Prep-HPLC to obtain 5-[2-fluoro-6-hydroxy-4-[(4-methylpiperazin-1-yl)methyl]phenyl]-1,1-dioxo-1,2,5-thiadiazolidin-3-one (12.3 mg, 0.0332 mmol, 23% yield) as a white solid. MS: m/z Calc'd for $C_{14}H_{19}FN_4O_4S$, $[M+H]^+$ 359, found 359. $^1H$ NMR (400 MHz, DMSO-d6) δ 9.42 (s, 1H), 6.63 (d, J=17.8 Hz, 2H), 3.95 (d, J=3.4 Hz, 2H), 2.78 (s, 4H), 2.54 (s, 6H), 2.48 (s, 3H).

Prep-HPLC purification conditions: XBridge Prep OBD C18 Column, 30*150 mm, 5 μm; Mobile Phase A: Water (10 mmol/L NH₄HCO₃), Mobile Phase B: ACN; Flow rate: 60 mL/min; Gradient: 2% B to 20% B in 7 min, 20% B; Wave Length: 254/220 nm.

Example 33: 5-(4-((4-(dimethylamino)piperidin-1-yl)methyl)-2-fluoro-6-hydroxyphenyl)-1,2,5-thiadiazolidin-3-one 1,1-dioxide

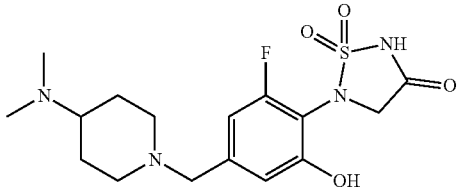 [SMILES: CN(C)C1CCN(Cc2cc(O)c(N3CC(=O)NS3(=O)=O)c(F)c2)CC1]

The title compound was prepared in 13% overall yield as a white solid according to the preparation of EXAMPLE 31 using N,N-dimethylpiperidin-4-amine in STEP 1. MS: m/z Calc'd for $C_{16}H_{23}FN_4O_4S$, $[M+H]^+$ 387, found 387. $^1H$ NMR (400 MHz, DMSO-d6) δ 9.40 (s, 1H), 6.67-6.57 (m, 2H), 3.95 (s, 2H), 3.39 (s, 2H), 2.89 (d, J=11.3 Hz, 2H), 2.81 (s, 1H), 2.59 (s, 1H), 2.51 (d, J=1.8 Hz, 6H), 1.96 (t, J=11.5 Hz, 2H), 1.87 (d, J=11.3 Hz, 2H), 1.61-1.48 (m, 2H).

Prep-HPLC purification conditions: XBridge Prep OBD C18 Column, 30*150 mm, 5 μm; Mobile Phase A: Water (10 mmol/L NH₄HCO₃), Mobile Phase B: ACN; Flow rate: 60 mL/min; Gradient: 2% B to 20% B in 7 min, 20% B; Wave Length: 254/220 nm.

Example 34: 5-[4-[(cyclohexylamino)methyl]-2-fluoro-6-hydroxy-phenyl]-1,1-dioxo-1,2,5-thiadiazolidin-3-one

Example 36: 5-(2-fluoro-6-hydroxy-4-((4-(3-methylbutanoyl)piperazin-1-yl)methyl)phenyl)-1,2,5-thiadiazolidin-3-one 1,1-dioxide

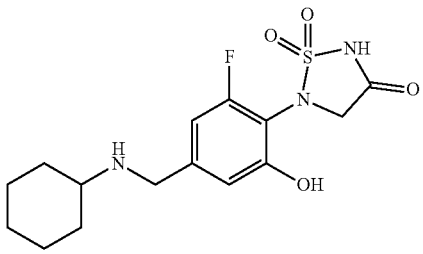 [SMILES: O=C1CN(c2c(O)cc(CNC3CCCCC3)cc2F)S(=O)(=O)N1]

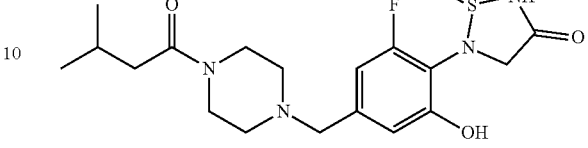

The title compound was prepared in 11% overall yield as a white solid according to the preparation of EXAMPLE 31 using cyclohexanamine in STEP 1. MS: m/z Calc'd for $C_{15}H_{20}FN_3O_4S$, $[M+H]^+$ 358, found 358. $^1H$ NMR (400 MHz, DMSO-d6) δ 9.57 (s, 1H), 8.37-8.31 (m, 1H), 6.86-6.78 (m, 2H), 3.99 (d, J=25.2 Hz, 4H), 2.93 (s, 1H), 2.09-2.02 (m, 2H), 1.80-1.73 (m, 2H), 1.61 (d, J=12.4 Hz, 1H), 1.45-0.95 (m, 5H).

Prep-HPLC purification conditions: Xselect CSH OBD Column 30*150 mm 5 um, n; Mobile Phase A: Water (0.05% TFA), Mobile Phase B: ACN; Flow rate: 60 m/min; Gradient: 2% B to 10% B in 10 min, 10% B; Wave Length: 254/220 nm.

Example 35: 5-[2-fluoro-6-hydroxy-4-[(tetrahydropyran-4-ylamino)methyl]phenyl]-1,1-dioxo-1,2,5-thiadiazolidin-3-one Scheme 12

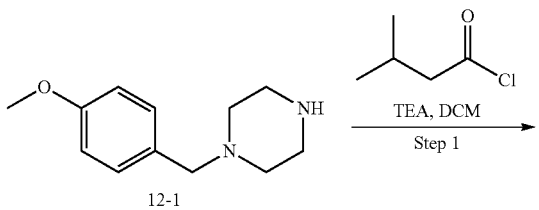

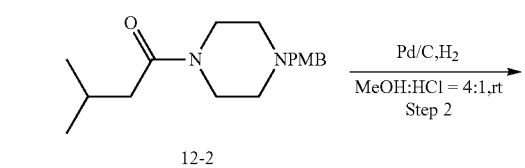

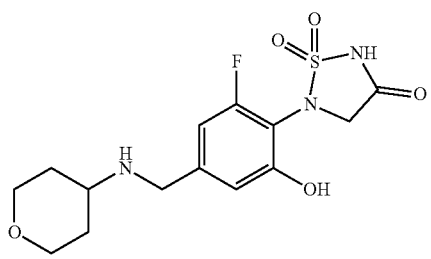 [SMILES: O=C1CN(c2c(O)cc(CNC3CCOCC3)cc2F)S(=O)(=O)N1]

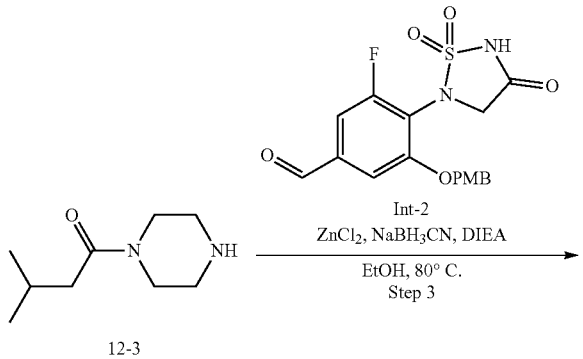

The title compound was prepared in 7.4% overall yield as an off-white semi-solid according to the preparation of EXAMPLE 31 using tetrahydropyran-4-amine in STEP 1. MS: m/z Calc'd for $C_{14}H_{18}FN_3O_5S$, $[M+H]^+$ 360, found 360. $^1H$ NMR (400 MHz, DMSO-d6) δ 9.82 (s, 1H), 8.85 (s, 2H), 6.97-6.69 (m, 2H), 4.11 (s, 2H), 3.97 (s, 2H), 3.93 (dd, J=11.1, 4.4 Hz, 2H), 3.30 (dd, J=11.9, 1.9 Hz, 3H), 2.05-1.96 (m, 2H), 1.65-1.51 (m, 2H), 1.24 (s, OH).

Prep-HPLC purification conditions: Xselect CSH OBD Column 30*150 mm 5 um, n; Mobile Phase A: Water (0.05% TFA), Mobile Phase B: ACN; Flow rate: 60 mL/min; Gradient: 2% B to 10% B in 11 min, 10% B; Wave Length: 254/220 nm.

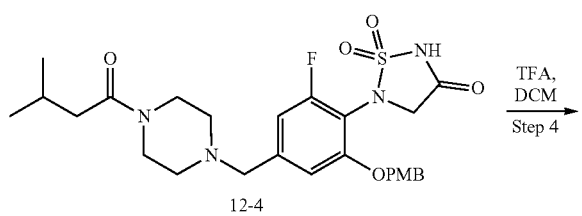

-continued

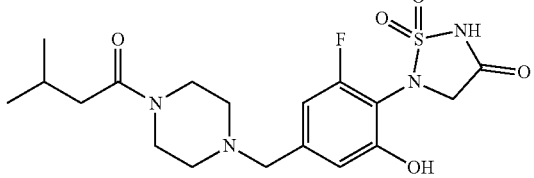

EXAMPLE 36

Step 1: To a solution of 1-[(4-methoxyphenyl)methyl]piperazine (300 mg, 1.45 mmol) and TEA (0.59 mL, 4.36 mmol) in DCM (15 mL) was added a solution of 3-methylbutanoyl chloride (263.05 mg, 2.18 mmol) in DCM (1 mL) at 0° C. and the resulting mixture was stirred for 1 h. Upon completion, the reaction mixture was quenched with water and extracted by EA, The combined organic layers were successively washed with brine, dried over anhydrous sodium sulfate, filtered and concentrated in vacuo to obtain the crude 1-[4-[(4-methoxyphenyl)methyl]piperazin-1-yl]-3-methyl-butan-1-one (240 mg, 0.83 mmol, 57% yield) as a white solid. MS: m/z: Calc'd for $C_{17}H_{26}N_2O_2[M+H]^+$ 291; Found 291.

Step 2: To a stirred mixture of 1-[4-[(4-methoxyphenyl)methyl]piperazin-1-yl]-3-methyl-butan-1-one (230 mg, 0.79 mmol) in Methanol (4 mL) and 2 M HCl (1 mL) was added Pd/C (230 mg) under $N_2$. $H_2$ was subsequently introduced and the resulting mixture was stirred at RT for 2 h. The resulting mixture was filtered through Celite and washed with Methanol. The filtrate was concentrated to obtain 3-methyl-1-piperazin-1-yl-butan-1-one as an off-white solid. MS: m/z: Calc'd for $C_9H_{18}N_2O$ $[M+H]^+$ 171; Found 171.

Step 3: To a mixture of 3-fluoro-5-[(4-methoxyphenyl)methoxy]-4-(1,1,4-trioxo-1,2,5-thiadiazolidin-2-yl)benzaldehyde (Int-2, 95 mg, 0.24 mmol), 3-methyl-1-piperazin-1-yl-butan-1-one hydrochloride (49.79 mg, 0.24 mmol) and DIEA (0.06 mL, 0.72 mmol) in Ethanol (1 mL) was added a solution of $ZnCl_2$ in THF (0.7M, 1.40 mL) and $NaBH_3CN$ (63.70 mg, 0.96 mmol) in Ethanol (2 mL), respectively. The resulting mixture was stirred at 80° C. for 2 h. Upon completion, the reaction mixture was concentrated. The resulting residue was purified by reversed-phase column to obtain 5-[2-fluoro-6-[(4-methoxyphenyl)methoxy]-4-[[4-(3-methylbutanoyl)piperazin-1-yl]methyl]phenyl]-1,1-dioxo-1,2,5-thiadiazolidin-3-one (100 mg, 0.18 mmol, 76% yield) as an off-white solid. MS: m/z: Calc'd for $C_{26}H_{33}FN_4O_6S$ $[M+H]^+$ 549; Found 549.

Step 4: To a stirred solution of 5-[2-fluoro-6-[(4-methoxyphenyl)methoxy]-4-[[4-(3-methylbutanoyl)piperazin-1-yl]methyl]phenyl]-1,1-dioxo-1,2,5-thiadiazolidin-3-one (100 mg, 0.18 mmol) in DCM (3 mL) was added TFA (3 mL), and the mixture was stirred at rt for 2 h. Upon completion, the reaction mixture was concentrated. The resulting residue was purified by Prep-HPLC to obtain 5-[2-fluoro-6-hydroxy-4-[[4-(3-methylbutanoyl)piperazin-1-yl]methyl]phenyl]-1,1-dioxo-1,2,5-thiadiazolidin-3-one (11.8 mg, 0.03 mmol, 15% yield) as an off-white solid. MS: m/z: Calc'd for $C_{13}H_{16}FN_3O_5S$ $[M+H]^+$ 429; Found 429. $^1H$ NMR (400 MHz, DMSO-d6) δ 6.67-6.63 (m, 2H), 3.96 (s, 2H), 3.46 (d, J=9.4 Hz, 6H), 2.38-2.27 (m, 4H), 2.17 (d, J=6.9 Hz, 2H), 2.02-1.89 (m, 1H), 0.88 (d, J=6.6 Hz, 6H).

Prep-HPLC purification conditions: XBridge Prep Phenyl OBD Column, 19*250 mm, 5 μm; Mobile Phase A: Water (10 mmol/L $NH_4HCO_3$), Mobile Phase B: ACN; Flow rate: 25 mL/min; Gradient: 17% B to 22% B in 8 min, 22% B; Wave Length: 254/220 nm.

Example 37: 5-(4-(((4,4-dimethylcyclohexyl)amino)methyl)-2-fluoro-6-hydroxyphenyl)-1,2,5-thiadiazolidin-3-one 1,1-dioxide

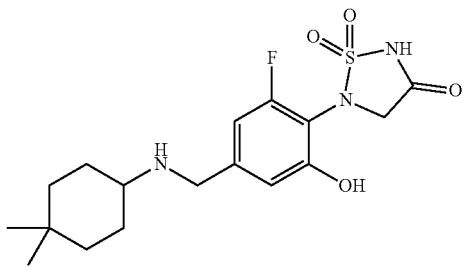 [SMILES: CC1(C)CCC(NCc2cc(O)c(N3CC(=O)NS3(=O)=O)c(F)c2)CC1]

The title compound was prepared in 18% overall yield as a white solid according to the preparation of EXAMPLE 36 using 4,4-dimethylcyclohexanamine in STEP 3. MS: m/z: Calc'd for $C_{17}H_{24}FN_3O_4S$ $[M+H]^+$ 386; Found 386. $^1H$ NMR (400 MHz, DMSO-d6) δ 6.82-6.78 (m, 2H), 4.02-3.98 (m, 4H), 2.89-2.84 (m, 1H), 1.92-1.82 (m, 2H), 1.58-1.32 (m, 4H), 1.25-1.12 (m, 2H), 0.90 (s, 6H).

Prep-HPLC conditions: Xselect CSH OBD Column 30*150 mm 5 um, n; Mobile Phase A: Water (0.05% $NH_4HCO_3$), Mobile Phase B: ACN; Flow rate: 60 mL/min; Gradient: 30% B to 60% B in 7 min, 60% B; Wave Length: 254/220 nm.

Example 38: 5-(4-((4-acetylpiperazin-1-yl)methyl)-2-fluoro-6-hydroxyphenyl)-1,2,5-thiadiazolidin-3-one 1,1-dioxide

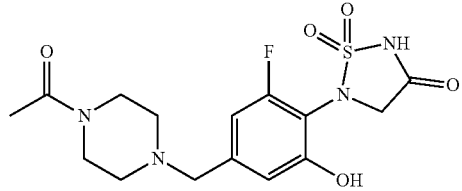

The title compound was prepared in 22% overall yield as a white solid according to the preparation of EXAMPLE 36 using 1-piperazin-1-ylethanone in STEP 3. MS: m/z: Calc'd for $C_{15}H_{19}FN_4O_5S$ $[M+H]^+$ 387; Found 387. $^1H$ NMR (400 MHz, DMSO-d6) δ 10.14 (s, 1H), 9.82 (br, 1H), 6.97-6.83 (m, 2H), 4.48-4.22 (m, 3H), 4.16-3.92 (m, 3H), 3.39-2.78 (m, 6H), 2.04 (s, 3H).

Prep-HPLC purification conditions: Xselect CSH OBD Column 30*150 mm 5 um; Mobile Phase A: Water (0.05% TFA), Mobile Phase B: ACN; Flow rate: 60 mL/min; Gradient: 5% B to 20% B in 10 min, 20% B; Wave Length: 254/220 nm.

Example 39: 5-(2-fluoro-6-hydroxy-4-((piperidin-4-ylamino)methyl)phenyl)-1,2,5-thiadiazolidin-3-one 1,1-dioxide

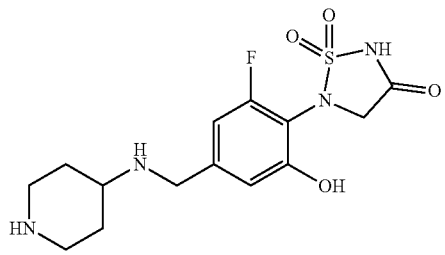 [SMILES: O=C1CN(c2c(O)cc(CNC3CCNCC3)cc2F)S(=O)(=O)N1]

The title compound was prepared in 11% overall yield as a white solid according to the preparation of EXAMPLE 36 using tert-butyl 4-aminopiperidine-1-carboxylate in STEP 3. MS: m/z: Calc'd for $C_{14}H_{19}FN_4O_4S$, $[M+H]^+$ 359; Found 359. $^1H$ NMR (400 MHz, DMSO-d6) δ 6.67-6.66 (m, 2H), 3.94 (s, 2H), 3.62 (s, 3H), 3.17-3.09 (m, 3H), 2.81-2.74 (m, 2H), 2.62-2.56 (m, 1H), 1.91-1.85 (m, 2H), 1.41-1.32 (m, 2H).

Example 40: 5-(4-(((1-ethylpiperidin-4-yl)amino)methyl)-2-fluoro-6-hydroxyphenyl)-1,2,5-thiadiazolidin-3-one 1,1-dioxide

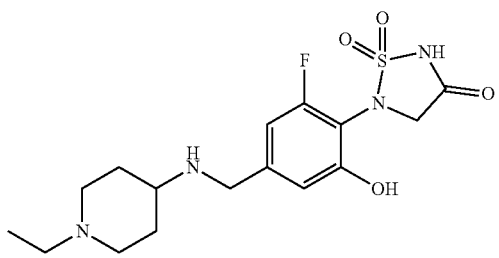 [SMILES: CCN1CCC(NCc2cc(O)c(N3CC(=O)NS3(=O)=O)c(F)c2)CC1]

The title compound was prepared in 22% overall yield as a white solid according to the preparation of EXAMPLE 36 using 1-ethylpiperidin-4-amine in STEP 3. MS: m/z: Calc'd for $C_{16}H_{23}FN_4O_4S$ $[M-H]^-$ 387; Found 387. $^1H$ NMR (300 MHz, DMSO-d6) δ 6.74-6.72 (m, 2H), 3.94 (s, 2H), 3.76 (s, 2H), 3.58-3.51 (m, 3H), 3.13-3.15 (m, 2H), 2.86-2.51 (m, 3H), 2.18-1.95 (m, 2H), 1.69-1.49 (m, 2H), 1.07 (t, J=7.2 Hz, 3H).

Prep-HPLC purification conditions: Xselect CSH OBD Column 30*150 mm 5 um; Mobile Phase A: Water (0.05% TFA), Mobile Phase B: ACN; Flow rate: 60 mL/min; Gradient: 5% B to 20% B in 10 min, 20% B; Wave Length: 254/220 nm.

Example 41: 5-(2-fluoro-6-hydroxy-4-(morpholinomethyl)phenyl)-1,2,5-thiadiazolidin-3-one 1,1-dioxide

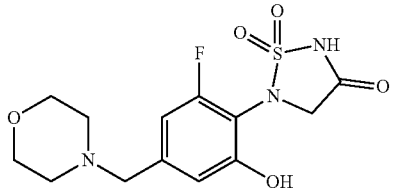 [SMILES: O=C1CN(c2c(O)cc(CN3CCOCC3)cc2F)S(=O)(=O)N1]

The title compound was prepared in 16% overall yield as a white solid according to the preparation of EXAMPLE 36 using morpholine in STEP 3. MS: m/z: Calc'd for $C_{13}H_{16}FN_3O_5S$ $[M+H]^+$ 346; Found 346. $^1H$ NMR (400 MHz, DMSO-d6) δ 10.45-9.87 (m, 2H), 6.94-6.84 (m, 2H), 4.31-4.12 (m, 4H), 3.95 (s, 2H), 3.62 (s, 2H), 3.27 (s, 2H), 3.12 (s, 2H).

Prep-HPLC purification conditions: Xselect CSH C18 OBD Column 30*150 mm 5 μm; Mobile Phase A: Water (0.05% TFA), Mobile Phase B: ACN; Flow rate: 60 mL/min; Gradient: 2% B to 15% B in 7 min, 15% B; Wave Length: 254/220 nm.

Example 42: 5-(2-fluoro-4-((4-fluoropiperidin-1-yl)methyl)-6-hydroxyphenyl)-1,2,5-thiadiazolidin-3-one 1,1-dioxide

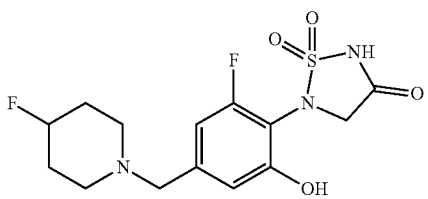 [SMILES: O=C1CN(c2c(O)cc(CN3CCC(F)CC3)cc2F)S(=O)(=O)N1]

The title compound was prepared in 27% overall yield as a white solid according to the preparation of EXAMPLE 36 using 4-fluoropiperidine hydrochloride in STEP 3. MS: m/z: Calc'd for $C_{14}H_{17}F_2N_3O_4S$ $[M-H]^+$360; Found 360. $^1H$ NMR (400 MHz, DMSO-d6) δ 10.05 (d, J=293.2 Hz, 2H), 6.95-6.85 (m, 2H), 4.99 (d, J=47.9 Hz, 1H), 4.50-4.06 (m, 4H), 3.47-2.85 (m, 4H), 2.38-1.77 (m, 4H).

Prep-HPLC conditions: Xselect CSH OBD Column 30*150 mm 5 um, n; Mobile Phase A: Water (0.05% TFA), Mobile Phase B: ACN; Flow rate: 60 mL/min; Gradient: 5% B to 20% B in 10 min, 20% B; Wave Length: 254/220 nm.

Example 43: 5-(4-((cyclohexyl(methyl)amino)methyl)-2-fluoro-6-hydroxyphenyl)-1,2,5-thiadiazolidin-3-one 1,1-dioxide

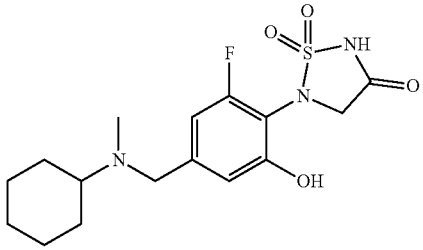 [SMILES: CN(Cc1cc(O)c(N2CC(=O)NS2(=O)=O)c(F)c1)C1CCCCC1]

The title compound was prepared in 17% overall yield as a white solid according to the preparation of EXAMPLE 36 using N-methylcyclohexanamine in STEP 3. MS: m/z: Calc'd for $C_{16}H_{22}FN_3O_4S$ $[M+H]^+$ 372; Found 372. $^1$H NMR (300 MHz, DMSO-d6) δ 10.17 (s, 1H), 9.19 (s, 1H), 6.98-6.84 (m, 2H), 4.42-4.31 (m, 1H), 4.15-4.01 (m, 3H), 3.24 (t, J=11.8 Hz, 1H), 2.61 (d, J=4.8 Hz, 3H), 2.03 (t, J=12.2 Hz, 2H), 1.84 (s, 2H), 1.62 (d, J=12.1 Hz, 1H), 1.57-1.39 (m, 2H), 1.36-1.08 (m, 3H).

Prep-HPLC purification conditions: Xselect CSH $C_{18}$ OBD Column 30*150 mm 5 μm; Mobile Phase A: Water (0.05% TFA), Mobile Phase B: ACN; Flow rate: 60 m/min; Gradient: 5% B to 30% B in 7 min, 30% B; Wave Length: 254/220 nm.

Example 44: 5-(2-fluoro-6-hydroxy-4-((4-(2-methoxyethyl)piperazin-1-yl)methyl)phenyl)-1,2,5-thiadiazolidin-3-one 1,1-dioxide

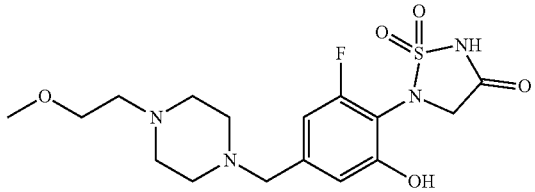 [SMILES: COCCN1CCN(Cc2cc(O)c(N3CC(=O)NS3(=O)=O)c(F)c2)CC1]

The title compound was prepared in 12% overall yield as a white solid according to the preparation of EXAMPLE 36 using 1-(2-methoxyethyl)piperazine in STEP 3. MS: m/z: Calc'd for $C_{16}H_{23}FN_4O_5S$ $[M+H]^+$ 403; Found 403. $^1$H NMR (400 MHz, DMSO-d6) δ 9.44-9.40 (m, 2H), 6.64 (d, J=12.5 Hz, 2H), 3.95 (s, 2H), 3.68 (s, 1H), 3.52 (s, 1H), 3.33 (s, 4H), 3.27 (s, 3H), 3.19-2.69 (m, 6H).

Prep-HPLC purification conditions: XBridge Prep OBD C18 Column, 19*250 mm, 5 μm; Mobile Phase A: Water (10 mmol/L $NH_4HCO_3$), Mobile Phase B: ACN; Flow rate: 25 mL/min; Gradient: 5% B to 20% B in 10 min, 20% B; Wave Length: 254/220 nm.

Example 45: 2-fluoro-5-[[[3-fluoro-5-hydroxy-4-(1,1,4-trioxo-1,2,5-thiadiazolidin-2-yl)phenyl]methylamino]methyl]benzonitrile

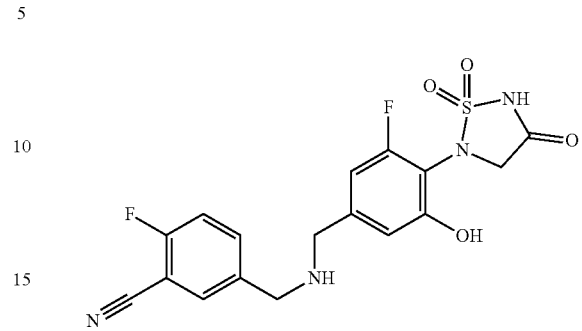

The title compound was prepared 30% overall yield as a white solid according to the preparation of EXAMPLE 36 using 5-(aminomethyl)-2-fluoro-benzonitrile in STEP 3. MS: m/z: Calc'd for $C_{17}H_{14}F_2N_4O_4S$, [M−H]−407; Found 407. $^1$H NMR (400 MHz, DMSO-d6) δ 10.01 (s, 1H), 9.20 (s, 2H), 8.06 (dd, J=6.2, 2.4 Hz, 1H), 7.90-7.87 (m, 1H), 7.65 (t, J=9.1 Hz, 1H), 6.89-6.78 (m, 2H), 4.25 (s, 2H), 4.20-4.01 (m, 4H).

Prep-HPLC purification conditions: Xselect CSH C18 OBD Column 30*150 mm 5 μm, n; Mobile Phase A: Water (0.05% TFA), Mobile Phase B: ACN; Flow rate: 60 mL/min; Gradient: 2% B to 25% B in 10 min, 25% B; Wave Length: 254 nm.

Example 46: 5-[2-fluoro-6-hydroxy-4-[[2-(1-methyl-4-piperidyl)ethylamino]methyl]phenyl]-1,1-dioxo-1,2,5-thiadiazolidin-3-one

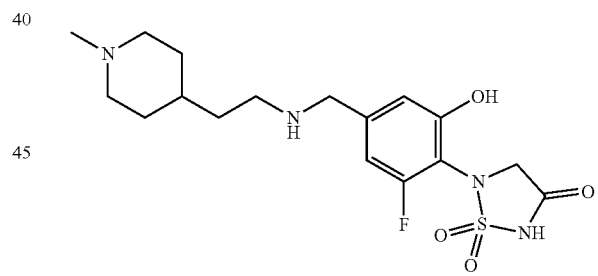

The title compound was prepared in 24% overall yield as a white solid according to the preparation of EXAMPLE 36 using 2-(1-methyl-4-piperidyl)ethanamine in STEP 3. MS: m/z: Calc'd for $C_{17}H_{25}FN_4O_4S$, $[M+H]^+$ 401; Found 401. $^1$H NMR (400 MHz, DMSO-d6) δ 9.88 (s, 1H), 9.33 (s, 1H), 8.81 (s, 1H), 6.89-6.80 (m, 2H), 4.07 (d, J=5.3 Hz, 2H), 4.00 (d, J=3.7 Hz, 2H), 3.42 (d, J=12.1 Hz, 2H), 2.96 (s, 2H), 2.93-2.79 (m, 2H), 2.76 (d, J=4.1 Hz, 3H), 1.85 (d, J=13.8 Hz, 2H), 1.71-1.54 (m, 3H), 1.31-1.29 (m, 2H).

Prep-HPLC purification conditions: Xselect CSH $C_{18}$ OBD Column 30*150 mm 5 μm, n; Mobile Phase A: Water (0.05% TFA), Mobile Phase B: ACN; Flow rate: 60 m/min; Gradient: 1% B to 8% B in 10 min, 8% B; Wave Length: 254 nm.

Example 47: 5-[2-fluoro-6-hydroxy-4-[(4-phenyl-1-piperidyl)methyl]phenyl]-1,1-dioxo-1,2,5-thiadiazolidin-3-one

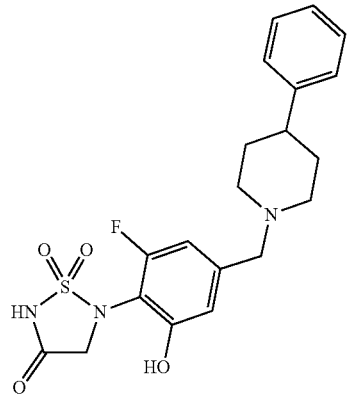 [SMILES: O=C1CN(c2c(O)cc(CN3CCC(c4ccccc4)CC3)cc2F)S(=O)(=O)N1]

The title compound was prepared in 22% overall yield as a white solid according to the preparation of EXAMPLE 36 using 4-phenylpiperidine in STEP 3. MS: m/z: Calc'd for $C_{20}H_{22}FN_3O_4S$, $[M+H]^+$ 420; Found 420. $^1H$ NMR (400 MHz, DMSO-d6) δ 9.79-9.19 (d, 1H), 7.33-7.23 (m, J=9.3, 5.6 Hz, 5H), 6.85 (d, J=11.0 Hz, 2H), 4.09-3.99 (m, 4H), 3.41 (s, 2H), 2.75 (d, 3H), 1.93-1.83 (m, 4H).

Prep-HPLC purification conditions: XBridge Prep OBD C18 Column, 19*250 mm, 5 µm; Mobile Phase A: Water (10 mmol/L $NH_4HCO_3$+0.1% $NH_3 \cdot H_2O$), Mobile Phase B: ACN; Flow rate: 25 mL/min; Gradient: 30% B to 40% B in 8 min, 40% B; Wave Length: 254/220 nm.

Example 48: 5-[4-[[cyclopropyl(propyl)amino]methyl]-2-fluoro-6-hydroxy-phenyl]-1,1-dioxo-1,2,5-thiadiazolidin-3-one

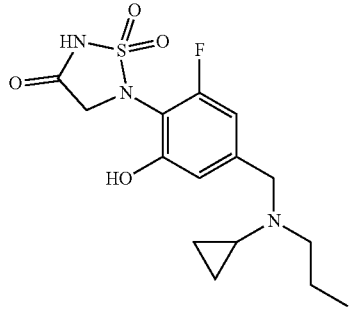 [SMILES: CCCN(Cc1cc(O)c(N2CC(=O)NS2(=O)=O)c(F)c1)C1CC1]

The title compound was prepared in 20% overall yield as a white solid according to the preparation of EXAMPLE 36 using N-propylcyclopropanamine in STEP 3. MS: m/z: Calc'd for $C_{15}H_{20}FN_3O_4S$, $[M+H]^+$ 358; Found 358. $^1H$ NMR (400 MHz, DMSO-d6) δ 10.00 (s, 1H), 9.11 (s, 1H), 6.91-6.75 (m, 2H), 4.34 (s, 2H), 4.07 (s, 2H), 3.08 (s, 2H), 2.85-2.65 (m, 1H), 1.94-1.60 (m, 2H), 1.00-0.60 (m, 7H).

Prep-HPLC purification conditions: Xselect CSH $C_{18}$ OBD Column 30*150 mm 5 µm, n; Mobile Phase A: Water (0.05% TFA), Mobile Phase B: ACN; Flow rate: 60 mL/min; Gradient: 2% B to 25% B in 10 min, 25% B; Wave Length: 254 nm.

Example 49: 5-[4-[[cyclobutylmethyl(methyl)amino]methyl]-2-fluoro-6-hydroxy-phenyl]-1,1-dioxo-1,2,5-thiadiazolidin-3-one

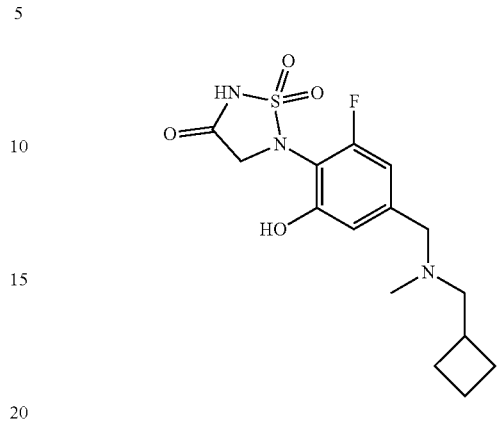

The title compound was prepared in 28% overall yield as a white solid according to the preparation of EXAMPLE 36 using 1-cyclobutyl-N-methyl-methanamine in STEP 3. MS: m/z: Calc'd for $C_{15}H_{20}FN_3O_4S$, $[M+H]^+$ 358; Found 358. 1H NMR (300 MHz, DMSO-d6) δ 6.80 (d, J=8.2 Hz, 2H), 4.03 (s, 2H), 4.01-3.91 (m, 2H), 2.85 (s, 2H), 2.77-2.65 (m, 1H), 2.45 (s, 3H), 2.07-2.01 (m, 2H), 1.92-1.60 (m, 4H).

Prep-HPLC purification conditions: XBridge Prep OBD C18 Column, 30*150 mm, 5 µm; Mobile Phase A: Water (10 mmol/L $NH_4HCO_3$+0.1% $NH_3 \cdot H_2O$), Mobile Phase B: ACN; Flow rate: 60 mL/min; Gradient: 28% B to 38% B in 8 min, 38% B; Wave Length: 254/220 nm.

Example 50: 3-[[[3-fluoro-5-hydroxy-4-(1,1,4-trioxo-1,2,5-thiadiazolidin-2-yl)phenyl]methyl-methyl-amino]methyl]benzonitrile

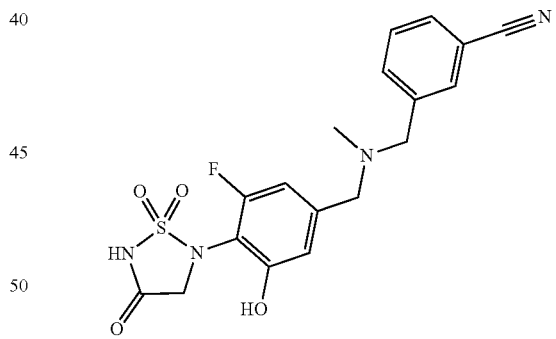

The title compound was prepared in 42% overall yield as a white solid according to the preparation of EXAMPLE 36 using 3-(methylaminomethyl)benzonitrile in STEP 3. MS: m/z: Calc'd for $C_{18}H_{17}FN_4O_4S$, $[M+H]^+$ 405; Found 405. $^1H$ NMR (400 MHz, DMSO-d6) δ 10.15 (s, 1H), 9.84 (s, 1H), 8.03 (d, J=1.7 Hz, 1H), 7.97-7.86 (m, 2H), 7.71 (t, J=7.8 Hz, 1H), 6.92 (dd, J=10.5, 1.9 Hz, 1H), 6.86 (t, J=1.5 Hz, 1H), 4.51-4.40 (m, 2H), 4.31-4.17 (m, 2H), 4.12 (s, 2H), 2.56 (s, 3H).

Prep-HPLC purification conditions: Xselect CSH C18 OBD Column 30*150 mm 5 µm, n; Mobile Phase A: Water (0.05% TFA), Mobile Phase B: ACN; Flow rate: 60 mL/min; Gradient: 9% B to 39% B in 10 min, 39% B; Wave Length: 254 nm.

Example 51: 5-[4-[[[(1R)-3,3-dimethylcyclohexyl]amino]methyl]-2-fluoro-6-hydroxy-phenyl]-1,1-dioxo-1,2,5-thiadiazolidin-3-one

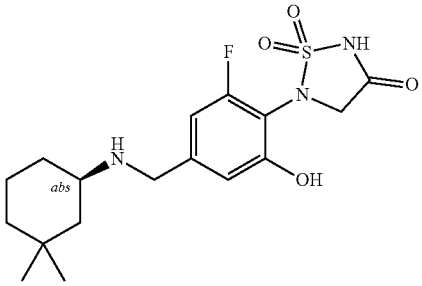 [SMILES: CC1(C)CCC[C@@H](NCc2cc(O)c(N3CC(=O)NS3(=O)=O)c(F)c2)C1]

The title compound was prepared in 21% overall yield as a white solid according to the preparation of EXAMPLE 36 using (1R)-3,3-dimethylcyclohexanamine in STEP 3. MS: m/z: Calc'd for $C_{17}H_{24}FN_3O_4S$, $[M+H]^+$ 386; Found 386. $^1$H NMR (400 MHz, DMSO-d6) δ 9.94 (s, 1H), 8.70-8.60 (m, 2H), 6.90-6.80 (m, 2H), 4.06 (d, J=22.5 Hz, 4H), 3.30-3.15 (m, 1H), 2.10 (d, J=12.0 Hz, 1H), 1.85-1.77 (m, 1H), 1.64 (dt, J=13.6, 3.0 Hz, 1H), 1.43 (dtd, J=13.4, 9.8, 3.5 Hz, 1H), 1.34 (d, J=13.6 Hz, 1H), 1.26-1.02 (m, 3H), 0.96 (s, 3H), 0.89 (s, 3H).

Prep-HPLC purification conditions: Xselect CSH C18 OBD Column 30*150 mm 5 μm, n; Mobile Phase A: Water (0.05% TFA), Mobile Phase B: ACN; Flow rate: 60 mL/min; Gradient: 2% B to 32% B in 10 min, 32% B; Wave Length: 254 nm.

Example 52: 5-[2-fluoro-6-hydroxy-4-[(4-hydroxy-1-piperidyl)methyl]phenyl]-1,1-dioxo-1,2,5-thiadiazolidin-3-one

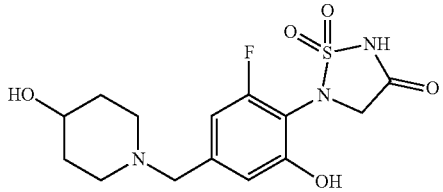 [SMILES: O=C1CN(c2c(O)cc(CN3CCC(O)CC3)cc2F)S(=O)(=O)N1]

The title compound was prepared in 26% overall yield as a white solid according to the preparation of EXAMPLE 36 using piperidin-4-ol in STEP 3. MS: m/z: Calc'd for $C_{14}H_{18}FN_3O_5S$, $[M+H]^+$ 360; Found 360. $^1$H NMR (400 MHz, DMSO-d6) δ 9.73 (s, 1H), 6.78 (s, 2H), 4.93 (s, 1H), 4.14 (s, 1H), 3.97 (s, 2H), 3.60-3.3 (m, 4H), 3.13 (s, 2H), 1.81 (s, 2H), 1.53 (s, 2H).

Prep-HPLC purification conditions: XBridge Prep OBD C18 Column, 30*150 mm, 5 μm; Mobile Phase A: Water (10 mmol/L $NH_4HCO_3$+0.1% $NH_3·H_2O$), Mobile Phase B: ACN; Flow rate: 60 mL/min; Gradient: 2% B to 12% B in 9 min, 12% B; Wave Length: 254/220 nm.

Example 53: 5-[2-fluoro-6-hydroxy-4-[(4-methoxy-1-piperidyl)methyl]phenyl]-1,1-dioxo-1,2,5-thiadiazolidin-3-one

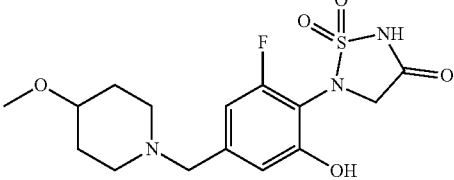

The title compound was prepared in 26% overall yield as a white solid according to the preparation of EXAMPLE 36 using 4-methoxypiperidine in STEP 3. MS: m/z: Calc'd for $C_{15}H_{20}FN_3O_5S$, $[M+H]^+$ 374; Found 374. $^1$H NMR (400 MHz, DMSO-d6) δ 6.79 (d, J=8.1 Hz, 2H), 3.99 (d, J=1.9 Hz, 2H), 3.90 (s, 1H), 3.76 (s, 1H), 3.37 (s, 1H), 3.24 (d, J=2.5 Hz, 3H), 2.98 (s, 2H), 2.84-2.62 (m, 2H), 2.21-1.33 (m, 4H).

Prep-HPLC purification conditions: XBridge Prep Phenyl OBD Column, 19*250 mm, 5 μm; Mobile Phase A: Water (10 mmol/L $NH_4HCO_3$+0.1% $NH_3·H_2O$), Mobile Phase B: ACN; Flow rate: 25 mL/min; Gradient: 5% B to 11% B in 8 min, 11% B; Wave Length: 254/220 nm.

Example 54: 5-[2-fluoro-6-hydroxy-4-[(4-isopropoxy-1-piperidyl)methyl]phenyl]-1,1-dioxo-1,2,5-thiadiazolidin-3-one

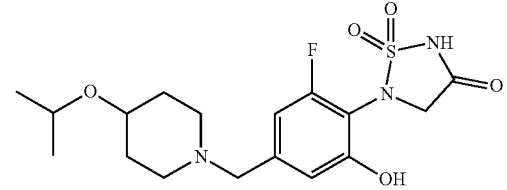 [SMILES: CC(C)OC1CCN(Cc2cc(O)c(N3CC(=O)NS3(=O)=O)c(F)c2)CC1]

The title compound was prepared in 29% overall yield as a white solid according to the preparation of EXAMPLE 36 using 4-(2-methoxyethyl)piperidine in STEP 3. MS: m/z: Calc'd for $C_{17}H_{24}FN_3O_5S$, $[M+H]^+$ 402; Found 402. $^1$H NMR (400 MHz, DMSO-d6) δ 9.73 (s, 1H), 6.79 (s, 2H), 4.14 (s, 1H), 3.96 (s, 2H), 3.66-3.61 (m, 1H), 3.03 (s, 5H), 1.84 (s, 2H), 1.52 (s, 2H), 1.07 (d, J=6.0 Hz, 6H).

Prep-HPLC purification conditions: XBridge Prep OBD C18 Column, 30*150 mm, 5 μm; Mobile Phase A: Water (10 mmol/L $NH_4HCO_3$+0.1% $NH_3·H_2O$), Mobile Phase B: ACN; Flow rate: 60 mL/min; Gradient: 17% B to 27% B in 9 min, 27% B; Wave Length: 254/220 nm.

Example 55: 5-[2-fluoro-6-hydroxy-4-[[4-(2-methoxyethyl)-1-piperidyl]methyl]phenyl]-1,1-dioxo-1,2,5-thiadiazolidin-3-one

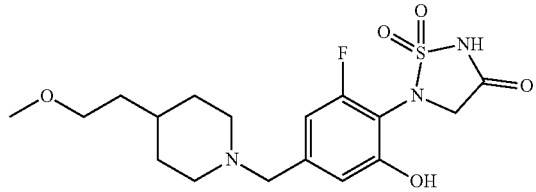

The title compound was prepared in 17% overall yield as a brown solid according to the preparation of EXAMPLE 36 using 4-(2-methoxyethyl)piperidine in STEP 3. MS: m/z: Calc'd for $C_{17}H_{24}FN_3O_5S$, $[M+H]^+$ 402; Found 402. $^1$H NMR (400 MHz, DMSO-d6) δ 10.24 (s, 1H), 9.35 (s, 1H), 6.94-6.82 (m, 2H), 4.18 (dd, J=9.9, 4.1 Hz, 4H), 3.35-3.22 (m, 4H), 3.21 (s, 3H), 2.95-2.86 (m, 2H), 1.85 (d, J=14.0 Hz, 2H), 1.74 (s, 1H), 1.48-1.27 (m, 4H).

Prep-HPLC purification conditions: Xselect Peptide CSH C18 19*150 mm 5 μm, 1; Mobile Phase A: Water (0.05% TFA), Mobile Phase B: ACN; Flow rate: 60 mL/min; Gradient: 2% B to 20% B in 10 min, 20% B; Wave Length: 254 nm.

Example 56: 5-[4-[[4-[(dimethylamino)methyl]-1-piperidyl]methyl]-2-fluoro-6-hydroxy-phenyl]-1,1-dioxo-1,2,5-thiadiazolidin-3-one

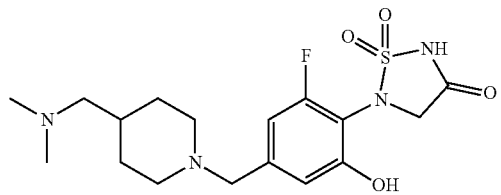 [SMILES: CN(C)CC1CCN(Cc2cc(O)c(N3CC(=O)NS3(=O)=O)c(F)c2)CC1]

The title compound was prepared in 25% overall yield as an off-white solid according to the preparation of EXAMPLE 36 using N,N-dimethyl-1-(4-piperidyl)methanamine in STEP 3. MS: m/z: Calc'd for $C_{17}H_{25}FN_4O_4S$, $[M+H]^+$ 401; Found 401. $^1$H NMR (400 MHz, DMSO-d6) δ 9.39 (s, 1H), 6.62 (d, J=20.8 Hz, 2H), 3.94 (s, 2H), 3.41 (s, 2H), 2.82 (s, 4H), 2.57 (s, 6H), 1.97 (s, 2H), 1.68 (d, J=12.4 Hz, 3H), 1.18 (d, J=12.2 Hz, 2H).

Prep-HPLC purification conditions: XBridge Prep Phenyl OBD Column, 19*250 mm, 5 μm; Mobile Phase A: Water (10 mmol/L $NH_4HCO_3$), Mobile Phase B: ACN; Flow rate: 25 mL/min; Gradient: 5% B to 10% B in 7 min, 10% B; Wave Length: 254/220 nm.

Example 57: 5-[4-[(4-butyl-1-piperidyl)methyl]-2-fluoro-6-hydroxy-phenyl]-1,1-dioxo-1,2,5-thiadiazolidin-3-one

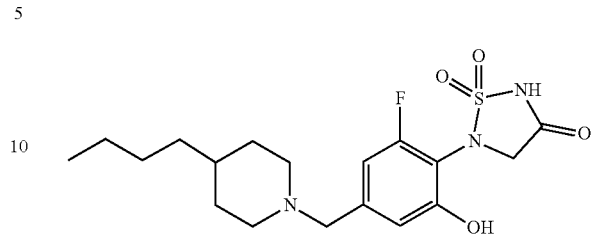

The title compound was prepared in 24% overall yield as a white solid according to the preparation of EXAMPLE 36 using 4-butylpiperidine in STEP 3. MS: m/z: Calc'd for $C_{18}H_{26}FN_3O_4S$, $[M+H]^+$ 400; Found 400. $^1$H NMR (400 MHz, DMSO-d6) δ 10.08 (s, 1H), 9.24 (s, 1H), 6.93-6.81 (m, 2H), 4.19 (d, J=4.8 Hz, 2H), 4.12-4.01 (m, 2H), 3.35 (d, J=12.2 Hz, 2H), 2.93-2.85 (m, 2H), 1.84 (d, J=13.7 Hz, 2H), 1.37-1.16 (m, 9H), 0.88-0.84 (m, 3H).

Prep-HPLC purification conditions: Xselect Peptide CSH C18 19*150 mm 5 μm, 1; Mobile Phase A: Water (0.05% TFA), Mobile Phase B: ACN; Flow rate: 60 mL/min; Gradient: 2% B to 20% B in 10 min, 20% B; Wave Length: 254 nm.

Example 58: (1r,4r)-4-((4-(1,1-dioxido-4-oxo-1,2,5-thiadiazolidin-2-yl)-3-fluoro-5-hydroxybenzyl)amino)-N-methylcyclohexane-1-carboxamide

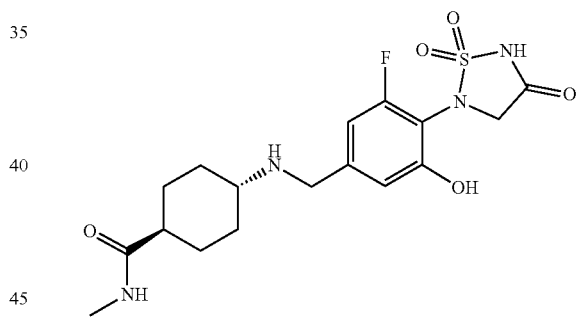

Scheme 13

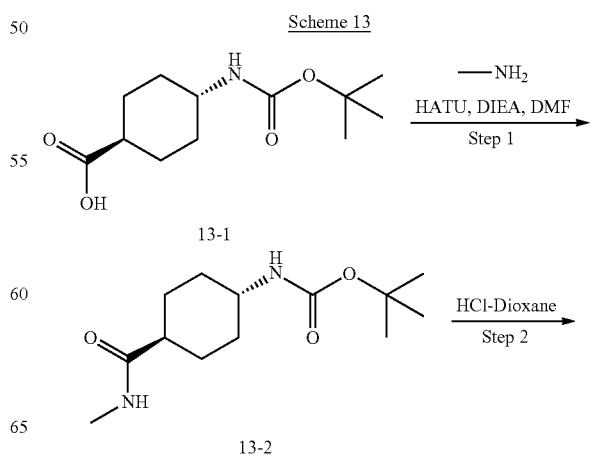

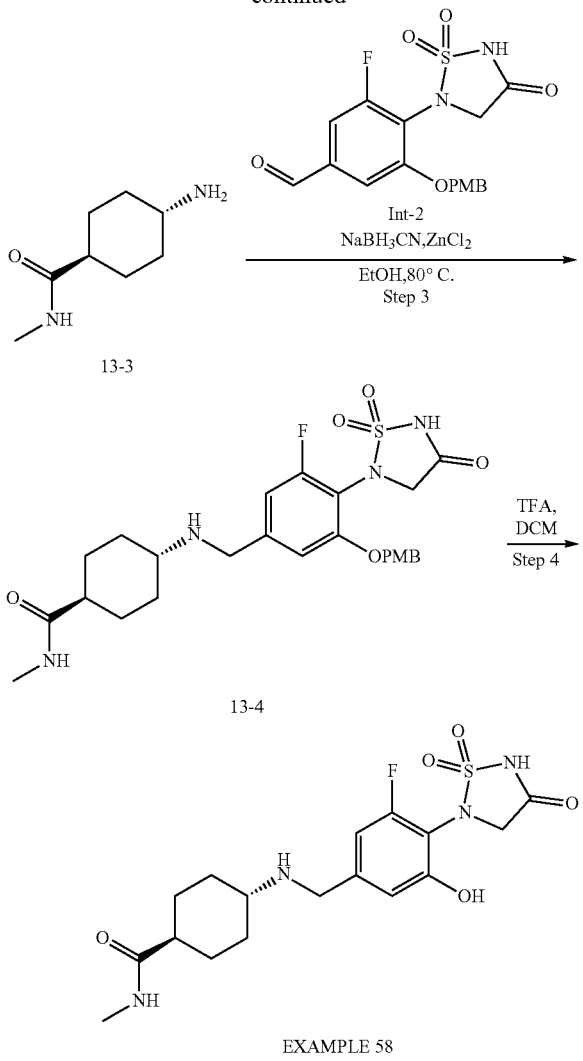

Step 1: To a stirred solution of 4-(tert-butoxycarbonylamino) cyclohexanecarboxylic acid (500 mg, 2.06 mmol) in DMF (20 mL) were added HATU (1170 mg, 3.08 mmol), methanamine (190 mg, 6.17 mmol) and DIEA (1.37 mL, 8.22 mmol) at 0° C., and the mixture was stirred at room temperature for overnight. The reaction was quenched by addition of brine (10 mL), and extracted with EA, dried, and concentrated to afford tert-butyl N-[4-(methylcarbamoyl)cyclohexyl] carbamate (500 mg, 1.95 mmol, 95% yield) as colorless oil.

$^1$H NMR (400 MHz, DMSO-d6) δ 7.66-7.63 (m, 1H), 6.70 (d, J=8.0 Hz, 1H), 3.20-3.07 (m, 1H), 2.61-2.53 (m, 3H), 2.01-1.96 (m, 1H), 1.82-1.73 (m, 2H), 1.73-1.65 (m, 2H), 1.40-1.29 (m, 11H), 1.19-1.04 (m, 2H).

Step 2: To a solution of tert-butyl N-[4-(methylcarbamoyl)cyclohexyl]carbamate (500 mg, 1.95 mmol) in 1,4-Dioxane (10 mL) was added HCl-dioxane (4 M, 10 mL). The reaction was stirred at room temperature for 3 h. After evaporation of the solvent, the resulting crude material was used for the next step without further purification.

Step 3: Compound 11-4 was prepared in 44% yield as a colorless semi-solid according to the preparation of EXAMPLE 36 using (1r,4r)-4-amino-N-methylcyclohexane-1-carboxamide hydrochloride in STEP 3. The compound was purified by reversed-phase column (0.5% NH$_4$HCO$_3$ in H$_2$O, MeCN). MS: m/z: Calc'd for C$_{25}$H$_{31}$FN$_4$O$_6$S, [M+H]$^+$ 535; Found 535.

Step 4: The title compound was prepared in 28% yield as a white solid according to the preparation of EXAMPLE 36 using 13-4 in STEP 4. MS: m/z: Calc'd for C$_{17}$H$_{23}$FN$_4$O$_5$S, [M+H]$^+$ 415; Found 415. $^1$H NMR (400 MHz, DMSO-d6) δ 9.79 (s, 1H), 8.65 (s, 2H), 7.72-7.69 (m, 1H), 6.87-6.78 (m, 2H), 4.10-4.07 (m, 2H), 3.97 (s, 2H), 3.06 (s, 1H), 2.61-2.55 (m, 3H), 2.19-2.01 (m, 3H), 1.83-1.79 (m, 2H), 1.46-1.24 (m, 4H).

Prep-HPLC purification condition: Xselect CSH OBD Column 30*150 mm 5 um, n; Mobile Phase A: Water (0.05% TFA), Mobile Phase B: ACN; Flow rate: 60 mL/min; Gradient: 20% B to 34% B in 10 min, 34% B to 100% B in 5 min; Wave Length: 254/220 nm.

Example 59: 2-(4-(4-(1,1-dioxido-4-oxo-1,2,5-thiadiazolidin-2-yl)-3-fluoro-5-hydroxybenzyl)piperazin-1-yl)-N-methylacetamide

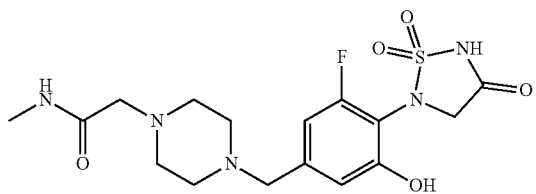

The title compound was prepared in 9.5% overall yield as a yellow solid according to the preparation of EXAMPLE 36 using N-methyl-2-(piperazin-1-yl)acetamide in STEP 3. MS: m/z: Calc'd for C$_{16}$H$_{22}$FN$_5$O$_5$S [M+H]$^+$ 416; Found 416. $^1$H NMR (300 MHz, DMSO-d6) δ 6.89-6.78 (m, 2H), 4.17 (s, 2H), 3.97 (s, 2H), 3.58 (d, J=4.3 Hz, 2H), 3.08 (s, 8H), 2.65 (s, 3H).

Prep-HPLC purification conditions: Atlantis Prep T3 OBD Column, 19*250 mm 10 μm; Mobile Phase A: Water (0.05% TFA), Mobile Phase B: ACN; Flow rate: 25 mL/min; Gradient: 2% B to 11% B in 10 min, 11% B; Wave Length: 254/220 nm.

Example 60: N-((1r,4r)-4-((4-(1,1-dioxido-4-oxo-1,2,5-thiadiazolidin-2-yl)-3-fluoro-5-hydroxybenzyl)amino)cyclohexyl)acetamide

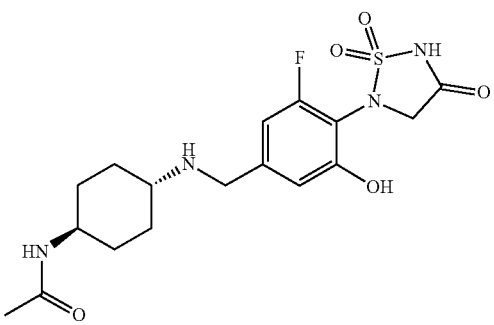 [SMILES: CC(=O)N[C@H]1CC[C@H](NCc2cc(O)c(N3CC(=O)NS3(=O)=O)c(F)c2)CC1]

The title compound was prepared in 6% overall yield as a white solid according to the preparation of EXAMPLE 59 using tert-butyl ((1r,4r)-4-aminocyclohexyl)carbamate in STEP 1. MS: m/z: Calc'd for $C_{17}H_{23}FN_4O_5S$ [M+H]$^+$ 415; Found 415. $^1$H NMR (400 MHz, DMSO-d6) δ 7.74 (d, J=7.8 Hz, 1H), 6.78 (d, J=9.0 Hz, 2H), 3.96 (s, 3H), 2.78-3.01 (m, 3H), 2.04 (d, J=12.2 Hz, 2H), 1.86-1.78 (m, 2H), 1.77 (s, 3H), 1.29 (d, J=10.8 Hz, 2H), 1.21-1.10 (m, 2H).

Prep-HPLC purification conditions: XBridge Prep OBD C18 Column, 30*150 mm, 5 µm; Mobile Phase A: Water (10 mmol/L NH$_4$HCO$_3$), Mobile Phase B: ACN; Flow rate: 60 mL/min; Gradient: 3% B to 27% B in 8 min, 27% B; Wave Length: 254/220 nm Example 61: (R)-5-(2-fluoro-6-hydroxy-4-((piperidin-3-ylamino)methyl)phenyl)-1,2,5-thiadiazolidin-3-one 1,1-dioxide

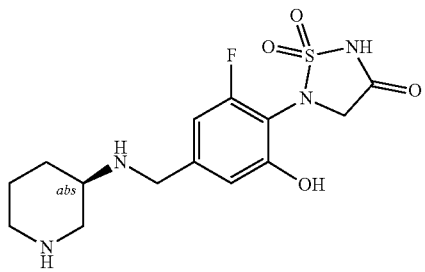 [SMILES: O=C1CN(c2c(O)cc(CN[C@@H]3CCCNC3)cc2F)S(=O)(=O)N1]

The title compound was prepared in 27% overall yield as a white solid according to the preparation of EXAMPLE 36 using tert-butyl (R)-3-aminopiperidine-1-carboxylate in STEP 3. MS: m/z: Calc'd for $C_{14}H_{19}FN_4O_4S$ [M+H]$^+$ 359; Found 359. $^1$H NMR (400 MHz, DMSO-d6) δ 6.74-6.66 (m, 2H), 4.00 (s, 2H), 3.61 (s, 2H), 3.11-2.96 (m, 2H), 2.74-2.53 (m, 3H), 1.92-1.71 (m, 2H), 1.42-1.27 (m, 2H).

Prep-HPLC conditions: XBridge Prep Phenyl OBD Column, 19*250 mm, 5 µm; Mobile Phase A: Water (10 mmol/L NH$_4$HCO$_3$+0.1% NH$_3$·H$_2$O), Mobile Phase B: ACN; Flow rate: 25 mL/min; Gradient: 8% B to 13% B in 10 min, 13% B; Wave Length: 254/220 nm.

Example 62: (R)-5-(2-fluoro-6-hydroxy-4-(((1-isopentylpiperidin-3-yl)amino)methyl)phenyl)-1,2,5-thiadiazolidin-3-one 1,1-dioxide

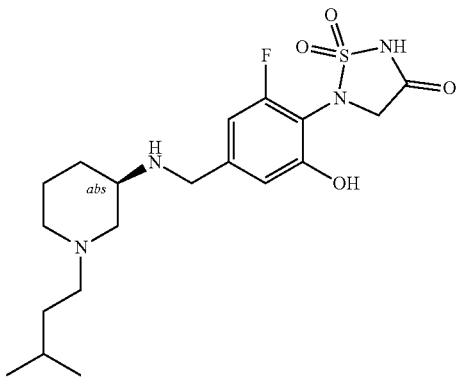 [SMILES: CC(C)CCN1CCC[C@@H](NCc2cc(O)c(N3CC(=O)NS3(=O)=O)c(F)c2)C1]

Scheme 14

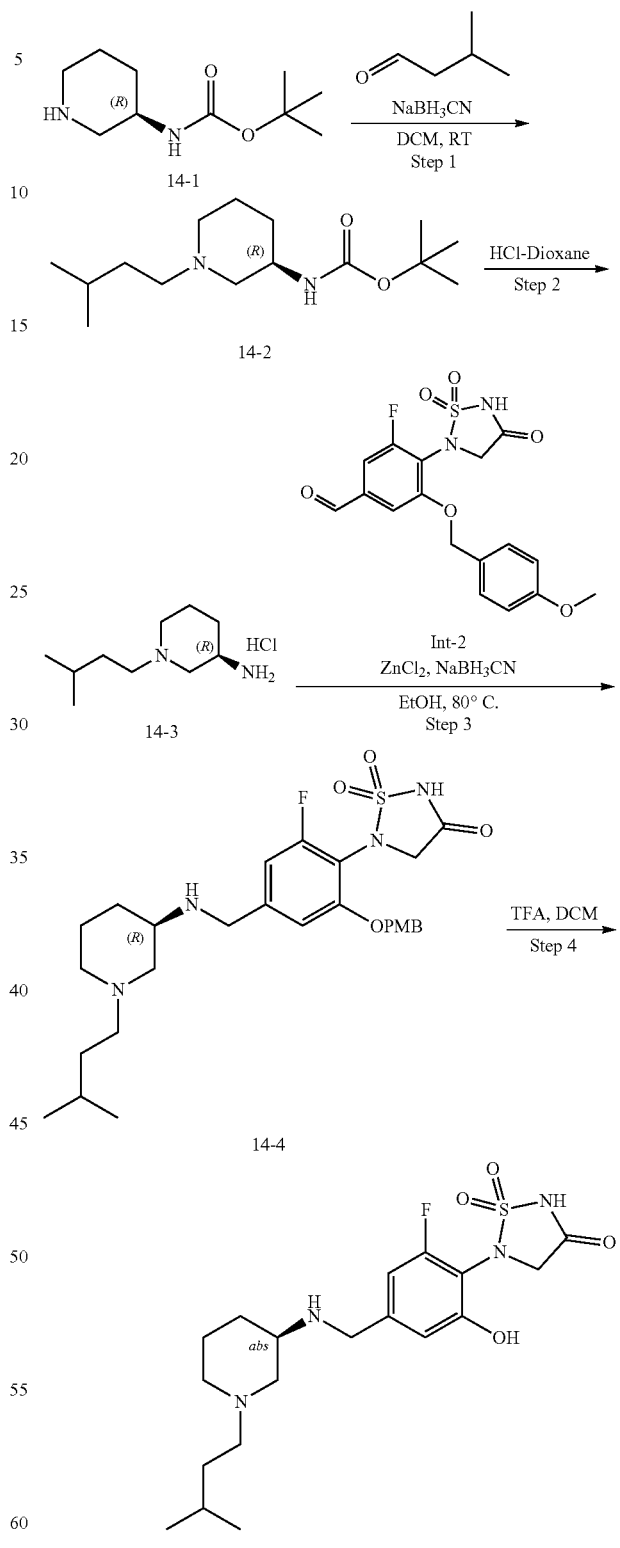

EXAMPLE 62

Step 1: To a solution of tert-butyl N-[(3R)-3-piperidyl]carbamate (500 mg, 2.5 mmol), 3-methylbutanal (430 mg, 4.99 mmol) were added DIEA (1.25 mL, 7.49 mmol) and AcOH (0.29 mL, 4.99 mmol), the mixture was stirred at room temperature for 0.5 h. NaBH₃CN (313.58 mg, 4.99 mmol) was added at 0° C., and the mixture was allowed to stir at room temperature for 2 h. The reaction was concentrated and diluted with EA, washed by brine, dried over anhydrous sodium sulfate, filtered and concentrated in vacuo. The crude was used for next step without further purification. MS: m/z: Calc'd for C₁₅H₃₀N₂O₂, [M+H]⁺ 271; Found 271.

Step 2: To a solution of tert-butyl N-[(3R)-1-isopentyl-3-piperidyl] carbamate (200 mg, 0.74 mmol) in 1,4-Dioxane (5 mL) was added HCl (g) (4 M in 1,4-dioxane, 5 mL), the mixture was stirred at room temperature for 3 h. The reaction was concentrated, and the resulting crude was used for next step without further purification. MS: m/z: Calc'd for C₁₀H₂₂N₂, [M+H]⁺ 171; Found 171.

Step 3: Compound 14-4 was prepared in 86% yield as an off-white semi-solid according to the preparation of EXAMPLE 36 using (R)-1-isopentylpiperidin-3-amine hydrochloride in STEP 3. MS: m/z: Calc'd for C₂₇H₃₇FN₄O₅S, [M+H]⁺ 549; Found 549.

Step 4: The title compound was prepared in 33% yield as an off-white solid according to the preparation of EXAMPLE 36 using 14-4 in STEP 4. MS: m/z: Calc'd for C₁₉H₂₉FN₄O₄S, [M+H]⁺ 429; Found 429. ¹H NMR (300 MHz, DMSO-d6) δ9.76-9.61 (m, 1H), 6.77-6.74 (m, 2H), 3.94 (s, 2H), 3.79 (s, 2H), 3.36-3.15 (m, 5H), 2.44-2.34 (m, 2H), 1.96-1.73 (m, 2H), 1.65-1.34 (m, 5H), 0.88 (d, J=6.5 Hz, 6H).

Prep-HPLC purification conditions: XBridge Shield RP18 OBD Column, 30*150 mm, 5 μm; Mobile Phase A: Water (10 mmol/L NH₄HCO₃), Mobile Phase B: ACN; Flow rate: 60 mL/min; Gradient: 8% B to 24% B in 10 min, 24% B; Wave Length: 254/220 nm.

Example 63: 5-[2-fluoro-6-hydroxy-4-[[[(3S)-1-isopentyl-3-piperidyl]amino]methyl]phenyl]-1,1-dioxo-1,2,5-thiadiazolidin-3-one

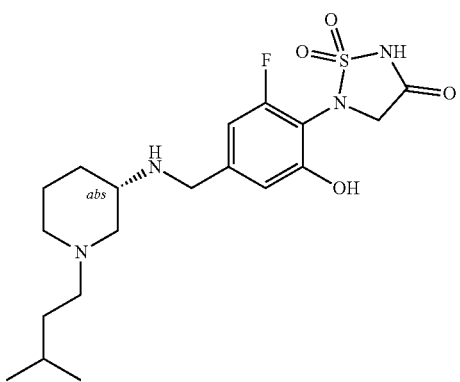 [SMILES: CC(C)CCN1CCC[C@H](NCc2cc(O)c(N3CC(=O)NS3(=O)=O)c(F)c2)C1]

The title compound was prepared in 3% overall yield as a purple semi-solid according to the preparation of EXAMPLE 62 using tert-butyl N-[(3S)-3-piperidyl]carbamate in STEP 3. MS: m/z: Calc'd for C₁₉H₂₉FN₄O₄S [M+H]⁺ 429; Found 429. ¹H NMR (300 MHz, DMSO-d6) δ 10.09-9.85 (m, 2H), 6.89 (d, J=10.8 Hz, 2H), 4.36 (s, 2H), 4.18 (s, 2H), 3.82 (s, 2H), 3.17 (p, J=6.5 Hz, 3H), 2.98-2.87 (m, 2H), 2.29-1.89 (m, 2H), 1.72-1.58 (m, 5H), 0.91 (d, J=5.8 Hz, 6H).

Prep-HPLC purification conditions: Column: XBridge Prep Phenyl OBD Column, 19*150 mm, 5 μm; Mobile Phase A: Water (0.05% TFA), Mobile Phase B: ACN; Flow rate: 60 mL/min; Gradient: 2% B to 20% B in 10 min, 20% B; Wave Length: 254 nm; RT1 (min): 7.98; Number Of Runs: 0.

Example 64: (R)-5-(2-fluoro-6-hydroxy-4-(((tetrahydro-2H-pyran-3-yl)amino)methyl)phenyl)-1,2,5-thiadiazolidin-3-one 1,1-dioxide

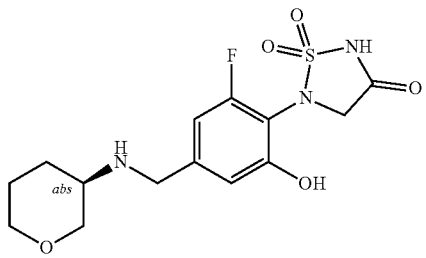 [SMILES: O=C1CN(c2c(O)cc(CN[C@@H]3CCCOC3)cc2F)S(=O)(=O)N1]

The title compound was prepared in 6.6% overall yield as a yellow solid according to the preparation of EXAMPLE 36 using (3R)-tetrahydropyran-3-amine in STEP 3. MS: m/z: Calc'd for C₁₄H₁₈FN₃O₅S, [M+H]⁺ 360; Found 360. ¹H NMR (300 MHz, DMSO-d6) δ 9.88 (s, 1H), 8.87 (s, 2H), 6.94-6.79 (m, 2H), 4.12 (s, 2H), 4.01 (s, 2H), 3.96-3.85 (m, 1H), 3.71-3.64 (m, 1H), 3.56-3.47 (m, 2H), 3.20 (s, 1H), 2.09-2.06 (m, 1H), 1.85-1.63 (m, 2H), 1.57-1.45 (m, 1H). Prep-HPLC purification conditions: Xselect CSH C18 OBD Column 30*150 mm 5 μm, n; Mobile Phase A: Water (0.05% TFA), Mobile Phase B: ACN; Flow rate: 60 mL/min; Gradient: 2% B to 12% B in 7 min, 12% B; Wave Length: 254/220 nm.

Example 65: (S)-5-(2-fluoro-6-hydroxy-4-((piperidin-3-ylamino)methyl)phenyl)-1,2,5-thiadiazolidin-3-one 1,1-dioxide

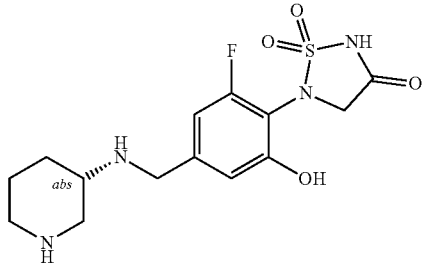

The title compound was prepared in 21% overall yield as a tan solid according to the preparation of EXAMPLE 36 using tert-butyl (S)-3-aminopiperidine-1-carboxylate in STEP 3. MS: m/z: Calc'd for C₁₄H₁₉FN₄O₄S [M+H]⁺ 359; Found 359. ¹H NMR (300 MHz, DMSO-d6) δ 6.78-6.72 (m, 2H), 3.98 (s, 2H), 3.64 (s, 2H), 3.17-2.89 (m, 2H), 2.79-2.54 (m, 3H), 2.01-1.69 (m, 2H), 1.35-1.14 (m, 2H).

Prep-HPLC conditions: XBridge Prep Phenyl OBD Column, 19*250 mm, 5 μm; Mobile Phase A: Water (10 mmol/L NH₄HCO₃+0.1% NH₃·H₂O), Mobile Phase B: ACN; Flow rate: 25 mL/min; Gradient: 7% B to 12% B in 10 min, 12% B; Wave Length: 254/220 nm.

Example 66: (S)-5-(4-(((3,3-dimethylcyclohexyl)amino)methyl)-2-fluoro-6-hydroxyphenyl)-1,2,5-thiadiazolidin-3-one 1,1-dioxide

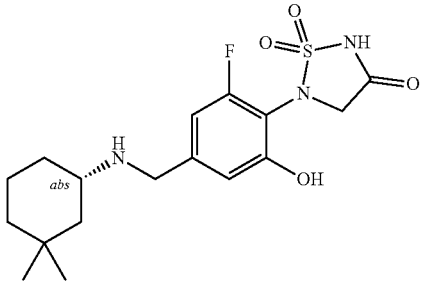 [SMILES: CC1(C)CCC[C@H](NCc2cc(O)c(N3CC(=O)NS3(=O)=O)c(F)c2)C1]

The title compound was prepared in 16% overall yield as a light-pink solid according to the preparation of EXAMPLE 36 using (1S)-3,3-dimethylcyclohexanamine hydrochloride in STEP 3. MS: m/z: Calc'd for $C_{17}H_{24}FN_3O_4S$ [M+H]$^+$ 386; Found 386. $^1$H NMR (300 MHz, DMSO-d6) δ 9.78 (s, 1H), 8.58 (s, 2H), 6.95-6.79 (m, 2H), 4.08 (t, J=6.2 Hz, 2H), 3.98 (s, 2H), 3.21 (s, 1H), 2.10 (d, J=12.1 Hz, 1H), 1.82 (d, J=12.4 Hz, 1H), 1.65 (d, J=13.6 Hz, 1H), 1.39 (dd, J=26.9, 13.5 Hz, 1H), 1.27-1.00 (m, 4H), 0.96 (s, 3H), 0.89 (s, 3H).

Prep-HPLC conditions: Xselect CSH C18 OBD Column 30*150 mm 5 μm, n; Mobile Phase A: Water (0.05% TFA), Mobile Phase B: ACN; Flow rate: 60 mL/min; Gradient: 12% B to 25% B in 10 min, 25% B; Wave Length: 254/220 nm.

Example 67: (S)-5-(2-fluoro-6-hydroxy-4-(((tetrahydro-2H-pyran-3-yl)amino)methyl)phenyl)-1,2,5-thiadiazolidin-3-one 1,1-dioxide

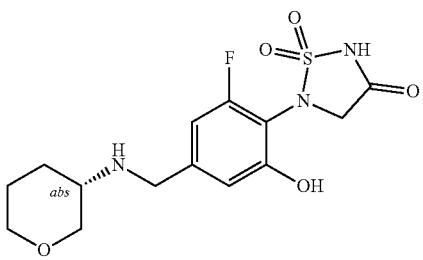 [SMILES: O=C1CN(c2c(O)cc(CN[C@H]3CCCOC3)cc2F)S(=O)(=O)N1]

The title compound was prepared in 22% overall yield as an off-white solid according to the preparation of EXAMPLE 36 using (S)-tetrahydro-2H-pyran-3-amine in STEP 3. MS: m/z: Calc'd for $C_{14}H_{18}FN_3O_5S$, [M+H]$^+$ 360; Found 360. $^1$H NMR (300 MHz, DMSO-d6) δ 6.72-6.69 (m, 2H), 3.94 (s, 2H), 3.87-3.73 (m, 2H), 3.69-3.66 (m, 2H), 3.31-3.17 (m, 3H), 1.96-1.91 (m, 1H), 1.76-1.64 (m, 1H), 1.47-1.44 (m, 2H).

Prep-HPLC purification conditions: XBridge Shield RP18 OBD Column, 30*150 mm, 5 μm; Mobile Phase A: Water (10 mmol/L NH$_4$HCO$_3$), Mobile Phase B: ACN; Flow rate: 60 mL/min; Gradient: 2% B to 17% B in 7 min, 17% B; Wave Length: 254/220 nm.

Example 68: 5-[4-[[[(3R)-1-acetyl-3-piperidyl]amino]methyl]-2-fluoro-6-hydroxy-phenyl]-1,1-dioxo-1,2,5-thiadiazolidin-3-one

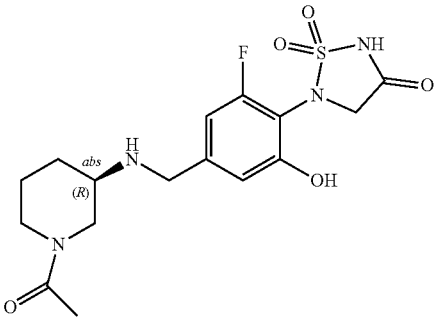

Scheme 15

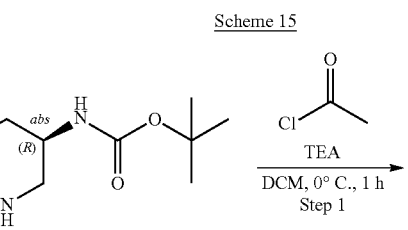

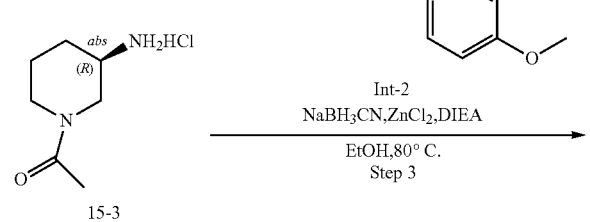

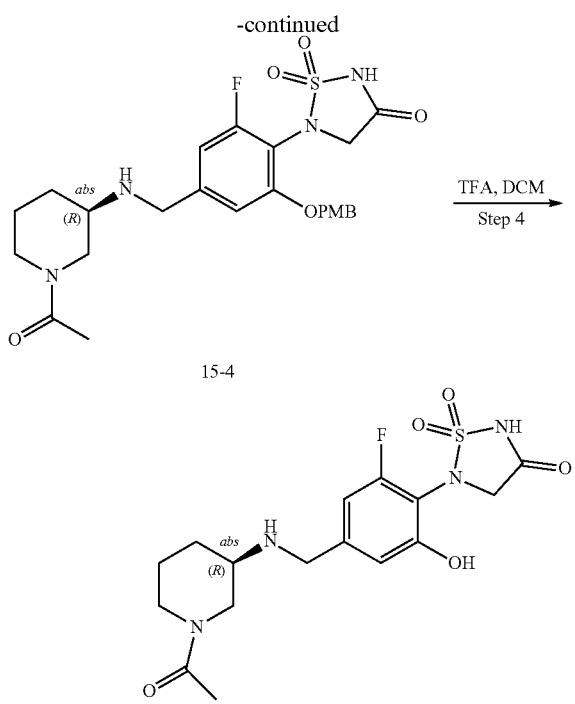

EXAMPLE 68

Step 1: To a mixture of tert-butyl N-[(3R)-3-piperidyl] carbamate (350 mg, 1.75 mmol) and TEA (0.91 mL, 5.24 mmol) in DCM (7 mL) were added acetyl chloride (205.77 mg, 2.62 mmol) dropwise at 0° C. The resulting mixture was stirred for 1 h. Upon completion, the resulting solution was concentrated in vacuo. The residue was purified by reversed phase column (0.05% NH$_4$HCO$_3$ in H$_2$O, MeCN) to obtain tert-butyl N-[(3R)-1-acetyl-3-piperidyl]carbamate (400 mg, 1.65 mmol, 94% yield) as a light-yellow oil. MS: m/z: Calc'd for C$_{12}$H$_{22}$N$_2$O$_3$, [M+H]$^+$ 243; Found 243.

Step 2: Into a 50 mL round-bottom flask was added a mixture of tert-butyl N-[(3R)-1-acetyl-3-piperidyl]carbamate (390 mg, 1.61 mmol) in DCM (3 mL) and 4 M HCl in EA (3 mL) at room temperature. The mixture was stirred at room temperature for 3 h. The reaction was concentrated, and the resulting crude was used for next step without further purification.

Step 3: Compound 15-4 was prepared in 63% yield as an off-white solid according to the preparation of EXAMPLE 36 using 1-[(3R)-3-amino-1-piperidyl]ethanone hydrochloride in STEP 3. MS: m/z: Calc'd for C$_{24}$H$_{29}$FN$_4$O$_6$S, [M+H]$^+$ 521; Found 521.

Step 4: The title compound was prepared in 29% yield as an off-white solid according to the preparation of EXAMPLE 36 using 15-4 in STEP 4. MS: m/z: Calc'd for C$_{16}$H$_{21}$FN$_4$O$_5$S, [M+H]$^+$ 401; Found 401. $^1$H NMR (300 MHz, DMSO-d6) δ 6.88 (dd, J=12.7, 2.2 Hz, 2H), 4.31-4.07 (m, 3H), 3.99 (s, 2H), 3.63-3.47 (m, 2H), 3.33-3.07 (m, 3H), 2.79 (d, J=30.6 Hz, OH), 2.03 (s, 4H), 1.73 (d, J=32.4 Hz, 2H), 1.50 (s, 1H).

Prep-HPLC purification conditions: XBridge Prep OBD C18 Column, 30*150 mm, 5 μm; Mobile Phase A: Water (0.05% TFA), Mobile Phase B: ACN; Flow rate: 60 m/min; Gradient: 3% B to 26% B in 8 min, 26% B; Wave Length: 254/220 nm.

Example 69: 5-[2-fluoro-4-[[[(3R)-1-(3-fluorophenyl)sulfonyl-3-piperidyl]amino]methyl]-6-hydroxyphenyl]-1,1-dioxo-1,2,5-thiadiazolidin-3-one

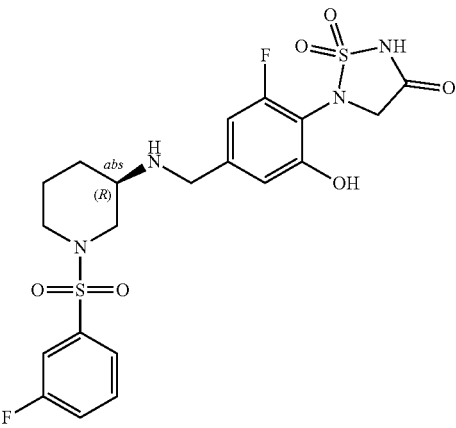

The title compound was prepared in 42% overall yield as a white solid according to the preparation of EXAMPLE 68 using 3-fluorobenzenesulfonyl chloride in STEP 1. MS: m/z: Calc'd for C$_{20}$H$_{22}$F$_2$N$_4$O$_6$S$_2$, [M+H]$^+$ 517; Found 517. $^1$H NMR (300 MHz, DMSO-d6) δ 7.85-7.48 (m, 4H), 6.77 (s, 2H), 3.99 (s, 2H), 3.91 (s, 2H), 3.62 (d, J=10.2 Hz, 2H), 3.35 (d, J=11.7 Hz, 1H), 2.95 (s, 1H), 2.47 (s, 1H), 2.01-1.74 (m, 2H), 1.62-1.08 (m, 2H).

Prep-HPLC purification conditions: XBridge Prep OBD C18 Column, 30*150 mm, 5 μm; Mobile Phase A: Water (0.05% TFA), Mobile Phase B: ACN; Flow rate: 60 m/min; Gradient: 3% B to 26% B in 8 min, 26% B; Wave Length: 254/220 nm.

Example 70: 5-[2-fluoro-4-[[[(3S)-1-(3-fluorophenyl)sulfonyl-3-piperidyl]amino]methyl]-6-hydroxyphenyl]-1,1-dioxo-1,2,5-thiadiazolidin-3-one

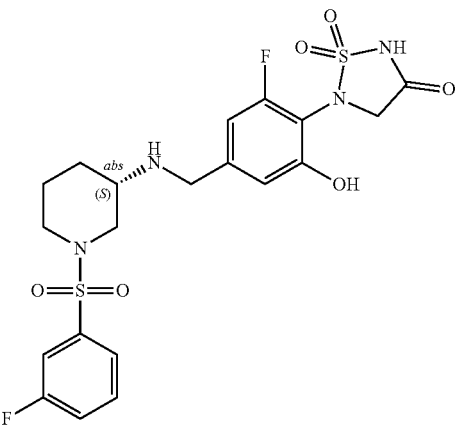

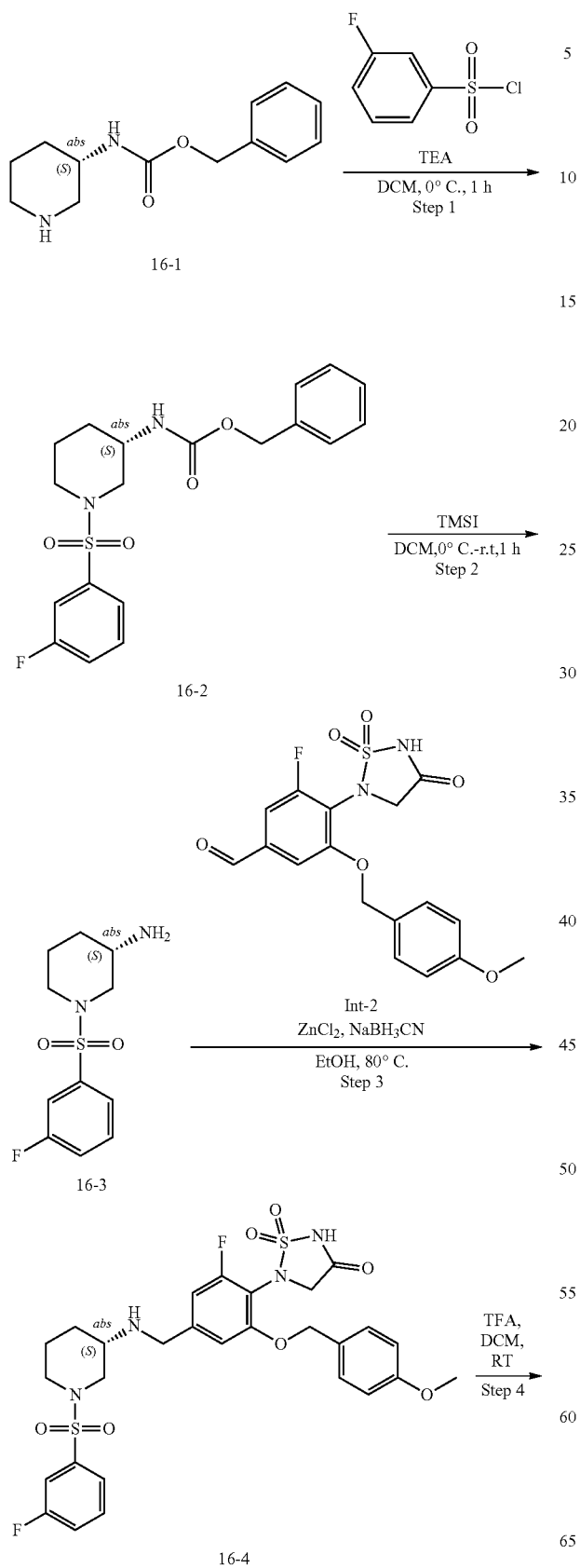

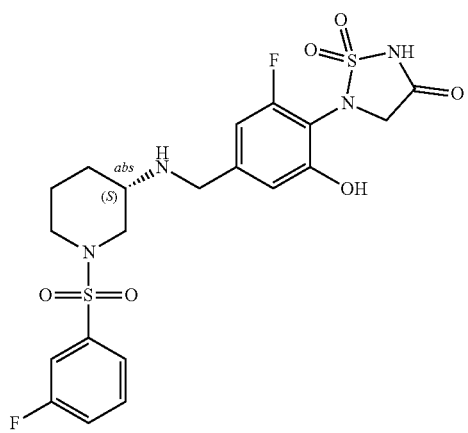

EXAMPLE 70

Step 1: Compound 16-2 was prepared in 93% yield as a white solid according to the preparation of EXAMPLE 68 using 3-fluorobenzenesulfonyl chloride in STEP 1. MS: m/z: Calc'd for $C_{19}H_{21}FN_2O_4S$, $[M-H]^-$ 391; Found 391.

Step 2: To a stirred mixture of benzyl N-[(3S)-1-(3-fluorophenyl)sulfonyl-3-piperidyl]carbamate (600 mg, 1.53 mmol) in DCM (10 mL) was added TMSI (458.88 mg, 2.29 mmol) at 0° C. The reaction mixture was stirred at room temperature for 2 h. After completion of the reaction monitored by LCMS, the mixture was concentrated. The resulting residue was purified by a reversed phase column to afford (3S)-1-(3-fluorophenyl)sulfonylpiperidin-3-amine (300 mg, 1.16 mmol, 76% yield) as a black solid. MS: m/z: Calc'd for $C_{11}H_{15}FN_2O_2S$, $[M+H]^+$ 259; Found 259.

Step 3: Compound 16-4 was prepared in 59% yield as a yellow solid according to the preparation of EXAMPLE 36 using (3S)-1-(3-fluorophenyl)sulfonylpiperidin-3-amine in STEP 3. MS: m/z: Calc'd for $C_{28}H_{30}F_2N_4O_7S_2$, $[M+H]^+$ 637; Found 637.

Step 4: The title compound was prepared in 44% yield as a white solid according to the preparation of EXAMPLE 36 using 16-4 in STEP 4. MS: m/z: Calc'd for $C_{20}H_{22}F_2N_4O_6S_2$, $[M+H]^+$ 517; Found 517. $^1$H NMR (400 MHz, DMSO-d6) δ 7.75-7.65 (m, 1H), 7.63-7.53 (m, 3H), 6.69-6.59 (m, 2H), 6.07 (s, 1H), 3.94 (s, 2H), 3.63 (d, J=2.6 Hz, 2H), 3.57-3.50 (m, 1H), 3.39 (d, J=11.6 Hz, 1H), 3.33 (s, 1H), 2.39-2.32 (m, 1H), 2.15-2.12 (m, 1H), 1.81-1.65 (m, 2H), 1.43 (t, J=11.4 Hz, 1H), 1.04-1.02 (m, 1H).

Prep-HPLC purification conditions: Xselect CSH C18 OBD Column 30*150 mm 5 μm; Mobile Phase A: Water (0.1% FA), Mobile Phase B: ACN; Flow rate: 60 mL/min; Gradient: 5% B to 35% B in 10 min, 35% B; Wave Length: 254 nm.

Example 71: 5-[4-[[[(3S)-1-acetyl-3-piperidyl]amino]methyl]-2-fluoro-6-hydroxy-phenyl]-1,1-dioxo-1,2,5-thiadiazolidin-3-one

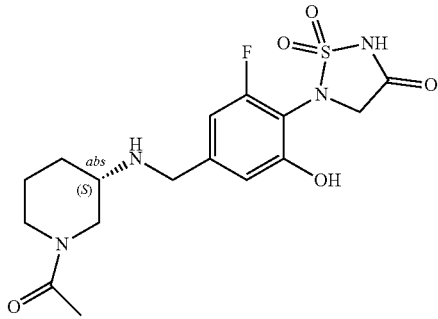

The title compound was prepared in 15% overall yield as a white solid according to the preparation of EXAMPLE 70 using acetyl chloride in STEP 1. MS: m/z: Calc'd for $C_{16}H_{21}FN_4O_5S$, $[M+H]^+$ 401; Found 401. $^1H$ NMR (400 MHz, DMSO-d6) δ 9.67 (s, 1H), 6.81 (dd, J=10.7, 5.1 Hz, 2H), 4.24 (d, J=11.6 Hz, 1H), 4.02 (s, 1H), 3.96 (s, 3H), 3.58 (dt, J=13.5, 4.4 Hz, 1H), 3.19-3.11 (m, 1H), 2.97 (s, 2H), 2.08-2.04 (m, 4H), 1.81-1.73 (m, 1H), 1.60-1.20 (m, 2H).

Prep-HPLC purification conditions: XBridge Prep OBD C18 Column, 30*150 mm, 5 μm; Mobile Phase A: Water (10 mmol/L $NH_4HCO_3$+0.1% $NH_3·H_2O$), Mobile Phase B: ACN; Flow rate: 60 mL/min; Gradient: 3% B to 20% B in 9 min, 20% B; Wave Length: 254/220 nm.

Example 72: 5-[2-fluoro-6-hydroxy-4-[[[(3R)-1-methylsulfonyl-3-piperidyl]amino]methyl]phenyl]-1,1-dioxo-1,2,5-thiadiazolidin-3-one

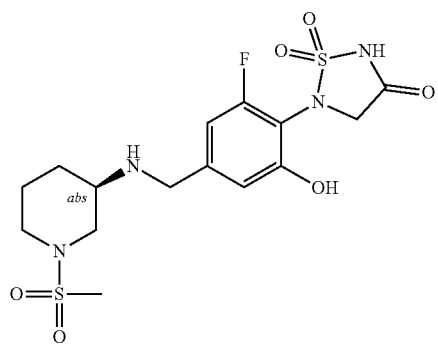 [SMILES: CS(=O)(=O)N1CCC[C@@H](NCc2cc(O)c(N3CC(=O)NS3(=O)=O)c(F)c2)C1]

The title compound was prepared in 20% overall yield as a white solid according to the preparation of EXAMPLE 70 using methanesulfonyl chloride in STEP 1. MS: m/z: Calc'd for $C_{15}H_{21}FN_4O_6S_2$, $[M+H]^+$ 437; Found 437. $^1H$ NMR (300 MHz, DMSO-d6) δ 6.93-6.82 (m, 2H), 4.22-4.05 (m, 2H), 4.02 (s, 2H), 3.70 (dd, J=12.0, 3.5 Hz, 1H), 3.38-3.28 (m, 2H), 2.94 (s, 5H), 2.07 (s, 1H), 1.90 (d, J=5.6 Hz, 1H), 1.59 (q, J=7.8, 6.1 Hz, 2H).

Prep-HPLC purification conditions XBridge Prep OBD C18 Column, 30*150 mm, 5 μm; Mobile Phase A: Water (0.05% TFA), Mobile Phase B: ACN; Flow rate: 60 m/min; Gradient: 2% B to 11% B in 9 min, 11% B; Wave Length: 254/220 nm.

Example 73: 5-[4-[[[(3S)-1-cyclopropylsulfonyl-3-piperidyl]amino]methyl]-2-fluoro-6-hydroxy-phenyl]-1,1-dioxo-1,2,5-thiadiazolidin-3-one

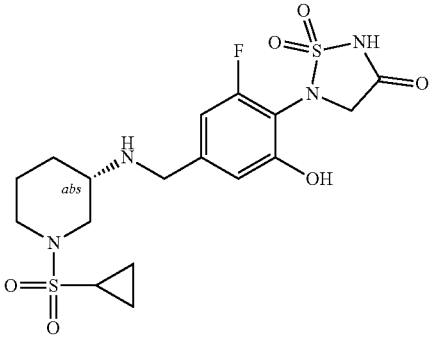 [SMILES: O=C1CN(c2c(O)cc(CN[C@H]3CCCN(S(=O)(=O)C4CC4)C3)cc2F)S(=O)(=O)N1]

The title compound was prepared in 17% overall yield as a white solid according to the preparation of EXAMPLE 70 using cyclopropanesulfonyl chloride in STEP 1. MS: m/z: Calc'd for $C_{17}H_{23}FN_4O_6S_2$, $[M+H]^+$ 463; Found 463. $^1H$ NMR (300 MHz, DMSO-d6) δ 6.93-6.81 (m, 2H), 4.13-4.06 (m, J=3.8 Hz, 4H), 3.75 (dd, J=12.1, 3.4 Hz, 1H), 3.39 (d, J=12.6 Hz, 2H), 3.12-2.93 (m, 2H), 2.68-2.52 (m, 1H), 2.06 (d, J=8.0 Hz, 2H), 1.89 (s, 2H), 1.08-0.89 (m, 4H).

Prep-HPLC purification conditions: Xselect CSH C18 OBD Column 30*150 mm 5 μm; Mobile Phase A: Water (0.05% TFA), Mobile Phase B: ACN; Flow rate: 60 m/min; Gradient: 5% B to 35% B in 10 min, 35% B; Wave Length: 254 nm.

Example 74: 5-[4-[[[(3R)-1-cyclopropylsulfonyl-3-piperidyl]amino]methyl]-2-fluoro-6-hydroxy-phenyl]-1,1-dioxo-1,2,5-thiadiazolidin-3-one

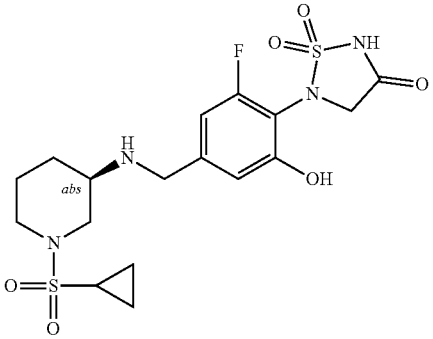 [SMILES: O=C1CN(c2c(O)cc(CN[C@@H]3CCCN(S(=O)(=O)C4CC4)C3)cc2F)S(=O)(=O)N1]

The title compound was prepared in 15% overall yield as a white solid according to the preparation of EXAMPLE 70 using cyclopropanesulfonyl chloride in STEP 1. MS: m/z: Calc'd for $C_{17}H_{23}FN_4O_6S_2$, $[M+H]^+$ 463; Found 463. $^1H$ NMR (400 MHz, DMSO-d6) δ 10.12 (s, 1H), 8.99-8.86 (d, 2H), 6.93-6.83 (m, 2H), 4.15-4.10 (d, 4H), 3.40 (d, J=11.6 Hz, 2H), 3.05 (dd, J=12.1, 8.6 Hz, 2H), 2.70-2.59 (m, 1H), 2.53 (s, 1H), 2.12 (s, 1H), 1.89 (s, 1H), 1.59 (t, J=10.4 Hz, 2H), 1.07-0.91 (m, 4H).

Prep-HPLC purification conditions: Xselect CSH C18 OBD Column 30*150 mm 5 um; Mobile Phase A: Water Example 75: 5-[2-fluoro-6-hydroxy-4-[[[(3S)-1-methylsulfonyl-3-piperidyl]amino]methyl]phenyl]-1,1-dioxo-1,2,5-thiadiazolidin-3-one

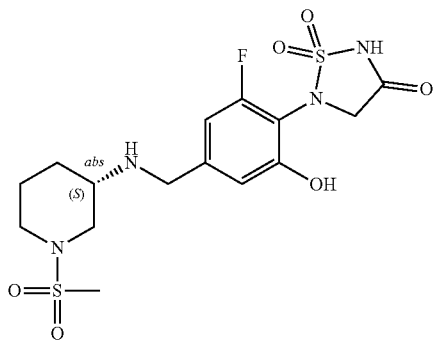

The title compound was prepared in 43% overall yield as a white solid according to the preparation of EXAMPLE 70 using methanesulfonyl chloride in STEP 1. MS: m/z: Calc'd for $C_{15}H_{21}FN_4O_6S_2$, $[M+H]^+$ 437; Found 437. $^1$H NMR (300 MHz, DMSO-d6) δ 9.99 (s, 1H), 9.02 (s, 1H), 8.91 (s, 1H), 6.93-6.81 (m, 2H), 4.14 (s, 2H), 4.05 (s, 2H), 3.70 (d, J=12.6 Hz, 1H), 3.34-3.30 (m, 2H), 3.06-2.88 (m, 2H), 2.95-2.90 (s, 3H), 2.05 (s, 1H), 1.89 (s, 1H), 1.59 (d, J=8.4 Hz, 2H).

Prep-HPLC purification conditions: Xselect CSH C18 OBD Column 30*150 mm 5 μm; Mobile Phase A: Water (0.1% FA), Mobile Phase B: ACN; Flow rate: 60 mL/min; Gradient: 2% B to 28% B in 7 min, 28% B; Wave Length: 254 nm.

Example 76: 3-[(3S)-3-[[3-fluoro-5-hydroxy-4-(1,1,4-trioxo-1,2,5-thiadiazolidin-2-yl) phenyl] methylamino]-1-piperidyl]-3-oxo-propanoic acid

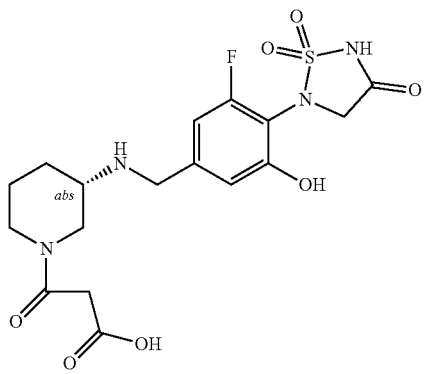 [SMILES: O=C(O)CC(=O)N1CCC[C@H](NCc2cc(O)c(N3CC(=O)NS3(=O)=O)c(F)c2)C1]

The title compound was prepared in 6% overall yield as a white solid according to the preparation of EXAMPLE 70 using 3-benzyloxy-3-oxo-propanoic acid in STEP 1. MS: m/z: Calc'd for $C_{17}H_{21}FN_4O_7S$, $[M+H]^+$ 445; Found 445. $^1$H NMR (300 MHz, DMSO-d6) δ 10.00 (s, 1H), 8.84 (s, 2H), 6.93-6.81 (m, 2H), 4.46-4.35 (m, 1H), 4.32-3.87 (m, 6H), 3.37-2.81 (m, 4H), 2.35-1.25 (m, 4H).

Prep-HPLC purification conditions: Xselect CSH C18 OBD Column 30*150 mm 5 μm; Mobile Phase A: Water (0.05% TFA), Mobile Phase B: ACN; Flow rate: 60 m/min; Gradient: 2% B to 20% B in 10 min, 20% B; Wave Length: 254 nm.

Example 77: 5-[4-[[(4,4-dimethylcyclohexyl)-methyl-amino]methyl]-2-fluoro-6-hydroxy-phenyl]-1,1-dioxo-1,2,5-thiadiazolidin-3-one

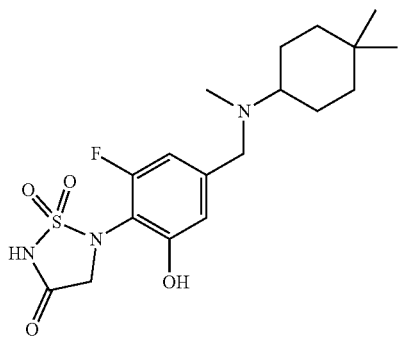 [SMILES: CN(Cc1cc(O)c(N2CC(=O)NS2(=O)=O)c(F)c1)C1CCC(C)(C)CC1]

Scheme 17

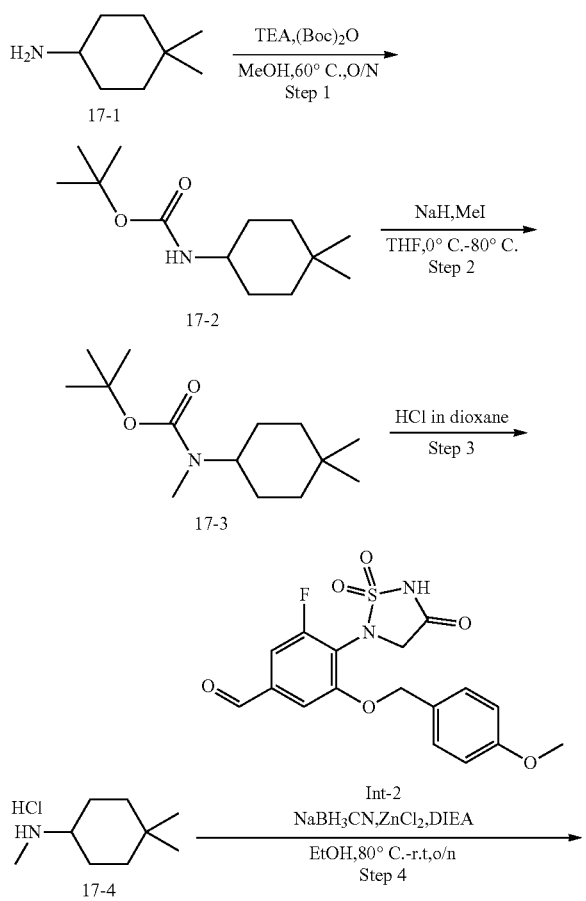

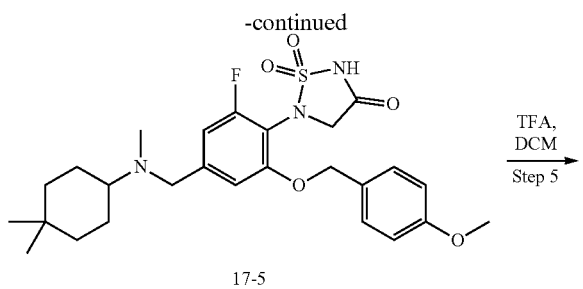

17-5

TFA, DCM
Step 5

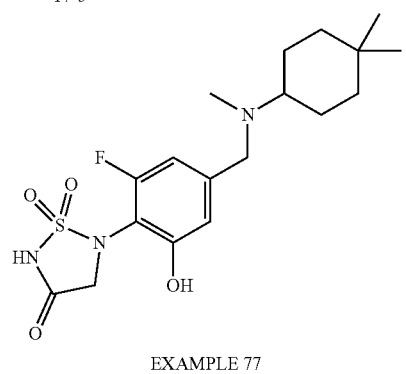

EXAMPLE 77

Step 1: To a mixture of 4,4-dimethylcyclohexanamine (400 mg, 3.14 mmol) and TEA (1.64 mL, 9.43 mmol) in Methanol (10 mL) was added di-tert-butyl dicarbonate (686.16 mg, 3.14 mmol) dropwise at 0° C. The resulting mixture was stirred at 60° C. for overnight. After completion of the reaction monitored by TLC, the mixture was quenched by ice water. The solution was extracted with ethyl acetate for 3 times. The organic phase was dried over anhydrous sodium sulfate, filtered and concentrated. The residue was purified by a silica gel column chromatography (PE:EA=8:1) to obtain tert-butyl N-(4,4-dimethylcyclohexyl)carbamate (700 mg, 3.07 mmol, 98% yield) as a white solid. MS: m/z: Calc'd for $C_{13}H_{25}NO_2$, $[M+H]^+$ 228; Found 228. $^1$H NMR (300 MHz, Chloroform-d) δ 4.42 (s, 1H), 3.37 (s, 1H), 1.77-1.75 (m, 2H), 1.44 (s, 9H), 1.38-1.21 (m, 6H), 0.90 (d, J=2.9 Hz, 6H).

Step 2: To a mixture of tert-butyl N-(4,4-dimethylcyclohexyl)carbamate (700. mg, 3.08 mmol) and iodomethane (1.31 g, 9.24 mmol) in THF (10 mL) was added NaH (221.7 mg, 9.24 mmol) dropwise at 0° C. The mixture was stirred at 80° C. for 2 h. LCMS showed the reaction was completed. The resulting solution was quenched by ice water, extracted with ethyl acetate. The organic phase was dried over anhydrous sodium sulfate, filtered and concentrated. The residue was purified by a silica gel column chromatography (PE:EA=8:1) to obtain tert-butyl N-(4,4-dimethylcyclohexyl)-N-methyl-carbamate (420 mg, 1.74 mmol, 57% yield) as a yellow oil. MS: m/z: Calc'd for $C_{14}H_{27}NO_2$, $[M+H-56+41]^+$ 227; Found 227.

Step 3: To a stirred solution of tert-butyl N-(4,4-dimethylcyclohexyl)-N-methyl-carbamate (400. mg, 1.66 mmol) in 1,4-Dioxane (4 mL) was added HCl (4 M in dioxane, 4 mL, 1.66 mmol). The mixture was stirred at room temperature for overnight. After completion of the reaction monitored by LCMS, the mixture was concentrated to obtain N,4,4-trimethylcyclohexanamine; hydrochloride (200 mg, 1.12 mmol, 68% yield) as a white solid. MS: m/z: Calc'd for $C_9H_{19}N$, $[M+H]^+$ 141; Found 141.

Step 4: To a stirred solution of 3-fluoro-5-[(4-methoxyphenyl)methoxy]-4-(1,1,4-trioxo-1,2,5-thiadiazolidin-2-yl)benzaldehyde (Int-2, 100 mg, 0.25 mmol), N,4,4-trimethylcyclohexanamine; hydrochloride (67.59 mg, 0.38 mmol) and DIEA (0.08 mL, 1.01 mmol) in Ethanol (8 mL) was added a solution of $ZnCl_2$ (0.7 M in THF, 1.45 mL, 1.01 mmol). The reaction mixture was stirred at 80° C. for 30 mins. $NaBH_3CN$ (64.91 mg, 1.01 mmol) was added to the mixture. The resulting mixture was stirred at room temperature for 12 h. After completion of the reaction monitored by LCMS, the mixture was concentrated. The resulting residue was purified by reverse phase column to obtain 5-[4-[[(4,4-dimethylcyclohexyl)-methyl-amino]methyl]-2-fluoro-6-[(4-methoxyphenyl)methoxy]phenyl]-1,1-dioxo-1,2,5-thiadiazolidin-3-one (44 mg, 0.08 mmol, 33% yield) as an off-white solid. MS: m/z: Calc'd for $C_{26}H_{34}FN_3O_5S$, $[M+H]^+$ 520; Found 520.

Step 5: The title compound was prepared in 35% yield as a white solid according to the preparation of EXAMPLE 36 using 17-5 in STEP 4. MS: m/z: Calc'd for $C_{18}H_{26}FN_3O_4S$, $[M+H]^+$ 400; Found 400. $^1$H NMR (400 MHz, DMSO-d6) δ 9.85 (s, 1H), 9.18 (s, 1H), 6.86 (d, J=15.2 Hz, 2H), 6.67 (s, 1H), 4.37 (s, 1H), 4.07 (s, 1H), 3.96 (s, 2H), 3.32 (s, 1H), 2.64 (s, 3H), 2.13 (s, 1H), 1.86 (s, 1H), 1.65 (s, 2H), 1.47 (s, 2H), 1.23 (s, 2H), 0.91 (d, J=7.4 Hz, 6H).

Prep-HPLC purification conditions: XBridge Prep OBD C18 Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 27% B to 37% B in 8 min, 37% B; Wave Length: 254/220 nm.

Example 78: 5-[4-[[cyclobutylmethyl(propyl)amino]methyl]-2-fluoro-6-hydroxy-phenyl]-1,1-dioxo-1,2,5-thiadiazolidin-3-one

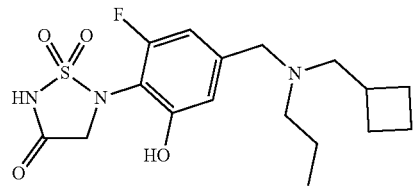 [SMILES: CCCN(Cc1cc(O)c(N2CC(=O)NS2(=O)=O)c(F)c1)CC1CCC1]

Scheme 18

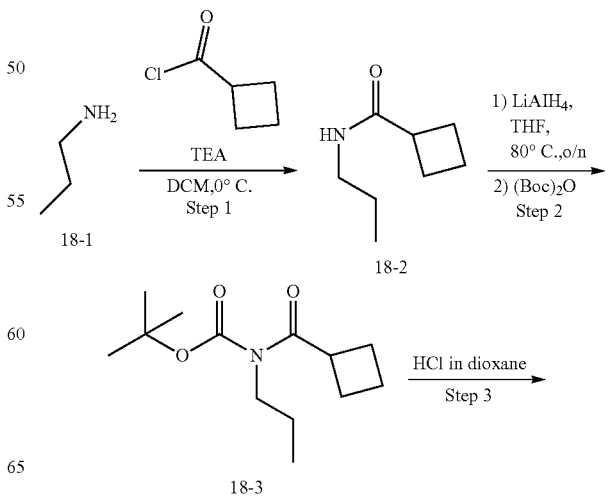

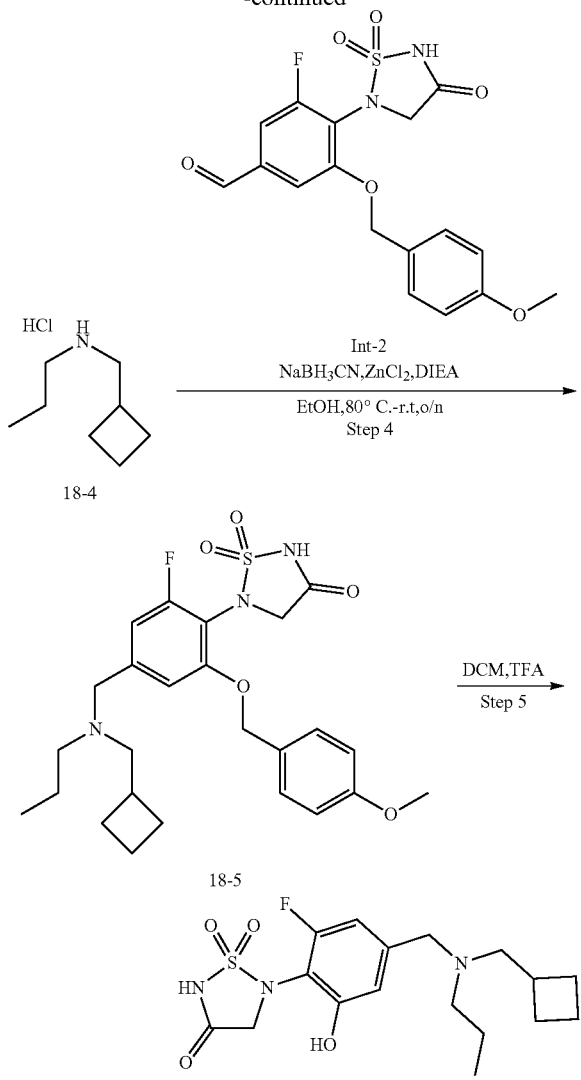

centrated. The resulting residue was purified by a silica gel column chromatography to obtain tert-butyl N-(cyclobutylmethyl)-N-propyl-carbamate (700 mg, 3.07 mmol, 87% yield) as a white solid. MS: m/z: Calc'd for $C_{13}H_{25}NO_2$, $[M+H]^+$ 228; Found 228.

Step 3: To a stirred solution of tert-butyl N-(cyclobutylmethyl)-N-propyl-carbamate (690 mg, 3.04 mmol) in 1,4-Dioxane (4 mL) was added a solution of HCl in dioxane (4 M, 4 mL). The mixture was stirred at room temperature for overnight. After completion of the reaction monitored by LCMS, the mixture was concentrated to obtain N-(cyclobutylmethyl)propan-1-amine; hydrochloride (350 mg, 2.1382 mmol, 70% yield) as a white solid. MS: m/z: Calc'd for $C_8H_{17}N$, $[M+H]^+$ 128; Found 128.

Step 4: The title compound was prepared in 51% yield as a white solid according to the preparation of EXAMPLE 77 using 18-4 in STEP 4. MS: m/z: Calc'd for $C_{25}H_{32}FN_3O_5S$, $[M+H]^+$ 505; Found 505.

Step 5: The title compound was prepared in 53% yield as a white solid according to the preparation of EXAMPLE 36 using 18-5 in STEP 4. MS: m/z: Calc'd for $C_{17}H_{24}FN_3O_4S$, $[M+H]^+$ 386; Found 386. $^1$H NMR (300 MHz, DMSO-d6) δ 10.16 (s, 1H), 9.28 (s, 1H), 6.91 (dd, J=10.6, 1.9 Hz, 1H), 6.84 (t, J=1.5 Hz, 1H), 4.20 (S, 2H), 4.19 (d, J=5.1 Hz, 2H), 3.11 (t, J=5.7 Hz, 2H), 2.91 (dt, J=12.9, 6.0 Hz, 2H), 2.75 (s, 1H), 2.09 (dd, J=8.3, 4.7 Hz, 2H), 1.96-1.75 (m, 3H), 1.73 (s, 3H), 0.88 (t, J=7.3 Hz, 3H).

Prep-HPLC purification conditions: Xselect CSH C18 OBD Column 30*150 mm 5 µm, n; Mobile Phase A: Water (0.05% TFA), Mobile Phase B: ACN; Flow rate: 60 mL/mm; Gradient: 7% B to 37% B in 10 min, 37% B; Wave Length: 254 nm.

Compound 80-1: 5-[2-fluoro-6-hydroxy-4-[(imidazo[1,2-a]pyridin-7-ylamino)methyl]phenyl]-1,1-dioxo-1,2,5-thiadiazolidin-3-one

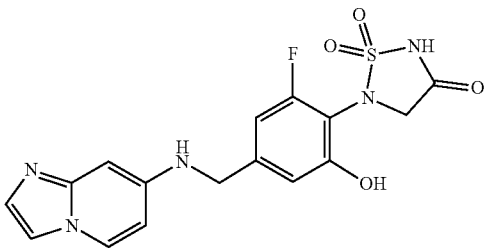 [SMILES: O=C1CN(c2c(O)cc(CNc3ccn4ccnc4c3)cc2F)S(=O)(=O)N1]

Scheme 19

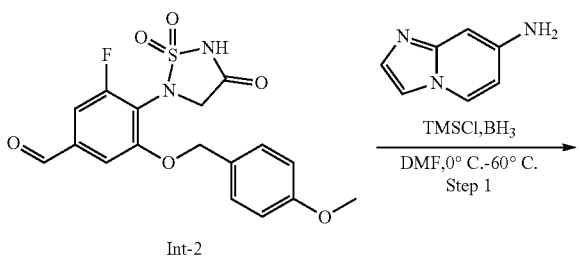

EXAMPLE 78

Step 1: To a stirred solution of propan-1-amine (500 mg, 8.46 mmol) and TEA (4.42 mL, 25.38 mmol) in DCM (8 mL) was added cyclobutanecarbonyl chloride (1.20 g, 10.15 mmol) at 0° C. The mixture was stirred at 0° C. for 1 h. After completion of the reaction monitored by LCMS, the mixture was diluted with DCM and washed with brine. The organic phase was dried over anhydrous $Na_2SO_4$, filtrated and concentrated. The resulting residue was purified by a silica gel column chromatography (PE:EA=4:1) to obtain N-propylcyclobutanecarboxamide (600 mg, 4.24 mmol, 50% yield) as an off-white solid. MS: m/z: Calc'd for $C_8H_{15}NO$, $[M+H]^+$ 142; Found 142.

Step 2: To a stirred solution of $LiAlH_4$ (393.03 mg, 10.62 mmol) in THF (8 mL) was added a solution of N-propylcyclobutanecarboxamide (500 mg, 3.54 mmol) in THF (2 mL). The mixture was stirred at 80° C. for overnight. LCMS showed the starting material was consumed completely. The mixture was quenched by water (4 mL). The suspension was filtrated, and $(Boc)_2O$ (1.15 g, 5.31 mmol) was added to the filtrate. The mixture was stirred for 1 h, the solution was extracted with ethyl acetate, the organic phase was combined and dried over anhydrous $Na_2SO_4$, filtrated and con-

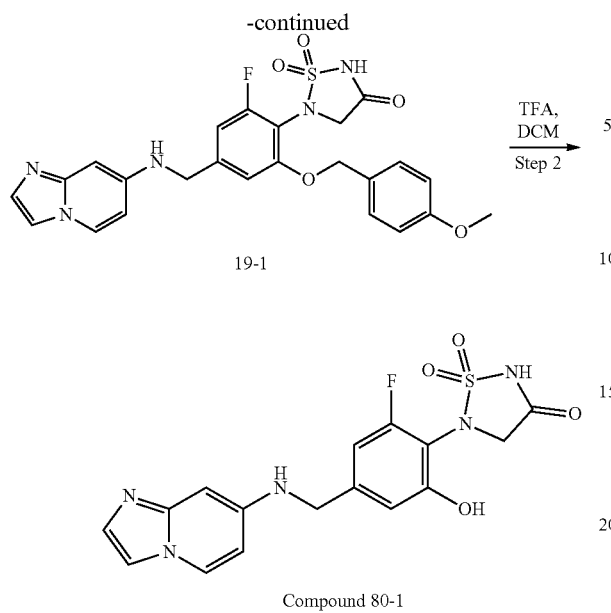

19-1

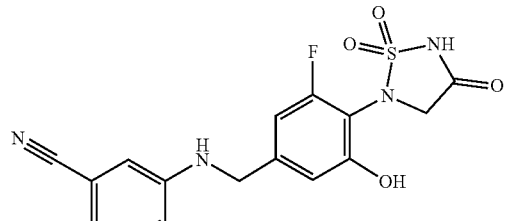

Compound 80-1

Step 1: To a stirred solution of 3-fluoro-5-[(4-methoxyphenyl)methoxy]-4-(1,1,4-trioxo-1,2,5-thiadiazolidin-2-yl)benzaldehyde (Int-2, 95 mg, 0.24 mmol) and imidazo[1,2-a]pyridin-7-amine (48.11 mg, 0.36 mmol) in dry DMF (5 mL) was added TMSCl (0.08 mL, 0.60 mmol) dropwise at 0° C., and the resulting mixture was stirred at 60° C. for 30 mins. The reaction mixture was then cooled to 0° C. and a solution of BH$_3$ in THF (1 M, 0.5 mL, 0.48 mmol) was added slowly with a syringe. After the addition, the reaction mixture was stirred at 60° C. for 1 h. LCMS showed the reaction was completed. The resulting solution was quenched with ice water (0.5 ml) and directly purified by reversed phase column (0.05% NH$_4$HCO$_3$ in H$_2$O and MeCN) to obtain 5-[2-fluoro-4-[(imidazo[1,2-a]pyridin-7-ylamino)methyl]-6-[(4-methoxyphenyl)methoxy]phenyl]-1,1-dioxo-1,2,5-thiadiazolidin-3-one (55 mg, 0.11 mmol, 45% yield) as a light yellow oil. MS: m/z: Calc'd for C$_{24}$H$_{22}$FN$_5$O$_5$S [M+H]$^+$ 512; Found, 512 [M+H]$^+$ Step 2: To a solution of 5-[2-fluoro-4-[(imidazo[1,2-a]pyridin-7-ylamino)methyl]-6-[(4-methoxyphenyl)methoxy]phenyl]-1,1-dioxo-1,2,5-thiadiazolidin-3-one (19-1, 50 mg, 0.10 mmol) in DCM (1 mL) was added TFA (2 mL) at 0° C. and the resulting mixture was stirred at room temperature for overnight. LCMS showed the reaction was completed, after concentration, the crude was purified by reversed phase column (0.05% NH$_4$HCO$_3$ in H$_2$O and MeCN) firstly, and then further purified by Prep-HPLC to obtain 5-[2-fluoro-6-hydroxy-4-[(imidazo[1,2-a]pyridin-7-ylamino)methyl]phenyl]-1,1-dioxo-1,2,5-thiadiazolidin-3-one (8.5 mg, 0.02 mmol, 22% yield) as a white solid. MS: m/z: Calc'd for C$_{16}$H$_{14}$FN$_5$O$_4$S [M+H]$^+$ 392; Found, 392 [M+H]$^+$. $^1$H NMR (300 MHz, DMSO-d6) δ 8.30 (d, J=7.4 Hz, 1H), 7.69 (d, J=1.9 Hz, 1H), 7.45 (d, J=1.9 Hz, 1H), 6.79-6.64 (m, 3H), 6.29 (d, J=2.2 Hz, 1H), 4.32 (s, 2H), 3.96 (s, 2H), 2.35 (s, OH).

Prep-HPLC purification conditions: XBridge Prep OBD C18 Column, 30*150 mm, 5 μm; Mobile Phase A: Water (10 mmol/L NH$_4$HCO$_3$+0.1% NH$_3$·H$_2$O), Mobile Phase B: ACN; Flow rate: 60 mL/min; Gradient: 2% B to 20% B in 9 min, 20% B; Wave Length: 254/220 nm.

Example 79: 5-[[3-fluoro-5-hydroxy-4-(1,1,4-trioxo-1,2,5-thiadiazolidin-2-yl)phenyl]methylamino]pyridine-3-carbonitrile

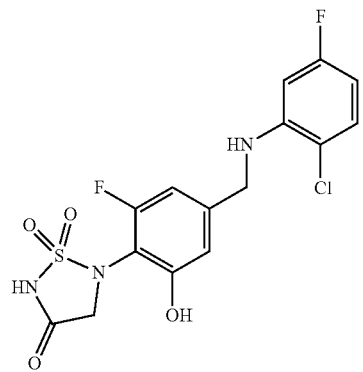

The title compound was prepared in 22% overall yield as a white solid according to the preparation of COMPOUND 80-1 using 5-aminopyridine-3-carbonitrile in STEP 1. MS: m/z: Calc'd for C$_{15}$H$_{12}$FN$_5$O$_4$S, [M+H]$^+$ 378; Found 378. $^1$H NMR (300 MHz, DMSO-d6) δ 6.95-6.52 (m, 4H), 4.41 (s, 2H), 3.95 (s, 2H), 2.38 (s, 6H).

Prep-HPLC purification conditions: XBridge Prep OBD C18 Column, 30*150 mm, 5 μm; Mobile Phase A: Water (10 mmol/L NH$_4$HCO$_3$+0.1% NH$_3$·H$_2$O), Mobile Phase B: ACN; Flow rate: 60 mL/min; Gradient: 3% B to 32% B in 8 min, 32% B; Wave Length: 254/220 nm.

Example 80: 5-[4-[(2-chloro-5-fluoro-anilino)methyl]-2-fluoro-6-hydroxy-phenyl]-1,1-dioxo-1,2,5-thiadiazolidin-3-one The title compound was prepared in 11% overall yield as a white solid according to the preparation of COMPOUND 80-1 using 2-chloro-5-fluoroaniline in STEP 1, the reductive amination was performed at room temperature instead of 60° C. MS: m/z: Calc'd for C$_{15}$H$_{12}$ClF$_2$N$_3$O$_4$S, [M+H]$^+$ 404; Found 404. $^1$H NMR (300 MHz, DMSO-d6) δ 7.28 (dd, J=8.7, 6.0 Hz, 1H), 6.71 (d, J=8.9 Hz, 2H), 6.58-6.13 (m, 2H), 4.49-4.12 (m, 4H).

Prep-HPLC purification conditions: Xselect CSH C18 OBD Column, 30*150 mm 5 μm; Mobile Phase A: Water (0.1% FA), Mobile Phase B: ACN; Flow rate: 60 mL/min; Gradient: 26% B to 56% B in 10 min, 56% B; Wave Length: 254 nm.

Example 81: 4-chloro-3-[[3-fluoro-5-hydroxy-4-(1,1,4-trioxo-1,2,5-thiadiazolidin-2-yl) phenyl] methylamino]benzonitrile

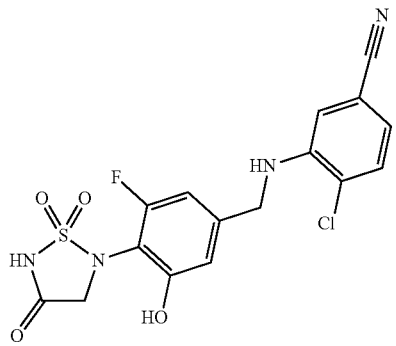 [SMILES: N#Cc1ccc(Cl)c(NCc2cc(O)c(N3CC(=O)NS3(=O)=O)c(F)c2)c1]

The title compound was prepared in 12% overall yield as a white solid according to the preparation of EXAMPLE 80 using 3-amino-4-chloro-benzonitrile in STEP 1. MS: m/z: Calc'd for $C_{16}H_{12}ClFN_4O_4S$, [M–H]$^-$ 409; Found 409. $^1$H NMR (300 MHz, DMSO-d6) δ 10.38 (s, 1H), 7.49 (d, J=8.1 Hz, 1H), 7.00 (dd, J=8.1, 1.9 Hz, 1H), 6.93 (d, J=1.9 Hz, 1H), 6.78-6.68 (m, 3H), 4.41 (d, J=4.6 Hz, 4H).

Prep-HPLC purification conditions: Xselect CSH C18 OBD Column 30*150 mm 5 μm, n; Mobile Phase A: Water (0.05% TFA), Mobile Phase B: ACN; Flow rate: 60 mL/min; Gradient: 30% B to 60% B in 10 min, 60% B; Wave Length: 254 nm.

Example 82: 5-[4-[[(4-cyclopropyl-2-pyridyl)amino]methyl]-2-fluoro-6-hydroxy-phenyl]-1,1-dioxo-1,2,5-thiadiazolidin-3-one

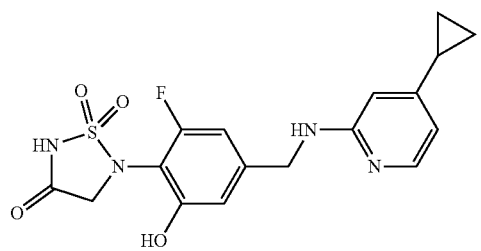 [SMILES: O=C1CN(c2c(O)cc(CNc3cc(C4CC4)ccn3)cc2F)S(=O)(=O)N1]

The title compound was prepared in 12% overall yield as a white solid according to the preparation of COMPOUND 80-1 using 4-cyclopropylpyridin-2-amine in STEP 1, the reductive amination was performed at 80° C. instead of 60° C. MS: m/z: Calc'd for $C_{17}H_{17}N_4O_4S$, [M+H]$^+$ 393; Found 393. $^1$H NMR (300 MHz, DMSO-d6) δ 7.77 (d, J=5.8 Hz, 1H), 6.68-6.57 (m, 2H), 6.43 (s, 1H), 6.30 (d, J=5.8 Hz, 1H), 4.39 (s, 2H), 3.94 (s, 2H), 1.84 (d, J=9.4 Hz, 1H), 1.09-0.96 (m, 2H), 0.82-0.65 (m, 2H).

Prep-HPLC purification conditions: Column: XBridge Prep OBD C18 Column, 30*150 mm, 5 μm; Mobile Phase A: Water (10 mmol/L NH$_4$HCO$_3$+0.1% NH$_3$·H$_2$O), Mobile Phase B: ACN; Flow rate: 60 mL/min; Gradient: 26% B to 36% B in 7 min, 36% B; Wave Length: 254/220 nm.

Example 83: 5-(2-fluoro-6-hydroxy-4-(4-isopentylpiperazin-1-yl)phenyl)-1,2,5-thiadiazolidin-3-one 1,1-dioxide

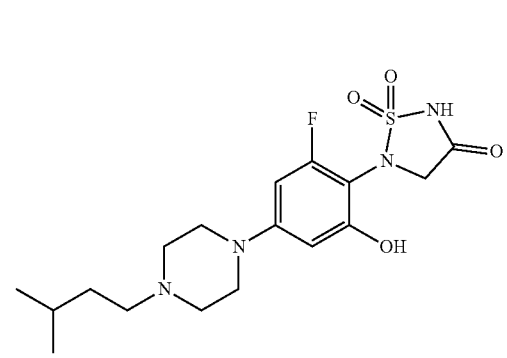 [SMILES: CC(C)CCN1CCN(c2cc(O)c(N3CC(=O)NS3(=O)=O)c(F)c2)CC1]

Scheme 22

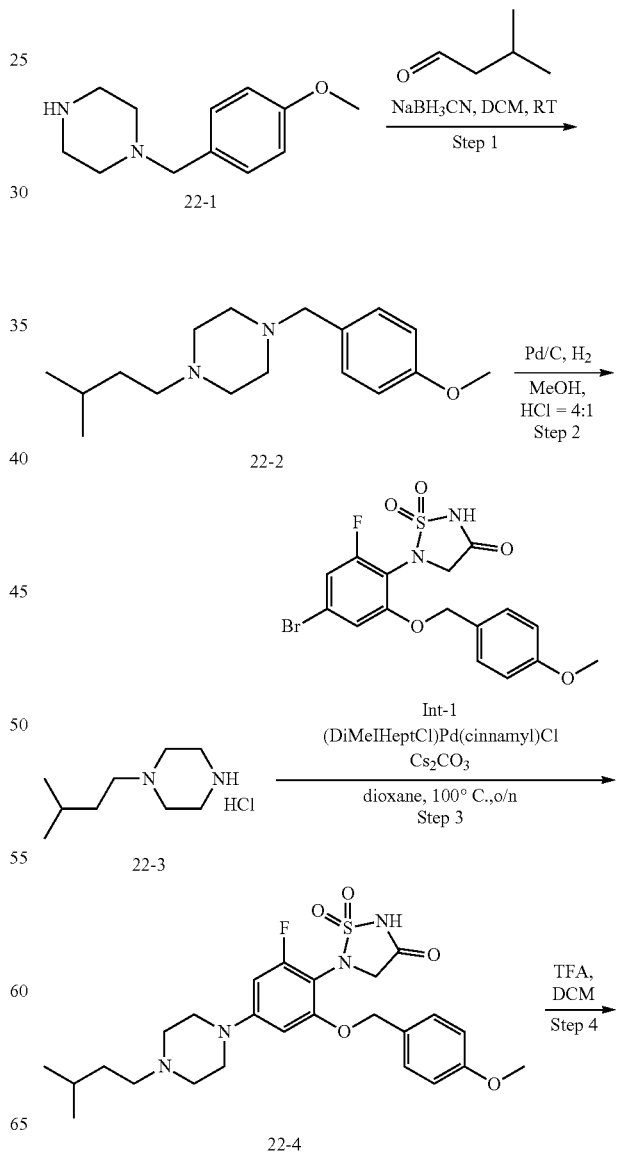

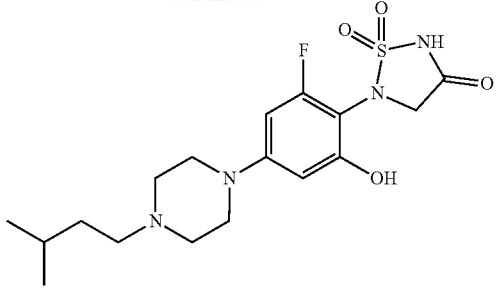

EXAMPLE 83

Step 1: To a stirred solution of 1-[(4-methoxyphenyl)methyl]piperazine (200 mg, 0.97 mmol) and 3-methylbutanal (167 mg, 1.94 mmol) in DCM (8.0 mL) was added CH$_3$COOH (0.11 mL, 1.94 mmol). The reaction mixture was stirred at ambient temperature for 30 mins. NaBH$_3$CN (0.17 mL, 1.94 mmol) was added at 0° C. The resulting mixture was stirred at ambient temperature for 2 h. LCMS showed the starting material was consumed completely. The reaction mixture was quenched with saturated aqueous NH$_4$Cl (5 mL), and extracted with ethyl acetate. The combined organic layers were dried over anhydrous sodium sulfate, filtrated and concentrated. The crude was purified by reversed-phase column to obtain 1-isopentyl-4-[(4-methoxyphenyl)methyl]piperazine (200 mg, 0.72 mmol, 75% yield). MS: m/z: Calc'd for C$_{17}$H$_{28}$N$_2$O [M+H]$^+$ 277; found 277.

Step 2: To a stirred solution of 1-isopentyl-4-[(4-methoxyphenyl)methyl]piperazine (200 mg, 0.72 mmol) in a mixed solvent of Methanol (8 mL) and 2 M HCl (2.0 mL) was added Pd/C (100. mg) under N$_2$. H$_2$ was then subsequently introduced into the reaction system, and the resulting mixture was stirred at ambient temperature for overnight. Upon completion, the mixture was filtrated, and the filtrate was concentrated. The residue was azeotroped twice with toluene to remove remaining water to give 1-isopentylpiperazine; hydrochloride as a white solid. MS: m/z: Calc'd for C$_9$H$_{20}$N$_2$ [M+H]$^+$ 157; found 157.

Step 3: To a stirred solution of 5-[4-bromo-2-fluoro-6-[(4-methoxyphenyl)methoxy]phenyl]-1,1-dioxo-1,2,5-thiadiazolidin-3-one (Int-1, 120 mg, 0.27 mmol) and 1-isopentylpiperazine; hydrochloride (103.88 mg, 0.54 mmol) in 1,4-Dioxane (8.0 mL) were added Cs$_2$CO$_3$ (0.07 mL, 0.81 mmol) and (DiMeIHeptCl)Pd(cinnamyl)Cl (27.89 mg, 0.03 mmol). The resulting suspension was degassed via vacuum/nitrogen backfills for 3 times, and stirred at 100° C. for 16 h. Upon completion, The mixture was concentrated. The resulting residue was purified by reversed-phase column (0.05% NH$_4$HCO$_3$ in water, MeCN) to obtain 5-[2-fluoro-4-(4-isopentylpiperazin-1-yl)-6-[(4-methoxyphenyl)methoxy]phenyl]-1,1-dioxo-1,2,5-thiadiazolidin-3-one (70 mg, 0.13 mmol, 50% yield). MS: m/z: Calc'd for C$_{25}$H$_{33}$FN$_4$O$_5$S [M+H]$^+$ 521; found 521.

Step 4: To a stirred solution of 5-[2-fluoro-4-(4-isopentylpiperazin-1-yl)-6-[(4-methoxyphenyl)methoxy]phenyl]-1,1-dioxo-1,2,5-thiadiazolidin-3-one (65 mg, 0.12 mmol) in DCM (3 mL) was added TFA (6 mL). The reaction mixture was stirred at room temperature for overnight. Upon completion, The mixture was concentrated and the resulting residue was purified by Prep-HPLC to obtain 5-[2-fluoro-6-hydroxy-4-(4-isopentylpiperazin-1-yl)phenyl]-1,2,5-thiadiazolidin-3-one (10.5 mg, 0.02 mmol, 20% yield) as a white solid. MS: m/z: Calc'd for C$_{17}$H$_{25}$FN$_4$O$_4$S [M+H]$^+$ 401; found 401. $^1$H NMR (400 MHz, DMSO-d6) δ 9.57 (s, 2H), 6.43 (dd, J=13.5, 2.7 Hz, 1H), 6.29 (s, 1H), 4.05 (d, J=16.3 Hz, 2H), 3.83 (d, J=13.1 Hz, 2H), 3.55 (d, J=11.7 Hz, 2H), 3.15 (d, J=11.0 Hz, 2H), 3.09 (d, J=8.8 Hz, 2H), 3.00 (d, J=13.0 Hz, 2H), 1.66-1.50 (m, 3H), 0.91 (d, J=6.1 Hz, 6H).

Prep-HPLC conditions: XBridge Prep OBD C18 Column, 30*150 mm, 5 μm; Mobile Phase A: Water (10 mmol/L NH$_4$HCO$_3$), Mobile Phase B: ACN; Flow rate: 60 mL/min; Gradient: 15% B to 30% B in 8 min, 30% B; Wave Length: 254/220 nm.

Example 84: 5-(4-(4-aminopiperidin-1-yl)-2-fluoro-6-hydroxyphenyl)-1,2,5-thiadiazolidin-3-one 1,1-dioxide

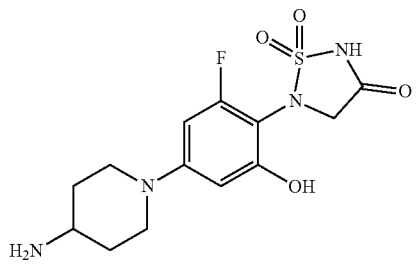 [SMILES: NC1CCN(c2cc(O)c(N3CC(=O)NS3(=O)=O)c(F)c2)CC1]

The title compound was prepared in 12% overall yield as a purple solid according to the preparation of EXAMPLE 83 using tert-butyl N-(4-piperidyl)carbamate in STEP 3. MS: m/z: Calc'd for C$_{13}$H$_{17}$FN$_4$O$_4$S [M+H]$^+$ 345; Found 345. $^1$H NMR (400 MHz, DMSO-d6) δ 7.93 (s, 2H), 6.31-6.21 (m, 2H), 3.88 (s, 2H), 3.75 (d, J=13.4 Hz, 2H), 3.51-3.21 (m, 1H), 2.89-2.78 (m, 2H), 1.91-1.80 (m, 2H), 1.54-1.51 (m, 2H).

Prep-HPLC purification conditions: XBridge Shield RP18 OBD Column, 19*250 mm, 10 μm; Mobile Phase A: Water (10 mmol/L NH$_4$HCO$_3$), Mobile Phase B: ACN; Flow rate: 25 mL/min; Gradient: 2% B to 20% B in 7 min, 20% B; Wave Length: 254/220 nm.

Example 85: 5-(2-fluoro-6-hydroxy-4-(piperazin-1-yl)phenyl)-1,2,5-thiadiazolidin-3-one 1,1-dioxide

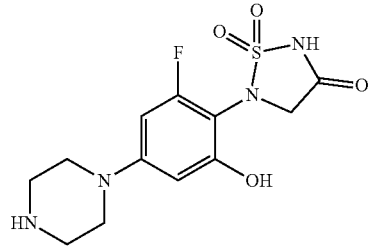

The title compound was prepared in 8% overall yield as a white solid according to the preparation of EXAMPLE 83 using tert-butyl piperazine-1-carboxylate in STEP 3. MS: m/z: Calc'd for C$_{12}$H$_{15}$FN$_4$O$_4$S [M−H]$^-$ 329; Found 329. $^1$H NMR (300 MHz, DMSO-d6) δ 9.91 (d, J=3.2 Hz, 1H), 9.24 (s, 1H), 6.28-6.45 (m, 2H), 4.01 (s, 2H), 3.38 (s, 4H), 3.18 (s, 4H).

Example 86: 5-(2-fluoro-6-hydroxy-4-(4-(2-methoxyethyl)piperazin-1-yl)phenyl)-1,2,5-thiadiazolidin-3-one 1,1-dioxide

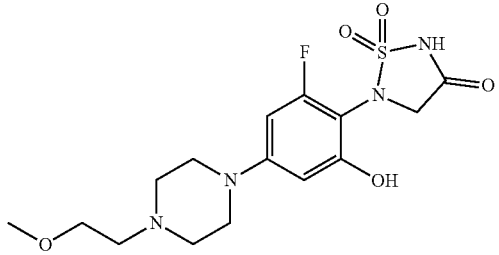 [SMILES: COCCN1CCN(c2cc(O)c(N3CC(=O)NS3(=O)=O)c(F)c2)CC1]

The title compound was prepared in 14% overall yield as an off-white solid according to the preparation of EXAMPLE 83 using 1-(2-methoxyethyl)piperazine in STEP 3. MS: m/z: Calc'd for $C_{15}H_{21}FN_4O_5S$ [M+H]$^+$ 389; Found 389. $^1$H NMR (400 MHz, DMSO-d6) δ 9.62 (s, 1H), 9.23 (s, 1H), 6.41 (dd, J=13.5, 2.6 Hz, 1H), 6.28 (d, J=2.7 Hz, 1H), 3.93 (s, 2H), 3.81 (d, J=12.3 Hz, 2H), 3.68 (t, J=4.8 Hz, 2H), 3.60-3.46 (m, 5H), 3.15-3.09 (m, 6H).

Prep-HPLC purification conditions: Xselect CSH OBD Column 30*150 mm 5 um, n; Mobile Phase A: Water (0.05% TFA), Mobile Phase B: ACN; Flow rate: 60 m/min; Gradient: 5% B to 20% B in 10 min, 20% B; Wave Length: 254/220 nm.

Example 87: 5-(4-(4-(dimethylamino)piperidin-1-yl)-2-fluoro-6-hydroxyphenyl)-1,2,5-thiadiazolidin-3-one 1,1-dioxide

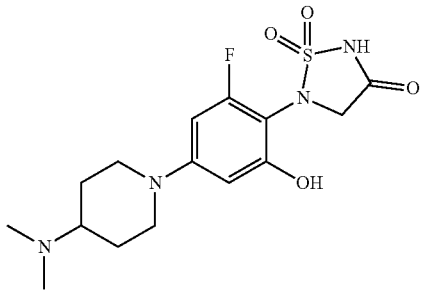 [SMILES: CN(C)C1CCN(c2cc(O)c(N3CC(=O)NS3(=O)=O)c(F)c2)CC1]

The title compound was prepared in 12% overall yield as an off-white solid according to the preparation of EXAMPLE 83 using N, N-dimethylpiperidin-4-amine in STEP 3. MS: m/z: Calc'd for $C_{15}H_{21}FN_4O_4S$, [M+H]$^+$ 373; Found 373. $^1$H NMR (400 MHz, DMSO-d6) δ 9.46-9.39 (m, 2H), 6.31 (dd, J=13.8, 2.7 Hz, 1H), 6.17 (d, J=2.7 Hz, 1H), 4.02 (s, 2H), 3.78 (d, J=13.1 Hz, 2H), 3.30-3.23 (m, 1H), 2.72-2.66 (m, 8H), 1.96-1.93 (m, 2H), 1.58-1.47 (in, 2H).

Prep-HPLC purification conditions: Xselect CSH C18 OBD Column 30*150 mm 5 μm; Mobile Phase A: Water (0.05% TFA), Mobile Phase B: ACN; Flow rate: 60 mL/min; Gradient: 2% B to 15% B in 7 min, 15% B; Wave Length: 254/220 nm.

Example 88: 5-(2-fluoro-6-hydroxy-4-(piperidin-4-ylamino)phenyl)-1,2,5-thiadiazolidin-3-one 1,1-dioxide

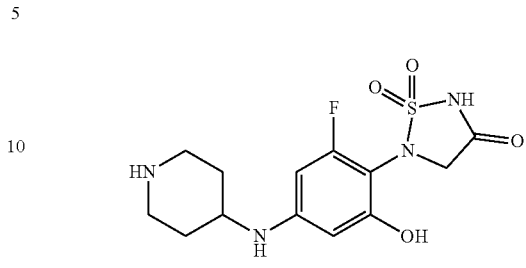

The title compound was prepared in 5% overall yield as whited solid according to the preparation of EXAMPLE 83 using tert-butyl 4-aminopiperidine-1-carboxylate in STEP 3. MS: m/z: Calc'd for $C_{13}H_{17}FN_4O_4S$, [M−H]$^+$343; Found 343. $^1$H NMR (400 MHz, DMSO-d6) δ 9.32 (s, 1H), 8.50 (s, 1H), 8.32 (s, 1H), 6.39-5.89 (m, 3H), 4.06 (s, 2H), 3.51-3.42 (m, 1H), 3.30-3.27 (m, 2H), 3.04-2.96 (m, 2H), 2.14-1.95 (m, 2H), 1.62-1.41 (m, 2H).

Prep-HPLC purification conditions: Xselect CSH OBD Column 30*150 mm 5 um, n; Mobile Phase A: Water (0.05% TFA), Mobile Phase B: ACN; Flow rate: 60 mL/min; Gradient: 20% B to 34% B in 10 min, 34% B to 100% B in 5 min; Wave Length: 254/220 nm.

Example 89: 5-(2-fluoro-6-hydroxy-4-((1-isopentylpiperidin-4-yl)amino)phenyl)-1,2,5-thiadiazolidin-3-one 1,1-dioxide

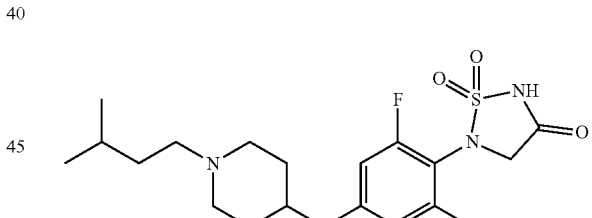

The title compound was prepared in 2.6% overall yield as a pink solid. according to the preparation of EXAMPLE 83 using 1-isopentylpiperidin-4-amine hydrochloride in STEP 3. MS: m/z: Calc'd for $C_{18}H_{27}FN_4O_4S$ [M+H]$^+$ 415; found 415. $^1$H NMR (400 MHz, DMSO-d6) δ 8.72 (s, 1H), 5.94-5.91 (m, 3H), 3.83 (s, 2H), 2.85 (s, 7H), 1.98 (s, 2H), 1.58-1.45 (m, 5H), 0.89 (d, J=6.5 Hz, 6H).

Prep-HPLC purification conditions: XBridge Prep OBD C18 Column, 30*150 mm, 5 μm; Mobile Phase A: Water (10 mmol/L NH$_4$HCO$_3$), Mobile Phase B: ACN; Flow rate: 60 mL/min; Gradient: 13% B to 33% B in 8 min, 33% B; Wave Length: 254/220 nm.

Example 90: 5-(2-fluoro-6-hydroxy-4-((1-(2-methoxyethyl)piperidin-4-yl)amino)phenyl)-1,2,5-thiadiazolidin-3-one 1,1-dioxide

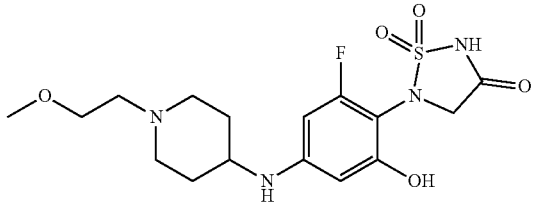 [SMILES: COCCN1CCC(Nc2cc(O)c(N3CC(=O)NS3(=O)=O)c(F)c2)CC1]

The title compound was prepared in 4.9% overall yield as a pink solid. according to the preparation of EXAMPLE 83 using 1-(2-methoxyethyl)piperidin-4-amine in STEP 3. MS: m/z: Calc'd for $C_{16}H_{23}FN_4O_5S$ [M+H]$^+$ 403; Found 403. $^1$H NMR (400 MHz, DMSO-d6) δ 8.70 (br, 1H), 5.95-5.70 (m, 3H), 3.85 (br, 2H), 3.61 (br, 2H), 3.53-2.95 (m, 10H), 2.12-1.93 (m, 2H), 1.68-1.47 (m, 2H).

Prep-HPLC purification conditions: Xselect CSH OBD Column 30*150 mm 5 um, n; Mobile Phase A: Water (0.1% NH$_4$HCO$_3$), Mobile Phase B: ACN; Flow rate: 60 m/min; Gradient: 5% B to 20% B in 10 min, 20% B; Wave Length: 254/220 nm.

Example 91: N-(2-(dimethylamino)ethyl)-4-(1,1-dioxido-4-oxo-1,2,5-thiadiazolidin-2-yl)-3-fluoro-5-hydroxybenzamide

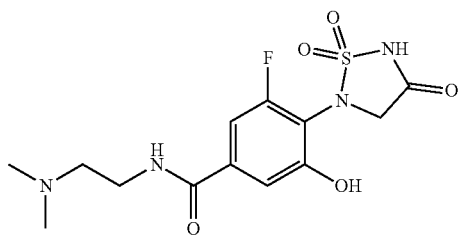 [SMILES: CN(C)CCNC(=O)c1cc(O)c(N2CC(=O)NS2(=O)=O)c(F)c1]

Scheme 23

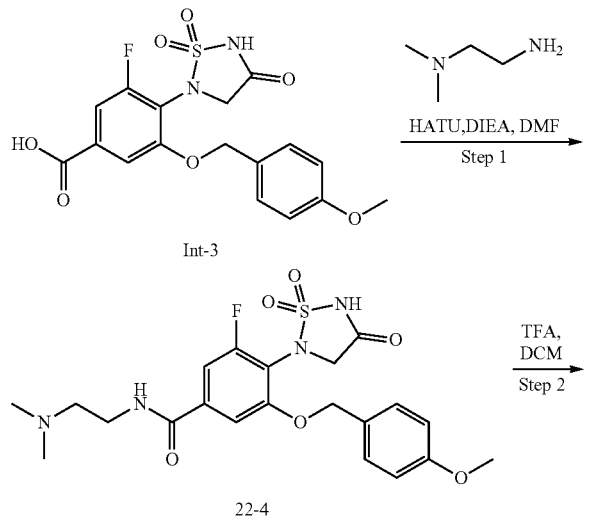

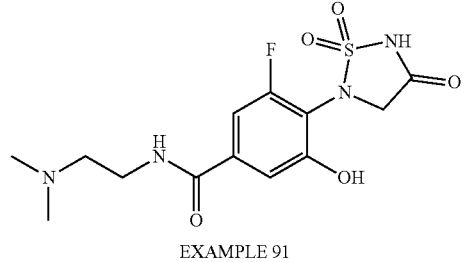

EXAMPLE 91

Step 1: To a stirred solution of 3-fluoro-5-[(4-methoxyphenyl)methoxy]-4-(1,1,4-trioxo-1,2,5-thiadiazolidin-2-yl)benzoic acid (Int-3, 100 mg, 0.24 mmol) and N',N'-dimethylethane-1,2-diamine (32.22 mg, 0.37 mmol) in DMF (4 mL) were added HATU (138.90 mg, 0.37 mmol) and DIEA (0.12 mL, 0.73 mmol). The reaction mixture was stirred at ambient temperature for 2 h. Upon completion, The reaction mixture was purified by reversed-phase column to obtain N-[2-(dimethylamino)ethyl]-3-fluoro-5-[(4-methoxyphenyl)methoxy]-4-(1,1,4-trioxo-1,2,5-thiadiazolidin-2-yl)benzamide (80 mg, 0.16 mmol, 68% yield). MS: m/z: Calc'd for $C_{21}H_{25}FN_4O_6S$ [M+H]$^+$ 481; found 481.

Step 2: To a stirred solution of N-[2-(dimethylamino)ethyl]-3-fluoro-5-[(4-methoxyphenyl)methoxy]-4-(1,1,4-trioxo-1,2,5-thiadiazolidin-2-yl)benzamide (23-1.70 mg, 0.15 mmol) in DCM (4 mL) was added TFA (8 mL) at 0° C. The mixture was stirred at ambient temperature for 3 h. Upon completion, the reaction mixture was concentrated and purified by Prep-HPLC to obtain N-[2-(dimethylamino)ethyl]-3-fluoro-5-hydroxy-4-(1,1,4-trioxo-1,2,5-thiadiazolidin-2-yl)benzamide (23.90 mg, 0.06 mmol, 44% yield) as a white solid. MS: m/z: Calc'd for $C_{13}H_{17}FN_4O_5S$ [M+H]$^+$ 361; Found 361. $^1$H NMR (300 MHz, DMSO-d6) δ 9.91 (d, J=3.2 Hz, 1H), 9.24 (s, 1H), 8.64 (t, J=5.6 Hz, 1H), 7.24-7.10 (m, 2H), 4.01 (s, 2H), 3.57 (d, J=5.8 Hz, 2H), 3.25 (t, J=5.9 Hz, 2H), 2.84 (s, 6H).

Prep-HPLC conditions: Xselect CSH C18 OBD Column 30*150 mm 5 μm; Mobile Phase A: Water (0.05% TFA), Mobile Phase B: ACN; Flow rate: 60 mL/min; Gradient: 12% B to 25% B in 10 min, 25% B; Wave Length: 254/220 nm.

Example 92: 4-(1,1-dioxido-4-oxo-1,2,5-thiadiazolidin-2-yl)-3-fluoro-5-hydroxy-N-(piperidin-4-yl)benzamide

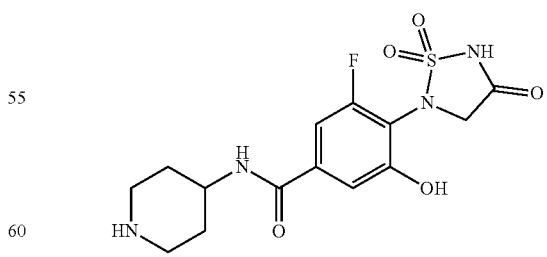

The title compound was prepared in 38% overall yield as an off-white solid according to the preparation of EXAMPLE 91 using tert-butyl 4-aminopiperidine-1-carboxylate in STEP 1. MS: m/z: Calc'd for $C_{14}H_{17}FN^4O_5S$, [M+H]$^+$ 373; Found 373. $^1$H NMR (300 MHz, DMSO-d6)

δ 10.04 (s, 1H), 8.61-8.41 (m, 2H), 8.26 (s, 1H), 7.21-7.11 (m, 2H), 4.16-4.03 (m, 3H), 3.34-3.29 (m, 2H), 3.07-3.00 (m, 2H), 1.98-1.94 (m, 2H), 1.80-1.58 (m, 2H).

Prep-HPLC purification conditions: Xselect CSH OBD Column 30*150 mm 5 um; Mobile Phase A: Water (0.05% TFA), Mobile Phase B: ACN; Flow rate: 60 mL/min; Gradient: 20% B to 34% B in 10 min, 34% B to 100% B in 5 min; Wave Length: 254/220 nm.

Example 93: (S)-4-(1,1-dioxido-4-oxo-1,2,5-thiadiazolidin-2-yl)-3-fluoro-5-hydroxy-N-(piperidin-3-yl)benzamide

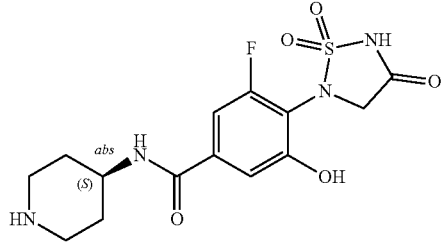

The title compound was prepared in 34% overall yield as a white solid according to the preparation of EXAMPLE 91 using tert-butyl (3S)-3-aminopiperidine-1-carboxylate in STEP 1. MS: m/z: Calc'd for $C_{14}H_{17}FN_4O_5S$, [M+H]$^+$ 373; Found 373. $^1$H NMR (400 MHz, DMSO-d6) δ 10.72-9.62 (m, 1H), 8.58 (s, 2H), 8.44 (s, 1H), 7.20-7.18 (m, 2H), 4.22-4.11 (m, 2H), 3.21-3.18 (m, 1H), 2.86-2.78 (m, 2H), 2.69 (s, 2H), 1.91-1.88 (m, 2H), 1.69-1.56 (m, 2H).

Prep-HPLC purification conditions: Xselect CSH OBD Column 30*150 mm 5 um; Mobile Phase A: Water (0.05% TFA), Mobile Phase B: ACN; Flow rate: 60 mL/min; Gradient: 20% B to 34% B in 10 min, 34% B to 100% B in 5 min; Wave Length: 254/220 nm.

Example 94: (R)-4-(1,1-dioxido-4-oxo-1,2,5-thiadiazolidin-2-yl)-3-fluoro-5-hydroxy-N-(piperidin-3-yl)benzamide

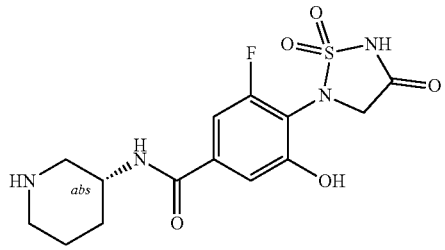 [SMILES: O=C1CN(c2c(O)cc(C(=O)N[C@@H]3CCCNC3)cc2F)S(=O)(=O)N1]

The title compound was prepared in 12% overall yield as a white solid according to the preparation of EXAMPLE 91 using tert-butyl (3R)-3-aminopiperidine-1-carboxylate in STEP 1. MS: m/z: Calc'd for $C_{14}H_{17}FN_4O_5S$ [M+H]$^+$ 373; Found 373. $^1$H NMR (300 MHz, DMSO-d6) δ 7.21-7.10 (m, 2H), 4.00 (s, 2H), 3.88 (d, J=10.0 Hz, 1H), 3.12-3.01 (m, 1H), 2.98-2.86 (m, 1H), 2.61-2.51 (m, 2H), 1.84 (s, 1H), 1.72 (s, 1H), 1.52 (q, J=10.2, 9.3 Hz, 2H).

Prep-HPLC purification conditions: XBridge Prep OBD C18 Column, 30*150 mm, 5 μm; Mobile Phase A: Water (10 mmol/L NH$_4$HCO$_3$), Mobile Phase B: ACN; Flow rate: 60 mL/min; Gradient: 3% B to 10% B in 8 min, 10% B; Wave Length: 254/220 nm.

Example 95: N-((1r,4r)-4-aminocyclohexyl)-4-(1,1-dioxido-4-oxo-1,2,5-thiadiazolidin-2-yl)-3-fluoro-5-hydroxybenzamide

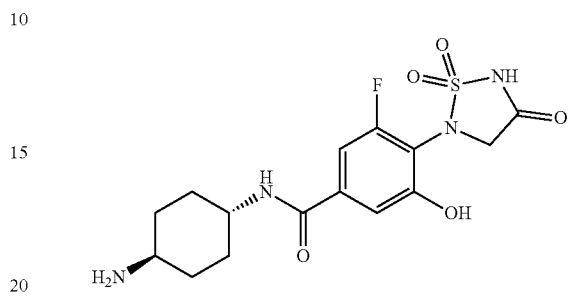

The title compound was prepared in 1.1% overall yield as a white solid according to the preparation of EXAMPLE 91 using tert-butyl N-(4-aminocyclohexyl)carbamate in STEP 1. MS: m/z: Calc'd for $C_{17}H_{23}FN_4O_5S$ [M+H]$^+$ 415; Found 415. $^1$H NMR (300 MHz, DMSO-d6) δ 8.30 (d, J=7.9 Hz, 1H), 7.22-7.08 (m, 2H), 4.00 (s, 2H), 3.76-3.68 (m, 1H), 2.98 (s, 1H), 1.96 (s, 2H), 1.90 (s, 2H), 1.40-1.29 (m, 4H).

Prep-HPLC purification conditions: XBridge Prep OBD C18 Column, 30*150 mm, 5 μm; Mobile Phase A: Water (0.05% TFA), Mobile Phase B: MeOH; Flow rate: 60 mL/min; Gradient: 2% B to 15% B in 9 min, 15% B; Wave Length: 254/220 nm.

Example 96: N-((1r,4r)-4-(dimethylamino)cyclohexyl)-4-(1,1-dioxido-4-oxo-1,2,5-thiadiazolidin-2-yl)-3-fluoro-5-hydroxybenzamide

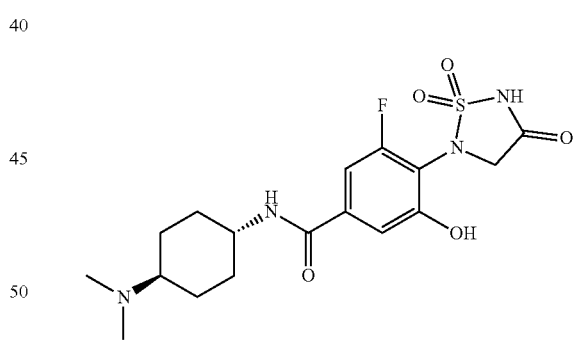

The title compound was prepared in 14% overall yield as an off-white solid according to the preparation of EXAMPLE 91 using (1r,4r)-N1,N1-dimethylcyclohexane-1,4-diamine in STEP 1. MS: m/z: Calc'd for $C_{17}H_{23}FN_4O_5S$ [M+H]$^+$ 415; Found 415. $^1$H NMR (400 MHz, DMSO-d6) δ 9.81 (s, 1H), 8.26 (d, J=7.6 Hz, 1H), 7.16-7.07 (m, 2H), 3.99 (s, 2H), 3.78-3.73 (m, 1H), 3.19-3.13 (m, 1H), 2.75 (s, 6H), 2.02-1.94 (m, 4H), 1.57-1.53 (m, 2H), 1.43-1.40 (m, 2H).

Prep-HPLC purification conditions: Xselect CSH OBD Column 30*150 mm 5 um, n; Mobile Phase A: Water (0.05% TFA), Mobile Phase B: ACN; Flow rate: 60 mL/min; Gradient: 5% B to 20% B in 10 min, 20% B; Wave Length: 254/220 nm.

Example 97: 5-(3-(((4,4-dimethylcyclohexyl)amino)methyl)-2-fluoro-6-hydroxyphenyl)-1,2,5-thiadiazolidin-3-one 1,1-dioxide

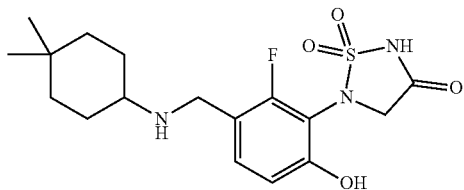 [SMILES: CC1(C)CCC(NCc2ccc(O)c(N3CC(=O)NS3(=O)=O)c2F)CC1]

Scheme 24

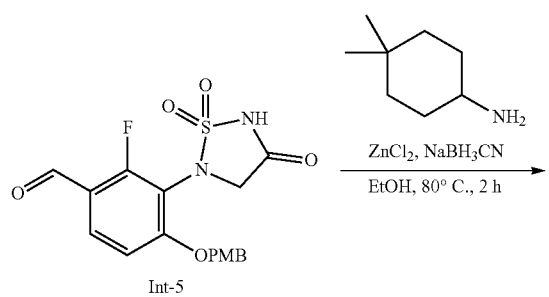

EXAMPLE 97

To a solution of 2-fluoro-4-[(4-methoxyphenyl)methoxy]-3-(1,1,4-trioxo-1,2,5-thiadiazolidin-2-yl)benzaldehyde (Int-5, 120 mg, 0.30 mmol) and 4,4-dimethylcyclohexanamine (77.43 mg, 0.61 mmol) in Ethanol (2 mL) were added a solution of $ZnCl_2$ in THF (0.7M, 1.22 mmol, 1.74 mL) and $NaBH_3CN$ (76.48 mg, 1.22 mmol) in Ethanol (8 mL). The reaction mixture was stirred at 80° C. for 2 h. Upon completion, the reaction mixture was concentrated and the resulting residue was purified by reversed-phase column to give a crude product, which was further purified by Prep-HPLC to obtain 5-[3-[[(4,4-dimethylcyclohexyl)amino]methyl]-2-fluoro-6-hydroxy-phenyl]-1,1-dioxo-1,2,5-thiadiazolidin-3-one (19.7 mg, 0.05 mmol, 17% yield) as a white solid. MS: m/z: Calc'd for $C_{17}H_{24}FN_3O_4S$ [M+H]$^+$ 386; Found 386. $^1$H NMR (400 MHz, DMSO-d6) δ 9.82 (s, 1H), 8.49 (s, 2H), 7.39-7.35 (m, 1H), 6.86-6.81 (m, 1H), 4.13-4.02 (m, 4H), 3.00 (s, 1H), 1.92-1.90 (m, 2H), 1.63-1.49 (m, 2H), 1.43 (d, J=13.6 Hz, 2H), 1.25-1.19 (m, 2H), 0.90 (s, 6H).

Prep-HPLC purification conditions: Xselect CSH C18 OBD Column 30*150 mm 5 μm Mobile Phase A: Water (0.05% TFA), Mobile Phase B: ACN; Flow rate: 60 mL/min; Gradient: 14% B to 36% B in 7 min, 36% B; Wave Length: 254/220 nm.

Example 98: 5-(2-fluoro-3-((4-fluoropiperidin-1-yl)methyl)-6-hydroxyphenyl)-1,2,5-thiadiazolidin-3-one 1,1-dioxide

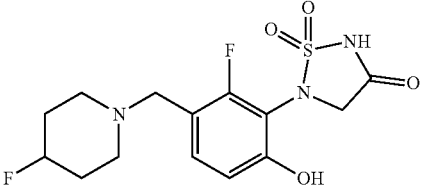

The title compound was prepared in 18% yield as an off-white solid according to the preparation of EXAMPLE 97 using 4-fluoropiperidine. MS: m/z: Calc'd for $C_{14}H_{17}F_2N_3O_4S$ [M+H]$^+$ 362; Found 362. $^1$H NMR (300 MHz, DMSO-d6) δ 7.43-7.11 (m, 1H), 6.99-6.82 (m, 1H), 5.06-4.87 (s, 1H), 4.30 (d, J=9.5 Hz, 2H), 4.06 (d, J=2.4 Hz, 2H), 3.32-3.17 (m, 4H), 2.29-1.78 (m, 4H).

Prep-HPLC purification conditions: Xselect CSH C18 OBD Column 30*150 mm 5 μm; Mobile Phase A: Water (0.05% TFA), Mobile Phase B: ACN; Flow rate: 60 m/min; Gradient: 2% B to 30% B in 7 min, 30% B; Wave Length: 254/220 nm.

Example 99: 5-(2-fluoro-6-hydroxy-3-(morpholinomethyl)phenyl)-1,2,5-thiadiazolidin-3-one 1,1-dioxide

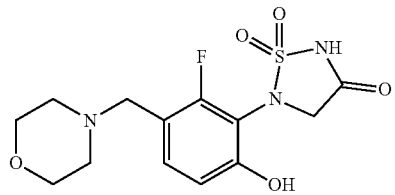 [SMILES: O=C1CN(c2c(O)ccc(CN3CCOCC3)c2F)S(=O)(=O)N1]

The title compound was prepared in 24% overall yield as an off-white solid according to the preparation of EXAMPLE 97 using morpholine. MS: m/z: Calc'd for $C_{13}H_{16}FN_3O_5S$, [M+H]$^+$ 346; Found 346. $^1$H NMR (300 MHz, Methanol-d4) δ 7.10-7.06 (m, 1H), 6.68-6.61 (m, 1H), 4.30 (s, 2H), 3.88-3.68 (m, 6H), 2.69 (s, 4H).

Prep-HPLC purification condition: Xselect CSH OBD Column 30*150 mm 5 um; Mobile Phase A: Water (0.05% $NH_4HCO_3$), Mobile Phase B: ACN; Flow rate: 60 mL/min; Gradient: 20% B to 34% B in 10 min, 34% B to 100% B in 6 min; Wavelength: 254/220 nm.

Example 100: 5-(3-((cyclohexylamino)methyl)-2-fluoro-6-hydroxyphenyl)-1,2,5-thiadiazolidin-3-one 1,1-dioxide

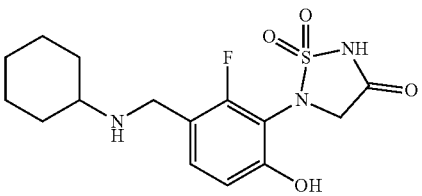 [SMILES: O=C1CN(c2c(O)ccc(CNC3CCCCC3)c2F)S(=O)(=O)N1]

The title compound was prepared in 19% yield as an off-white solid according to the preparation of EXAMPLE 97 using cyclohexanamine. MS: m/z: Calc'd for $C_{15}H_{20}FN_3O_4S$ [M+H]$^+$ 358; Found 358. $^1$H NMR (300 MHz, DMSO-d6) δ 9.63 (br, 1H), 8.50 (br, 2H), 7.34 (dd, J=8.6, 6.1 Hz, 1H), 6.88-6.75 (m, 1H), 4.08 (s, 2H), 3.95 (s, 2H), 3.04 (s, 1H), 2.09 (d, J=10.3 Hz, 2H), 1.77 (d, J=11.4 Hz, 2H), 1.61 (d, J=12.2 Hz, 1H), 1.59-1.27 (m, 5H).

Prep-HPLC-condition: Xselect CSH C18 OBD Column 30*150 mm 5 μm; Mobile Phase A: Water (0.05% TFA), Mobile Phase B: ACN; Flow rate: 60 mL/min; Gradient: 2% B to 30% B in 10 min, 30% B; Wave Length: 254 nm.

Example 101: 5-(2-fluoro-6-hydroxy-3-(((tetrahydro-2H-pyran-4-yl)amino)methyl)phenyl)-1,2,5-thiadiazolidin-3-one 1,1-dioxide

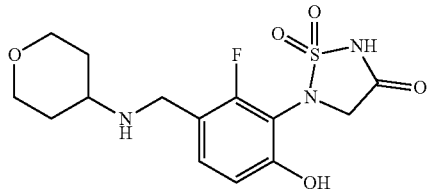 [SMILES: O=C1CN(c2c(O)ccc(CNC3CCOCC3)c2F)S(=O)(=O)N1]

The title compound was prepared in 14% yield as an off-white solid according to the preparation of EXAMPLE 97 using tetrahydro-2H-pyran-4-amine. MS: m/z: Calc'd for $C_{14}H_{18}FN_3O_5S$ [M+H]$^+$ 360; Found 360. $^1$H NMR (300 MHz, DMSO-d6) δ 9.75 (s, 1H), 8.66 (s, 2H), 7.36 (dd, J=8.6, 6.1 Hz, 1H), 6.94-6.77 (m, 1H), 4.10 (s, 2H), 3.94 (d, J=21.4 Hz, 4H), 3.31 (t, J=11.5 Hz, 3H), 2.01 (d, J=12.4 Hz, 2H), 1.68-1.50 (m, 2H).

Prep-HPLC condition: Xselect CSH C18 OBD Column 30*150 mm 5 μm; Mobile Phase A: Water (0.05% TFA), Mobile Phase B: ACN; Flow rate: 60 mL/min; Gradient: 2% B to 13% B in 7 min, 13% B; Wave Length: 254/220 nm.

Example 102: 5-(3-((4-(dimethylamino)piperidin-1-yl)methyl)-2-fluoro-6-hydroxyphenyl)-1,2,5-thiadiazolidin-3-one 1,1-dioxide

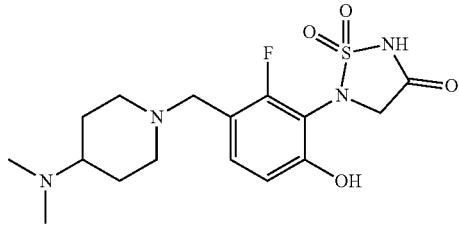 [SMILES: CN(C)C1CCN(Cc2ccc(O)c(N3CC(=O)NS3(=O)=O)c2F)CC1]

The title compound was prepared in 12% yield as a white solid according to the preparation of EXAMPLE 97 using N,N-dimethylpiperidin-4-amine. MS: m/z: Calc'd for $C_{16}H_{23}FN_4O_4S$ [M+H]$^+$ 387; Found 387. $^1$H NMR (300 MHz, DMSO-d6) δ 7.19-7.01 (m, 1H), 6.69-6.63 (m, 1H), 3.99 (s, 2H), 3.60 (s, 2H), 2.99 (d, J=11.8 Hz, 3H), 2.69 (s, 6H), 2.17-2.03 (m, 2H), 2.02-1.89 (m, 2H), 1.72-1.55 (m, 2H).

Prep-HPLC purification conditions: Atlantis Prep T3 OBD Column, 19*250 mm 10 μm; Mobile Phase A: Water (10 mmol/L NH$_4$HCO$_3$), Mobile Phase B: ACN; Flow rate: 25 mL/min; Gradient: 10% B to 20% B in 9 min, 20% B; Wave Length: 254/220 nm.

Example 103: 5-(2-fluoro-6-hydroxy-3-((4-methylpiperazin-1-yl)methyl)phenyl)-1,2,5-thiadiazolidin-3-one 1,1-dioxide

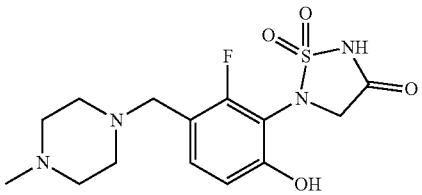

The title compound was prepared in 13% overall yield as an off-white solid according to the preparation of EXAMPLE 97 using 1-methylpiperazine. MS: m/z: Calc'd for $C_{14}H_{19}FN_4O_4S$ [M+H]$^+$ 359; Found 359. $^1$H NMR (400 MHz, DMSO-d6) δ 7.11-7.07 (m, 1H), 6.86-6.64 (m, 1H), 4.00 (s, 2H), 3.61 (s, 2H), 2.74-2.53 (m, 8H), 2.44-2.27 (m, 3H).

Prep-HPLC conditions: XBridge Prep Phenyl OBD Column, 19*250 mm, 5 μm; Mobile Phase A: Water (10 mmol/L NH$_4$HCO$_3$+0.1% NH$_3$·H$_2$O), Mobile Phase B: ACN; Flow rate: 25 mL/min; Gradient: 5% B to 10% B in 8 min; Wave Length: 254/220 nm.

Example 104: 5-[2-fluoro-6-hydroxy-3-[(4-isopentylpiperazin-1-yl)methyl]phenyl]-1,1-dioxo-1,2,5-thiadiazolidin-3-one

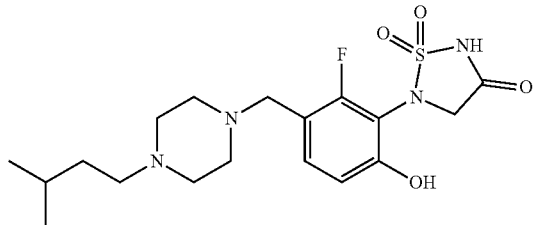 [SMILES: CC(C)CCN1CCN(Cc2ccc(O)c(N3CC(=O)NS3(=O)=O)c2F)CC1]

The title compound was prepared in 17% overall yield as a white solid according to the preparation of EXAMPLE 97 using 1-isopentylpiperazine. MS: m/z: Calc'd for $C_{18}H_{27}FN_4O_4S$ [M+H]$^+$ 415; Found 415. $^1$H NMR (400 MHz, DMSO-d6) δ 7.31 (dd, J=8.6, 6.3 Hz, 1H), 6.81 (dd, J=10.0, 8.6 Hz, 1H), 4.09 (s, 2H), 4.04-3.97 (m, 2H), 3.56 (s, 1H), 3.41-2.83 (m, 7H), 2.55-2.45 (m, 2H), 1.55-1.45 (m, 3H), 0.90 (d, J=6.5 Hz, 6H).

Prep-HPLC conditions: Column: Xselect CSH C18 OBD Column 30*150 mm 5 μm, n; Mobile Phase A: Water (0.05% TFA), Mobile Phase B: ACN; Flow rate: 60 mL/min; Gradient: 2% B to 17% B in 7 min, 17% B; Wave Length: 254/220 nm.

Example 105: 5-(2-fluoro-6-hydroxy-3-(piperidin-4-yl)phenyl)-1,2,5-thiadiazolidin-3-one 1,1-dioxide

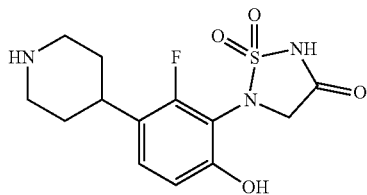 [SMILES: O=C1CN(c2c(O)ccc(C3CCNCC3)c2F)S(=O)(=O)N1]

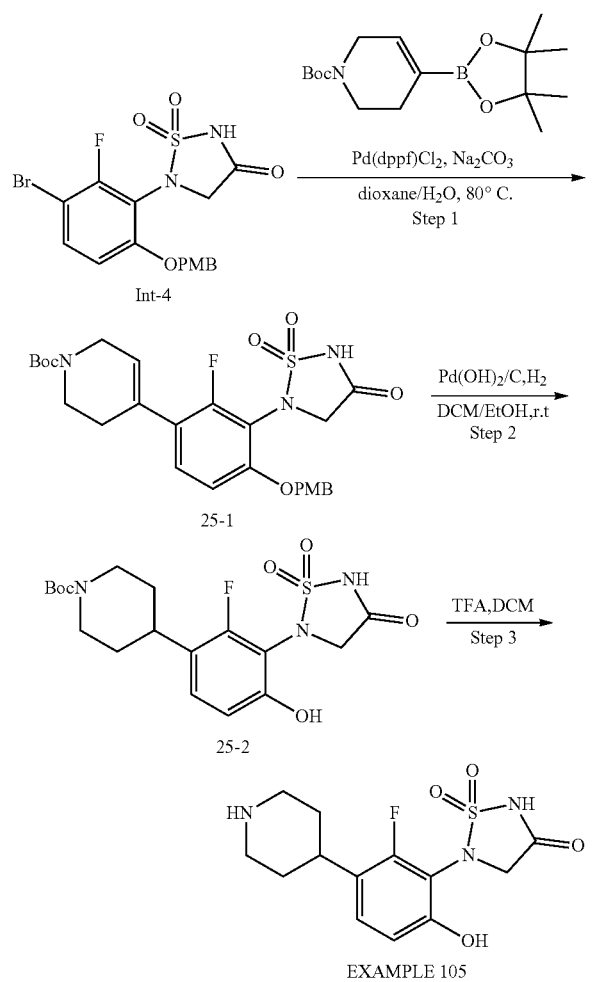

Scheme 25

EXAMPLE 105

Step 1: To a suspension of 5-[3-bromo-2-fluoro-6-[(4-methoxyphenyl)methoxy]phenyl]-1,1-dioxo-1,2,5-thiadiazolidin-3-one (Int-4, 110 mg, 0.25 mmol) in 1,4-Dioxane (3 mL) and Water (0.30 mL) were added tert-butyl 4-(4,4,5,5-tetramethyl-1,3,2-dioxaborolan-2-yl)-3,6-dihydro-2H-pyridine-1-carboxylate (114.58 mg, 0.37 mmol), Pd(dppf)Cl$_2$ (40.35 mg, 0.05 mmol), and Na$_2$CO$_3$ (78.56 mg, 0.74 mmol). The resulting mixture was purged with N$_2$ and allowed to stir at 80° C. for 3 h. Upon completion, the solvent was concentrated in vacuo and the crude residue was purified by reversed-phase column (0.5% TFA in H$_2$O, MeCN) to obtain tert-butyl 4-[2-fluoro-4-[(4-methoxyphenyl)methoxy]-3-(1,1,4-trioxo-1,2,5-thiadiazolidin-2-yl)phenyl]-3,6-dihydro-2H-pyridine-1-carboxylate (120 mg, 0.22 mmol, 89% yield) as a light-yellow solid.

MS: m/z: Calc'd for C$_{26}$H$_{30}$FN$_3$O$_7$S [M+H]$^+$ 548; Found 448.

Step 2: To a solution of tert-butyl 4-[2-fluoro-4-[(4-methoxyphenyl)methoxy]-3-(1,1,4-trioxo-1,2,5-thiadiazolidin-2-yl)phenyl]-3,6-dihydro-2H-pyridine-1-carboxylate (110 mg, 0.20 mmol) in Ethanol (3 mL) and DCM (3 mL) was added Pd(OH)$_2$/C (50 mg, 0.47 mmol), the resulting mixture was degassed and purged with H$_2$ for 3 times, then stirred under H$_2$ at room temperature for 12 hr. The reaction mixture was filtered, and concentrated to obtain tert-butyl 4-[2-fluoro-4-hydroxy-3-(1,1,4-trioxo-1,2,5-thiadiazolidin-2-yl)phenyl]piperidine-1-carboxylate (70 mg, 0.16 mmol, 81% yield) as a light yellow oil, which was used directly in the next step without further purification. MS: m/z: Calc'd for C$_{18}$H$_{24}$FN$_3$O$_6$S [M+H]$^+$ 430; Found 374 [M+H−56]$^+$ Step 3: To a solution of tert-butyl 4-[2-fluoro-4-hydroxy-3-(1,1,4-trioxo-1,2,5-thiadiazolidin-2-yl)phenyl]piperidine-1-carboxylate (110 mg, 0.26 mmol) in DCM (2 mL) was added TFA (1 mL), the mixture was stirred at room temperature for 2 h. After evaporation of the solvent, the crude product was purified by Prep-HPLC to obtain 5-[2-fluoro-6-hydroxy-3-(4-piperidyl)phenyl]-1,1-dioxo-1,2,5-thiadiazolidin-3-one (13.8 mg, 0.04 mmol, 16% yield) as a purple solid. MS: m/z: Calc'd for C$_{13}$H$_{16}$FN$_3$O$_4$S [M+H]$^+$ 330; Found 330.

1H NMR (400 MHz, DMSO-d6) δ 7.14-7.07 (m, 1H), 6.79-6.73 (m, 1H), 3.97 (s, 2H), 3.42-3.36 (m, 2H), 3.16-2.95 (m, 3H), 2.02-1.65 (m, 4H).

Prep-HPLC conditions: XBridge Prep OBD C18 Column, 30*150 mm, 5 μm; Mobile Phase A: Water (10 mmol/L NH$_4$HCO$_3$), Mobile Phase B: ACN; Flow rate: 60 mL/min; Gradient: 2% B to 15% B in 8 min, 15% B; Wave Length: 254/220 nm.

Example 106: 5-(2-fluoro-6-hydroxy-3-(1-methylpiperidin-4-yl)phenyl)-1,2,5-thiadiazolidin-3-one 1,1-dioxide

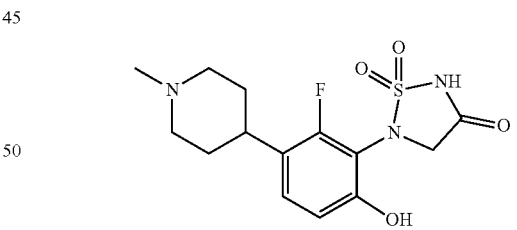

The title compound was prepared in 29% overall yield as a white solid according to the preparation of EXAMPLE 105 using 1-methyl-4-(4,4,5,5-tetramethyl-1,3,2-dioxaborolan-2-yl)-1,2,3,6-tetrahydropyridine in STEP 1. MS: m/z: Calc'd for C$_{14}$H$_{18}$FN$_3$O$_4$S [M+H]$^+$ 344; Found 344. $^1$H NMR (400 MHz, DMSO-d6) δ 8.90 (s, 1H), 7.12-7.05 (m, 1H), 6.75-6.63 (m, 1H), 3.95 (s, 2H), 3.42-3.33 (m, 2H), 2.98-2.94 (m, 3H), 2.69 (s, 3H), 2.03-1.70 (m, 4H).

Prep-HPLC conditions: XBridge Prep OBD C18 Column, 30*150 mm, 5 μm; Mobile Phase A: Water (10 mmol/L NH$_4$HCO$_3$), Mobile Phase B: ACN; Flow rate: 60 mL/min; Gradient: 2% B to 20% B in 7 min, 20% B; Wave Length: 254/220 nm.

Example Compounds Prepared in this Procedure are listed in Table 1

TABLE 1

| Compound number | Structure | Chemical name |
|---|---|---|
| EXAMPLE 1 | 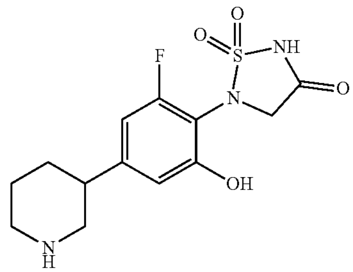 [SMILES: O=C1CN(c2c(O)cc(C3CCCNC3)cc2F)S(=O)(=O)N1] | 5-(2-fluoro-6-hydroxy-4-(piperidin-3-yl)phenyl)-1,2,5-thiadiazolidin-3-one 1,1-dioxide |
| EXAMPLE 2 | 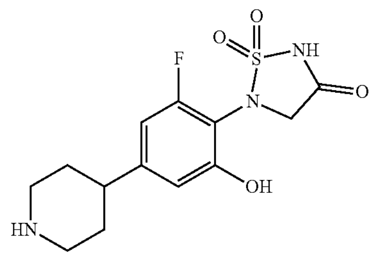 [SMILES: O=C1CN(c2c(O)cc(C3CCNCC3)cc2F)S(=O)(=O)N1] | 5-[2-fluoro-6-hydroxy-4-(4-piperidyl)phenyl]-1,1-dioxo-1,2,5-thiadiazolidin-3-one |
| EXAMPLE 3 | 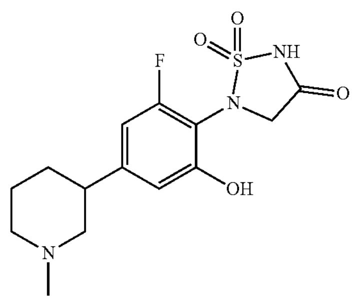 [SMILES: CN1CCCC(c2cc(O)c(N3CC(=O)NS3(=O)=O)c(F)c2)C1] | 5-(2-fluoro-6-hydroxy-4-(1-methylpiperidin-3-yl)phenyl)-1,2,5-thiadiazolidin-3-one 1,1-dioxide |
| EXAMPLE 4 | 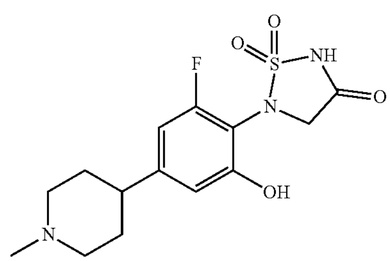 [SMILES: CN1CCC(c2cc(O)c(N3CC(=O)NS3(=O)=O)c(F)c2)CC1] | 5-[2-fluoro-6-hydroxy-4-(1-methyl-4-piperidyl)phenyl]-1,1-dioxo-1,2,5-thiadiazolidin-3-one |
| EXAMPLE 5 | 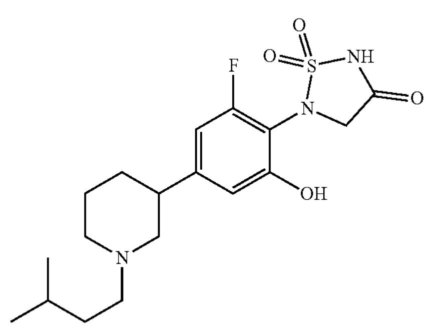 [SMILES: CC(C)CCN1CCCC(c2cc(O)c(N3CC(=O)NS3(=O)=O)c(F)c2)C1] | 5-(2-fluoro-6-hydroxy-4-(1-isopentylpiperidin-3-yl)phenyl)-1,2,5-thiadiazolidin-3-one 1,1-dioxide |

TABLE 1-continued

| Compound number | Structure | Chemical name |
|---|---|---|
| EXAMPLE 6 | 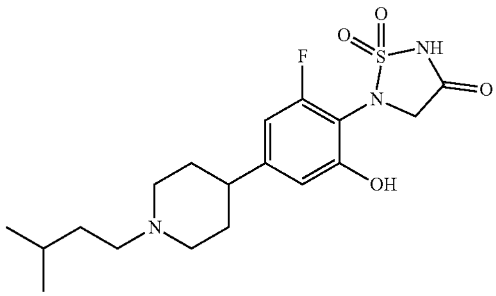 | 5-[2-fluoro-6-hydroxy-4-(1-isopentyl-4-piperidyl)phenyl]-1,1-dioxo-1,2,5-thiadiazolidin-3-one |
| EXAMPLE 7 | 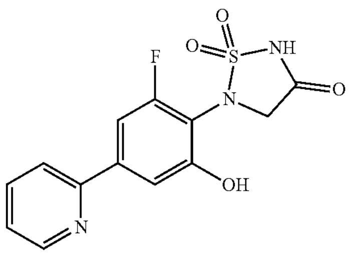 [SMILES: O=C1CN(c2c(O)cc(-c3ccccn3)cc2F)S(=O)(=O)N1] | 5-(2-fluoro-6-hydroxy-4-(pyridin-2-yl)phenyl)-1,2,5-thiadiazolidin-3-one 1,1-dioxide |
| EXAMPLE 8 | 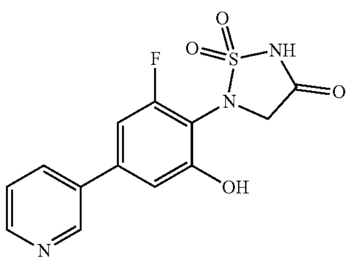 [SMILES: O=C1CN(c2c(O)cc(-c3cccnc3)cc2F)S(=O)(=O)N1] | 5-(2-fluoro-6-hydroxy-4-(pyridin-3-yl)phenyl)-1,2,5-thiadiazolidin-3-one 1,1-dioxide |
| EXAMPLE 9 | 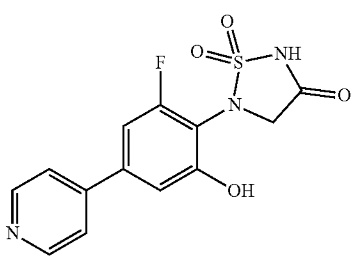 [SMILES: O=C1CN(c2c(O)cc(-c3ccncc3)cc2F)S(=O)(=O)N1] | 5-(2-fluoro-6-hydroxy-4-(pyridin-4-yl)phenyl)-1,2,5-thiadiazolidin-3-one 1,1-dioxide |
| EXAMPLE 10 | 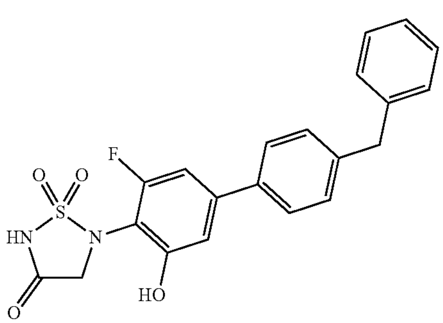 [SMILES: O=C1CN(c2c(O)cc(-c3ccc(Cc4ccccc4)cc3)cc2F)S(=O)(=O)N1] | 5-[4-(4-benzylphenyl)-2-fluoro-6-hydroxy-phenyl]-1,1-dioxo-1,2,5-thiadiazolidin-3-one |

TABLE 1-continued

| Compound number | Structure | Chemical name |
|---|---|---|
| EXAMPLE 11 | 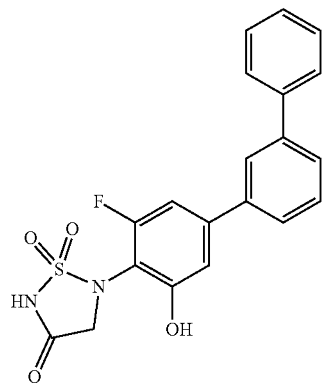 [SMILES: O=C1CN(c2c(O)cc(-c3cccc(-c4ccccc4)c3)cc2F)S(=O)(=O)N1] | 5-[2-fluoro-6-hydroxy-4-(3-phenylphenyl)phenyl]-1,1-dioxo-1,2,5-thiadiazolidin-3-one |
| EXAMPLE 12 | 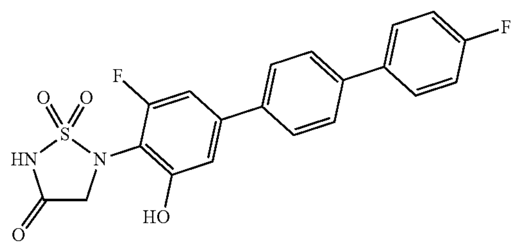 [SMILES: O=C1CN(c2c(O)cc(-c3ccc(-c4ccc(F)cc4)cc3)cc2F)S(=O)(=O)N1] | 5-[2-fluoro-4-[4-(4-fluorophenyl)phenyl]-6-hydroxy-phenyl]-1,1-dioxo-1,2,5-thiadiazolidin-3-one |
| EXAMPLE 13 | 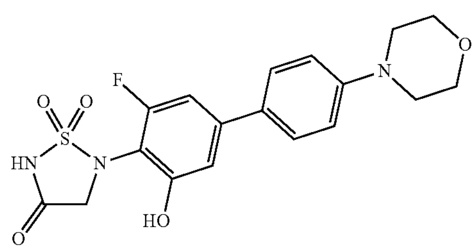 [SMILES: O=C1CN(c2c(O)cc(-c3ccc(N4CCOCC4)cc3)cc2F)S(=O)(=O)N1] | 5-[2-fluoro-6-hydroxy-4-(4-morpholinophenyl)phenyl]-1,1-dioxo-1,2,5-thiadiazolidin-3-one |
| EXAMPLE 14 | 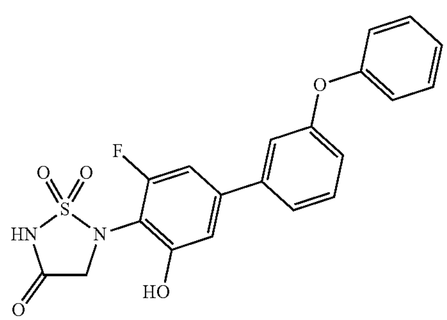 [SMILES: O=C1CN(c2c(O)cc(-c3cccc(Oc4ccccc4)c3)cc2F)S(=O)(=O)N1] | 5-[2-fluoro-6-hydroxy-4-(3-phenoxyphenyl)phenyl]-1,1-dioxo-1,2,5-thiadiazolidin-3-one |
| EXAMPLE 15 | 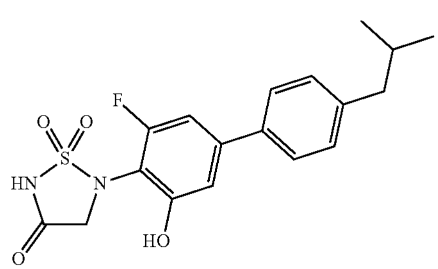 [SMILES: CC(C)Cc1ccc(-c2cc(O)c(N3CC(=O)NS3(=O)=O)c(F)c2)cc1] | 5-[2-fluoro-6-hydroxy-4-(4-isobutylphenyl)phenyl]-1,1-dioxo-1,2,5-thiadiazolidin-3-one |

TABLE 1-continued

| Compound number | Structure | Chemical name |
| --- | --- | --- |
| EXAMPLE 16 | 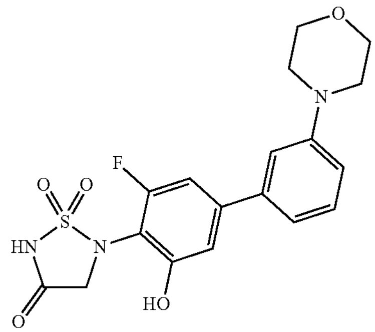 [SMILES: O=C1CN(c2c(O)cc(-c3cccc(N4CCOCC4)c3)cc2F)S(=O)(=O)N1] | 5-[2-fluoro-6-hydroxy-4-(3-morpholinophenyl)phenyl]-1,1-dioxo-1,2,5-thiadiazolidin-3-one |
| EXAMPLE 17 | 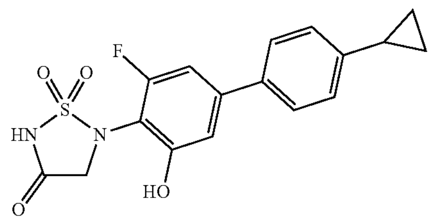 [SMILES: O=C1CN(c2c(O)cc(-c3ccc(C4CC4)cc3)cc2F)S(=O)(=O)N1] | 5-[4-(4-cyclopropylphenyl)-2-fluoro-6-hydroxy-phenyl]-1,1-dioxo-1,2,5-thiadiazolidin-3-one |
| EXAMPLE 18 | 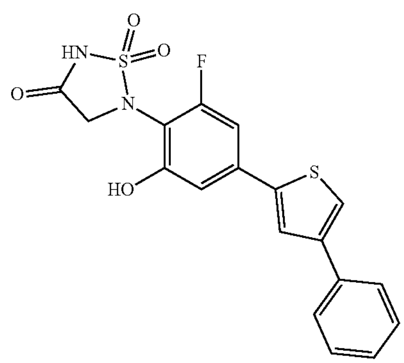 [SMILES: O=C1CN(c2c(O)cc(-c3cc(-c4ccccc4)cs3)cc2F)S(=O)(=O)N1] | 5-[2-fluoro-6-hydroxy-4-(4-phenyl-2-thienyl)phenyl]-1,1-dioxo-1,2,5-thiadiazolidin-3-one |
| EXAMPLE 19 | 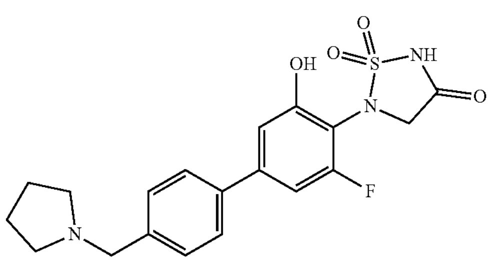 [SMILES: O=C1CN(c2c(O)cc(-c3ccc(CN4CCCC4)cc3)cc2F)S(=O)(=O)N1] | 5-[2-fluoro-6-hydroxy-4-[4-(pyrrolidin-1-ylmethyl)phenyl]phenyl]-1,1-dioxo-1,2,5-thiadiazolidin-3-one |
| EXAMPLE 20 | 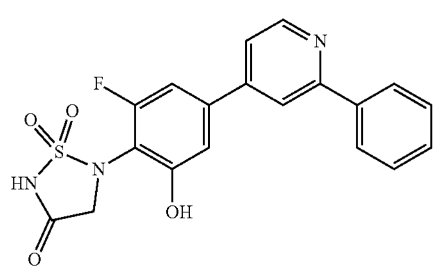 [SMILES: O=C1CN(c2c(O)cc(-c3ccnc(-c4ccccc4)c3)cc2F)S(=O)(=O)N1] | 5-[2-fluoro-6-hydroxy-4-(2-phenyl-4-pyridyl)phenyl]-1,1-dioxo-1,2,5-thiadiazolidin-3-one |

TABLE 1-continued

| Compound number | Structure | Chemical name |
| --- | --- | --- |
| EXAMPLE 21 | 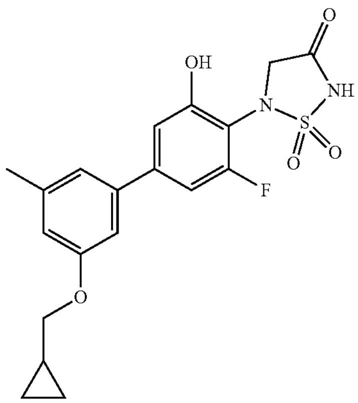 [SMILES: Cc1cc(OCC2CC2)cc(-c2cc(O)c(N3CC(=O)NS3(=O)=O)c(F)c2)c1] | 5-[4-[3-(cyclopropylmethoxy)-5-methyl-phenyl]-2-fluoro-6-hydroxy-phenyl]-1,1-dioxo-1,2,5-thiadiazolidin-3-one |
| EXAMPLE 22 | 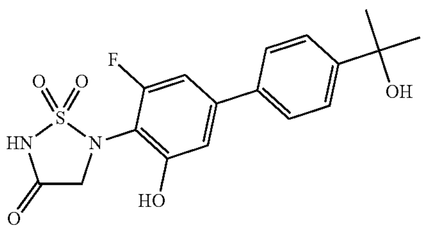 [SMILES: CC(C)(O)c1ccc(-c2cc(O)c(N3CC(=O)NS3(=O)=O)c(F)c2)cc1] | 5-[2-fluoro-6-hydroxy-4-[4-(1-hydroxy-1-methyl-ethyl)phenyl]phenyl]-1,1-dioxo-1,2,5-thiadiazolidin-3-one |
| EXAMPLE 23 | 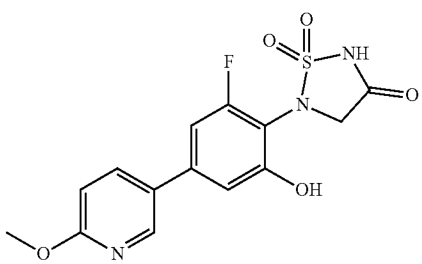 [SMILES: COc1ccc(-c2cc(O)c(N3CC(=O)NS3(=O)=O)c(F)c2)cn1] | 5-[2-fluoro-6-hydroxy-4-(6-methoxy-3-pyridyl)phenyl]-1,1-dioxo-1,2,5-thiadiazolidin-3-one |
| EXAMPLE 24 | 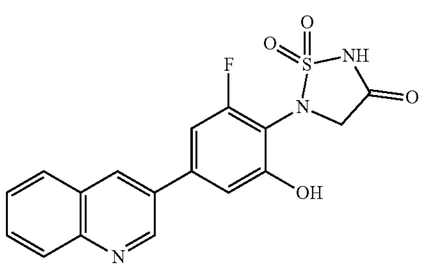 [SMILES: O=C1CN(c2c(O)cc(-c3cnc4ccccc4c3)cc2F)S(=O)(=O)N1] | 5-[2-fluoro-6-hydroxy-4-(3-quinolyl)phenyl]-1,1-dioxo-1,2,5-thiadiazolidin-3-one |
| EXAMPLE 25 | 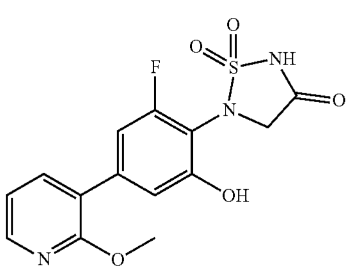 [SMILES: COc1ncccc1-c1cc(O)c(N2CC(=O)NS2(=O)=O)c(F)c1] | 5-[2-fluoro-6-hydroxy-4-(2-methoxy-3-pyridyl)phenyl]-1,1-dioxo-1,2,5-thiadiazolidin-3-one |

TABLE 1-continued

| Compound number | Structure | Chemical name |
|---|---|---|
| EXAMPLE 26 | 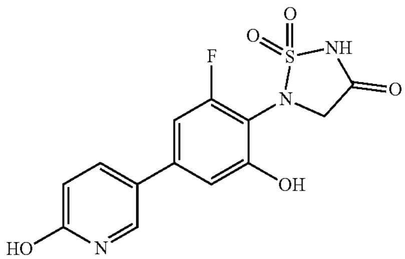 [SMILES: O=C1CN(c2c(O)cc(-c3ccc(O)nc3)cc2F)S(=O)(=O)N1] | 5-[2-fluoro-6-hydroxy-4-(6-hydroxy-3-pyridyl)phenyl]-1,1-dioxo-1,2,5-thiadiazolidin-3-one |
| EXAMPLE 27 | 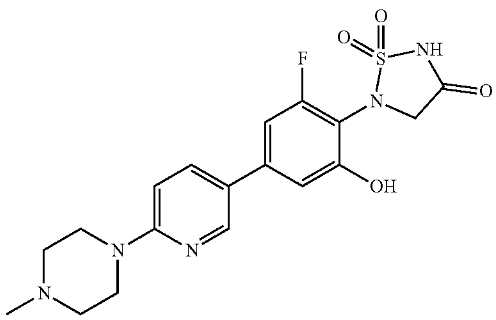 [SMILES: CN1CCN(c2ccc(-c3cc(O)c(N4CC(=O)NS4(=O)=O)c(F)c3)cn2)CC1] | 5-[2-fluoro-6-hydroxy-4-[6-(4-methylpiperazin-1-yl)-3-pyridyl]phenyl]-1,1-dioxo-1,2,5-thiadiazolidin-3-one |
| EXAMPLE 28 | 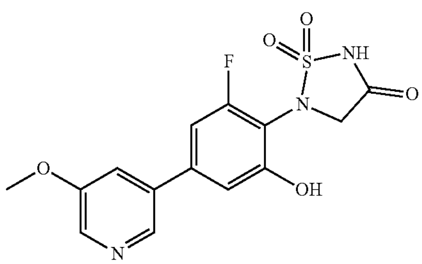 [SMILES: COc1cncc(-c2cc(O)c(N3CC(=O)NS3(=O)=O)c(F)c2)c1] | 5-[2-fluoro-6-hydroxy-4-(5-methoxy-3-pyridyl)phenyl]-1,1-dioxo-1,2,5-thiadiazolidin-3-one |
| EXAMPLE 29 | 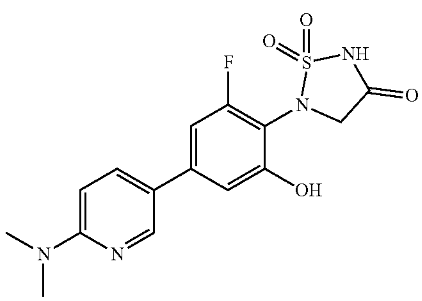 [SMILES: CN(C)c1ccc(-c2cc(O)c(N3CC(=O)NS3(=O)=O)c(F)c2)cn1] | 5-[4-[6-(dimethylamino)-3-pyridyl]-2-fluoro-6-hydroxy-phenyl]-1,1-dioxo-1,2,5-thiadiazolidin-3-one |
| EXAMPLE 30 | 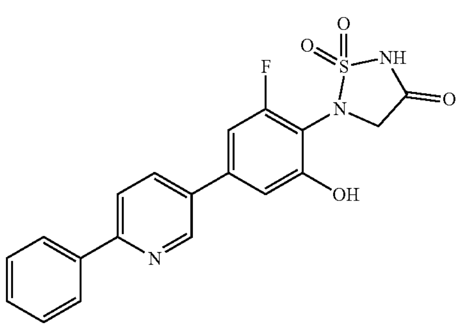 [SMILES: O=C1CN(c2c(O)cc(-c3ccc(-c4ccccc4)nc3)cc2F)S(=O)(=O)N1] | 5-[2-fluoro-6-hydroxy-4-(6-phenyl-3-pyridyl)phenyl]-1,1-dioxo-1,2,5-thiadiazolidin-3-one |

TABLE 1-continued

| Compound number | Structure | Chemical name |
| --- | --- | --- |
| EXAMPLE 31 | 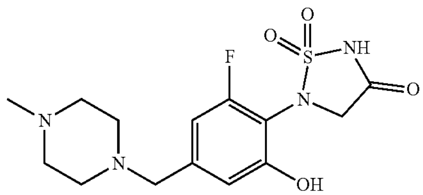 [SMILES: CN1CCN(Cc2cc(O)c(N3CC(=O)NS3(=O)=O)c(F)c2)CC1] | 5-(2-fluoro-6-hydroxy-4-((4-methylpiperazin-1-yl)methyl)phenyl)-1,2,5-thiadiazolidin-3-one 1,1-dioxide |
| EXAMPLE 32 | 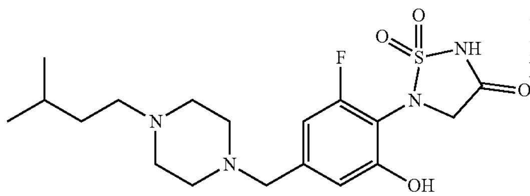 [SMILES: CC(C)CCN1CCN(Cc2cc(O)c(N3CC(=O)NS3(=O)=O)c(F)c2)CC1] | 5-(2-fluoro-6-hydroxy-4-((4-isopentylpiperazin-1-yl)methyl)phenyl)-1,2,5-thiadiazolidin-3-one 1,1-dioxide |
| EXAMPLE 33 | 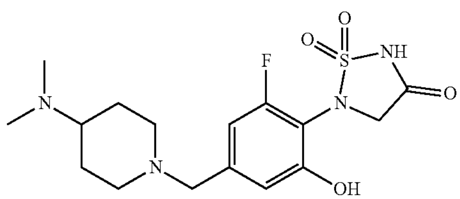 [SMILES: CN(C)C1CCN(Cc2cc(O)c(N3CC(=O)NS3(=O)=O)c(F)c2)CC1] | 5-(4-((4-(dimethylamino)piperidin-1-yl)methyl)-2-fluoro-6-hydroxyphenyl)-1,2,5-thiadiazolidin-3-one 1,1-dioxide |
| EXAMPLE 34 | 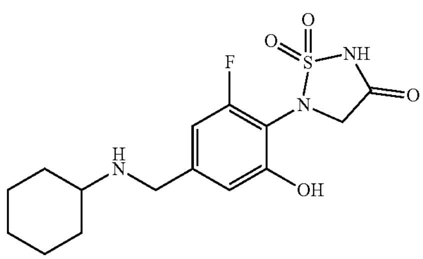 | 5-[4-[(cyclohexylamino)methyl]-2-fluoro-6-hydroxy-phenyl]-1,1-dioxo-1,2,5-thiadiazolidin-3-one |
| EXAMPLE 35 | 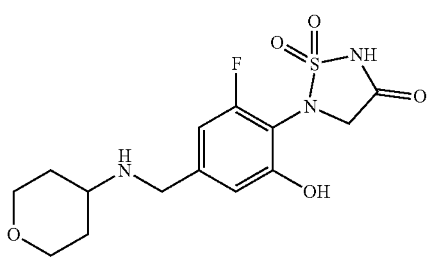 [SMILES: O=C1CN(c2c(O)cc(CNC3CCOCC3)cc2F)S(=O)(=O)N1] | 5-[2-fluoro-6-hydroxy-4-[(tetrahydropyran-4-ylamino)methyl]phenyl]-1,1-dioxo-1,2,5-thiadiazolidin-3-one |
| EXAMPLE 36 | 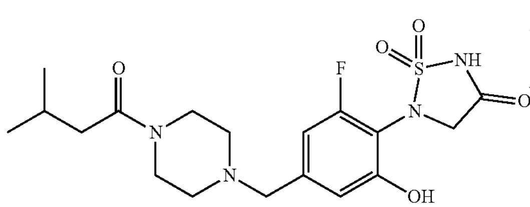 [SMILES: CC(C)CC(=O)N1CCN(Cc2cc(O)c(N3CC(=O)NS3(=O)=O)c(F)c2)CC1] | 5-(2-fluoro-6-hydroxy-4-((4-(3-methylbutanoyl)piperazin-1-yl)methyl)phenyl)-1,2,5-thiadiazolidin-3-one 1,1-dioxide |

TABLE 1-continued

| Compound number | Structure | Chemical name |
|---|---|---|
| EXAMPLE 37 | 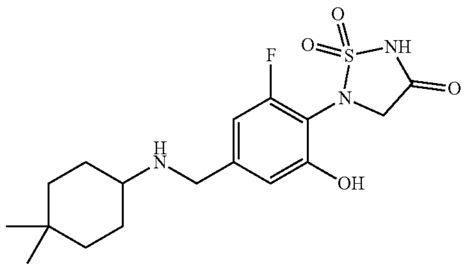 [SMILES: CC1(C)CCC(NCc2cc(O)c(N3CC(=O)NS3(=O)=O)c(F)c2)CC1] | 5-(4-(((4,4-dimethylcyclohexyl)amino)methyl)-2-fluoro-6-hydroxyphenyl)-1,2,5-thiadiazolidin-3-one 1,1-dioxide |
| EXAMPLE 38 | 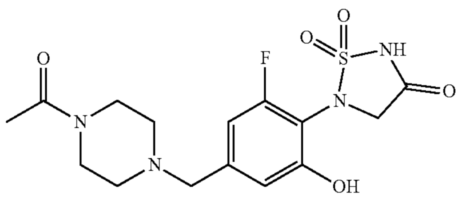 [SMILES: CC(=O)N1CCN(Cc2cc(O)c(N3CC(=O)NS3(=O)=O)c(F)c2)CC1] | 5-(4-((4-acetylpiperazin-1-yl)methyl)-2-fluoro-6-hydroxyphenyl)-1,2,5-thiadiazolidin-3-one 1,1-dioxide |
| EXAMPLE 39 | 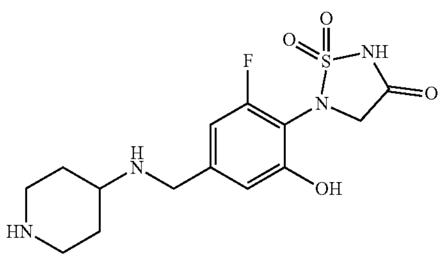 [SMILES: O=C1CN(c2c(O)cc(CNC3CCNCC3)cc2F)S(=O)(=O)N1] | 5-(2-fluoro-6-hydroxy-4-((piperidin-4-ylamino)methyl)phenyl)-1,2,5-thiadiazolidin-3-one 1,1-dioxide |
| EXAMPLE 40 | 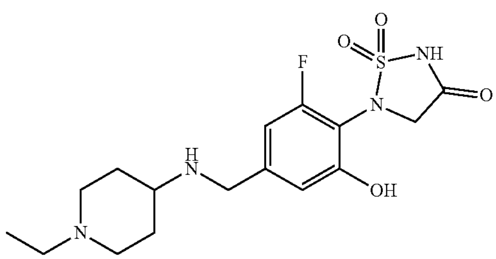 [SMILES: CCN1CCC(NCc2cc(O)c(N3CC(=O)NS3(=O)=O)c(F)c2)CC1] | 5-(4-(((1-ethylpiperidin-4-yl)amino)methyl)-2-fluoro-6-hydroxyphenyl)-1,2,5-thiadiazolidin-3-one 1,1-dioxide |
| EXAMPLE 41 | 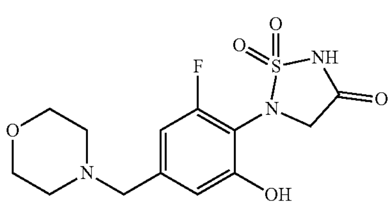 [SMILES: O=C1CN(c2c(O)cc(CN3CCOCC3)cc2F)S(=O)(=O)N1] | 5-(2-fluoro-6-hydroxy-4-(morpholinomethyl)phenyl)-1,2,5-thiadiazolidin-3-one 1,1-dioxide |
| EXAMPLE 42 | 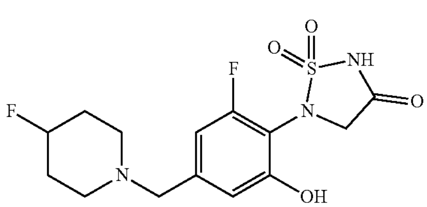 [SMILES: O=C1CN(c2c(O)cc(CN3CCC(F)CC3)cc2F)S(=O)(=O)N1] | 5-(2-fluoro-4-((4-fluoropiperidin-1-yl)methyl)-6-hydroxyphenyl)-1,2,5-thiadiazolidin-3-one 1,1-dioxide |

TABLE 1-continued

| Compound number | Structure | Chemical name |
|---|---|---|
| EXAMPLE 43 | 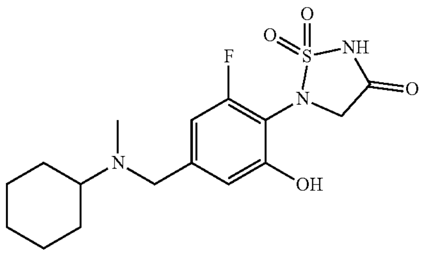 | 5-(4-((cyclohexyl(methyl)amino)methyl)-2-fluoro-6-hydroxyphenyl)-1,2,5-thiadiazolidin-3-one 1,1-dioxide |
| EXAMPLE 44 | 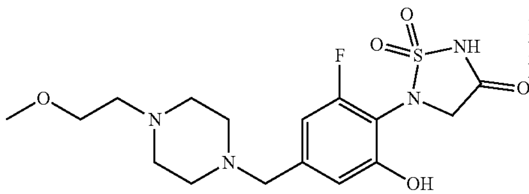 [SMILES: COCCN1CCN(Cc2cc(O)c(N3CC(=O)NS3(=O)=O)c(F)c2)CC1] | 5-(2-fluoro-6-hydroxy-4-((4-(2-methoxyethyl)piperazin-1-yl)methyl)phenyl)-1,2,5-thiadiazolidin-3-one 1,1-dioxide |
| EXAMPLE 45 | 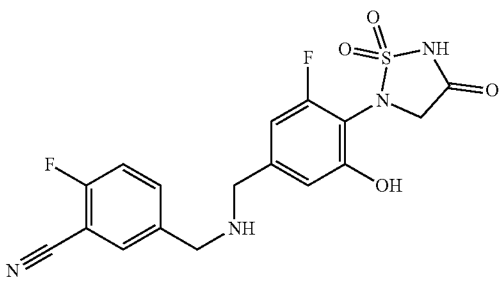 [SMILES: N#Cc1cc(CNCc2cc(O)c(N3CC(=O)NS3(=O)=O)c(F)c2)ccc1F] | 2-fluoro-5-[[[3-fluoro-5-hydroxy-4-(1,1,4-trioxo-1,2,5-thiadiazolidin-2-yl)phenyl]methylamino]methyl]benzonitrile |
| EXAMPLE 46 | 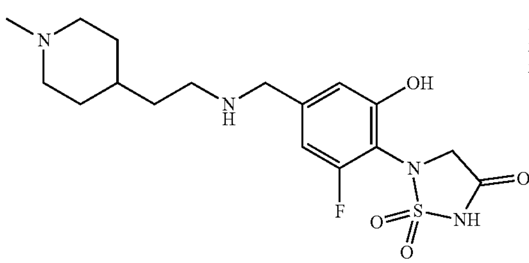 [SMILES: CN1CCC(CCNCc2cc(O)c(N3CC(=O)NS3(=O)=O)c(F)c2)CC1] | 5-[2-fluoro-6-hydroxy-4-[[2-(1-methyl-4-piperidyl)ethylamino]methyl]phenyl]-1,1-dioxo-1,2,5-thiadiazolidin-3-one |
| EXAMPLE 47 | 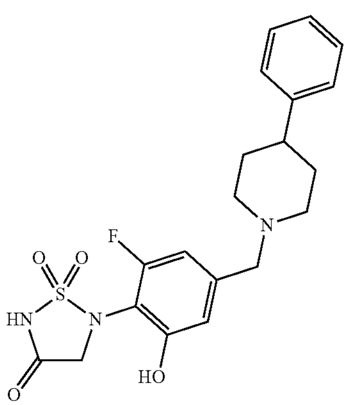 [SMILES: O=C1CN(c2c(O)cc(CN3CCC(c4ccccc4)CC3)cc2F)S(=O)(=O)N1] | 5-[2-fluoro-6-hydroxy-4-[(4-phenyl-1-piperidyl)methyl]phenyl]-1,1-dioxo-1,2,5-thiadiazolidin-3-one |

TABLE 1-continued

| Compound number | Structure | Chemical name |
|---|---|---|
| EXAMPLE 48 | 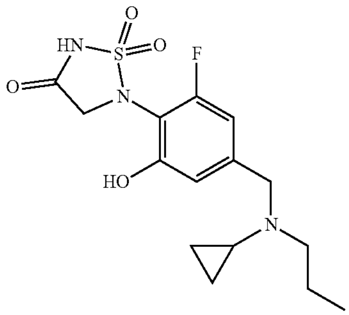 [SMILES: CCCN(Cc1cc(O)c(N2CC(=O)NS2(=O)=O)c(F)c1)C1CC1] | 5-[4-[cyclopropyl(propyl)amino]methyl]-2-fluoro-6-hydroxy-phenyl]-1,1-dioxo-1,2,5-thiadiazolidin-3-one |
| EXAMPLE 49 | 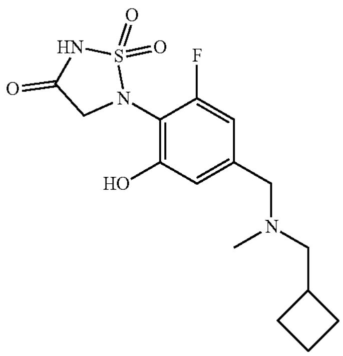 [SMILES: CN(Cc1cc(O)c(N2CC(=O)NS2(=O)=O)c(F)c1)CC1CCC1] | 5-[4-[[cyclobutylmethyl(methyl)amino]methyl]-2-fluoro-6-hydroxy-phenyl]-1,1-dioxo-1,2,5-thiadiazolidin-3-one |
| EXAMPLE 50 | 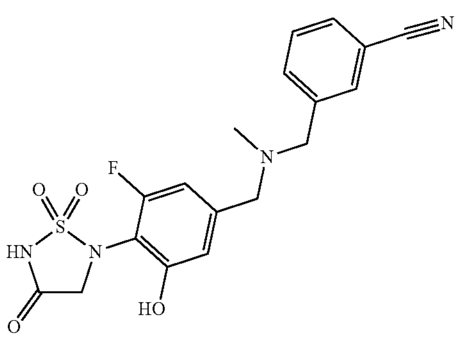 [SMILES: CN(Cc1cccc(C#N)c1)Cc1cc(O)c(N2CC(=O)NS2(=O)=O)c(F)c1] | 3-[[[3-fluoro-5-hydroxy-4-(1,1,4-trioxo-1,2,5-thiadiazolidin-2-yl)phenyl]methyl-methyl-amino]methyl]benzonitrile |
| EXAMPLE 51 | 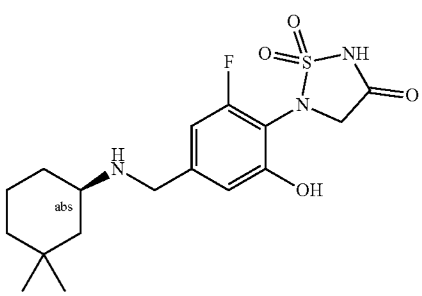 [SMILES: CC1(C)CCC[C@@H](NCc2cc(O)c(N3CC(=O)NS3(=O)=O)c(F)c2)C1] | 5-[4-[[[(1R)-3,3-dimethyl-cyclohexyl]amino]methyl]-2-fluoro-6-hydroxy-phenyl]-1,1-dioxo-1,2,5-thiadiazolidin-3-one |
| EXAMPLE 52 | 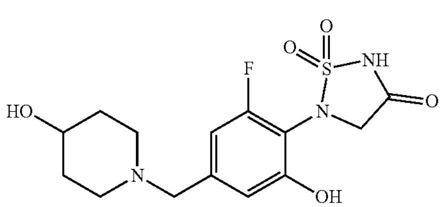 [SMILES: O=C1CN(c2c(O)cc(CN3CCC(O)CC3)cc2F)S(=O)(=O)N1] | 5-[2-fluoro-6-hydroxy-4-[(4-hydroxy-1-piperidyl)methyl]phenyl]-1,1-dioxo-1,2,5-thiadiazolidin-3-one |

TABLE 1-continued

| Compound number | Structure | Chemical name |
|---|---|---|
| EXAMPLE 53 | 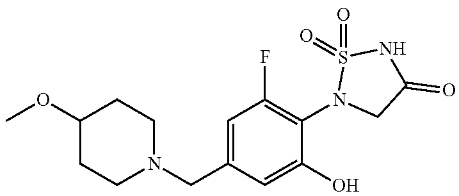 [SMILES: COC1CCN(Cc2cc(O)c(N3CC(=O)NS3(=O)=O)c(F)c2)CC1] | 5-[2-fluoro-6-hydroxy-4-[(4-methoxy-1-piperidyl)methyl]phenyl]-1,1-dioxo-1,2,5-thiadiazolidin-3-one |
| EXAMPLE 54 | 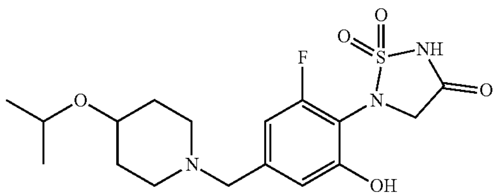 [SMILES: CC(C)OC1CCN(Cc2cc(O)c(N3CC(=O)NS3(=O)=O)c(F)c2)CC1] | 5-[2-fluoro-6-hydroxy-4-[(4-isopropoxy-1-piperidyl)methyl]phenyl]-1,1-dioxo-1,2,5-thiadiazolidin-3-one |
| EXAMPLE 55 | 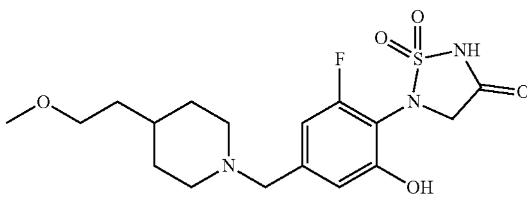 [SMILES: COCCC1CCN(Cc2cc(O)c(N3CC(=O)NS3(=O)=O)c(F)c2)CC1] | 5-[2-fluoro-6-hydroxy-4-[4-(2-methoxyethyl)-1-piperidyl]methyl]phenyl]-1,1-dioxo-1,2,5-thiadiazolidin-3-one |
| EXAMPLE 56 | 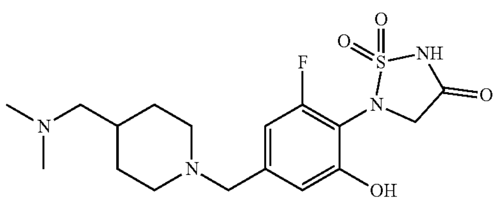 [SMILES: CN(C)CC1CCN(Cc2cc(O)c(N3CC(=O)NS3(=O)=O)c(F)c2)CC1] | 5-[4-[[4-[(dimethylamino)methyl]-1-piperidyl]methyl]-2-fluoro-6-hydroxy-phenyl]-1,1-dioxo-1,2,5-thiadiazolidin-3-one |
| EXAMPLE 57 | 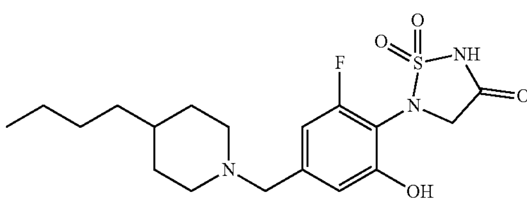 | 5-[4-[(4-butyl-1-piperidyl)methyl]-2-fluoro-6-hydroxy-phenyl]-1,1-dioxo-1,2,5-thiadiazolidin-3-one |
| EXAMPLE 58 | 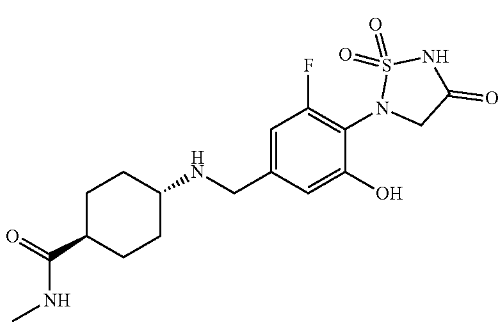 [SMILES: CNC(=O)[C@H]1CC[C@H](NCc2cc(O)c(N3CC(=O)NS3(=O)=O)c(F)c2)CC1] | (1r,4r)-4-((4-(1,1-dioxido-4-oxo-1,2,5-thiadiazolidin-2-yl)-3-fluoro-5-hydroxybenzyl)amino)-N-methylcyclohexane-1-carboxamide |
| EXAMPLE 59 | 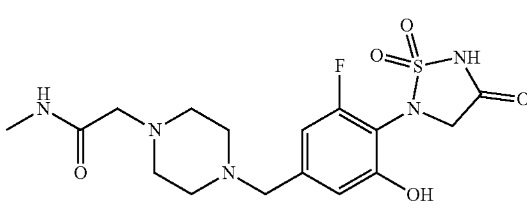 [SMILES: CNC(=O)CN1CCN(Cc2cc(O)c(N3CC(=O)NS3(=O)=O)c(F)c2)CC1] | 2-(4-(4-(1,1-dioxido-4-oxo-1,2,5-thiadiazolidin-2-yl)-3-fluoro-5-hydroxy benzyl)piperazin-1-yl)-N-methylacetamide |

TABLE 1-continued

| Compound number | Structure | Chemical name |
|---|---|---|
| EXAMPLE 60 | 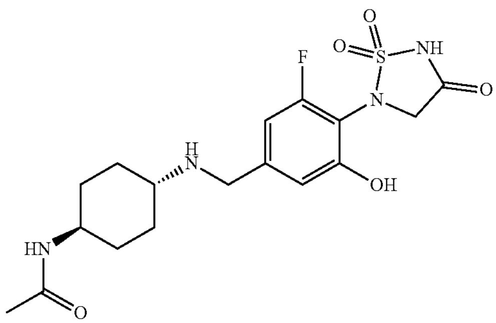 [SMILES: CC(=O)N[C@H]1CC[C@H](NCc2cc(O)c(N3CC(=O)NS3(=O)=O)c(F)c2)CC1] | N-((1r,4r)-4-((4-(1,1-dioxido-4-oxo-1,2,5-thiadiazolidin-2-yl)-3-fluoro-5-hydroxybenzyl)amino)cyclohexyl)acetamide |
| EXAMPLE 61 | 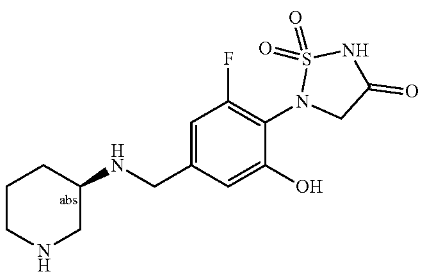 [SMILES: O=C1CN(c2c(O)cc(CN[C@@H]3CCCNC3)cc2F)S(=O)(=O)N1] | (R)-5-(2-fluoro-6-hydroxy-4-((piperidin-3-ylamino)methyl)phenyl)-1,2,5-thiadiazolidin-3-one 1,1-dioxide |
| EXAMPLE 62 | 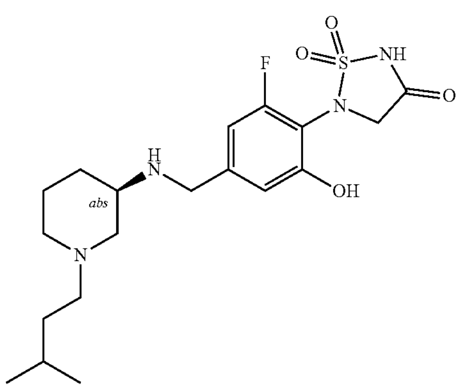 [SMILES: CC(C)CCN1CCC[C@@H](NCc2cc(O)c(N3CC(=O)NS3(=O)=O)c(F)c2)C1] | (R)-5-(2-fluoro-6-hydroxy-4-(((1-isopentylpiperidin-3-yl)amino)methyl)phenyl)-1,2,5-thiadiazolidin-3-one 1,1-dioxide |
| EXAMPLE 63 | 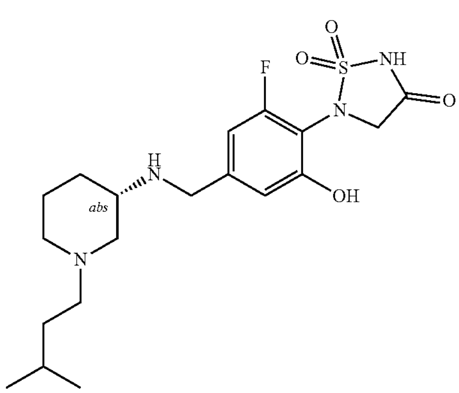 [SMILES: CC(C)CCN1CCC[C@H](NCc2cc(O)c(N3CC(=O)NS3(=O)=O)c(F)c2)C1] | 5-[2-fluoro-6-hydroxy-4-[[[(3S)-1-isopentyl-3-piperidyl]amino]methyl]phenyl]-1,1-dioxo-1,2,5-thiadiazolidin-3-one |

TABLE 1-continued

| Compound number | Structure | Chemical name |
|---|---|---|
| EXAMPLE 64 | 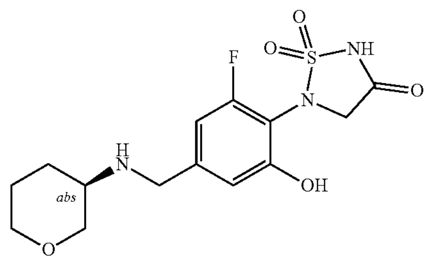 [SMILES: O=C1CN(c2c(O)cc(CN[C@@H]3CCCOC3)cc2F)S(=O)(=O)N1] | (R)-5-(2-fluoro-6-hydroxy-4-(((tetrahydro-2H-pyran-3-yl)amino)methyl)phenyl)-1,2,5-thiadiazolidin-3-one 1,1-dioxide |
| EXAMPLE 65 | 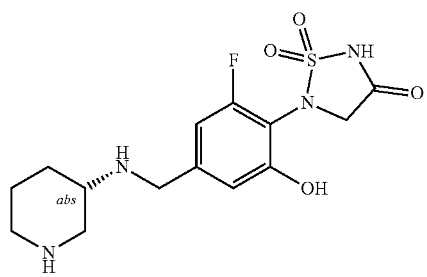 | (S)-5-(2-fluoro-6-hydroxy-4-((piperidin-3-ylamino)methyl)phenyl)-1,2,5-thiadiazolidin-3-one 1,1-dioxide |
| EXAMPLE 66 | 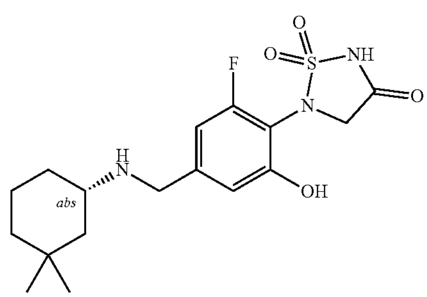 [SMILES: CC1(C)CCC[C@H](NCc2cc(O)c(N3CC(=O)NS3(=O)=O)c(F)c2)C1] | (S)-5-(4-(((3,3-dimethylcyclohexyl)amino)methyl)-2-fluoro-6-hydroxyphenyl)-1,2,5-thiadiazolidin-3-one 1,1-dioxide |
| EXAMPLE 67 | 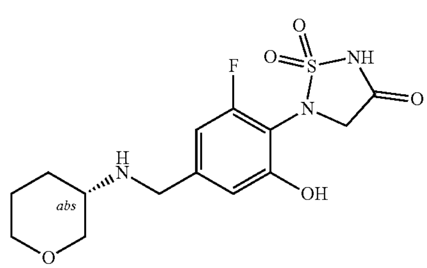 [SMILES: O=C1CN(c2c(O)cc(CN[C@H]3CCCOC3)cc2F)S(=O)(=O)N1] | (S)-5-(2-fluoro-6-hydroxy-4-(((tetrahydro-2H-pyran-3-yl)amino)methyl)phenyl)-1,2,5-thiadiazolidin-3-one 1,1-dioxide |
| EXAMPLE 68 | 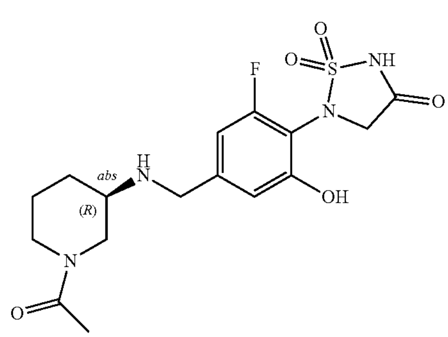 | 5-[4-[[[(3R)-1-acetyl-3-piperidyl]amino]methyl]-2-fluoro-6-hydroxy-phenyl]-1,1-dioxo-1,2,5-thiadiazolidin-3-one |

TABLE 1-continued

| Compound number | Structure | Chemical name |
|---|---|---|
| EXAMPLE 69 | 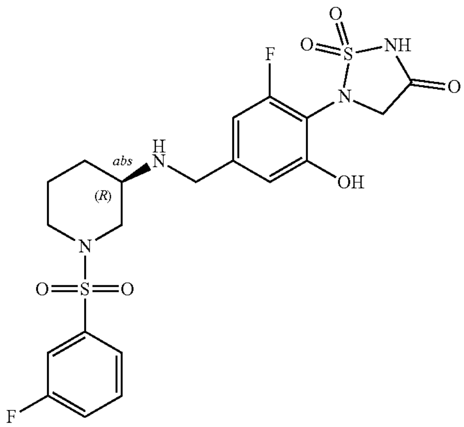 | 5-[2-fluoro-4-[[[(3R)-1-(3-fluorophenyl)sulfonyl-3-piperidyl]amino]methyl]-6-hydroxy-phenyl]-1,1-dioxo-1,2,5-thiadiazolidin-3-one |
| EXAMPLE 70 | 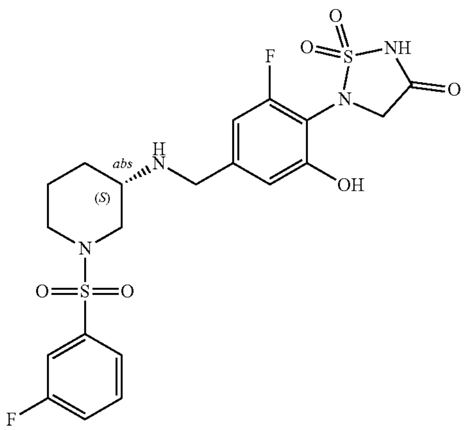 | 5-[2-fluoro-4-[[[(3S)-1-(3-fluorophenyl)sulfonyl-3-piperidyl]amino]methyl]-6-hydroxy-phenyl]-1,1-dioxo-1,2,5-thiadiazolidin-3-one |
| EXAMPLE 71 | 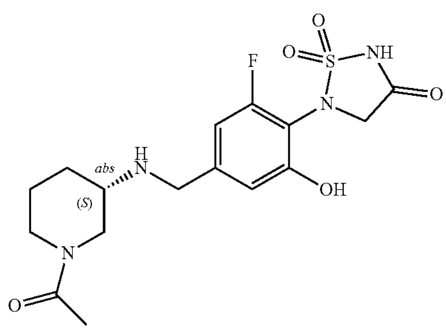 | 5-[4-[[[(3S)-1-acetyl-3-piperidyl]amino]methyl]-2-fluoro-6-hydroxy-phenyl]-1,1-dioxo-1,2,5-thiadiazolidin-3-one |
| EXAMPLE 72 | 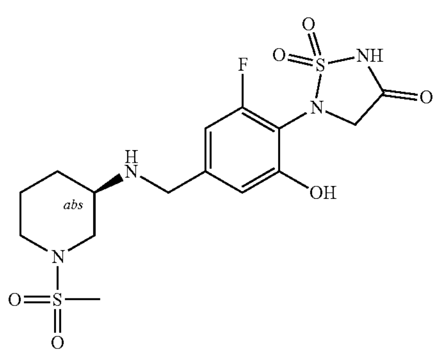 [SMILES: CS(=O)(=O)N1CCC[C@@H](NCc2cc(O)c(N3CC(=O)NS3(=O)=O)c(F)c2)C1] | 5-[2-fluoro-6-hydroxy-4-[[[(3R)-1-methylsulfonyl-3-piperidyl]amino]methyl]phenyl]-1,1-dioxo-1,2,5-thiadiazolidin-3-one |

TABLE 1-continued

| Compound number | Structure | Chemical name |
|---|---|---|
| EXAMPLE 73 | 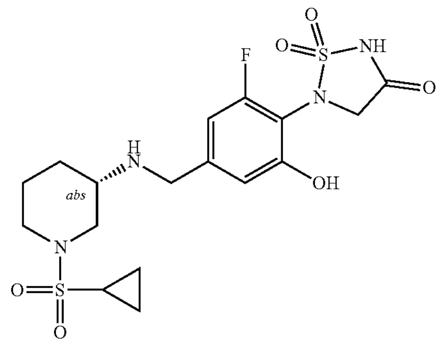 [SMILES: O=C1CN(c2c(O)cc(CN[C@H]3CCCN(S(=O)(=O)C4CC4)C3)cc2F)S(=O)(=O)N1] | 5-[4-[[[(3S)-1-cyclopropyl-sulfonyl-3-piperidyl]amino]methyl]-2-fluoro-6-hydroxy-phenyl]-1,1-dioxo-1,2,5-thiadiazolidin-3-one |
| EXAMPLE 74 | 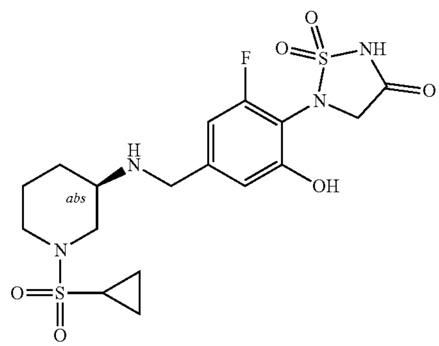 [SMILES: O=C1CN(c2c(O)cc(CN[C@@H]3CCCN(S(=O)(=O)C4CC4)C3)cc2F)S(=O)(=O)N1] | 5-[4-[[[(3R)-1-cyclopropyl-sulfonyl-3-piperidyl]amino]methyl]-2-fluoro-6-hydroxy-phenyl]-1,1-dioxo-1,2,5-thiadiazolidin-3-one |
| EXAMPLE 75 | 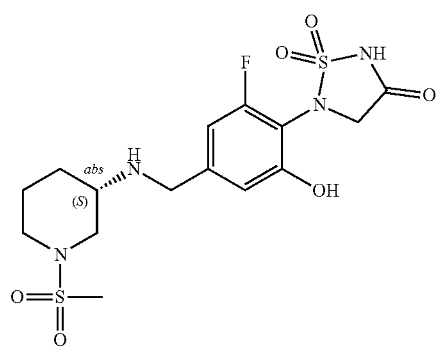 | 5-[2-fluoro-6-hydroxy-4-[[[(3S)-1-methylsulfonyl-3-piperidyl]amino]methyl]phenyl]-1,1-dioxo-1,2,5-thiadiazolidin-3-one |
| EXAMPLE 76 | 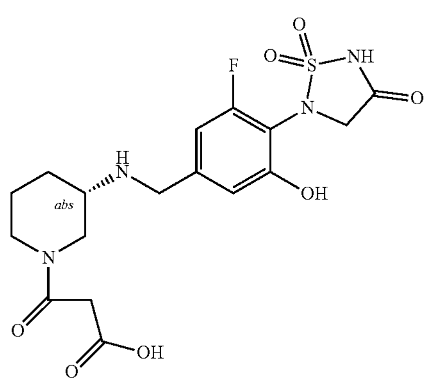 [SMILES: O=C(O)CC(=O)N1CCC[C@H](NCc2cc(O)c(N3CC(=O)NS3(=O)=O)c(F)c2)C1] | 3-[(3S)-3-[[3-fluoro-5-hydroxy-4-(1,1,4-trioxo-1,2,5-thiadiazolidin-2-yl)phenyl]methylamino]-1-piperidyl]-3-oxo-propanoic acid |

TABLE 1-continued

| Compound number | Structure | Chemical name |
|---|---|---|
| EXAMPLE 77 | 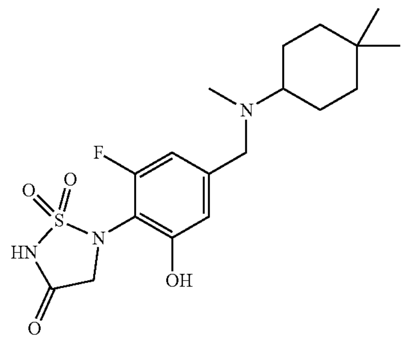 [SMILES: CN(Cc1cc(O)c(N2CC(=O)NS2(=O)=O)c(F)c1)C1CCC(C)(C)CC1] | 5-[4-[[(4,4-dimethylcyclohexyl)-methyl-amino]methyl]-2-fluoro-6-hydroxy-phenyl]-1,1-dioxo-1,2,5-thiadiazolidin-3-one |
| EXAMPLE 78 | 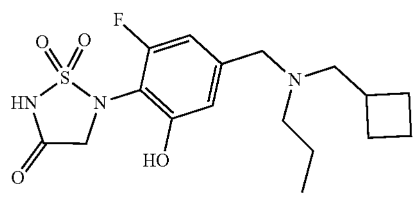 [SMILES: CCCN(Cc1cc(O)c(N2CC(=O)NS2(=O)=O)c(F)c1)CC1CCC1] | 5-[4-[cyclobutylmethyl(propyl)amino]methyl]-2-fluoro-6-hydroxy-phenyl]-1,1-dioxo-1,2,5-thiadiazolidin-3-one |
| EXAMPLE 79 | 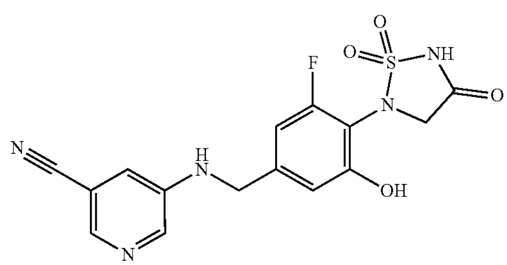 [SMILES: N#Cc1cncc(NCc2cc(O)c(N3CC(=O)NS3(=O)=O)c(F)c2)c1] | 5-[[3-fluoro-5-hydroxy-4-(1,1,4-trioxo-1,2,5-thiadiazolidin-2-yl)phenyl]methylamino]pyridine-3-carbonitrile |
| EXAMPLE 80 | 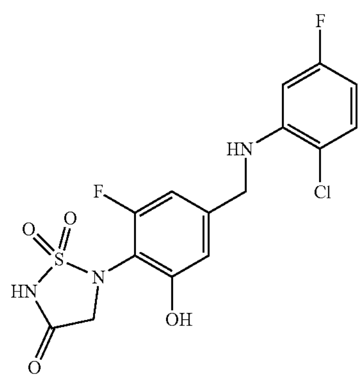 [SMILES: O=C1CN(c2c(O)cc(CNc3cc(F)ccc3Cl)cc2F)S(=O)(=O)N1] | 5-[4-[(2-chloro-5-fluoro-anilino)methyl]-2-fluoro-6-hydroxy-phenyl]-1,1-dioxo-1,2,5-thiadiazolidin-3-one |
| EXAMPLE 81 | 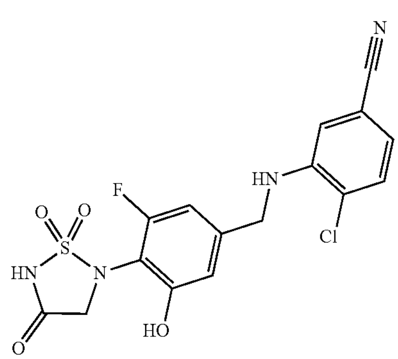 [SMILES: N#Cc1ccc(Cl)c(NCc2cc(O)c(N3CC(=O)NS3(=O)=O)c(F)c2)c1] | 4-chloro-3-[[3-fluoro-5-hydroxy-4-(1,1,4-trioxo-1,2,5-thiadiazolidin-2-yl)phenyl]methylamino]benzonitrile |

TABLE 1-continued

| Compound number | Structure | Chemical name |
|---|---|---|
| EXAMPLE 82 | 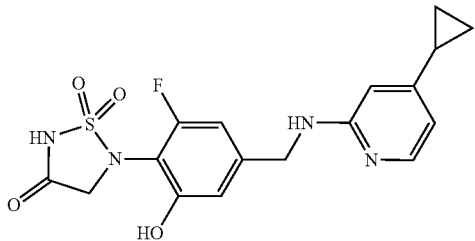 [SMILES: O=C1CN(c2c(O)cc(CNc3cc(C4CC4)ccn3)cc2F)S(=O)(=O)N1] | 5-[4-[[(4-cyclopropyl-2-pyridyl)amino]methyl]-2-fluoro-6-hydroxyphenyl]-1,1-dioxo-1,2,5-thiadiazolidin-3-one |
| EXAMPLE 83 | 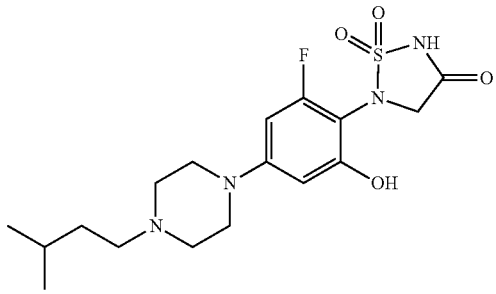 [SMILES: CC(C)CCN1CCN(c2cc(O)c(N3CC(=O)NS3(=O)=O)c(F)c2)CC1] | 5-(2-fluoro-6-hydroxy-4-(4-isopentylpiperazin-1-yl)phenyl)-1,2,5-thiadiazolidin-3-one 1,1-dioxide |
| EXAMPLE 84 | 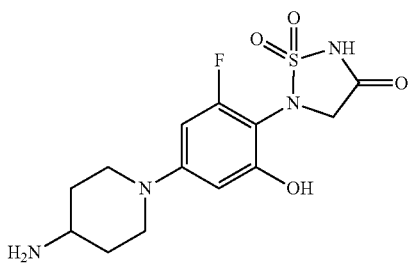 [SMILES: NC1CCN(c2cc(O)c(N3CC(=O)NS3(=O)=O)c(F)c2)CC1] | 5-(4-(4-aminopiperidin-1-yl)-2-fluoro-6-hydroxyphenyl)-1,2,5-thiadiazolidin-3-one 1,1-dioxide |
| EXAMPLE 85 | 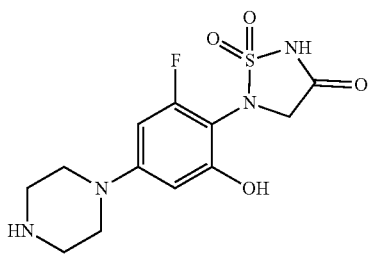 [SMILES: O=C1CN(c2c(O)cc(N3CCNCC3)cc2F)S(=O)(=O)N1] | 5-(2-fluoro-6-hydroxy-4-(piperazin-1-yl)phenyl)-1,2,5-thiadiazolidin-3-one 1,1-dioxide |
| EXAMPLE 86 | 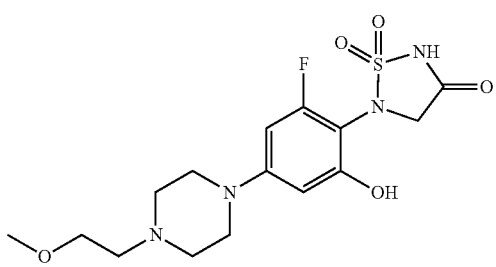 [SMILES: COCCN1CCN(c2cc(O)c(N3CC(=O)NS3(=O)=O)c(F)c2)CC1] | 5-(2-fluoro-6-hydroxy-4-(4-(2-methoxyethyl)piperazin-1-yl)phenyl)-1,2,5-thiadiazolidin-3-one 1,1-dioxide |

TABLE 1-continued

| Compound number | Structure | Chemical name |
| --- | --- | --- |
| EXAMPLE 87 | 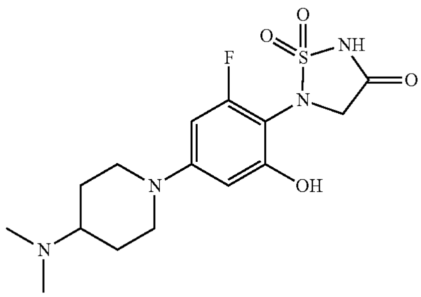 [SMILES: CN(C)C1CCN(c2cc(O)c(N3CC(=O)NS3(=O)=O)c(F)c2)CC1] | 5-(4-(4-(dimethylamino)piperidin-1-yl)-2-fluoro-6-hydroxyphenyl)-1,2,5-thiadiazolidin-3-one 1,1-dioxide |
| EXAMPLE 88 | 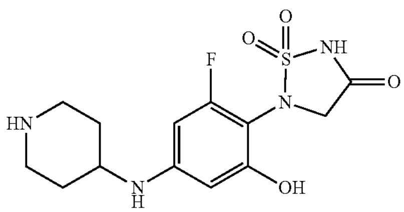 [SMILES: O=C1CN(c2c(O)cc(NC3CCNCC3)cc2F)S(=O)(=O)N1] | 5-(2-fluoro-6-hydroxy-4-(piperidin-4-ylamino)phenyl)-1,2,5-thiadiazolidin-3-one 1,1-dioxide |
| EXAMPLE 89 | 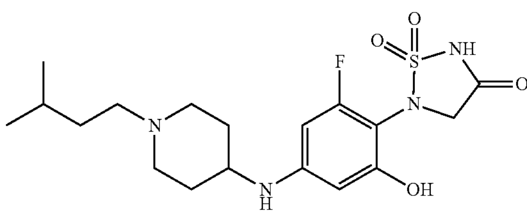 [SMILES: CC(C)CCN1CCC(Nc2cc(O)c(N3CC(=O)NS3(=O)=O)c(F)c2)CC1] | 5-(2-fluoro-6-hydroxy-4-((1-isopentylpiperidin-4-yl)amino)phenyl)-1,2,5-thiadiazolidin-3-one 1,1-dioxide |
| EXAMPLE 90 | 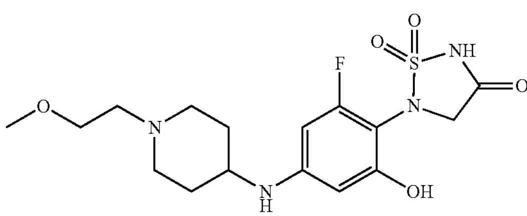 [SMILES: COCCN1CCC(Nc2cc(O)c(N3CC(=O)NS3(=O)=O)c(F)c2)CC1] | 5-(2-fluoro-6-hydroxy-4-((1-(2-methoxyethyl)piperidin-4-yl)amino)phenyl)-1,2,5-thiadiazolidin-3-one 1,1-dioxide |
| EXAMPLE 91 | 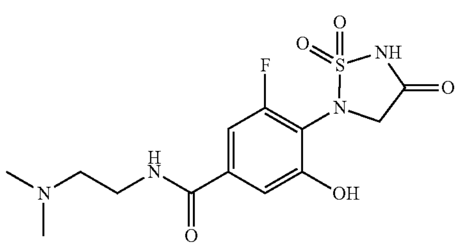 [SMILES: CN(C)CCNC(=O)c1cc(O)c(N2CC(=O)NS2(=O)=O)c(F)c1] | N-(2-(dimethylamino)ethyl)-4-(1,1-dioxido-4-oxo-1,2,5-thiadiazolidin-2-yl)-3-fluoro-5-hydroxybenzamide |
| EXAMPLE 92 | 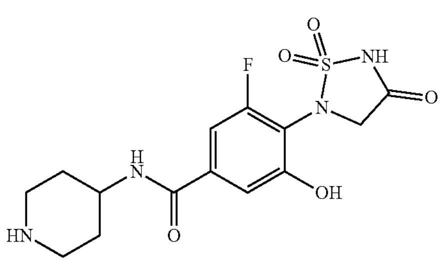 [SMILES: O=C1CN(c2c(O)cc(C(=O)NC3CCNCC3)cc2F)S(=O)(=O)N1] | 4-(1,1-dioxido-4-oxo-1,2,5-thiadiazolidin-2-yl)-3-fluoro-5-hydroxy-N-(piperidin-4-yl)benzamide |

TABLE 1-continued

| Compound number | Structure | Chemical name |
|---|---|---|
| EXAMPLE 93 | 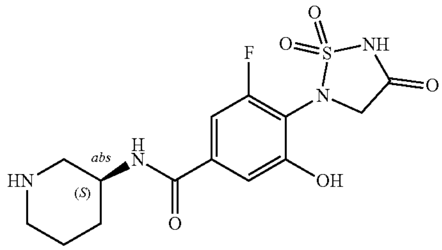 | (S)-4-(1,1-dioxido-4-oxo-1,2,5-thiadiazolidin-2-yl)-3-fluoro-5-hydroxy-N-(piperidin-3-yl)benzamide |
| EXAMPLE 94 | 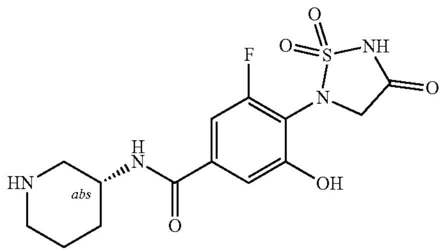 [SMILES: O=C1CN(c2c(O)cc(C(=O)N[C@@H]3CCCNC3)cc2F)S(=O)(=O)N1] | (R)-4-(1,1-dioxido-4-oxo-1,2,5-thiadiazolidin-2-yl)-3-fluoro-5-hydroxy-N-(piperidin-3-yl)benzamide |
| EXAMPLE 95 | 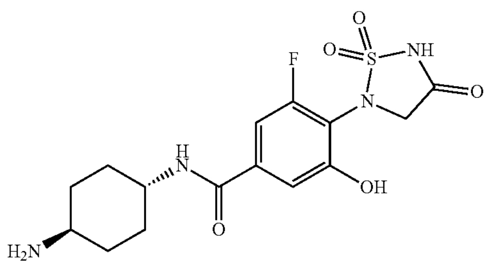 [SMILES: N[C@H]1CC[C@H](NC(=O)c2cc(O)c(N3CC(=O)NS3(=O)=O)c(F)c2)CC1] | N-((1r,4r)-4-aminocyclohexyl)-4-(1,1-dioxido-4-oxo-1,2,5-thiadiazolidin-2-yl)-3-fluoro-5-hydroxybenzamide |
| EXAMPLE 96 | 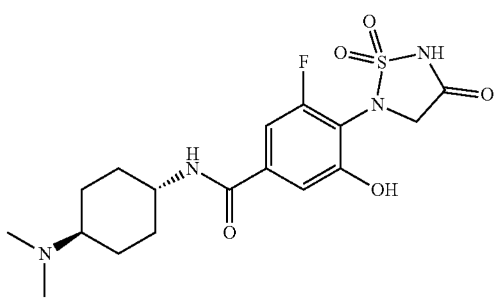 [SMILES: CN(C)[C@H]1CC[C@H](NC(=O)c2cc(O)c(N3CC(=O)NS3(=O)=O)c(F)c2)CC1] | N-((1r,4r)-4-(dimethylamino)cyclohexyl)-4-(1,1-dioxido-4-oxo-1,2,5-thiadiazolidin-2-yl)-3-fluoro-5-hydroxybenzamide |
| EXAMPLE 97 | 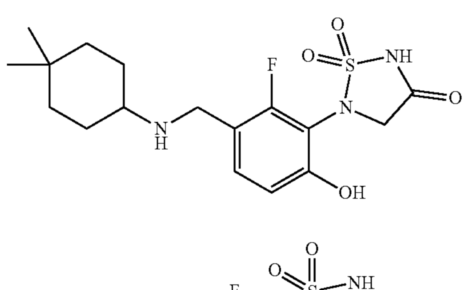 | 5-(3-(((4,4-dimethylcyclohexyl)amino)methyl)-2-fluoro-6-hydroxyphenyl)-1,2,5-thiadiazolidin-3-one 1,1-dioxide |
| EXAMPLE 98 | 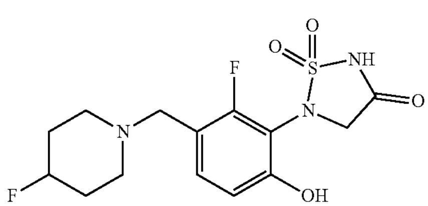 [SMILES: O=C1CN(c2c(O)ccc(CN3CCC(F)CC3)c2F)S(=O)(=O)N1] | 5-(2-fluoro-3-((4-fluoropiperidin-1-yl)methyl)-6-hydroxyphenyl)-1,2,5-thiadiazolidin-3-one 1,1-dioxide |

TABLE 1-continued

| Compound number | Structure | Chemical name |
|---|---|---|
| EXAMPLE 99 | 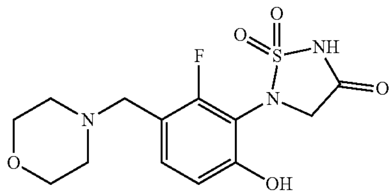 [SMILES: O=C1CN(c2c(O)ccc(CN3CCOCC3)c2F)S(=O)(=O)N1] | 5-(2-fluoro-6-hydroxy-3-(morpholinomethyl)phenyl)-1,2,5-thiadiazolidin-3-one 1,1-dioxide |
| EXAMPLE 100 | 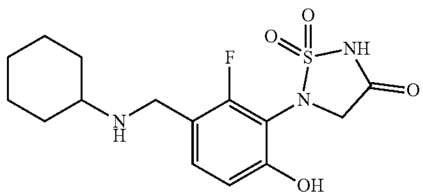 [SMILES: O=C1CN(c2c(O)ccc(CNC3CCCCC3)c2F)S(=O)(=O)N1] | 5-(3-((cyclohexylamino)methyl)-2-fluoro-6-hydroxyphenyl)-1,2,5-thiadiazolidin-3-one 1,1-dioxide |
| EXAMPLE 101 | 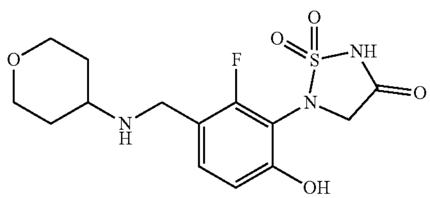 [SMILES: O=C1CN(c2c(O)ccc(CNC3CCOCC3)c2F)S(=O)(=O)N1] | 5-(2-fluoro-6-hydroxy-3-(((tetrahydro-2H-pyran-4-yl)amino)methyl)phenyl)-1,2,5-thiadiazolidin-3-one 1,1-dioxide |
| EXAMPLE 102 | 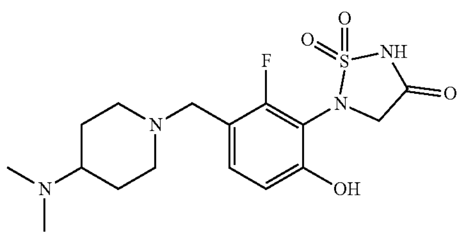 [SMILES: CN(C)C1CCN(Cc2ccc(O)c(N3CC(=O)NS3(=O)=O)c2F)CC1] | 5-(3-((4-(dimethylamino)piperidin-1-yl)methyl)-2-fluoro-6-hydroxyphenyl)-1,2,5-thiadiazolidin-3-one 1,1-dioxide |
| EXAMPLE 103 | 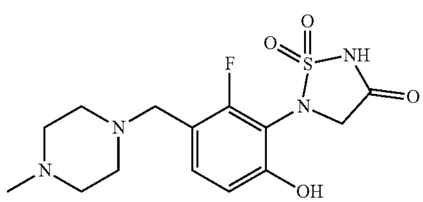 [SMILES: CN1CCN(Cc2ccc(O)c(N3CC(=O)NS3(=O)=O)c2F)CC1] | 5-(2-fluoro-6-hydroxy-3-((4-methylpiperazin-1-yl)methyl)phenyl)-1,2,5-thiadiazolidin-3-one 1,1-dioxide |
| EXAMPLE 104 | 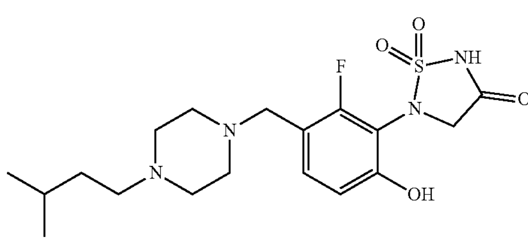 [SMILES: CC(C)CCN1CCN(Cc2ccc(O)c(N3CC(=O)NS3(=O)=O)c2F)CC1] | 5-[2-fluoro-6-hydroxy-3-[(4-isopentylpiperazin-1-yl)methyl]phenyl]-1,1-dioxo-1,2,5-thiadiazolidin-3-one |
| EXAMPLE 105 | 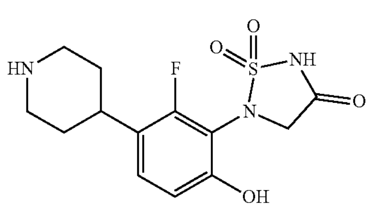 [SMILES: O=C1CN(c2c(O)ccc(C3CCNCC3)c2F)S(=O)(=O)N1] | 5-(2-fluoro-6-hydroxy-3-(piperidin-4-yl)phenyl)-1,2,5-thiadiazolidin-3-one 1,1-dioxide |

TABLE 1-continued

| Compound number | Structure | Chemical name |
|---|---|---|
| EXAMPLE 106 | 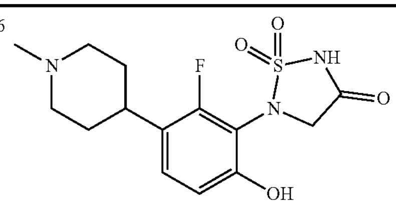 | 5-(2-fluoro-6-hydroxy-3-(1-methylpiperidin-4-yl)phenyl)-1,2,5-thiadiazolidin-3-one 1,1-dioxide |

Biological Assays

The pharmacological properties of the compounds of this invention may be confirmed by a number of biological assays known in the art. The exemplified biological assays which follow, have been carried out with compounds of the invention.

Assays

A PhosphoSens® kinase assay was performed as described by the vendor (AssayQuant Technologies, Marlborough, MA). Briefly, 1000×solutions of compounds were prepared in DMSO via serial dilution of the 10 mM DMSO stocks using 3-fold intervals in a 384-well reagent plate. 50 nL of the compound dilution series was then added to the corresponding wells of a 384-well assay plate. 40 mL of 1.25×substrate (AQT0264) in 1× assay buffer (50 mM HEPES pH 7.5, 500 µM EGTA, 10 nM MgCl2, 0.01% Brij-35, 1% Glycerol, 1 mM DTT, and 0.2 mg/mL BSA) was transferred to each well of the assay plate to achieve a final substrate concentration of 20 µM. Finally, 10 mL of 5×PTPN2 enzyme stock was added to each well of the assay plate for a final enzyme concentration of 150 µM. Reaction progress curves were collected by sampling fluorescence intensity at the excitation wavelength 360 nm ($\lambda_{ex}$360) and emission wavelength 480 nm ($\lambda_{em}$480) every 71 seconds for one hour using a Synergy H4 plate reader (BioTek Instruments/Agilent Technologies, Winooski, VT) at room temperature.

Cell Proliferation Assay Protocol

B16-F10 cells (ATCC, Manassas, VA, #CRL-6475) were cultured in DMEM growth medium (ThermoFisher Scientific, Waltham, MA, #11995-040) supplemented with 10% heat inactivated FBS (ThermoFisher Scientific, #16140-071) and 1% pen/strep (ThermoFisher Scientific, #15140-122). The cells were seeded into two white opaque 384-well tissue culture treated microplates (PerkinElmer, Waltham, MA, #6007688) at a density of 100 cells/well in 20 uL total volume and incubated overnight at 37 C and 5% CO2. 30 nL of compounds dissolved in DMSO were then transferred from a source plate into target wells with the Echo650 acoustic liquid handler (Beckman Coulter, Indianapolis, IN). Negative control wells received 30 nL of DMSO only (0.15% final concentration). Plates were returned to the incubator for 1 hour and then cells treated with either 5 uL of growth medium or 5 uL of growth medium containing 50 ng/mL of recombinant mouse IFN-gamma protein (R&D Systems, Minneapolis, MN, #485-MI/CF, 10 ng/mL final concentration) using the Assist automated pipetting platform (INTEGRA Biosciences, Hudson, NH). Plates were incubated at 37 C for 4 days and cell proliferation assayed with the CellTiter-Glo reagent (Promega, Madison, WI, #G7573, 25 uL per well). Luminescence signal intensity was collected with the EnVision 2105 plate reader (PerkinElmer) 15 minutes after CellTiter-Glo reagent addition and analyzed with the Dotmatics software platform to calculate compound IC50 values. Off-target compound mediated cytotoxicity was identified by checking for growth inhibition in the absence of IFNg.

Phospho-STAT1 Assay Protocol

B16-F10 cells (ATCC, Manassas, VA, #CRL-6475) were cultured in DMEM growth medium (ThermoFisher Scientific, Waltham, MA, #11995-040) supplemented with 10% heat inactivated FBS (ThermoFisher Scientific, #16140-071) and 1% pen/strep (ThermoFisher Scientific, #15140-122). The cells were seeded into a white opaque 384-well tissue culture treated microplate (PerkinElmer, Waltham, MA, #6007688) at a density of 10,000 cells/well in 20 uL total volume and incubated overnight at 37 C and 5% CO2. 30 nL of compounds dissolved in DMSO were then transferred from a source plate into target wells with the Echo650 acoustic liquid handler (Beckman Coulter, Indianapolis, IN). Negative control wells received 30 nL of DMSO only (0.15% final concentration). Plates were returned to the incubator for 1 hour and then cells treated with either 5 uL of growth medium or 5 uL of growth medium containing 500 ng/mL of recombinant mouse IFN-gamma protein (R&D Systems, Minneapolis, MN, #485-MI/CF, 100 ng/mL final concentration) using the Assist automated pipetting platform (INTEGRA Biosciences, Hudson, NH). Plates were incubated at 37 C for 1 hour and assayed for phosphorylated STAT1 protein levels with the phospho-STAT1 (Tyr701) HTRF kit (Cisbio, Bedford, MA, #63ADK026PEH) according to manufacturer's instructions. HTRF signal intensity was collected with the EnVision 2105 plate reader (PerkinElmer) 24 hours later and analyzed with the Dotmatics software platform to calculate compound IC50 values.

| Compound | IUPAC NAME | PTPN2 BCHEM IC50 (uM) | pSTAT1 HTRF B16 EC50 (uM) | PTPN2 Prolif 5d B16F10 EC50 (uM) |
|---|---|---|---|---|
| EXAMPLE 1 | 5-[2-fluoro-6-hydroxy-4-(piperidin-3-yl)phenyl]-1λ6,2,5-thiadiazolidine-1,1,3-trione | 0.119 | 1.280 | 0.882 |
| EXAMPLE 2 | 5-[2-fluoro-6-hydroxy-4-(piperidin-4-yl)phenyl]-1λ6,2,5-thiadiazolidine-1,1,3-trione | 1.300 | | |
| EXAMPLE 3 | 5-[2-fluoro-6-hydroxy-4-(1-methylpiperidin-3-yl)phenyl]-1λ6,2,5-thiadiazolidine-1,1,3-trione | 4.726 | | |
| EXAMPLE 4 | 5-[2-fluoro-6-hydroxy-4-(1-methylpiperidin-4-yl)phenyl]-1λ6,2,5-thiadiazolidine-1,1,3-trione | 0.807 | 15 | 15 |

-continued

| Compound | IUPAC NAME | PTPN2 BCHEM IC50 (uM) | pSTAT1 HTRF B16 EC50 (uM) | PTPN2 Prolif 5d B16F10 EC50 (uM) |
|---|---|---|---|---|
| EXAMPLE 5 | 5-{2-fluoro-6-hydroxy-4-[1-(3-methylbutyl)piperidin-3-yl]phenyl}-1λ6,2,5-thiadiazolidine-1,1,3-trione | 1.023 | 15 | 15 |
| EXAMPLE 6 | 5-{2-fluoro-6-hydroxy-4-[1-(3-methylbutyl)piperidin-4-yl]phenyl}-1λ6,2,5-thiadiazolidine-1,1,3-trione | 2.754 | | |
| EXAMPLE 7 | 5-[2-fluoro-6-hydroxy-4-(pyridin-2-yl)phenyl]-1λ6,2,5-thiadiazolidine-1,1,3-trione | 0.568 | 14.993 | 14.993 |
| EXAMPLE 8 | 5-[2-fluoro-6-hydroxy-4-(pyridin-3-yl)phenyl]-1λ6,2,5-thiadiazolidine-1,1,3-trione | 0.199 | 2.429 | 14.993 |
| EXAMPLE 9 | 5-[2-fluoro-6-hydroxy-4-(pyridin-4-yl)phenyl]-1λ6,2,5-thiadiazolidine-1,1,3-trione | 0.322 | 14.993 | 14.993 |
| EXAMPLE 10 | 5-{4'-benzyl-3-fluoro-5-hydroxy-[1,1'-biphenyl]-4-yl}-1λ6,2,5-thiadiazolidine-1,1,3-trione | 6.144 | 14.993 | 14.993 |
| EXAMPLE 11 | 5-{3-fluoro-5-hydroxy-3'-phenyl-[1,1'-biphenyl]-4-yl}-1λ6,2,5-thiadiazolidine-1,1,3-trione | 1.338 | 14.993 | 14.993 |
| EXAMPLE 12 | 5-[3-fluoro-4'-(4-fluorophenyl)-5-hydroxy-[1,1'-biphenyl]-4-yl]-1λ6,2,5-thiadiazolidine-1,1,3-trione | 1.989 | 14.993 | 14.993 |
| EXAMPLE 13 | 5-[3-fluoro-5-hydroxy-4'-(morpholin-4-yl)-[1,1'-biphenyl]-4-yl]-1λ6,2,5-thiadiazolidine-1,1,3-trione | 0.466 | 14.993 | 14.993 |
| EXAMPLE 14 | 5-{3-fluoro-5-hydroxy-3'-phenoxy-[1,1'-biphenyl]-4-yl}-1λ6,2,5-thiadiazolidine-1,1,3-trione | 2.212 | 14.993 | 14.993 |
| EXAMPLE 15 | 5-[3-fluoro-5-hydroxy-4'-(2-methylpropyl)-[1,1'-biphenyl]-4-yl]-1λ6,2,5-thiadiazolidine-1,1,3-trione | 2.484 | 14.993 | 14.993 |
| EXAMPLE 16 | 5-[3-fluoro-5-hydroxy-3'-(morpholin-4-yl)-[1,1'-biphenyl]-4-yl]-1λ6,2,5-thiadiazolidine-1,1,3-trione | 0.423 | 14.993 | 14.993 |
| EXAMPLE 17 | 5-{4'-cyclopropyl-3-fluoro-5-hydroxy-[1,1'-biphenyl]-4-yl}-1λ6,2,5-thiadiazolidine-1,1,3-trione | 1.408 | 7.949 | 14.993 |
| EXAMPLE 18 | 5-[2-fluoro-6-hydroxy-4-(4-phenylthiophen-2-yl)phenyl]-1λ6,2,5-thiadiazolidine-1,1,3-trione | 1.185 | 14.993 | 14.993 |
| EXAMPLE 19 | 5-{3-fluoro-5-hydroxy-4'-[(pyrrolidin-1-yl)methyl]-[1,1'-biphenyl]-4-yl}-1λ6,2,5-thiadiazolidine-1,1,3-trione | 0.483 | 14.993 | 14.993 |
| EXAMPLE 20 | 5-[2-fluoro-6-hydroxy-4-(2-phenylpyridin-4-yl)phenyl]-1λ6,2,5-thiadiazolidine-1,1,3-trione | 0.205 | 14.993 | 14.993 |
| EXAMPLE 21 | 5-[3'-(cyclopropylmethoxy)-3-fluoro-5-hydroxy-5'-methyl-[1,1'-biphenyl]-4-yl]-1λ6,2,5-thiadiazolidine-1,1,3-trione | 6.961 | 14.993 | 14.993 |
| EXAMPLE 22 | 5-[3-fluoro-5-hydroxy-4'-(2-hydroxypropan-2-yl)-[1,1'-biphenyl]-4-yl]-1λ6,2,5-thiadiazolidine-1,1,3-trione | 0.179 | 14.993 | 14.993 |
| EXAMPLE 23 | 5-[2-fluoro-6-hydroxy-4-(6-methoxypyridin-3-yl)phenyl]-1λ6,2,5-thiadiazolidine-1,1,3-trione | 0.142 | 14.993 | 14.993 |
| EXAMPLE 24 | 5-[2-fluoro-6-hydroxy-4-(quinolin-3-yl)phenyl]-1λ6,2,5-thiadiazolidine-1,1,3-trione | 0.190 | 14.993 | 14.993 |
| EXAMPLE 25 | 5-[2-fluoro-6-hydroxy-4-(2-methoxypyridin-3-yl)phenyl]-1λ6,2,5-thiadiazolidine-1,1,3-trione | 0.266 | 9.736 | |
| EXAMPLE 26 | 5-[2-fluoro-6-hydroxy-4-(6-hydroxypyridin-3-yl)phenyl]-1λ6,2,5-thiadiazolidine-1,1,3-trione | 0.010 | 2.177 | 3.107 |
| EXAMPLE 27 | 5-{2-fluoro-6-hydroxy-4-[6-(4-methylpiperazin-1-yl)pyridin-3-yl]phenyl}-1λ6,2,5-thiadiazolidine-1,1,3-trione | 0.457 | 14.993 | 14.993 |
| EXAMPLE 28 | 5-[2-fluoro-6-hydroxy-4-(5-methoxypyridin-3-yl)phenyl]-1λ6,2,5-thiadiazolidine-1,1,3-trione | 0.089 | 14.993 | 7.825 |
| EXAMPLE 29 | 5-{4-[6-(dimethylamino)pyridin-3-yl]-2-fluoro-6-hydroxyphenyl}-1λ6,2,5-thiadiazolidine-1,1,3-trione | 0.090 | 14.993 | 14.993 |
| EXAMPLE 30 | 5-[2-fluoro-6-hydroxy-4-(6-phenylpyridin-3-yl)phenyl]-1λ6,2,5-thiadiazolidine-1,1,3-trione | 0.148 | 14.993 | 14.993 |
| EXAMPLE 31 | 5-{2-fluoro-6-hydroxy-4-[(4-methylpiperazin-1-yl)methyl]phenyl}-1λ6,2,5-thiadiazolidine-1,1,3-trione | 0.104 | 2.414 | 1.307 |
| EXAMPLE 32 | 5-(2-fluoro-6-hydroxy-4-{[4-(3-methylbutyl)piperazin-1-yl]methyl}phenyl)-1λ6,2,5-thiadiazolidine-1,1,3-trione | 0.065 | 15 | 15 |
| EXAMPLE 33 | 5-(4-{[4-(dimethylamino)piperidin-1-yl]methyl}-2-fluoro-6-hydroxyphenyl)-1λ6,2,5-thiadiazolidine-1,1,3-trione | 0.094 | 15 | 15 |
| EXAMPLE 34 | 5-{4-[(cyclohexylamino)methyl]-2-fluoro-6-hydroxyphenyl}-1λ6,2,5-thiadiazolidine-1,1,3-trione | 0.090 | 1.737 | 1.716 |
| EXAMPLE 35 | 5-(2-fluoro-6-hydroxy-4-{[(oxan-4-yl)amino methyl}phenyl)-1λ6,2,5-thiadiazolidine-1,1,3-trione | 1.565 | 15 | 15 |
| EXAMPLE 36 | 5-(2-fluoro-6-hydroxy-4-{[4-(3-methylbutanoyl)piperazin-1-yl]methyl}phenyl)-1λ6,2,5-thiadiazolidine-1,1,3-trione | 0.079 | 15 | 15 |
| EXAMPLE 37 | 5-(4-{[(4,4-dimethylcyclohexyl)amino]methyl}-2-fluoro-6-hydroxyphenyl)-1λ6,2,5-thiadiazolidine-1,1,3-trione | 0.035 | 1.335 | 0.812 |
| EXAMPLE 38 | 5-{4-[(4-acetylpiperazin-1-yl)methyl]-2-fluoro-6-hydroxyphenyl}-1λ6,2,5-thiadiazolidine-1,1,3-trione | 0.083 | | |
| EXAMPLE 39 | 5-(2-fluoro-6-hydroxy-4-{[(piperidin-4-yl)amino]methyl}phenyl)-1λ6,2,5-thiadiazolidine-1,1,3-trione | 0.086 | 15 | 15 |
| EXAMPLE 40 | 5-(4-{[(1-ethylpiperidin-4-yl)amino]methyl}-2-fluoro-6-hydroxyphenyl)-1λ6,2,5-thiadiazolidine-1,1,3-trione | 0.131 | 2.341 | 3.262 |
| EXAMPLE 41 | 5-{2-fluoro-6-hydroxy-4-[(morpholin-4-yl)methyl]phenyl}-1λ6,2,5-thiadiazolidine-1,1,3-trione | 0.070 | 3.379 | 3.556 |
| EXAMPLE 42 | 5-{2-fluoro-4-[(4-fluoropiperidin-1-yl)methyl]-6-hydroxyphenyl}-1λ6,2,5-thiadiazolidine-1,1,3-trione | 0.060 | 2.571 | 4.718 |
| EXAMPLE 43 | 5-(4-{[cyclohexyl(methyl)amino]methyl}-2-fluoro-6-hydroxyphenyl)-1λ6,2,5-thiadiazolidine-1,1,3-trione | 0.239 | 4.274 | 4.352 |
| EXAMPLE 44 | 5-(2-fluoro-6-hydroxy-4-{[4-(2-methoxyethyl)piperazin-1-yl]methyl}phenyl)-1λ6,2,5-thiadiazolidine-1,1,3-trione | 0.131 | 14.993 | 14.993 |
| EXAMPLE 45 | 2-fluoro-5-[({[3-fluoro-5-hydroxy-4-(1,1,4-trioxo-1λ6,2,5-thiadiazolidin-2-yl)phenyl]methyl}amino)methyl]benzonitrile | 0.070 | 1.867 | |

| Compound | IUPAC NAME | PTPN2 BCHEM IC50 (uM) | pSTAT1 HTRF B16 EC50 (uM) | PTPN2 Prolif 5d B16F10 EC50 (uM) |
|---|---|---|---|---|
| EXAMPLE 46 | 5-(4-{[(2,4-dimethylpyridin-3-yl)amino]methyl}-2-fluoro-6-hydroxyphenyl)-1¿6,2,5-thiadiazolidine-1,1,3-trione | 0.039 | 8.875 | 14.993 |
| EXAMPLE 47 | 5-(4-{[cyclohexyl(cyclopropyl)amino]methyl}-2-fluoro-6-hydroxyphenyl)-1¿6,2,5-thiadiazolidine-1,1,3-trione | 0.354 | 5.215 | |
| EXAMPLE 48 | 5-(4-{[(4,4-dimethylcyclohexyl)(methyl)amino]methyl}-2-fluoro-6-hydroxyphenyl)-1¿6,2,5-thiadiazolidine-1,1,3-trione | 0.442 | 14.993 | |
| EXAMPLE 49 | 5-(4-{[(cyclobutylmethyl)(propyl)amino]methyl}-2-fluoro-6-hydroxyphenyl)-1¿6,2,5-thiadiazolidine-1,1,3-trione | 0.806 | 14.993 | |
| EXAMPLE 50 | 4-[{{[3-fluoro-5-hydroxy-4-(1,1,4-trioxo-1¿6,2,5-thiadiazolidin-2-yl)phenyl]methyl}(methyl)amino)methyl]benzonitrile | 0.027 | 14.993 | 9.526 |
| EXAMPLE 51 | 5-[4-({[(1R)-3,3-dimethylcyclohexyl]amino}methyl)-2-fluoro-6-hydroxyphenyl]-1¿6,2,5-thiadiazolidine-1,1,3-trione | 0.035 | 1.153 | 0.656 |
| EXAMPLE 52 | 5-{2-fluoro-6-hydroxy-4-[(4-hydroxypiperidin-1-yl)methyl]phenyl}-1¿6,2,5-thiadiazolidine-1,1,3-trione | 0.114 | 4.607 | 6.937 |
| EXAMPLE 53 | 5-{2-fluoro-6-hydroxy-4-[(4-methoxypiperidin-1-yl)methyl]phenyl}-1¿6,2,5-thiadiazolidine-1,1,3-trione | 0.102 | 3.196 | 2.980 |
| EXAMPLE 54 | 5-(2-fluoro-6-hydroxy-4-{[4-(propan-2-yloxy)piperidin-1-yl]methyl}phenyl)-1¿6,2,5-thiadiazolidine-1,1,3-trione | 0.331 | 13.073 | |
| EXAMPLE 55 | 5-(2-fluoro-6-hydroxy-4-{[4-(2-methoxyethyl)piperidin-1-yl]methyl}phenyl)-1¿6,2,5-thiadiazolidine-1,1,3-trione | 0.401 | 11.257 | |
| EXAMPLE 56 | 5-[4-({4-[(dimethylamino)methyl]piperidin-1-yl}methyl)-2-fluoro-6-hydroxyphenyl]-1¿6,2,5-thiadiazolidine-1,1,3-trione | 0.226 | 14.993 | 14.993 |
| EXAMPLE 57 | 5-{4-[(4-butylpiperidin-1-yl)methyl]-2-fluoro-6-hydroxyphenyl}-1¿6,2,5-thiadiazolidine-1,1,3-trione | 0.381 | 10.868 | |
| EXAMPLE 58 | (1r,4r)-4-({[3-fluoro-5-hydroxy-4-(1,1,4-trioxo-1¿6,2,5-thiadiazolidin-2-yl)phenyl]methyl}amino)-N-methylcyclohexane-1-carboxamide | 0.376 | 5.078 | 14.993 |
| EXAMPLE 59 | 2-(4-{[3-fluoro-5-hydroxy-4-(1,1,4-trioxo-1¿6,2,5-thiadiazolidin-2-yl)phenyl]methyl}piperazin-1-yl)-N-methylacetamide | 0.477 | 14.993 | 14.993 |
| EXAMPLE 60 | N-[(1r,4r)-4-({[3-fluoro-5-hydroxy-4-(1,1,4-trioxo-1¿6,2,5-thiadiazolidin-2-yl)phenyl]methyl}amino)cyclohexyl]acetamide | 0.410 | 14.993 | 14.993 |
| EXAMPLE 61 | 5-[2-fluoro-6-hydroxy-4-({[(3R)-piperidin-3-yl]amino}methyl)phenyl]-1¿6,2,5-thiadiazolidine-1,1,3-trione | 0.121 | 4.975 | 2.565 |
| EXAMPLE 62 | 5-[2-fluoro-6-hydroxy-4-({[(3R)-1-(3-methylbutyl)piperidin-3-yl]amino}methyl)phenyl]-1¿6,2,5-thiadiazolidine-1,1,3-trione | 0.088 | 14.993 | 14.603 |
| EXAMPLE 63 | 5-[2-fluoro-6-hydroxy-4-({[(3S)-1-(3-methylbutyl)piperidin-3-yl]amino}methyl)phenyl]-1¿6,2,5-thiadiazolidine-1,1,3-trione | 0.153 | 14.993 | 14.993 |
| EXAMPLE 64 | 5-[2-fluoro-6-hydroxy-4-({[(3R)-oxan-3-yl]amino}methyl)phenyl]-1¿6,2,5-thiadiazolidine-1,1,3-trione | 0.139 | 2.183 | 2.716 |
| EXAMPLE 65 | 5-[2-fluoro-6-hydroxy-4-({[(3S)-piperidin-3-yl]amino}methyl)phenyl]-1¿6,2,5-thiadiazolidine-1,1,3-trione | 0.130 | 5.199 | 6.859 |
| EXAMPLE 66 | 5-[4-({[(1S)-3,3-dimethylcyclohexyl]amino}methyl)-2-fluoro-6-hydroxyphenyl]-1¿6,2,5-thiadiazolidine-1,1,3-trione | 0.042 | 0.782 | 0.772 |
| EXAMPLE 67 | 5-[2-fluoro-6-hydroxy-4-({[(3S)-oxan-3-yl]amino}methyl)phenyl]-1¿6,2,5-thiadiazolidine-1,1,3-trione | 0.126 | 2.695 | 1.669 |
| EXAMPLE 68 | 5-[4-({[(3R)-1-acetylpiperidin-3-yl]amino}methyl)-2-fluoro-6-hydroxyphenyl]-1¿6,2,5-thiadiazolidine-1,1,3-trione | 0.032 | 6.676 | |
| EXAMPLE 69 | 5-[2-fluoro-4-({[(3R)-1-(3-fluorobenzenesulfonyl)piperidin-3-yl]amino}methyl)-6-hydroxyphenyl]-1¿6,2,5-thiadiazolidine-1,1,3-trione | 0.088 | 14.993 | |
| EXAMPLE 70 | 5-[2-fluoro-4-({[(3S)-1-(3-fluorobenzenesulfonyl)piperidin-3-yl]amino}methyl)-6-hydroxyphenyl]-1¿6,2,5-thiadiazolidine-1,1,3-trione | 0.030 | 14.993 | |
| EXAMPLE 71 | 5-[4-({[(3S)-1-acetylpiperidin-3-yl]amino}methyl)-2-fluoro-6-hydroxyphenyl]-1¿6,2,5-thiadiazolidine-1,1,3-trione | 0.025 | 2.914 | 1.894 |
| EXAMPLE 72 | 5-[2-fluoro-6-hydroxy-4-({[(3R)-1-methanesulfonylpiperidin-3-yl]amino}methyl)phenyl]-1¿6,2,5-thiadiazolidine-1,1,3-trione | 0.054 | 3.564 | 4.693 |
| EXAMPLE 73 | 5-[4-({[(3S)-1-(cyclopropanesulfonyl)piperidin-3-yl]amino}methyl)-2-fluoro-6-hydroxyphenyl]-1¿6,2,5-thiadiazolidine-1,1,3-trione | 0.010 | 7.796 | 9.839 |
| EXAMPLE 74 | 5-[4-({[(3R)-1-(cyclopropanesulfonyl)piperidin-3-yl]amino}methyl)-2-fluoro-6-hydroxyphenyl]-1¿6,2,5-thiadiazolidine-1,1,3-trione | 0.017 | 10.986 | 5.646 |
| EXAMPLE 75 | 5-[2-fluoro-6-hydroxy-4-({[(3S)-1-methanesulfonylpiperidin-3-yl]amino}methyl)phenyl]-1¿6,2,5-thiadiazolidine-1,1,3-trione | 0.037 | 3.217 | 2.189 |
| EXAMPLE 76 | 3-[(3S)-3-({[3-fluoro-5-hydroxy-4-(1,1,4-trioxo-1¿6,2,5-thiadiazolidin-2-yl)phenyl]methyl}amino)piperidin-1-yl]-3-oxopropanoic acid | 0.012 | 14.993 | 14.993 |
| EXAMPLE 77 | 4-chloro-3-({[3-fluoro-5-hydroxy-4-(1,1,4-trioxo-1¿6,2,5-thiadiazolidin-2-yl)phenyl]methyl}amino)benzonitrile | 0.050 | 14.993 | 14.993 |
| EXAMPLE 78 | 5-{2-fluoro-6-hydroxy-4-[(4-phenylpiperidin-1-yl)methyl]phenyl}-1¿6,2,5-thiadiazolidine-1,1,3-trione | 0.229 | 10.801 | 14.993 |
| EXAMPLE 79 | 5-[4-({cyclopropyl[(1-methyl-1H-pyrazol-4-yl)methyl]amino}methyl)-2-fluoro-6-hydroxyphenyl]-1¿6,2,5-thiadiazolidine-1,1,3-trione | 0.051 | 2.547 | 2.027 |
| EXAMPLE 80 | 5-(4-{[(2-chloro-5-fluorophenyl)amino]methyl}-2-fluoro-6-hydroxyphenyl)-1¿6,2,5-thiadiazolidine-1,1,3-trione | 0.050 | 14.993 | 14.993 |

| Compound | IUPAC NAME | PTPN2 BCHEM IC50 (uM) | pSTAT1 HTRF B16 EC50 (uM) | PTPN2 Prolif 5d B16F10 EC50 (uM) |
|---|---|---|---|---|
| EXAMPLE 81 | 5-({[3-fluoro-5-hydroxy-4-(1,1,4-trioxo-1¿6,2,5-thiadiazolidin-2-yl)phenyl]methyl}amino)-2-methylpyridine-3-carbonitrile | 0.012 | 5.606 | 5.191 |
| EXAMPLE 82 | 5-(4-{[(4-cyclopropylpyridin-2-yl)amino]methyl}-2-fluoro-6-hydroxyphenyl)-1¿6,2,5-thiadiazolidine-1,1,3-trione | 0.010 | 0.197 | |
| EXAMPLE 83 | 5-{2-fluoro-6-hydroxy-4-[4-(3-methylbutyl)piperazin-1-yl]phenyl}-1¿6,2,5-thiadiazolidine-1,1,3-trione | 0.896 | 14.993 | 14.993 |
| EXAMPLE 84 | 5-[4-(4-aminopiperidin-1-yl)-2-fluoro-6-hydroxyphenyl]-1¿6,2,5-thiadiazolidine-1,1,3-trione | 0.745 | 14.993 | 14.993 |
| EXAMPLE 85 | 5-[2-fluoro-6-hydroxy-4-(piperazin-1-yl)phenyl]-1¿6,2,5-thiadiazolidine-1,1,3-trione | 0.682 | 5.482 | 14.993 |
| EXAMPLE 86 | 5-{2-fluoro-6-hydroxy-4-[4-(2-methoxyethyl)piperazin-1-yl]phenyl}-1¿6,2,5-thiadiazolidine-1,1,3-trione | 0.336 | 15 | 15 |
| EXAMPLE 87 | 5-{4-[4-(dimethylamino)piperidin-1-yl]-2-fluoro-6-hydroxyphenyl}-1¿6,2,5-thiadiazolidine-1,1,3-trione | 0.318 | 15 | 15 |
| EXAMPLE 88 | 5-{2-fluoro-6-hydroxy-4-[(piperidin-4-yl)amino]phenyl}-1¿6,2,5-thiadiazolidine-1,1,3-trione | 1.199 | | |
| EXAMPLE 89 | 5-(2-fluoro-6-hydroxy-4-{[1-(3-methylbutyl)piperidin-4-yl]amino}phenyl)-1¿6,2,5-thiadiazolidine-1,1,3-trione | 0.757 | 14.993 | 14.993 |
| EXAMPLE 90 | 5-(2-fluoro-6-hydroxy-4-{[1-(2-methoxyethyl)piperidin-4-yl]amino}phenyl)-1¿6,2,5-thiadiazolidine-1,1,3-trione | 2.127 | 14.993 | 14.993 |
| EXAMPLE 91 | N-[2-(dimethylamino)ethyl]-3-fluoro-5-hydroxy-4-(1,1,4-trioxo-1¿6,2,5-thiadiazolidin-2-yl)benzamide | 1 | 14.993 | 14.993 |
| EXAMPLE 92 | 3-fluoro-5-hydroxy-N-(piperidin-4-yl)-4-(1,1,4-trioxo-1¿6,2,5-thiadiazolidin-2-yl)benzamide | 1 | 14.993 | 14.993 |
| EXAMPLE 93 | 3-fluoro-5-hydroxy-N-[(3S)-piperidin-3-yl]-4-(1,1,4-trioxo-1¿6,2,5-thiadiazolidin-2-yl)benzamide | 1 | 14.993 | 14.993 |
| EXAMPLE 94 | 3-fluoro-5-hydroxy-N-[(3R)-piperidin-3-yl]-4-(1,1,4-trioxo-1¿6,2,5-thiadiazolidin-2-yl)benzamide | 1 | 14.993 | 14.993 |
| EXAMPLE 95 | 3-fluoro-5-hydroxy-N-[(1r,4r)-4-aminocyclohexyl]-4-(1,1,4-trioxo-1¿6,2,5-thiadiazolidin-2-yl)benzamide | 6.885 | | |
| EXAMPLE 96 | 3-fluoro-5-hydroxy-N-[(1r,4r)-4-(dimethylamino)cyclohexyl]-4-(1,1,4-trioxo-1¿6,2,5-thiadiazolidin-2-yl)benzamide | 1 | 14.993 | 14.993 |
| EXAMPLE 97 | 5-(3-{[(4,4-dimethylcyclohexyl)amino]methyl}-2-fluoro-6-hydroxyphenyl)-1¿6,2,5-thiadiazolidine-1,1,3-trione | 10 | 14.993 | 14.993 |
| EXAMPLE 98 | 5-{2-fluoro-3-[(4-fluoropiperidin-1-yl)methyl]-6-hydroxyphenyl}-1¿6,2,5-thiadiazolidine-1,1,3-trione | 10 | 14.993 | |
| EXAMPLE 99 | 5-{2-fluoro-6-hydroxy-3-[(morpholin-4-yl)methyl]phenyl}-1¿6,2,5-thiadiazolidine-1,1,3-trione | 10 | 14.993 | 14.993 |
| EXAMPLE 100 | 5-{3-[(cyclohexylamino)methyl]-2-fluoro-6-hydroxyphenyl}-1¿6,2,5-thiadiazolidine-1,1,3-trione | 10 | 14.993 | 14.993 |
| EXAMPLE 101 | 5-(2-fluoro-6-hydroxy-3-{[(oxan-4-yl)amino]methyl}phenyl)-1¿6,2,5-thiadiazolidine-1,1,3-trione | 10 | 14.993 | 14.993 |
| EXAMPLE 102 | 5-(3-{[4-(dimethylamino)piperidin-1-yl]methyl}-2-fluoro-6-hydroxyphenyl)-1¿6,2,5-thiadiazolidine-1,1,3-trione | 10 | 14.993 | |
| EXAMPLE 103 | 5-{2-fluoro-6-hydroxy-3-[(4-methylpiperazin-1-yl)methyl]phenyl}-1¿6,2,5-thiadiazolidine-1,1,3-trione | 10 | 14.993 | 14.993 |
| EXAMPLE 104 | 5-(2-fluoro-6-hydroxy-3-{[4-(3-methylbutyl)piperazin-1-yl]methyl}phenyl)-1¿6,2,5-thiadiazolidine-1,1,3-trione | 10 | 14.993 | |
| EXAMPLE 105 | 5-[2-fluoro-6-hydroxy-3-(piperidin-4-yl)phenyl]-1¿6,2,5-thiadiazolidine-1,1,3-trione | 10 | 14.993 | 14.993 |
| EXAMPLE 106 | 5-[2-fluoro-6-hydroxy-3-(1-methylpiperidin-4-yl)phenyl]-1¿6,2,5-thiadiazolidine-1,1,3-trione | 4.473 | 14.993 | 14.993 |

What is claimed is:

1. A compound of Formula (I):

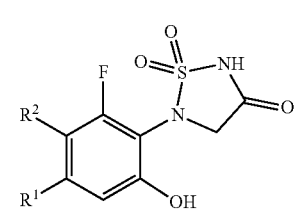

Formula (I)

wherein:

$R^1$ is selected from the group consisting of: —CONHR$^3$, —CH$_2$N(R$^5$)CH$_2$R$^4$, 4-aminopiperidin-1-yl,

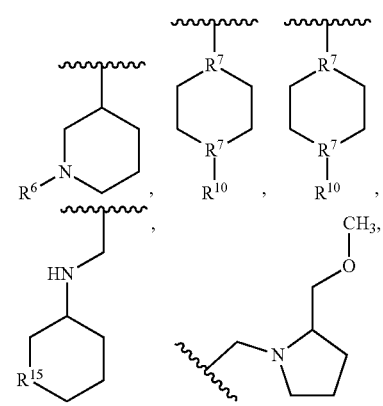

-continued

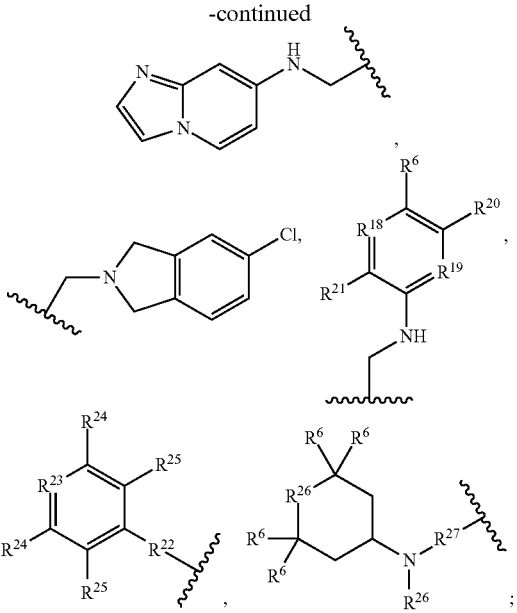

R² is selected from the group consisting of —H,

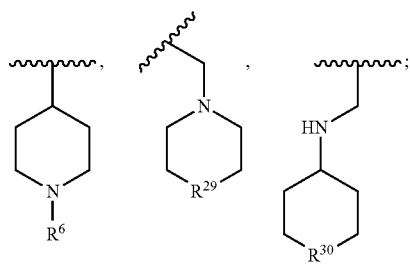

R³ is selected from the group consisting of -heteroalicyclyl and —CH₂CH₂N(CH₃)₂;
R⁴ is selected from the group consisting of -alkyl, -heteroaryl, -carboalicyclyl, and 1-methyl-1H-pyrazol-4-yl;
R⁵ is selected from the group consisting of -alkyl and -carboalicyclyl;
R⁶ is selected from the group consisting of —H and -alkyl;
R⁷ is selected from the group consisting of and N;
R⁸ is selected from the group consisting of —NH—, —CH₂CH₂NHCH₂—,

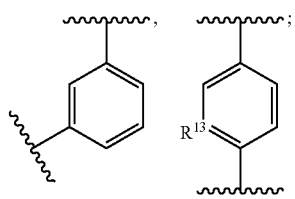

R⁹ is selected from the group consisting of —CH₂—, —NH—, —O—, —CH(R³¹)—, and —N(R³²)—;
R¹⁰ is selected from the group consisting of —H, -alkyl, —N(CH₃)₂, and —CH₂CH₂OCH₃;
R¹¹ is selected from the group consisting of —CH=, —N=, and —C(R³³)=;

R¹² is selected from the group consisting of —CH=, —N=, and —C(R³⁴)=;
R¹³ is selected from the group consisting of —CH= and —N=;
R¹⁴ is selected from the group consisting of —H, -alkyl, phenoxy, and

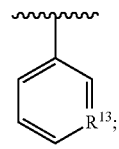

R¹⁵ is selected from the group consisting of —NH—, —O—, and —N(R³⁵)—;
R¹⁶ is selected from the group consisting of —H, —OH, —OCH₃, and —N(CH₃)₂;
R¹⁷ is selected from the group consisting of —H and —OCH₃;
R¹⁸ is selected from the group consisting of —CH=, —N=, and

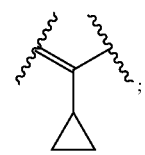 [SMILES: *C(=*)C1CC1]

R¹⁹ is selected from the group consisting of —CH=, —N=, and —CCH₃=;
R²⁰ is selected from the group consisting of —H and —CN;
R²¹ is selected from the group consisting of —H, -alkyl, and -halogen;
R²² is selected from the group consisting of —NHCH₂—, —CH₂N(R⁶)CH₂—, and

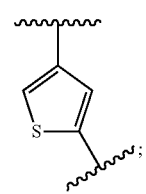 [SMILES: *c1csc(*)c1]

R²³ is selected from the group consisting of —CH=, —N=, and —C(R³⁶)=;
R²⁴ is selected from the group consisting of —H, -alkyl, -halogen, and —CN;
R²⁵ is selected from the group consisting of —H and -halogen;
R²⁶ is selected from the group consisting of —CH₂—, —NH—, —O—, —CH(R³⁷)—, —C(CH₃)₂—, and

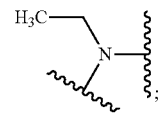

R²⁷ is selected from the group consisting of —CH₂— and —CO—;

R²⁸ is selected from the group consisting of —H, -alkyl, and -carboalicyclyl;

R²⁹ is selected from the group consisting of —O—, —CH(R³⁸)—, and —N(R³⁹)—;

R³⁰ is selected from the group consisting of —CH₂—, —O—, and —C(CH₃)₂—;

R³¹ is selected from the group consisting of —OH, -halogen, -carboaryl, —OCH₃, —N(CH₃)₂, —CH₂N(CH₃)₂, —OCH(CH₃)₂, and —CH₂CH₂R⁴⁰CH₃;

R³² is selected from the group consisting of -alkyl, —CCH₃O, —CH₂CH₂OCH₃, —CH₂CONHCH₃, and —R²⁷CH₂CH(CH₃)₂;

R³³ is selected from the group consisting of -halogen, —OCH₃, and cyclopropylmethoxy;

R³⁴ is selected from the group consisting of -alkyl, -halogen, —OCH₂CH₃, —C(CH₃)₂R⁴¹, —CH₂NHCCH₃O, (pyrrolidin-1-yl)methyl, benzyl,

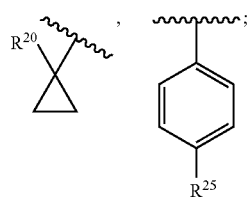

R³⁵ is selected from the group consisting of —CCH₃O, —R²⁷CH₂R⁴², and —SO₂R⁴³;

R³⁶ is selected from the group consisting of -halogen and —CN;

R³⁷ is selected from the group consisting of —NH₂, —N(CH₃)₂, —CONHCH₃, and —NHCCH₃O;

R³⁸ is selected from the group consisting of -halogen and —N(CH₃)₂;

R³⁹ is -alkyl;

R⁴⁰ is selected from the group consisting of —CH₂— and —O—;

R⁴¹ is selected from the group consisting of —OH, -alkyl, and —CN;

R⁴² is selected from the group consisting of -alkyl and —COOH;

R⁴³ is selected from the group consisting of -alkyl, -carboalicyclyl, and 3-fluorophenyl.

2. The compound according to claim 1, wherein:

R¹ is selected from the group consisting of —H, 1H-pyrrol-2-yl, furan-2-yl, 1H-imidazol-5-yl, 1,2-oxazol-5-yl, 1H-1,2,3-triazol-5-yl, 1,3,4-oxadiazol-2-yl, 1H-1,2,3,4-tetrazol-5-yl, thiophen-2-yl, 1,3-thiazol-2-yl, 1,3,4-thiadiazol-2-yl, pyridin-2-yl, pyrimidin-4-yl, 1,3,5-triazin-2-yl, 1,2,4-triazin-3-yl, 1λ⁴-pyran-1-ylium-4-yl, —CONHR³, —CH₂N(R⁵)CH₂R⁴, 4-aminopiperidin-1-yl,

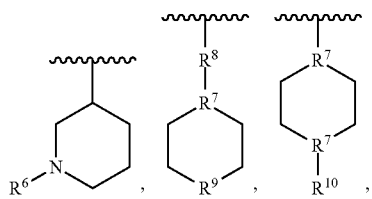

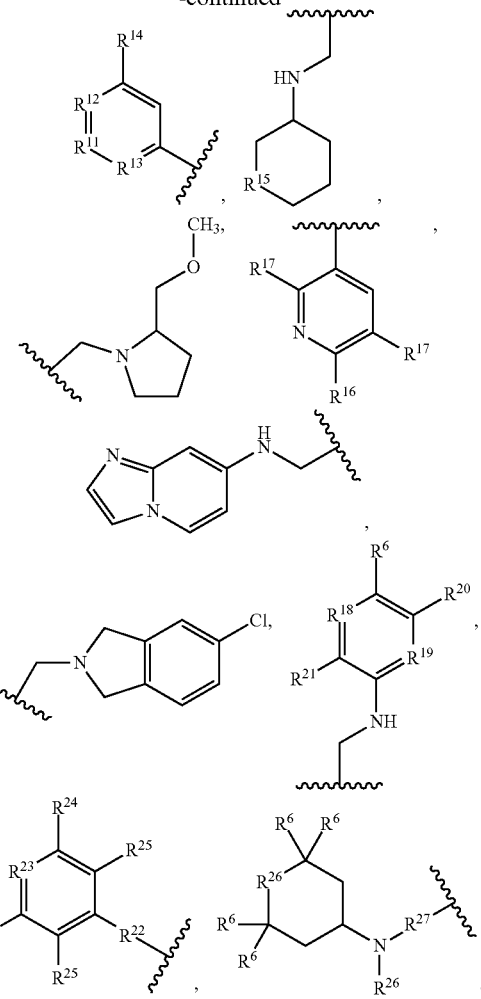

3. The compound according to claim 1, wherein:

R³ is selected from the group consisting of aziridin-1-yl, 2,5-dihydro-1H-pyrrol-1-yl, 2,5-dihydrofuran-3-yl, 4,5-dihydro-1H-imidazol-2-yl, pyrrolidin-1-yl, oxolan-2-yl, imidazolidin-4-yl, 1,3-dioxolan-2-yl, 1,3-thiazolidin-3-yl, piperidin-1-yl, oxan-2-yl, 1,3-diazinan-5-yl, morpholin-4-yl, 1,3,5-triazinan-2-yl, 1,3-dioxan-2-yl, and —CH₂CH₂N(CH₃)₂.

4. The compound according to claim 1, wherein:

R³ is selected from the group consisting of aziridin-1-yl, 2,5-dihydro-1H-pyrrol-1-yl, 2,5-dihydrofuran-3-yl, 4,5-dihydro-1H-imidazol-2-yl, pyrrolidin-1-yl, oxolan-2-yl, imidazolidin-4-yl, 1,3-dioxolan-2-yl, 1,3-thiazolidin-3-yl, piperidin-1-yl, oxan-2-yl, 1,3-diazinan-5-yl, morpholin-4-yl, 1,3,5-triazinan-2-yl, 1,3-dioxan-2-yl, and —CH₂CH₂N(CH₃)₂;

R⁴ is selected from the group consisting of —CH₃, —CH₂CH₃, —CH₂CH₂CH₃, —CH₂CH₂CH₂CH₃, —C(CH₃)₃, pentyl, —CH₂CH₂CH(CH₃)₂, —CH₂C(CH₃)₃, hexyl, heptyl, 6-methylheptan-2-yl, decyl, hexadecyl, 4,8,12-trimethyltridecyl, 1H-pyrrol-2-yl, furan-2-yl, 1H-imidazol-5-yl, 1,2-oxazol-5-yl, 1H-1,2,3-triazol-5-yl, 1,3,4-oxadiazol-2-yl, thiophen-2-yl, 1,3-thiazol-2-yl, 1,3,4-thiadiazol-2-yl, pyridin-2-yl, pyrimidin-4-yl, 1,3,5-triazin-2-yl, 1,2,4-triazin-3-yl, 1λ⁴-pyran-1-ylium-4-yl, cyclopropyl, cyclobutyl, cyclopent-2-en-1-yl, cyclopentyl, cyclohexa-1,4-dien- 1-yl, cyclohex-3-en-1-yl, cyclohexyl, adamantan-1-yl, decahydronaphthalen-1-yl, 1-methyl-1H-pyrazol-4-yl,

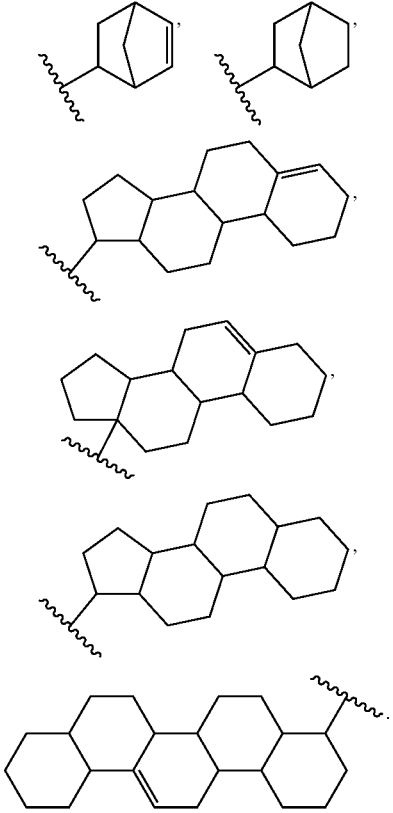

5. The compound according to claim 1, wherein:
R⁵ is selected from the group consisting of —CH₃, —CH₂CH₃, —CH₂CH₂CH₃, —CH₂CH₂CH₂CH₃, —C(CH₃)₃, pentyl, —CH₂CH₂CH(CH₃)₂, —CH₂C(CH₃)₃, hexyl, heptyl, 6-methylheptan-2-yl, decyl, hexadecyl, 4,8,12-trimethyltridecyl, cyclopropyl, cyclobutyl, cyclopent-2-en-1-yl, cyclopentyl, cyclohexa-1,4-dien-1-yl, cyclohex-3-en-1-yl, cyclohexyl, adamantan-1-yl, decahydronaphthalen-1-yl,

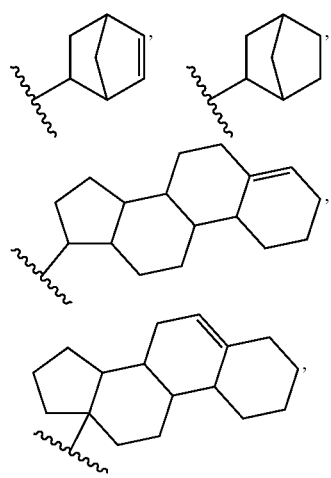

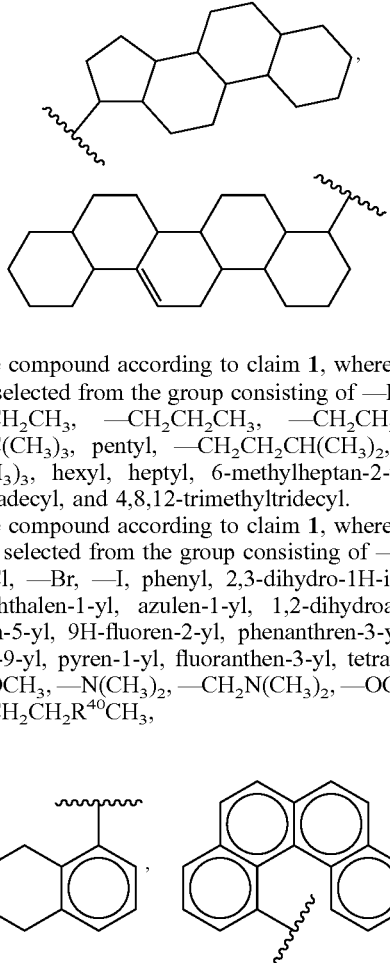

6. The compound according to claim 1, wherein:
R⁶ is selected from the group consisting of —H, —CH₃, —CH₂CH₃, —CH₂CH₂CH₃, —CH₂CH₂CH₂CH₃, —C(CH₃)₃, pentyl, —CH₂CH₂CH(CH₃)₂, —CH₂C(CH₃)₃, hexyl, heptyl, 6-methylheptan-2-yl, decyl, hexadecyl, and 4,8,12-trimethyltridecyl.

7. The compound according to claim 1, wherein:
R³¹ is selected from the group consisting of —OH, —F, —Cl, —Br, —I, phenyl, 2,3-dihydro-1H-inden-5-yl, naphthalen-1-yl, azulen-1-yl, 1,2-dihydroacenaphthylen-5-yl, 9H-fluoren-2-yl, phenanthren-3-yl, anthracen-9-yl, pyren-1-yl, fluoranthen-3-yl, tetraphen-7-yl, —OCH₃, —N(CH₃)₂, —CH₂N(CH₃)₂, —OCH(CH₃)₂, —CH₂CH₂R⁴⁰CH₃,

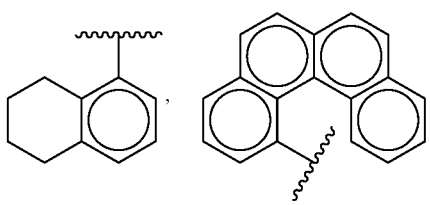

8. The compound according to claim 1, wherein:
R³² is selected from the group consisting of —CH₃, —CH₂CH₃, —CH₂CH₂CH₃, —CH₂CH₂CH₂CH₃, —C(CH₃)₃, pentyl, —CH₂CH₂CH(CH₃)₂, —CH₂C(CH₃)₃, hexyl, heptyl, 6-methylheptan-2-yl, decyl, hexadecyl, 4,8,12-trimethyltridecyl, —CCH₃O, —CH₂CH₂OCH₃, —CH₂CONHCH₃, and —R²⁷CH₂CH(CH₃)₂.

9. The compound according to claim 1, wherein:
R¹⁰ is selected from the group consisting of —H, —CH₃, —CH₂CH₃, —CH₂CH₂CH₃, —CH₂CH₂CH₂CH₃, —C(CH₃)₃, pentyl, —CH₂CH₂CH(CH₃)₂, —CH₂C(CH₃)₃, hexyl, heptyl, 6-methylheptan-2-yl, decyl, hexadecyl, 4,8,12-trimethyltridecyl, —N(CH₃)₂, and —CH₂CH₂OCH₃.

10. The compound according to claim 1, wherein:
R¹⁰ is selected from the group consisting of —H, —CH₃, —CH₂CH₃, —CH₂CH₂CH₃, —CH₂CH₂CH₂CH₃, —C(CH₃)₃, pentyl, —CH₂CH₂CH(CH₃)₂, —CH₂C(CH₃)₃, hexyl, heptyl, 6-methylheptan-2-yl, decyl, hexadecyl, 4,8,12-trimethyltridecyl, —N(CH₃)₂, and —CH₂CH₂OCH₃;
R³³ is selected from the group consisting of —F, —Cl, —Br, —I, —OCH₃, and cyclopropylmethoxy.

11. The compound according to claim 1, wherein:
R³⁴ is selected from the group consisting of —CH₃, —CH₂CH₃, —CH₂CH₂CH₃, —CH₂CH₂CH₂CH₃, —C(CH₃)₃, pentyl, —CH₂CH₂CH(CH₃)₂, —CH₂C ($CH_3$)$_3$, hexyl, heptyl, 6-methylheptan-2-yl, decyl, hexadecyl, 4,8,12-trimethyltridecyl, —F, —Cl, —Br, —I, —$OCH_2CH_3$, —$C(CH_3)_2R^{41}$, —$CH_2NHCCH_3O$, (pyrrolidin-1-yl)methyl, benzyl,

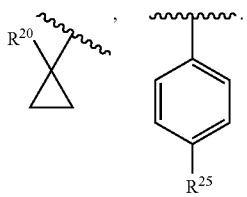

12. The compound according to claim 1, wherein:
$R^{14}$ is selected from the group consisting of —H, —$CH_3$, —$CH_2CH_3$, —$CH_2CH_2CH_3$, —$CH_2CH_2CH_2CH_3$, —$C(CH_3)_3$, pentyl, —$CH_2CH_2CH(CH_3)_2$, —$CH_2C(CH_3)_3$, hexyl, heptyl, 6-methylheptan-2-yl, decyl, hexadecyl, 4,8,12-trimethyltridecyl, phenoxy, and

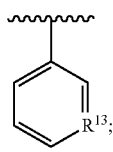

$R^{25}$ is selected from the group consisting of —H, —F, —Cl, —Br, and —I;
$R^{41}$ is selected from the group consisting of —OH, —$CH_3$, —$CH_2CH_3$, —$CH_2CH_2CH_3$, —$CH_2CH_2CH_2CH_3$, —$C(CH_3)_3$, pentyl, —$CH_2CH_2CH(CH_3)_2$, —$CH_2C(CH_3)_3$, hexyl, heptyl, 6-methylheptan-2-yl, decyl, hexadecyl, 4,8,12-trimethyltridecyl, and —CN.

13. The compound according to claim 1, wherein:
$R^{42}$ is selected from the group consisting of —$CH_3$, —$CH_2CH_3$, —$CH_2CH_2CH_3$, —$CH_2CH_2CH_2CH_3$, —$C(CH_3)_3$, pentyl, —$CH_2CH_2CH(CH_3)_2$, —$CH_2C(CH_3)_3$, hexyl, heptyl, 6-methylheptan-2-yl, decyl, hexadecyl, 4,8,12-trimethyltridecyl, and —COOH.

14. The compound according to claim 1, wherein:
$R^{43}$ is selected from the group consisting of —$CH_3$, —$CH_2CH_3$, —$CH_2CH_2CH_3$, —$CH_2CH_2CH_2CH_3$, —$C(CH_3)_3$, pentyl, —$CH_2CH_2CH(CH_3)_2$, —$CH_2C(CH_3)_3$, hexyl, heptyl, 6-methylheptan-2-yl, decyl, hexadecyl, 4,8,12-trimethyltridecyl, -carboalicyclyl, and 3-fluorophenyl.

15. The compound according to claim 1, wherein:
$R^6$ is selected from the group consisting of —H, —$CH_3$, —$CH_2CH_3$, —$CH_2CH_2CH_3$, —$CH_2CH_2CH_2CH_3$, —$C(CH_3)_3$, pentyl, —$CH_2CH_2CH(CH_3)_2$, —$CH_2C(CH_3)_3$, hexyl, heptyl, 6-methylheptan-2-yl, decyl, hexadecyl, and 4,8,12-trimethyltridecyl;
$R^{21}$ is selected from the group consisting of —H, —$CH_3$, —$CH_2CH_3$, —$CH_2CH_2CH_3$, —$CH_2CH_2CH_2CH_3$, —$C(CH_3)_3$, pentyl, —$CH_2CH_2CH(CH_3)_2$, —$CH_2C(CH_3)_3$, hexyl, heptyl, 6-methylheptan-2-yl, decyl, hexadecyl, 4,8,12-trimethyltridecyl, —F, —Cl, —Br, and —I;
$R^{24}$ is selected from the group consisting of —H, —$CH_3$, —$CH_2CH_3$, —$CH_2CH_2CH_3$, —$CH_2CH_2CH_2CH_3$, —$C(CH_3)_3$, pentyl, —$CH_2CH_2CH(CH_3)_2$, —$CH_2C(CH_3)_3$, hexyl, heptyl, 6-methylheptan-2-yl, decyl, hexadecyl, 4,8,12-trimethyltridecyl, —F, —Cl, —Br, —I, and —CN;
$R^{28}$ is selected from the group consisting of —H, —$CH_3$, —$CH_2CH_3$, —$CH_2CH_2CH_3$, —$CH_2CH_2CH_2CH_3$, —$C(CH_3)_3$, pentyl, —$CH_2CH_2CH(CH_3)_2$, —$CH_2C(CH_3)_3$, hexyl, heptyl, 6-methylheptan-2-yl, decyl, hexadecyl, 4,8,12-trimethyltridecyl, and -carboalicyclyl;
$R^{36}$ is selected from the group consisting of —F, —Cl, —Br, —I, and —CN;
$R^{38}$ is selected from the group consisting of —F, —Cl, —Br, —I, and —$N(CH_3)_2$;
$R^{39}$ is selected from the group consisting of —$CH_3$, —$CH_2CH_3$, —$CH_2CH_2CH_3$, —$CH_2CH_2CH_2CH_3$, —$C(CH_3)_3$, pentyl, —$CH_2CH_2CH(CH_3)_2$, —$CH_2C(CH_3)_3$, hexyl, heptyl, 6-methylheptan-2-yl, decyl, hexadecyl, and 4,8,12-trimethyltridecyl.

16. A compound selected from the group consisting of:

| Compound number | Structure | Chemical name |
|---|---|---|
| EXAMPLE 1 | ![structure] | 5-(2-fluoro-6-hydroxy-4-(piperidin-3-yl)phenyl)-1,2,5-thiadiazolidin-3-one 1,1-dioxide |

| Compound number | Structure | Chemical name |
|---|---|---|
| EXAMPLE 2 | 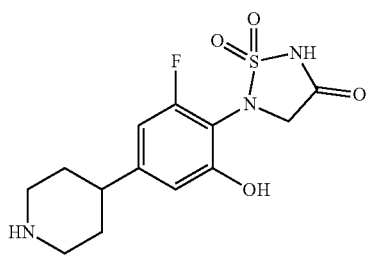 | -[2-fluoro-6-hydroxy-4-(4-piperidyl)phenyl]-1,1-dioxo-1,2,5-thiadiazolidin-3-one |
| EXAMPLE 3 | 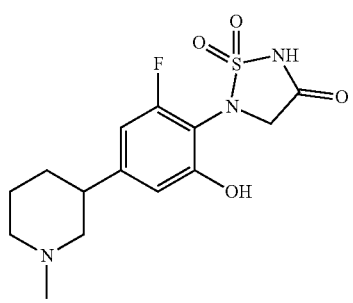 [SMILES: CN1CCCC(c2cc(O)c(N3CC(=O)NS3(=O)=O)c(F)c2)C1] | 5-(2-fluoro-6-hydroxy-4-(1-methylpiperidin-3-yl)phenyl)-1,2,5-thiadiazolidin-3-one 1,1-dioxide |
| EXAMPLE 4 | 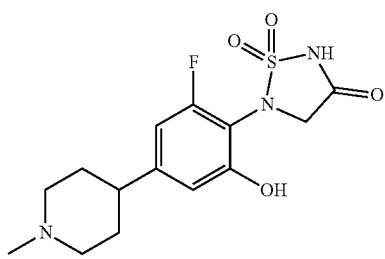 [SMILES: CN1CCC(c2cc(O)c(N3CC(=O)NS3(=O)=O)c(F)c2)CC1] | 5-[2-fluoro-6-hydroxy-4-(1-methyl-4-piperidyl)phenyl]-1,1-dioxo-1,2,5-thiadiazolidin-3-one |
| EXAMPLE 5 | 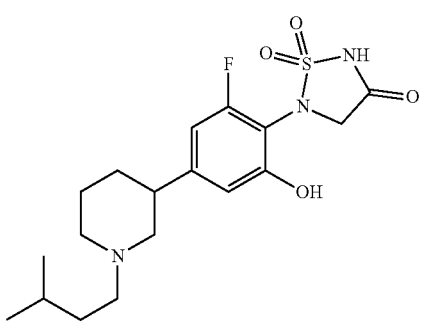 [SMILES: CC(C)CCN1CCCC(c2cc(O)c(N3CC(=O)NS3(=O)=O)c(F)c2)C1] | 5-(2-fluoro-6-hydroxy-4-(1-isopentylpiperidin-3-yl)phenyl)-1,2,5-thiadiazolidin-3-one 1,1-dioxide |
| EXAMPLE 6 | 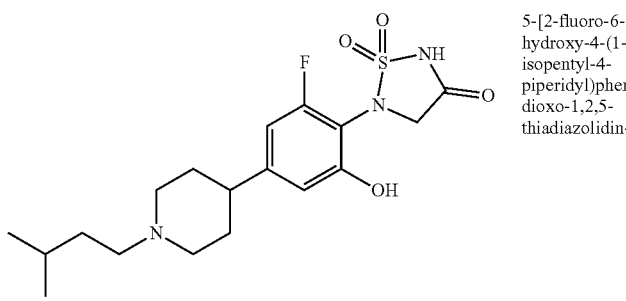 | 5-[2-fluoro-6-hydroxy-4-(1-isopentyl-4-piperidyl)phenyl]-1,1-dioxo-1,2,5-thiadiazolidin-3-one |

-continued

| Compound number | Structure | Chemical name |
|---|---|---|
| EXAMPLE 7 | 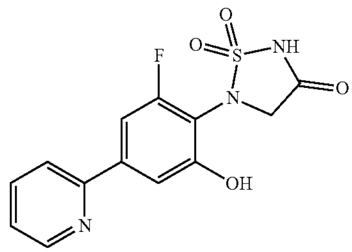 [SMILES: O=C1CN(c2c(O)cc(-c3ccccn3)cc2F)S(=O)(=O)N1] | 5-(2-fluoro-6-hydroxy-4-(pyridin-2-yl)phenyl)-1,2,5-thiadiazolidin-3-one 1,1-dioxide |
| EXAMPLE 8 | 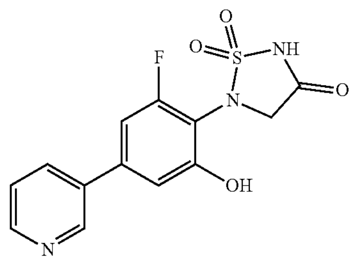 [SMILES: O=C1CN(c2c(O)cc(-c3cccnc3)cc2F)S(=O)(=O)N1] | 5-(2-fluoro-6-hydroxy-4-(pyridin-3-yl)phenyl)-1,2,5-thiadiazolidin-3-one 1,1-dioxide |
| EXAMPLE 9 | 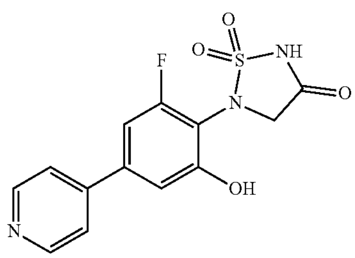 [SMILES: O=C1CN(c2c(O)cc(-c3ccncc3)cc2F)S(=O)(=O)N1] | 5-(2-fluoro-6-hydroxy-4-(pyridin-4-yl)phenyl)-1,2,5-thiadiazolidin-3-one 1,1-dioxide |
| EXAMPLE 10 | 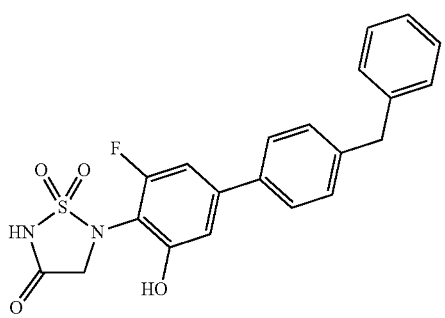 [SMILES: O=C1CN(c2c(O)cc(-c3ccc(Cc4ccccc4)cc3)cc2F)S(=O)(=O)N1] | 5-[4-(4-benzylphenyl)-2-fluoro-6-hydroxy-phenyl]-1,1-dioxo-1,2,5-thiadiazolidin-3-one |
| EXAMPLE 11 | 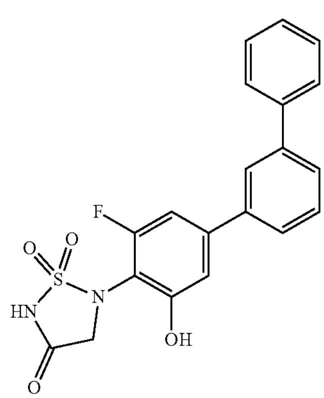 [SMILES: O=C1CN(c2c(O)cc(-c3cccc(-c4ccccc4)c3)cc2F)S(=O)(=O)N1] | 5-[2-fluoro-6-hydroxy-4-(3-phenylphenyl)phenyl]-1,1-dioxo-1,2,5-thiadiazolidin-3-one |

-continued

| Compound number | Structure | Chemical name |
|---|---|---|
| EXAMPLE 12 | 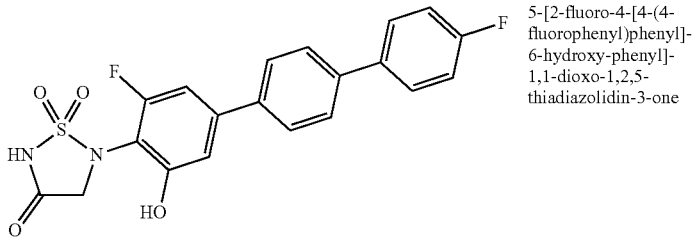 | 5-[2-fluoro-4-[4-(4-fluorophenyl)phenyl]-6-hydroxy-phenyl]-1,1-dioxo-1,2,5-thiadiazolidin-3-one |
| EXAMPLE 13 | 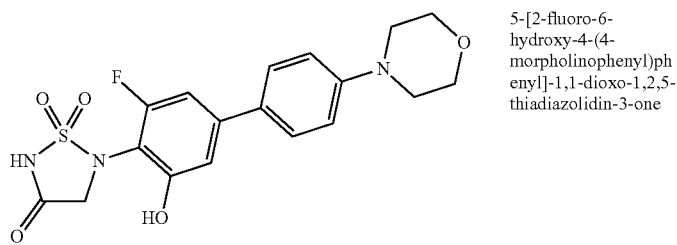 | 5-[2-fluoro-6-hydroxy-4-(4-morpholinophenyl)phenyl]-1,1-dioxo-1,2,5-thiadiazolidin-3-one |
| EXAMPLE 14 | 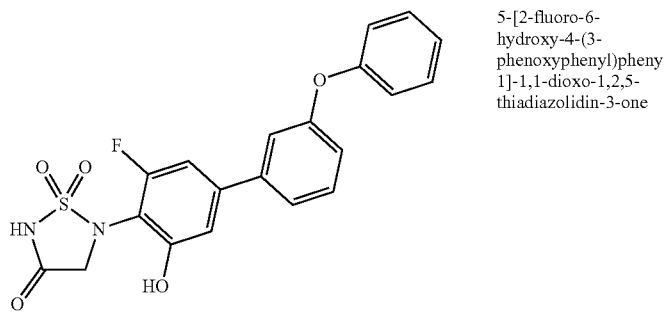 | 5-[2-fluoro-6-hydroxy-4-(3-phenoxyphenyl)phenyl]-1,1-dioxo-1,2,5-thiadiazolidin-3-one |
| EXAMPLE 15 | 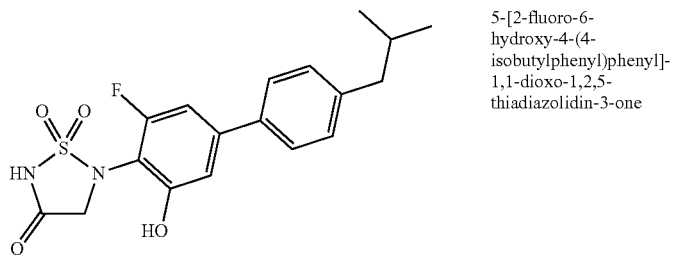 | 5-[2-fluoro-6-hydroxy-4-(4-isobutylphenyl)phenyl]-1,1-dioxo-1,2,5-thiadiazolidin-3-one |
| EXAMPLE 16 | 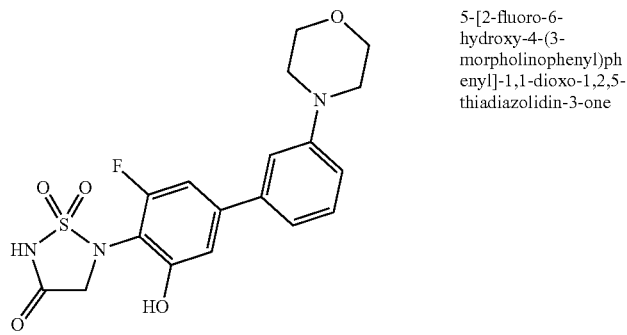 | 5-[2-fluoro-6-hydroxy-4-(3-morpholinophenyl)phenyl]-1,1-dioxo-1,2,5-thiadiazolidin-3-one |

-continued

| Compound number | Structure | Chemical name |
|---|---|---|
| EXAMPLE 17 | 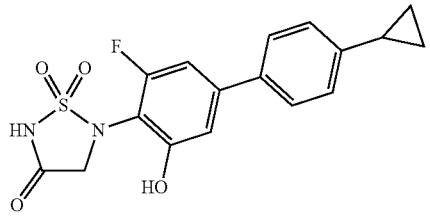 [SMILES: O=C1CN(c2c(O)cc(-c3ccc(C4CC4)cc3)cc2F)S(=O)(=O)N1] | 5-[4-(4-cyclopropylphenyl)-2-fluoro-6-hydroxy-phenyl]-1,1-dioxo-1,2,5-thiadiazolidin-3-one |
| EXAMPLE 18 | 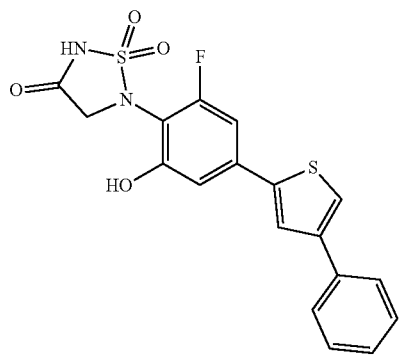 [SMILES: O=C1CN(c2c(O)cc(-c3cc(-c4ccccc4)cs3)cc2F)S(=O)(=O)N1] | 5-[2-fluoro-6-hydroxy-4-(4-phenyl-2-thienyl)phenyl]-1,1-dioxo-1,2,5-thiadiazolidin-3-one |
| EXAMPLE 19 | 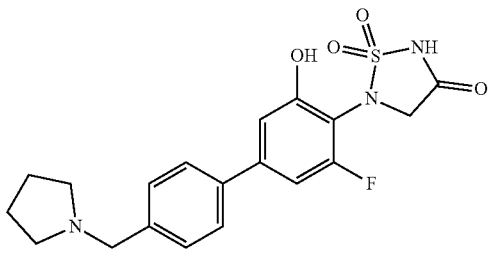 [SMILES: O=C1CN(c2c(O)cc(-c3ccc(CN4CCCC4)cc3)cc2F)S(=O)(=O)N1] | 5-[2-fluoro-6-hydroxy-4-[4-(pyrrolidin-1-ylmethyl)phenyl]phenyl]-1,1-dioxo-1,2,5-thiadiazolidin-3-one |
| EXAMPLE 20 | 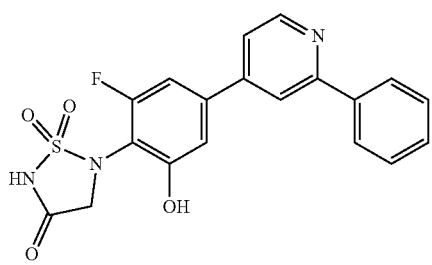 [SMILES: O=C1CN(c2c(O)cc(-c3ccnc(-c4ccccc4)c3)cc2F)S(=O)(=O)N1] | 5-[2-fluoro-6-hydroxy-4-(2-phenyl-4-pyridyl)phenyl]-1,1-dioxo-1,2,5-thiadiazolidin-3-one |
| EXAMPLE 21 | 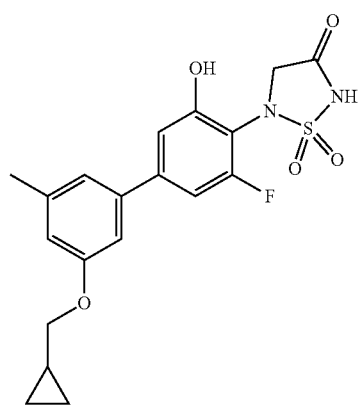 [SMILES: Cc1cc(OCC2CC2)cc(-c2cc(O)c(N3CC(=O)NS3(=O)=O)c(F)c2)c1] | 5-[4-[3-(cyclopropylmethoxy)-5-methyl-phenyl]-2-fluoro-6-hydroxy-phenyl]-1,1-dioxo-1,2,5-thiadiazolidin-3-one |

-continued

| Compound number | Structure | Chemical name |
|---|---|---|
| EXAMPLE 22 | 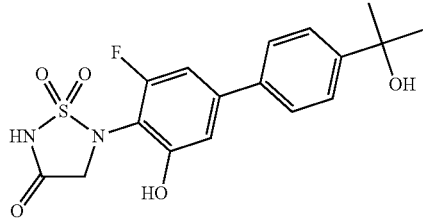 [SMILES: CC(C)(O)c1ccc(-c2cc(O)c(N3CC(=O)NS3(=O)=O)c(F)c2)cc1] | 5-[2-fluoro-6-hydroxy-4-[4-(1-hydroxy-1-methyl-ethyl)phenyl]phenyl]-1,1-dioxo-1,2,5-thiadiazolidin-3-one |
| EXAMPLE 23 | 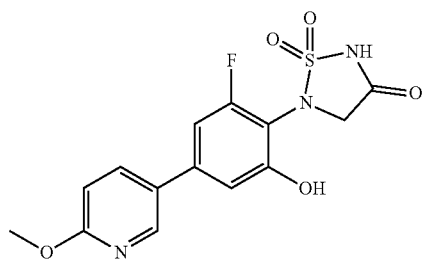 [SMILES: COc1ccc(-c2cc(O)c(N3CC(=O)NS3(=O)=O)c(F)c2)cn1] | 5-[2-fluoro-6-hydroxy-4-(6-methoxy-3-pyridyl)phenyl]-1,1-dioxo-1,2,5-thiadiazolidin-3-one |
| EXAMPLE 24 | 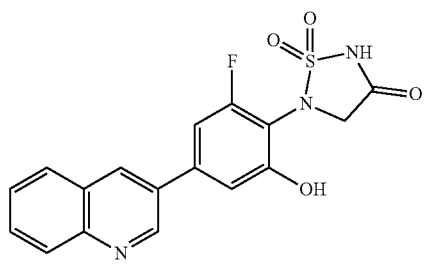 [SMILES: O=C1CN(c2c(O)cc(-c3cnc4ccccc4c3)cc2F)S(=O)(=O)N1] | 5-[2-fluoro-6-hydroxy-4-(3-quinolyl)phenyl]-1,1-dioxo-1,2,5-thiadiazolidin-3-one |
| EXAMPLE 25 | 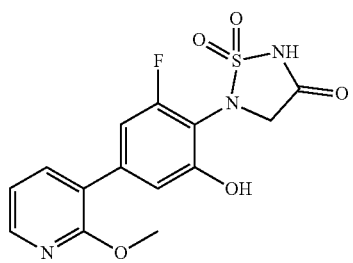 [SMILES: COc1ncccc1-c1cc(O)c(N2CC(=O)NS2(=O)=O)c(F)c1] | 5-[2-fluoro-6-hydroxy-4-(2-methoxy-3-pyridyl)phenyl]-1,1-dioxo-1,2,5-thiadiazolidin-3-one |
| EXAMPLE 26 | 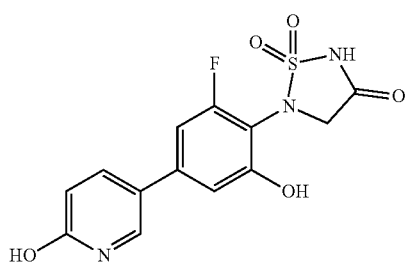 | 5-[2-fluoro-6-hydroxy-4-(6-hydroxy-3-pyridyl)phenyl]-1,1-dioxo-1,2,5-thiadiazolidin-3-one |

-continued

| Compound number | Structure | Chemical name |
|---|---|---|
| EXAMPLE 27 | 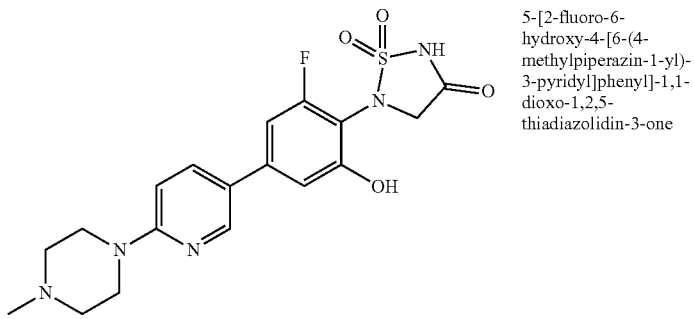 | 5-[2-fluoro-6-hydroxy-4-[6-(4-methylpiperazin-1-yl)-3-pyridyl]phenyl]-1,1-dioxo-1,2,5-thiadiazolidin-3-one |
| EXAMPLE 28 | 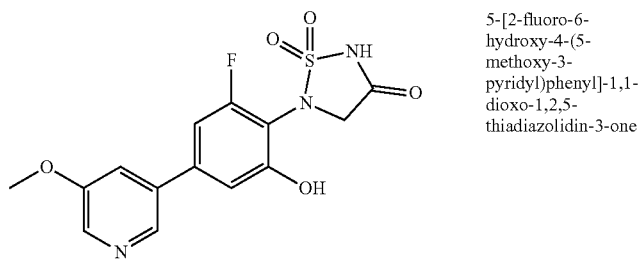 | 5-[2-fluoro-6-hydroxy-4-(5-methoxy-3-pyridyl)phenyl]-1,1-dioxo-1,2,5-thiadiazolidin-3-one |
| EXAMPLE 29 | 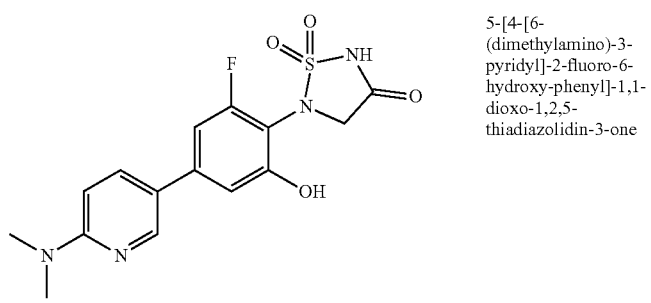 | 5-[4-[6-(dimethylamino)-3-pyridyl]-2-fluoro-6-hydroxy-phenyl]-1,1-dioxo-1,2,5-thiadiazolidin-3-one |
| EXAMPLE 30 | 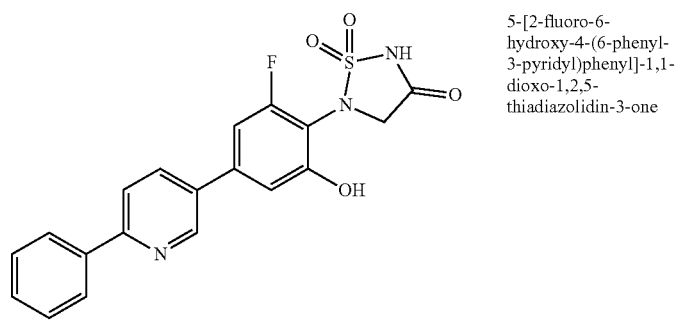 | 5-[2-fluoro-6-hydroxy-4-(6-phenyl-3-pyridyl)phenyl]-1,1-dioxo-1,2,5-thiadiazolidin-3-one |
| EXAMPLE 31 | 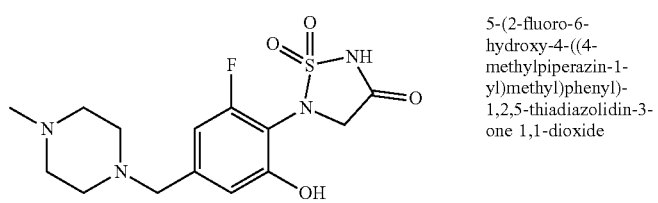 | 5-(2-fluoro-6-hydroxy-4-((4-methylpiperazin-1-yl)methyl)phenyl)-1,2,5-thiadiazolidin-3-one 1,1-dioxide |

| Compound number | Structure | Chemical name |
|---|---|---|
| EXAMPLE 32 | 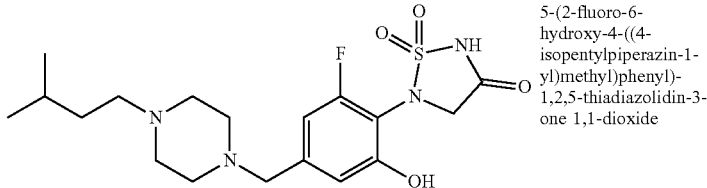 | 5-(2-fluoro-6-hydroxy-4-((4-isopentylpiperazin-1-yl)methyl)phenyl)-1,2,5-thiadiazolidin-3-one 1,1-dioxide |
| EXAMPLE 33 | 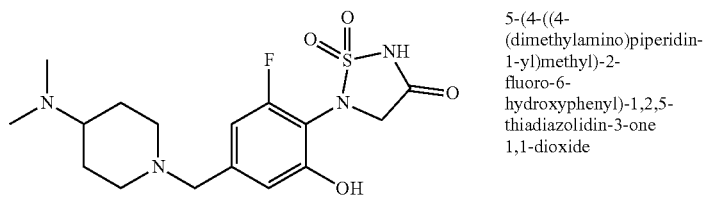 | 5-(4-((4-(dimethylamino)piperidin-1-yl)methyl)-2-fluoro-6-hydroxyphenyl)-1,2,5-thiadiazolidin-3-one 1,1-dioxide |
| EXAMPLE 34 | 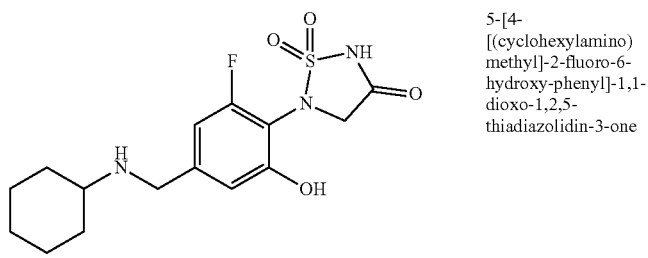 | 5-[4-[(cyclohexylamino)methyl]-2-fluoro-6-hydroxy-phenyl]-1,1-dioxo-1,2,5-thiadiazolidin-3-one |
| EXAMPLE 35 | 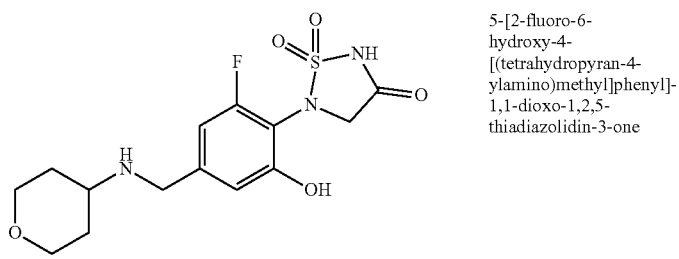 | 5-[2-fluoro-6-hydroxy-4-[(tetrahydropyran-4-ylamino)methyl]phenyl]-1,1-dioxo-1,2,5-thiadiazolidin-3-one |
| EXAMPLE 36 | 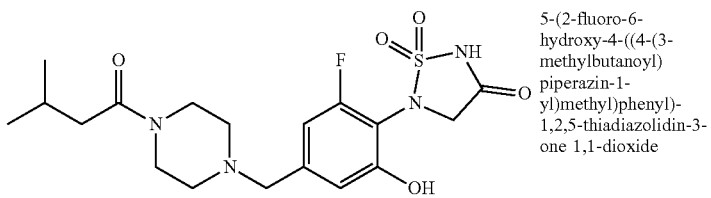 | 5-(2-fluoro-6-hydroxy-4-((4-(3-methylbutanoyl)piperazin-1-yl)methyl)phenyl)-1,2,5-thiadiazolidin-3-one 1,1-dioxide |
| EXAMPLE 37 | 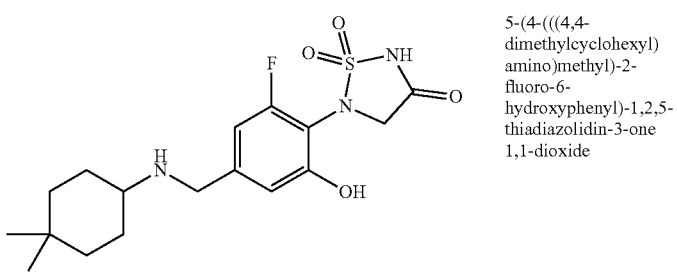 | 5-(4-(((4,4-dimethylcyclohexyl)amino)methyl)-2-fluoro-6-hydroxyphenyl)-1,2,5-thiadiazolidin-3-one 1,1-dioxide |

-continued

| Compound number | Structure | Chemical name |
|---|---|---|
| EXAMPLE 38 | 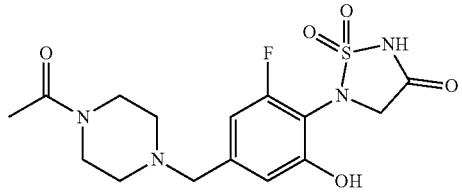 [SMILES: CC(=O)N1CCN(Cc2cc(O)c(N3CC(=O)NS3(=O)=O)c(F)c2)CC1] | 5-(4-((4-acetylpiperazin-1-yl)methyl)-2-fluoro-6-hydroxyphenyl)-1,2,5-thiadiazolidin-3-one 1,1-dioxide |
| EXAMPLE 39 | 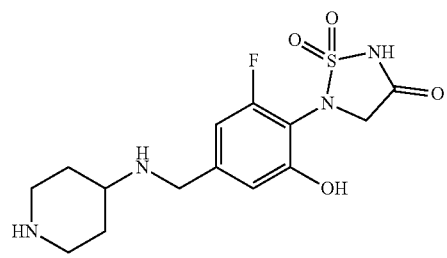 | 5-(2-fluoro-6-hydroxy-4-((piperidin-4-ylamino)methyl)phenyl)-1,2,5-thiadiazolidin-3-one 1,1-dioxide |
| EXAMPLE 40 | 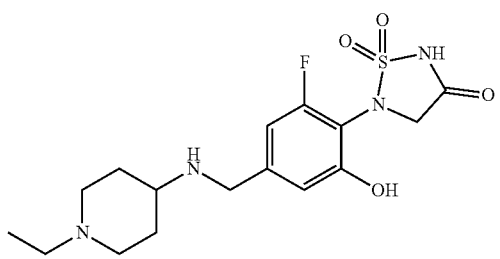 [SMILES: CCN1CCC(NCc2cc(O)c(N3CC(=O)NS3(=O)=O)c(F)c2)CC1] | 5-(4-(((1-ethylpiperidin-4-yl)amino)methyl)-2-fluoro-6-hydroxyphenyl)-1,2,5-thiadiazolidin-3-one 1,1-dioxide |
| EXAMPLE 41 | 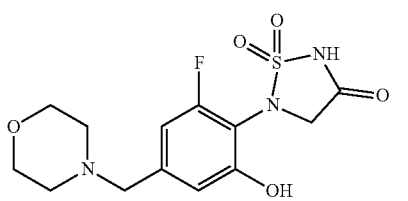 [SMILES: O=C1CN(c2c(O)cc(CN3CCOCC3)cc2F)S(=O)(=O)N1] | 5-(2-fluoro-6-hydroxy-4-(morpholinomethyl)phenyl)-1,2,5-thiadiazolidin-3-one 1,1-dioxide |
| EXAMPLE 42 | 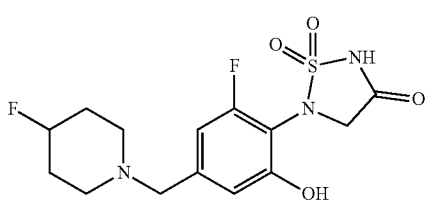 [SMILES: O=C1CN(c2c(O)cc(CN3CCC(F)CC3)cc2F)S(=O)(=O)N1] | 5-(2-fluoro-4-((4-fluoropiperidin-1-yl)methyl)-6-hydroxyphenyl)-1,2,5-thiadiazolidin-3-one 1,1-dioxide |
| EXAMPLE 43 | 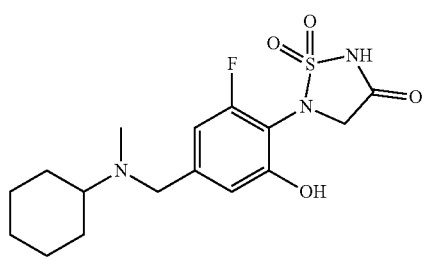 [SMILES: CN(Cc1cc(O)c(N2CC(=O)NS2(=O)=O)c(F)c1)C1CCCCC1] | 5-(4-((cyclohexyl(methyl)amino)methyl)-2-fluoro-6-hydroxyphenyl)-1,2,5-thiadiazolidin-3-one 1,1-dioxide |

-continued

| Compound number | Structure | Chemical name |
|---|---|---|
| EXAMPLE 44 | 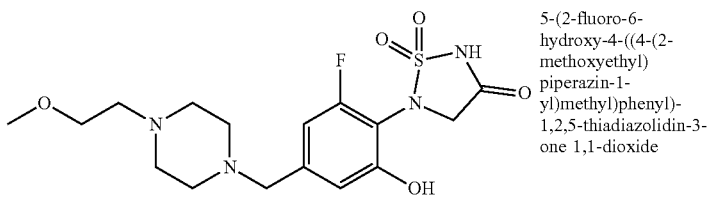 | 5-(2-fluoro-6-hydroxy-4-((4-(2-methoxyethyl)piperazin-1-yl)methyl)phenyl)-1,2,5-thiadiazolidin-3-one 1,1-dioxide |
| EXAMPLE 45 | 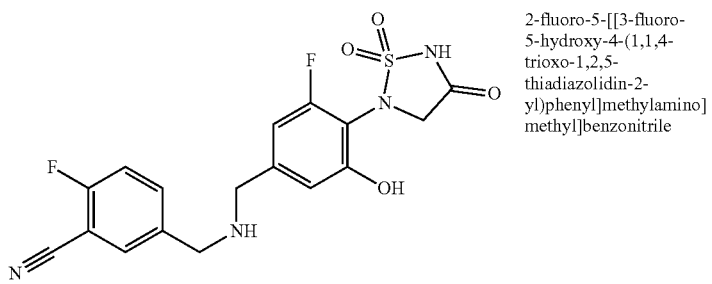 | 2-fluoro-5-[[3-fluoro-5-hydroxy-4-(1,1,4-trioxo-1,2,5-thiadiazolidin-2-yl)phenyl]methylamino]methyl]benzonitrile |
| EXAMPLE 46 | 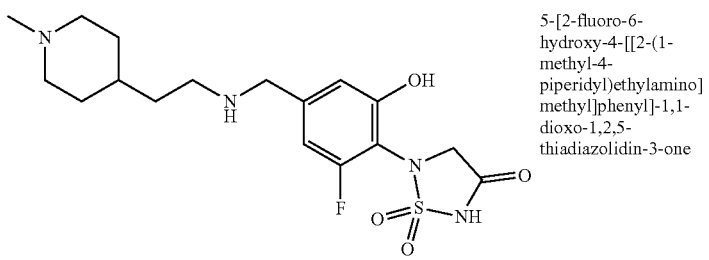 | 5-[2-fluoro-6-hydroxy-4-[[2-(1-methyl-4-piperidyl)ethylamino]methyl]phenyl]-1,1-dioxo-1,2,5-thiadiazolidin-3-one |
| EXAMPLE 47 | 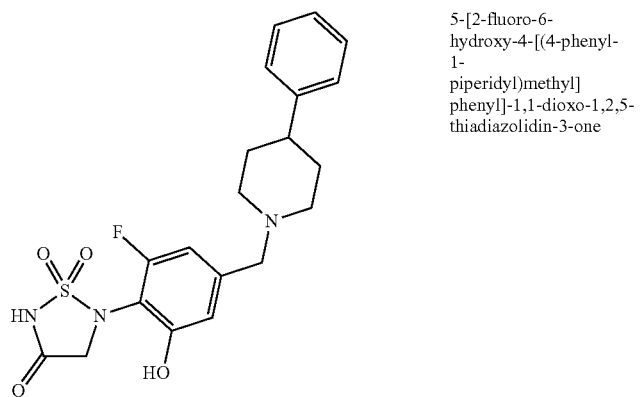 | 5-[2-fluoro-6-hydroxy-4-[(4-phenyl-1-piperidyl)methyl]phenyl]-1,1-dioxo-1,2,5-thiadiazolidin-3-one |
| EXAMPLE 48 | 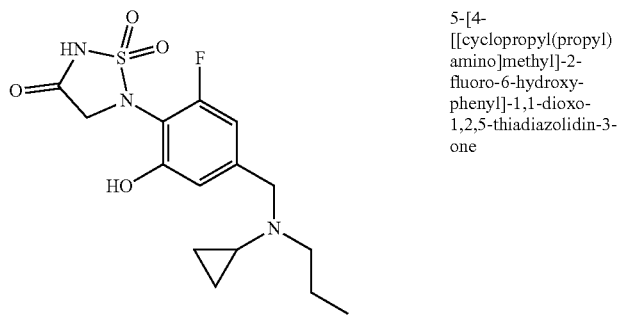 | 5-[4-[[cyclopropyl(propyl)amino]methyl]-2-fluoro-6-hydroxy-phenyl]-1,1-dioxo-1,2,5-thiadiazolidin-3-one |

| Compound number | Structure | Chemical name |
|---|---|---|
| EXAMPLE 49 | 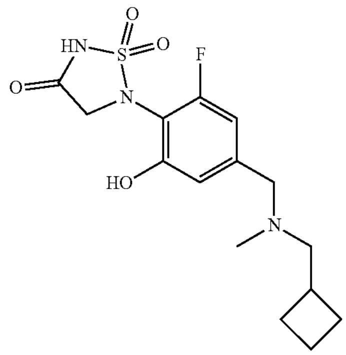 [SMILES: CN(Cc1cc(O)c(N2CC(=O)NS2(=O)=O)c(F)c1)CC1CCC1] | 5-[4-[[cyclobutylmethyl(methyl)amino]methyl]-2-fluoro-6-hydroxy-phenyl]-1,1-dioxo-1,2,5-thiadiazolidin-3-one |
| EXAMPLE 50 | 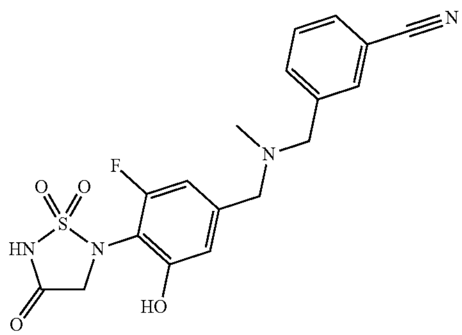 [SMILES: CN(Cc1cccc(C#N)c1)Cc1cc(O)c(N2CC(=O)NS2(=O)=O)c(F)c1] | 3-[[[3-fluoro-5-hydroxy-4-(1,1,4-trioxo-1,2,5-thiadiazolidin-2-yl)phenyl]methyl-methyl-amino]methyl]benzonitrile |
| EXAMPLE 51 | 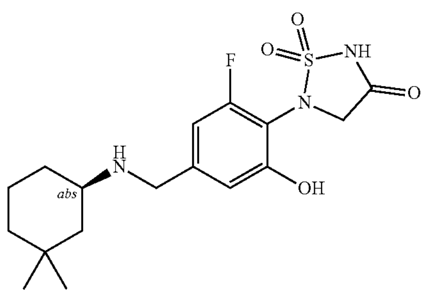 [SMILES: CC1(C)CCC[C@@H](NCc2cc(O)c(N3CC(=O)NS3(=O)=O)c(F)c2)C1] | 5-[4-[[[(1R)-3,3-dimethylcyclohexyl]amino]methyl]-2-fluoro-6-hydroxy-phenyl]-1,1-dioxo-1,2,5-thiadiazolidin-3-one |
| EXAMPLE 52 | 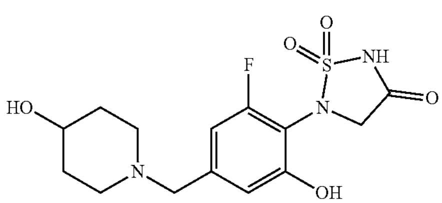 [SMILES: O=C1CN(c2c(O)cc(CN3CCC(O)CC3)cc2F)S(=O)(=O)N1] | 5-[2-fluoro-6-hydroxy-4-[(4-hydroxy-1-piperidyl)methyl]phenyl]-1,1-dioxo-1,2,5-thiadiazolidin-3-one |
| EXAMPLE 53 | 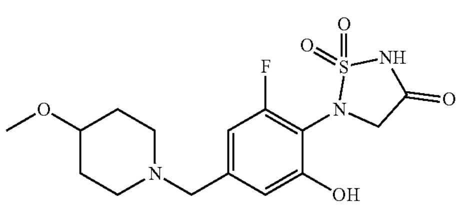 [SMILES: COC1CCN(Cc2cc(O)c(N3CC(=O)NS3(=O)=O)c(F)c2)CC1] | 5-[2-fluoro-6-hydroxy-4-[(4-methoxy-1-piperidyl)methyl]phenyl]-1,1-dioxo-1,2,5-thiadiazolidin-3-one |

| Compound number | Structure | Chemical name |
|---|---|---|
| EXAMPLE 54 | 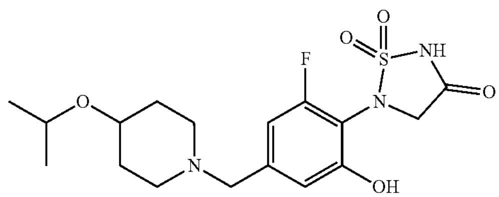 [SMILES: CC(C)OC1CCN(Cc2cc(O)c(N3CC(=O)NS3(=O)=O)c(F)c2)CC1] | 5-[2-fluoro-6-hydroxy-4-[(4-isopropoxy-1-piperidyl)methyl]phenyl]-1,1-dioxo-1,2,5-thiadiazolidin-3-one |
| EXAMPLE 55 | 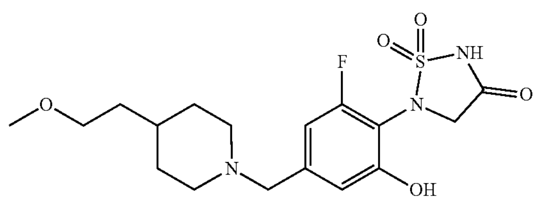 | 5-[2-fluoro-6-hydroxy-4-[[4-(2-methoxyethyl)-1-piperidyl]methyl]phenyl]-1,1-dioxo-1,2,5-thiadiazolidin-3-one |
| EXAMPLE 56 | 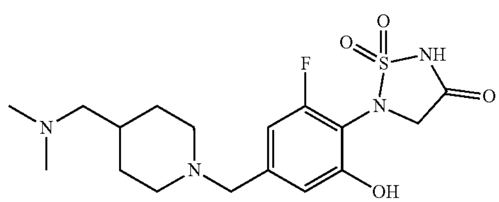 | 5-[4-[[4-[(dimethylamino)methyl]-1-piperidyl]methyl]-2-fluoro-6-hydroxyphenyl]-1,1-dioxo-1,2,5-thiadiazolidin-3-one |
| EXAMPLE 57 | 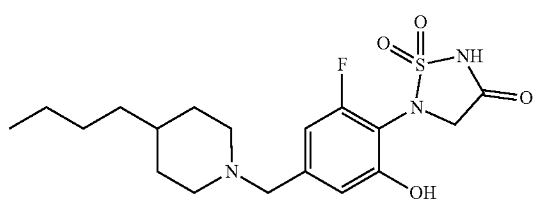 [SMILES: CCCCC1CCN(Cc2cc(O)c(N3CC(=O)NS3(=O)=O)c(F)c2)CC1] | 5-[4-[(4-butyl-1-piperidyl)methyl]-2-fluoro-6-hydroxyphenyl]-1,1-dioxo-1,2,5-thiadiazolidin-3-one |
| EXAMPLE 58 | 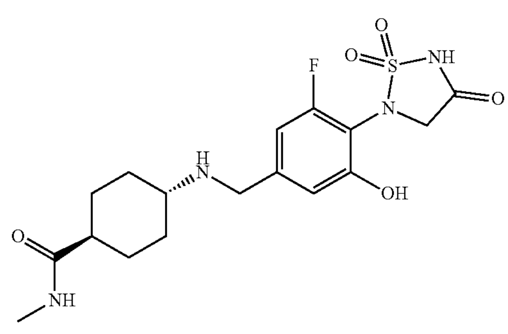 [SMILES: CNC(=O)[C@H]1CC[C@H](NCc2cc(O)c(N3CC(=O)NS3(=O)=O)c(F)c2)CC1] | (1r,4r)-4-((4-(1,1-dioxido-4-oxo-1,2,5-thiadiazolidin-2-yl)-3-fluoro-5-hydroxybenzyl)amino)-N-methylcyclohexane-1-carboxamide |
| EXAMPLE 59 | 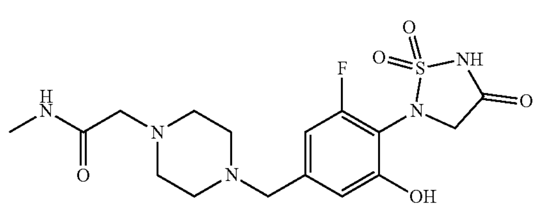 [SMILES: CNC(=O)CN1CCN(Cc2cc(O)c(N3CC(=O)NS3(=O)=O)c(F)c2)CC1] | 2-(4-(4-(1,1-dioxido-4-oxo-1,2,5-thiadiazolidin-2-yl)-3-fluoro-5-hydroxybenzyl)piperazin-1-yl)-N-methylacetamide |

| Compound number | Structure | Chemical name |
|---|---|---|
| EXAMPLE 60 | 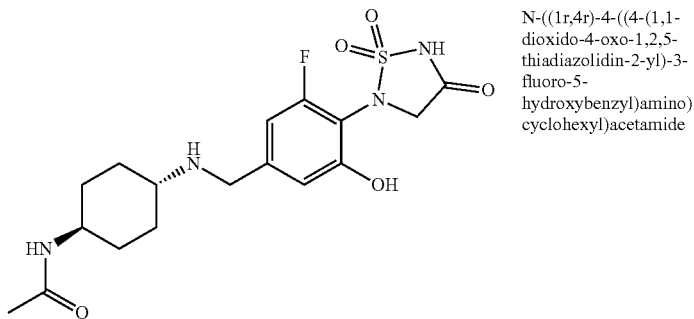 | N-((1r,4r)-4-((4-(1,1-dioxido-4-oxo-1,2,5-thiadiazolidin-2-yl)-3-fluoro-5-hydroxybenzyl)amino)cyclohexyl)acetamide |
| EXAMPLE 61 | 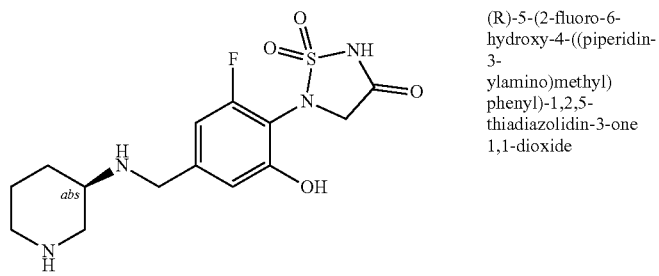 | (R)-5-(2-fluoro-6-hydroxy-4-((piperidin-3-ylamino)methyl)phenyl)-1,2,5-thiadiazolidin-3-one 1,1-dioxide |
| EXAMPLE 62 | 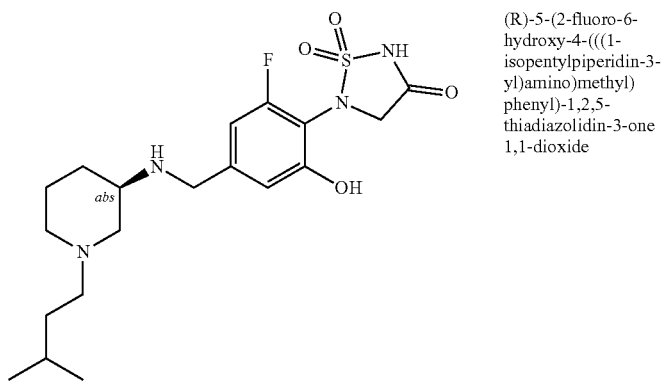 | (R)-5-(2-fluoro-6-hydroxy-4-(((1-isopentylpiperidin-3-yl)amino)methyl)phenyl)-1,2,5-thiadiazolidin-3-one 1,1-dioxide |
| EXAMPLE 63 | 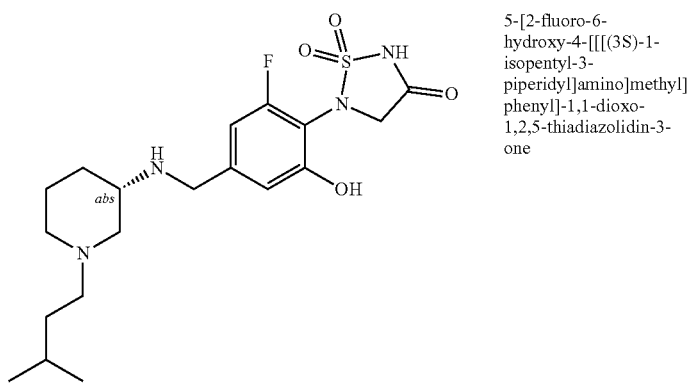 | 5-[2-fluoro-6-hydroxy-4-[[[(3S)-1-isopentyl-3-piperidyl]amino]methyl]phenyl]-1,1-dioxo-1,2,5-thiadiazolidin-3-one |

| Compound number | Structure | Chemical name |
|---|---|---|
| EXAMPLE 64 | 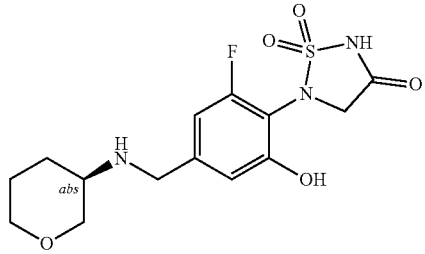 [SMILES: O=C1CN(c2c(O)cc(CN[C@@H]3CCCOC3)cc2F)S(=O)(=O)N1] | (R)-5-(2-fluoro-6-hydroxy-4-(((tetrahydro-2H-pyran-3-yl)amino)methyl)phenyl)-1,2,5-thiadiazolidin-3-one 1,1-dioxide |
| EXAMPLE 65 | 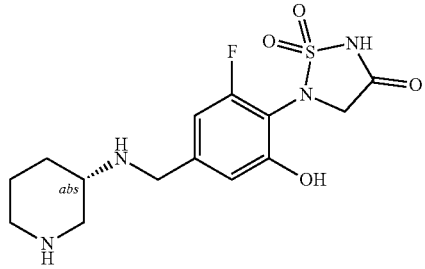 [SMILES: O=C1CN(c2c(O)cc(CN[C@H]3CCCNC3)cc2F)S(=O)(=O)N1] | (S)-5-(2-fluoro-6-hydroxy-4-((piperidin-3-ylamino)methyl)phenyl)-1,2,5-thiadiazolidin-3-one 1,1-dioxide |
| EXAMPLE 66 | 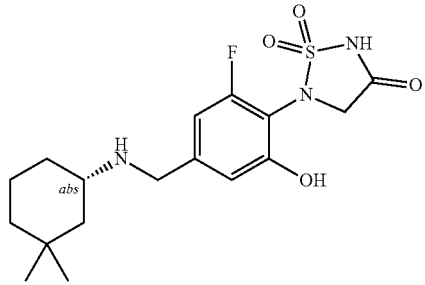 [SMILES: CC1(C)CCC[C@H](NCc2cc(O)c(N3CC(=O)NS3(=O)=O)c(F)c2)C1] | (S)-5-(4-(((3,3-dimethylcyclohexyl)amino)methyl)-2-fluoro-6-hydroxyphenyl)-1,2,5-thiadiazolidin-3-one 1,1-dioxide |
| EXAMPLE 67 | 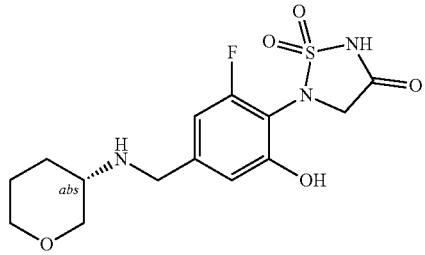 [SMILES: O=C1CN(c2c(O)cc(CN[C@H]3CCCOC3)cc2F)S(=O)(=O)N1] | (S)-5-(2-fluoro-6-hydroxy-4-(((tetrahydro-2H-pyran-3-yl)amino)methyl)phenyl)-1,2,5-thiadiazolidin-3-one 1,1-dioxide |
| EXAMPLE 68 | 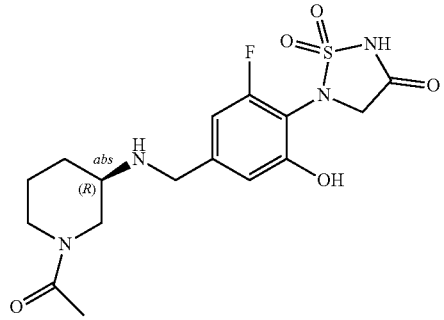 | 5-[4-[[[(3R)-1-acetyl-3-piperidyl]amino]methyl]-2-fluoro-6-hydroxy-phenyl]-1,1-dioxo-1,2,5-thiadiazolidin-3-one |

| Compound number | Structure | Chemical name |
|---|---|---|
| EXAMPLE 69 | 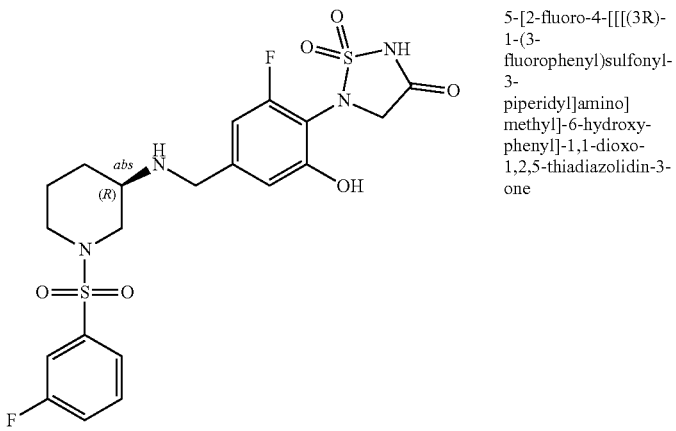 | 5-[2-fluoro-4-[[[(3R)-1-(3-fluorophenyl)sulfonyl-3-piperidyl]amino]methyl]-6-hydroxy-phenyl]-1,1-dioxo-1,2,5-thiadiazolidin-3-one |
| EXAMPLE 70 | 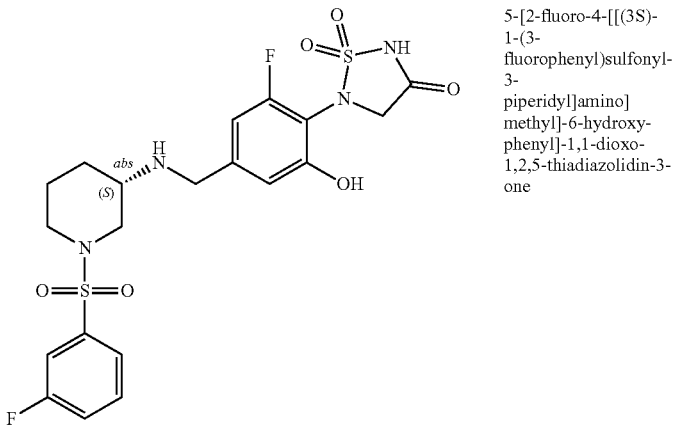 | 5-[2-fluoro-4-[[[(3S)-1-(3-fluorophenyl)sulfonyl-3-piperidyl]amino]methyl]-6-hydroxy-phenyl]-1,1-dioxo-1,2,5-thiadiazolidin-3-one |
| EXAMPLE 71 | 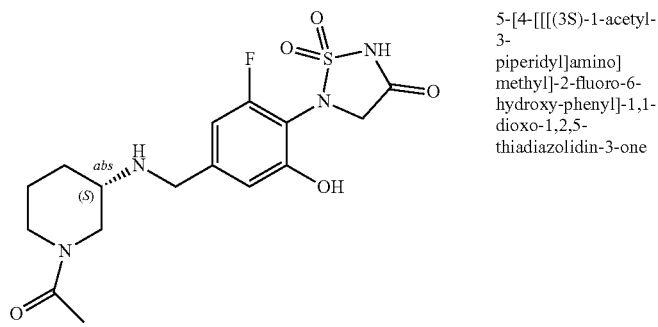 | 5-[4-[[[(3S)-1-acetyl-3-piperidyl]amino]methyl]-2-fluoro-6-hydroxy-phenyl]-1,1-dioxo-1,2,5-thiadiazolidin-3-one |
| EXAMPLE 72 | 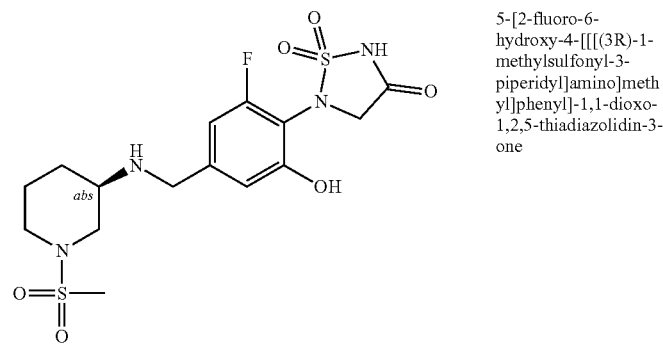 | 5-[2-fluoro-6-hydroxy-4-[[[(3R)-1-methylsulfonyl-3-piperidyl]amino]methyl]phenyl]-1,1-dioxo-1,2,5-thiadiazolidin-3-one |

-continued

| Compound number | Structure | Chemical name |
|---|---|---|
| EXAMPLE 73 | 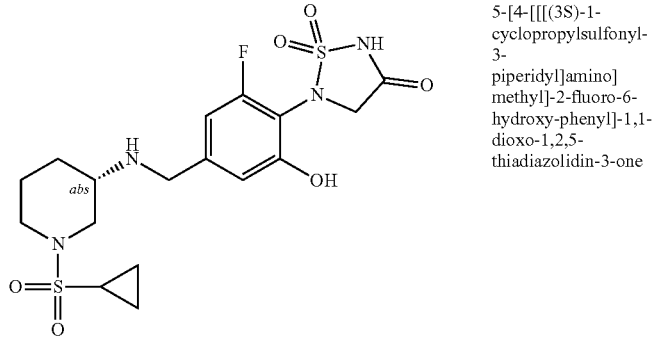 | 5-[4-[[[(3S)-1-cyclopropylsulfonyl-3-piperidyl]amino]methyl]-2-fluoro-6-hydroxy-phenyl]-1,1-dioxo-1,2,5-thiadiazolidin-3-one |
| EXAMPLE 74 | 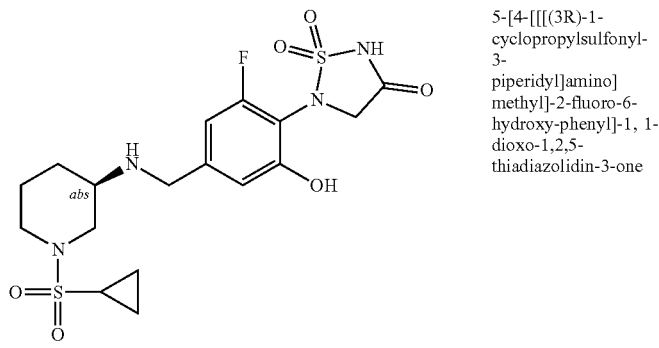 | 5-[4-[[[(3R)-1-cyclopropylsulfonyl-3-piperidyl]amino]methyl]-2-fluoro-6-hydroxy-phenyl]-1, 1-dioxo-1,2,5-thiadiazolidin-3-one |
| EXAMPLE 75 | 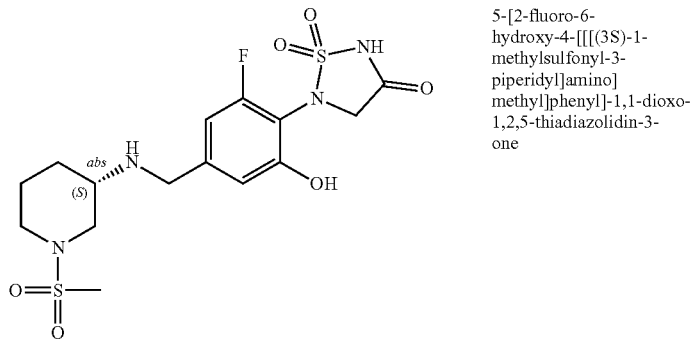 | 5-[2-fluoro-6-hydroxy-4-[[[(3S)-1-methylsulfonyl-3-piperidyl]amino]methyl]phenyl]-1,1-dioxo-1,2,5-thiadiazolidin-3-one |
| EXAMPLE 76 | 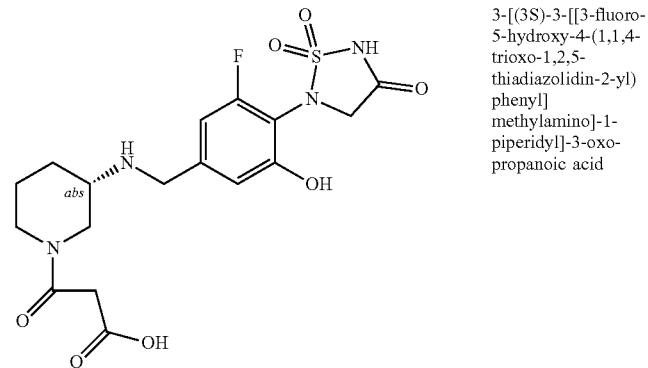 | 3-[(3S)-3-[[3-fluoro-5-hydroxy-4-(1,1,4-trioxo-1,2,5-thiadiazolidin-2-yl)phenyl]methylamino]-1-piperidyl]-3-oxo-propanoic acid |

-continued

| Compound number | Structure | Chemical name |
|---|---|---|
| EXAMPLE 77 | 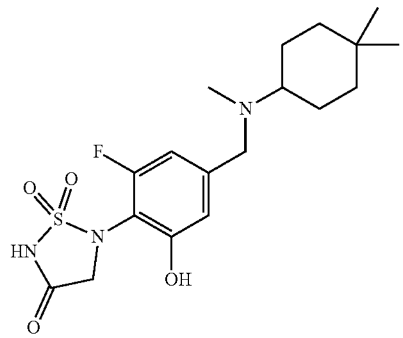 [SMILES: CN(Cc1cc(O)c(N2CC(=O)NS2(=O)=O)c(F)c1)C1CCC(C)(C)CC1] | 5-[4-[[(4,4-dimethylcyclohexyl)-methyl-amino]methyl]-2-fluoro-6-hydroxy-phenyl]-1,1-dioxo-1,2,5-thiadiazolidin-3-one |
| EXAMPLE 78 | 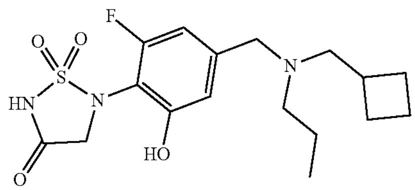 [SMILES: CCCN(Cc1cc(O)c(N2CC(=O)NS2(=O)=O)c(F)c1)CC1CCC1] | 5-[4-[cyclobutylmethyl(propyl)amino]methyl]-2-fluoro-6-hydroxy-phenyl]-1,1-dioxo-1,2,5-thiadiazolidin-3-one |
| EXAMPLE 79 | 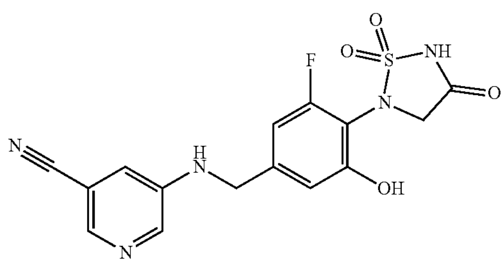 [SMILES: N#Cc1cncc(NCc2cc(O)c(N3CC(=O)NS3(=O)=O)c(F)c2)c1] | 5-[[3-fluoro-5-hydroxy-4-(1,1,4-trioxo-1,2,5-thiadiazolidin-2-yl)phenyl]methylamino]pyridine-3-carbonitrile |
| EXAMPLE 80 | 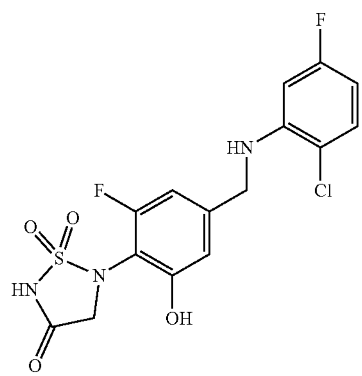 [SMILES: O=C1CN(c2c(O)cc(CNc3cc(F)ccc3Cl)cc2F)S(=O)(=O)N1] | 5-[4-[(2-chloro-5-fluoro-anilino)methyl]-2-fluoro-6-hydroxy-phenyl]-1,1-dioxo-1,2,5-thiadiazolidin-3-one |
| EXAMPLE 81 | 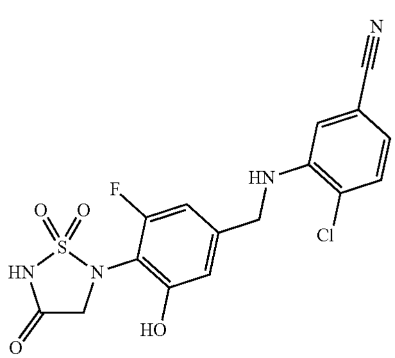 [SMILES: N#Cc1ccc(Cl)c(NCc2cc(O)c(N3CC(=O)NS3(=O)=O)c(F)c2)c1] | 4-chloro-3-[[3-fluoro-5-hydroxy-4-(1,1,4-trioxo-1,2,5-thiadiazolidin-2-yl)phenyl]methylamino]benzonitrile |

| Compound number | Structure | Chemical name |
|---|---|---|
| EXAMPLE 82 | 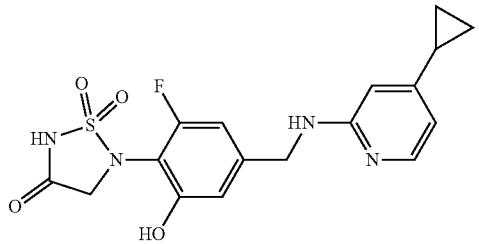 [SMILES: O=C1CN(c2c(O)cc(CNc3cc(C4CC4)ccn3)cc2F)S(=O)(=O)N1] | 5-[4-[[(4-cyclopropyl-2-pyridyl)amino]methyl]-2-fluoro-6-hydroxy-phenyl]-1,1-dioxo-1,2,5-thiadiazolidin-3-one |
| EXAMPLE 83 | 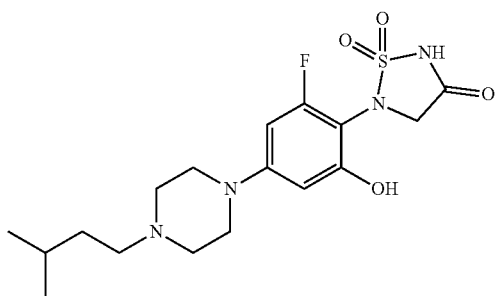 [SMILES: CC(C)CCN1CCN(c2cc(O)c(N3CC(=O)NS3(=O)=O)c(F)c2)CC1] | 5-(2-fluoro-6-hydroxy-4-(4-isopentylpiperazin-1-yl)phenyl)-1,2,5-thiadiazolidin-3-one 1,1-dioxide |
| EXAMPLE 84 | 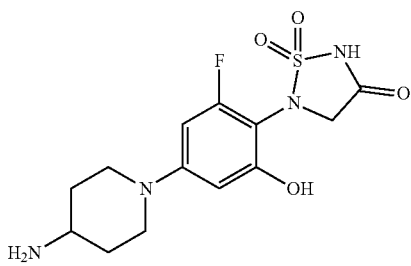 | 5-(4-(4-aminopiperidin-1-yl)-2-fluoro-6-hydroxyphenyl)-1,2,5-thiadiazolidin-3-one 1,1-dioxide |
| EXAMPLE 85 | 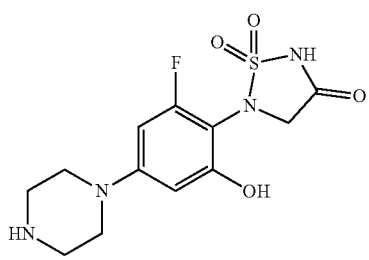 [SMILES: O=C1CN(c2c(O)cc(N3CCNCC3)cc2F)S(=O)(=O)N1] | 5-(2-fluoro-6-hydroxy-4-(piperazin-1-yl)phenyl)-1,2,5-thiadiazolidin-3-one 1,1-dioxide |
| EXAMPLE 86 | 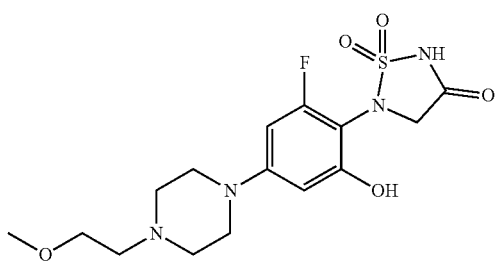 [SMILES: COCCN1CCN(c2cc(O)c(N3CC(=O)NS3(=O)=O)c(F)c2)CC1] | 5-(2-fluoro-6-hydroxy-4-(4-(2-methoxyethyl)piperazin-1-yl)phenyl)-1,2,5-thiadiazolidin-3-one 1,1-dioxide |

-continued

| Compound number | Structure | Chemical name |
|---|---|---|
| EXAMPLE 87 | 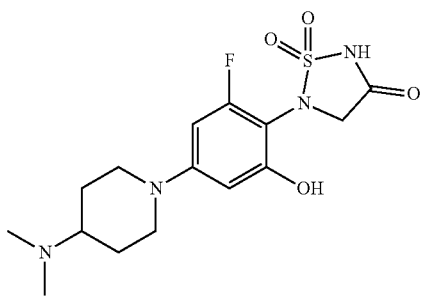 [SMILES: CN(C)C1CCN(c2cc(O)c(N3CC(=O)NS3(=O)=O)c(F)c2)CC1] | 5-(4-(4-(dimethylamino)piperidin-1-yl)-2-fluoro-6-hydroxyphenyl)-1,2,5-thiadiazolidin-3-one 1,1-dioxide |
| EXAMPLE 88 | 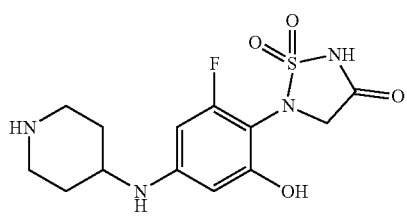 [SMILES: O=C1CN(c2c(O)cc(NC3CCNCC3)cc2F)S(=O)(=O)N1] | 5-(2-fluoro-6-hydroxy-4-(piperidin-4-ylamino)phenyl)-1,2,5-thiadiazolidin-3-one 1,1-dioxide |
| EXAMPLE 89 | 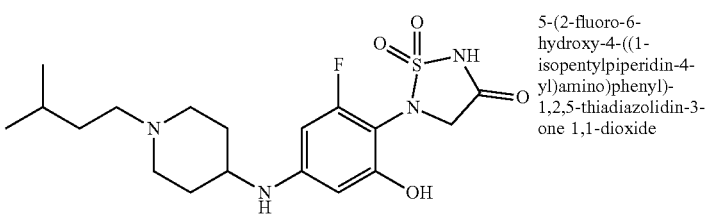 | 5-(2-fluoro-6-hydroxy-4-((1-isopentylpiperidin-4-yl)amino)phenyl)-1,2,5-thiadiazolidin-3-one 1,1-dioxide |
| EXAMPLE 90 | 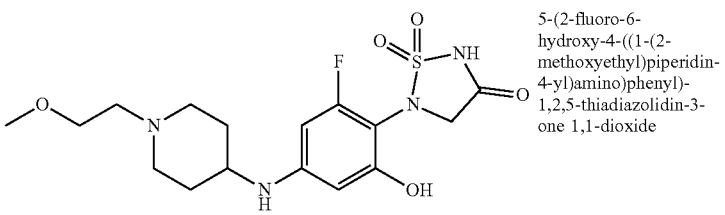 | 5-(2-fluoro-6-hydroxy-4-((1-(2-methoxyethyl)piperidin-4-yl)amino)phenyl)-1,2,5-thiadiazolidin-3-one 1,1-dioxide |
| EXAMPLE 91 | 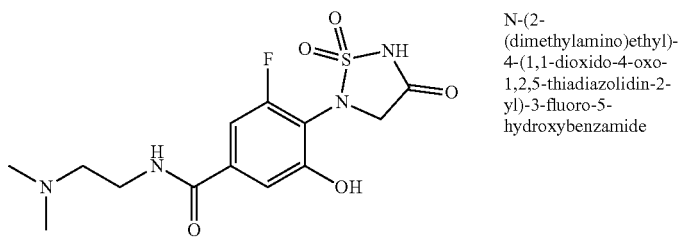 | N-(2-(dimethylamino)ethyl)-4-(1,1-dioxido-4-oxo-1,2,5-thiadiazolidin-2-yl)-3-fluoro-5-hydroxybenzamide |
| EXAMPLE 92 | 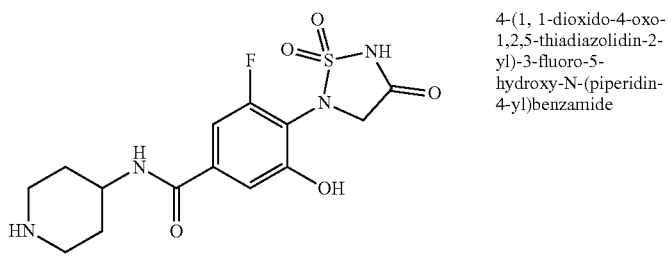 | 4-(1, 1-dioxido-4-oxo-1,2,5-thiadiazolidin-2-yl)-3-fluoro-5-hydroxy-N-(piperidin-4-yl)benzamide |

-continued

| Compound number | Structure | Chemical name |
|---|---|---|
| EXAMPLE 93 | 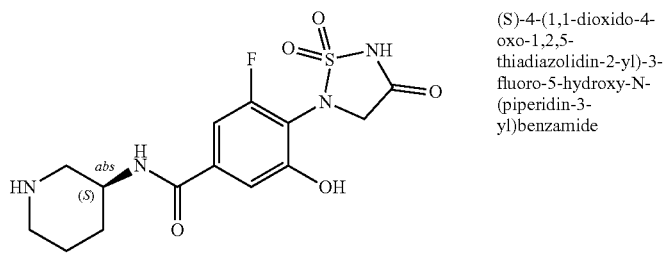 | (S)-4-(1,1-dioxido-4-oxo-1,2,5-thiadiazolidin-2-yl)-3-fluoro-5-hydroxy-N-(piperidin-3-yl)benzamide |
| EXAMPLE 94 | 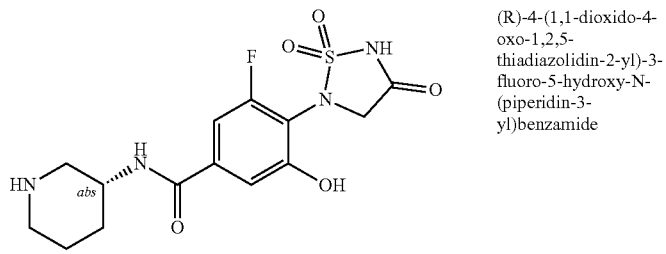 | (R)-4-(1,1-dioxido-4-oxo-1,2,5-thiadiazolidin-2-yl)-3-fluoro-5-hydroxy-N-(piperidin-3-yl)benzamide |
| EXAMPLE 95 | 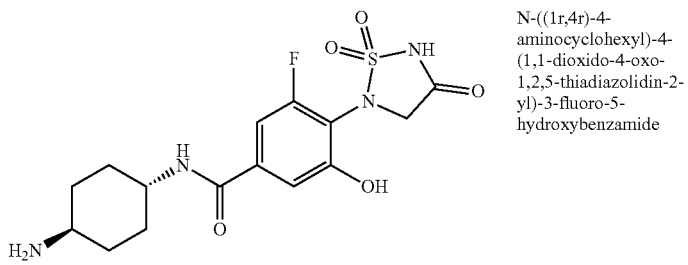 | N-((1r,4r)-4-aminocyclohexyl)-4-(1,1-dioxido-4-oxo-1,2,5-thiadiazolidin-2-yl)-3-fluoro-5-hydroxybenzamide |
| EXAMPLE 96 | 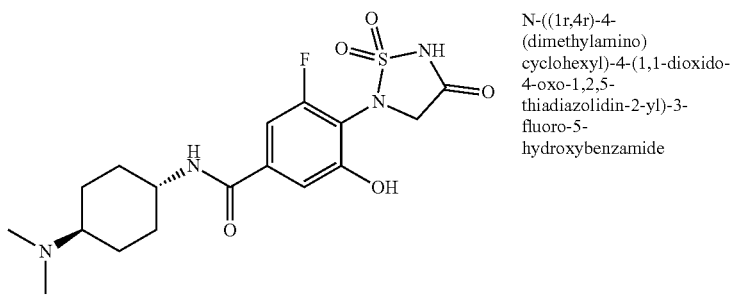 | N-((1r,4r)-4-(dimethylamino)cyclohexyl)-4-(1,1-dioxido-4-oxo-1,2,5-thiadiazolidin-2-yl)-3-fluoro-5-hydroxybenzamide |
| EXAMPLE 97 | 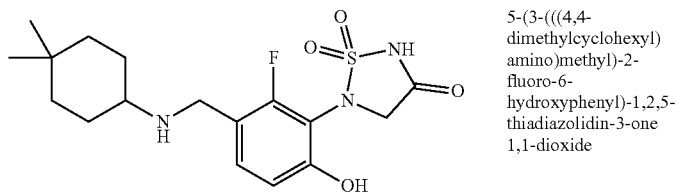 | 5-(3-(((4,4-dimethylcyclohexyl)amino)methyl)-2-fluoro-6-hydroxyphenyl)-1,2,5-thiadiazolidin-3-one 1,1-dioxide |
| EXAMPLE 98 | 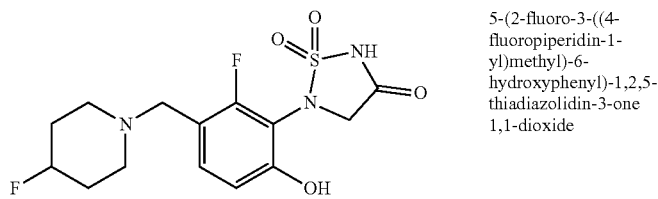 | 5-(2-fluoro-3-((4-fluoropiperidin-1-yl)methyl)-6-hydroxyphenyl)-1,2,5-thiadiazolidin-3-one 1,1-dioxide |

-continued

| Compound number | Structure | Chemical name |
|---|---|---|
| EXAMPLE 99 | 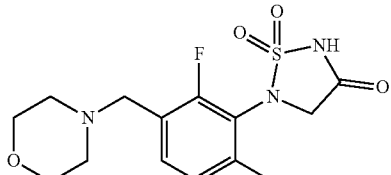 | 5-(2-fluoro-6-hydroxy-3-(morpholinomethyl)phenyl)-1,2,5-thiadiazolidin-3-one 1,1-dioxide |
| EXAMPLE 100 | 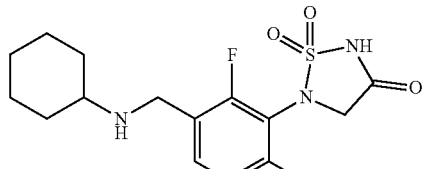 | 5-(3-((cyclohexylamino)methyl)-2-fluoro-6-hydroxyphenyl)-1,2,5-thiadiazolidin-3-one 1,1-dioxide |
| EXAMPLE 101 | 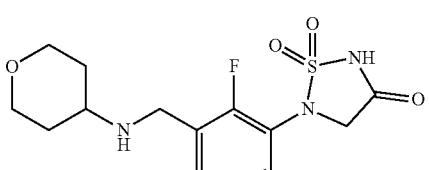 | 5-(2-fluoro-6-hydroxy-3-(((tetrahydro-2H-pyran-4-yl)amino)methyl)phenyl)-1,2,5-thiadiazolidin-3-one 1,1-dioxide |
| EXAMPLE 102 | 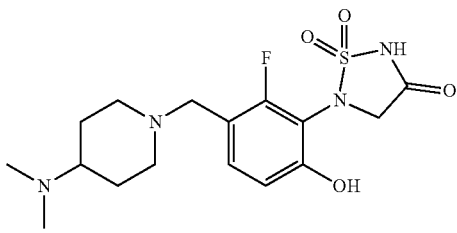 [SMILES: CN(C)C1CCN(Cc2ccc(O)c(N3CC(=O)NS3(=O)=O)c2F)CC1] | 5-(3-((4-(dimethylamino)piperidin-1-yl)methyl)-2-fluoro-6-hydroxyphenyl)-1,2,5-thiadiazolidin-3-one 1,1-dioxide |
| EXAMPLE 103 | 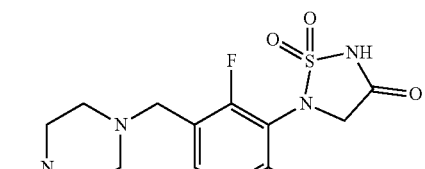 | 5-(2-fluoro-6-hydroxy-3-((4-methylpiperazin-1-yl)methyl)phenyl)-1,2,5-thiadiazolidin-3-one 1,1-dioxide |
| EXAMPLE 104 | 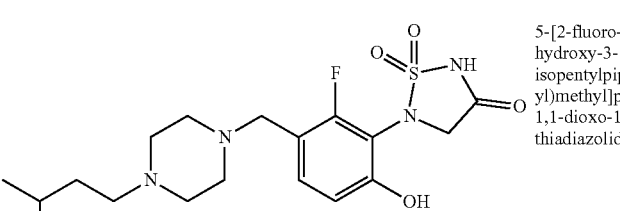 | 5-[2-fluoro-6-hydroxy-3-[(4-isopentylpiperazin-1-yl)methyl]phenyl]-1,1-dioxo-1,2,5-thiadiazolidin-3-one |
| EXAMPLE 105 | 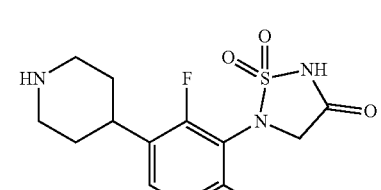 | 5-(2-fluoro-6-hydroxy-3-(piperidin-4-yl)phenyl)-1,2,5-thiadiazolidin-3-one 1,1-dioxide |

-continued

| Compound number | Structure | Chemical name |
|---|---|---|
| EXAMPLE 106 | 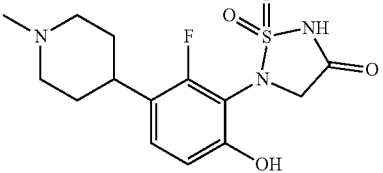 | 5-(2-fluoro-6-hydroxy-3-(1-methylpiperidin-4-yl)phenyl)-1,2,5-thiadiazolidin-3-one 1,1-dioxide | or pharmaceutically acceptable salts thereof.

17. A pharmaceutical composition comprising a compound of Formula (I) according to claim 1, or a pharmaceutically acceptable salt thereof, and at least one pharmaceutically acceptable carrier.

* * * * *

UNITED STATES PATENT AND TRADEMARK OFFICE
CERTIFICATE OF CORRECTION

PATENT NO. : 12,162,848 B2
APPLICATION NO. : 18/161184
DATED : December 10, 2024
INVENTOR(S) : Haibo Liu et al.

Page 1 of 3

It is certified that error appears in the above-identified patent and that said Letters Patent is hereby corrected as shown below:

In the Claims

Claim 1, Column 153, Lines 17-25 (approximately):

DELETE " 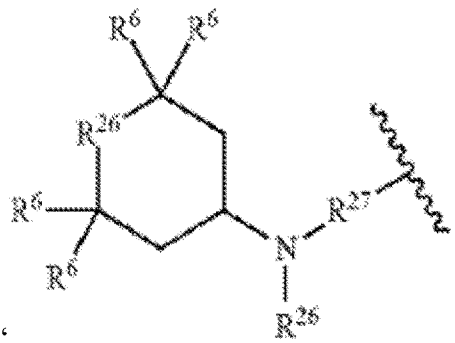 " and INSERT

-- 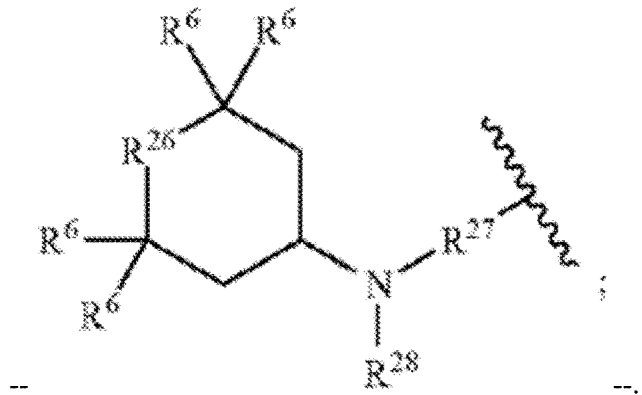 --.

Signed and Sealed this
Twenty-fifth Day of March, 2025

Coke Morgan Stewart
*Acting Director of the United States Patent and Trademark Office*

Claim 2, Column 156, Lines 33-40 (approximately):

DELETE " 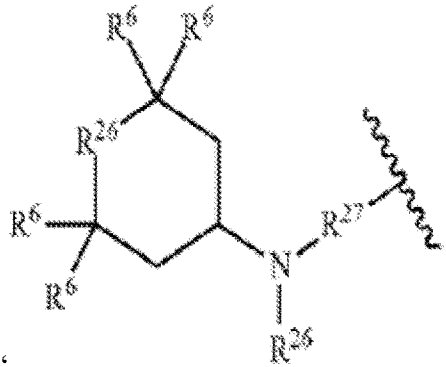 " and INSERT

-- 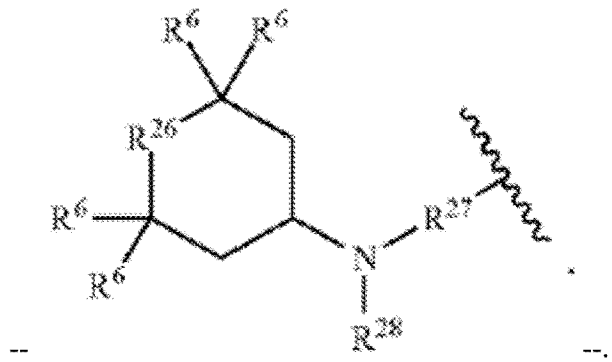 --.

Claim 16, Columns 165-166, Lines 15-16 (approximately):
DELETE "pheny 1" and INSERT -- phenyl --.

Claim 16, Columns 177-178, Line 11 (approximately):
DELETE "2-fluoro-5-[[3-fluoro-" and INSERT -- 2-fluoro-5-[[[3-fluoro - --.

Claim 16, Columns 179-180, Line 19 (approximately):
DELETE "5-[4[[(1R)-3,3-" and INSERT -- 5-[4-[[[(1R)-3,3 - --.

Claim 16, Columns 187-188, Line 13 (approximately):
DELETE "5-[2-fluoro-4-[[(3S)-" and INSERT -- 5-[2-fluoro-4[[[(3S) - --.

Claim 16, Columns 191-192, Line 13 (approximately):
DELETE "[cyclobutylmethyl" and INSERT -- [[cyclobutylmethyl --.

Claim 16, Column 201, Line 15:
DELETE "or" and INSERT -- ; or --.

CERTIFICATE OF CORRECTION (continued)
U.S. Pat. No. 12,162,848 B2

Claim 16, Columns 201-202, Line 3 (approximately):

DELETE " 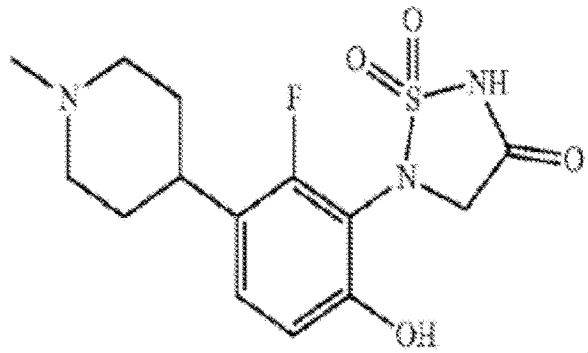 " and INSERT

-- and, 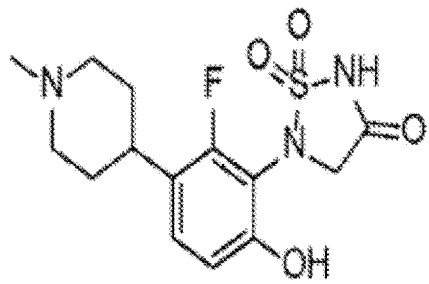 --.